United States Patent
Yamazaki et al.

(10) Patent No.: US 7,098,215 B2
(45) Date of Patent: Aug. 29, 2006

(54) NITROGENOUS COMPOUNDS AND ANTIVIRAL DRUGS CONTAINING THE SAME

(75) Inventors: Toru Yamazaki, Tokyo (JP); Hiroshi Maruoka, Osaka (JP); Shigeru Suzuki, Kanagawa (JP); Tsutomu Mukade, Saitama (JP); Kunitaka Hirose, Tokyo (JP); Mikiro Yanaka, Chiba (JP); Naoki Yamamoto, Tokyo (JP)

(73) Assignee: Kureha Chemical Industry Co., Ltd., Tokyo (JP)

( * ) Notice: Subject to any disclaimer, the term of this patent is extended or adjusted under 35 U.S.C. 154(b) by 246 days.

(21) Appl. No.: 10/257,340

(22) PCT Filed: Apr. 11, 2001

(86) PCT No.: PCT/JP01/03123
§ 371 (c)(1),
(2), (4) Date: Nov. 21, 2002

(87) PCT Pub. No.: WO01/79168
PCT Pub. Date: Oct. 25, 2001

(65) Prior Publication Data
US 2004/0092556 A1 May 13, 2004

(30) Foreign Application Priority Data
Apr. 14, 2000 (JP) ..................... 2000-114067

(51) Int. Cl.
*A61K 31/495* (2006.01)
*C07D 24/36* (2006.01)

(52) U.S. Cl. .................. 514/254.01; 514/343; 544/338; 546/192

(58) Field of Classification Search ............ 514/254.01, 514/343; 544/338; 546/192
See application file for complete search history.

(56) References Cited

U.S. PATENT DOCUMENTS

| | | | |
|---|---|---|---|
| 5,086,069 A * | 2/1992 | Klein et al. | 514/399 |
| 5,633,231 A | 5/1997 | Habich et al. | |
| 5,886,044 A | 3/1999 | Widdowson et al. | |
| 6,096,773 A | 8/2000 | Scott et al. | |
| 2004/0157818 A1 | 8/2004 | Yanaka et al. | |
| 2004/0254221 A1 | 12/2004 | Yamazaki et al. | |

FOREIGN PATENT DOCUMENTS

| | | |
|---|---|---|
| EP | 183271 A2 | 6/1986 |
| EP | 628551 | 12/1994 |
| EP | 0 646 598 A1 | 4/1995 |
| EP | 1 389 460 A1 | 2/2004 |
| JP | 7-89988 | 4/1995 |
| WO | WO 98/06397 A1 | 2/1998 |
| WO | WO 99/33787 A1 | 7/1999 |
| WO | WO 01/10842 A | 2/2001 |
| WO | WO 02/094261 A1 | 5/2002 |

OTHER PUBLICATIONS

U.S. Appl. No. 10/516,158, filed Nov. 30, 2004, Yamazaki et al.
Molino, M., et al., "CXCR4 on human endothelial cells can serve as both a mediator of biological responses and as a receptor for HIV-2," Biochimica et Biophysica Acta (BBA), Molecular Basis of Disease, vol. 1500, Issue 2, Feb. 21, 2000, p. 227–240.

* cited by examiner

Primary Examiner—Kamal A. Saeed
(74) Attorney, Agent, or Firm—Hollander Law Firm, P.L.C.

(57) ABSTRACT

The present invention provides novel compounds having antiviral activities and antiviral drugs containing the compounds as the active ingredient. The compounds are shown by the following general formula (1), wherein typically $A^1$ and $A^2$ are each guanidine or a group of the general formula (ia); $A^3$ is a mono- or poly-cyclic heteroaromatic ring containing 1 or 2 heteroatoms; $B^1$ is a single bond or alkylene group; $R^1$ is hydrogen or alkyl group; W is an alkylene having 2–3 carbons, a cycloalkylene having 5–10 carbons, aromatic ring having 6–10 carbons, or a heteroaromatic ring having 5–10 carbons; y is $C(=O)$—; x is —$C(=O)$—NH—; $n^1$ is an integer of 1–2; $n^2$ is an integer of 2–3; D is a substituent selected from among various groups

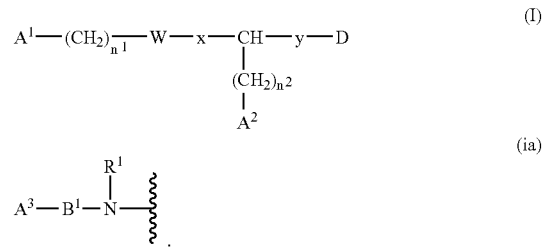

19 Claims, No Drawings

NITROGENOUS COMPOUNDS AND ANTIVIRAL DRUGS CONTAINING THE SAME

FIELD OF THE INVENTION

The present invention relates to a nitrogen-containing compound, particularly to a nitrogen-containing compound which exhibits antiviral activity.

BACKGROUND OF THE INVENTION

There are a reverse transcriptase inhibitor and a protease inhibitor as the remedies for the acquired immune deficiency syndrome (AIDS) induced by infection with human immunodeficiency virus (HIV) However, the therapeutic effects are lost by appearance of drug-resistant HIV variants (SAISHIN IGAKU, Vol. 53, No. 9, 2031 (1998)). Therapy by the combined use of these drugs is complicated due to a number of requirements to be followed. In addition, there are many drugs to be administered and some of them exhibit various side effects (NIKKEI SCIENCE, Oct. 29 (1998)). In particular, a protease inhibitor, which requires a complicated method of administration and has a risk of involving various side effects, is known to increase the probability of inducing production and selection of resistant strains unless almost 100% of a required dose is administered (Molecular Medicine, Vol. 36, No. 9, 1012 (1999)).

Development of vaccines has been undertaken in view of the past experiences in which many viral diseases were exterminated or significantly reduced by vaccines. However, the use of vaccines in HIV is thought to be very difficult due to frequent occurrences of HIV variants (NIKKEI SCIENCE, October 42 (1998)).

As mentioned above, several compounds exhibiting anti-HIV effects have been reported. However, development of a novel antiviral agent having excellent antiretroviral activity, capable of withstanding expression of resistance, being free from toxicity and side effect, and capable of being subjected to a long use has been strongly desired.

DISCLOSURE OF THE INVENTION

An objective of the present invention is to provide a drug possessing excellent antiretroviral activity and high safety.

As a result of extensive studies to develop a useful compound as a novel antiretroviral drug, the inventors of the present invention have found a series of nitrogen-containing compounds which demonstrate properties of protecting cells inoculated by HIV-1 and, therefore, possess potentiality of curing AIDS, AIDS-related complications, and the like. Accordingly, an object of the present invention is to provide a compound of the following formula (I) possessing antiviral activity mainly against HIV and a drug used for curing virus-infected patients.

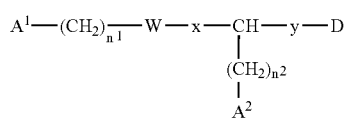
(I)

wherein $n^1$ is an integer of 0–3; $n^2$ is an integer of 0–4;
$A^1$ and $A^2$ independently represent a guanidino group or amidino group which may be substituted with a nitro group, a cyano group, an alkyl group having 1–6 carbon atoms, or an alkylene group having 2–3 carbon atoms, or a group of the following formula (i),

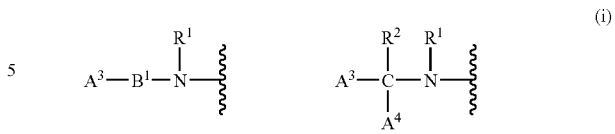

wherein $A^3$ and $A^4$ independently represent a 5–12 member, preferably 5–10 member monocyclic or polycyclic heteroaromatic ring containing 1–4 nitrogen atoms and, optionally, 1–2 other hetero atoms, the nitrogen atoms being either substituted or unsubstituted, or a 5–12 member, preferably 5–10 member monocyclic or polycyclic heteroaromatic ring, either partially saturated or unsaturated and containing 1–3 nitrogen atoms and, optionally, 1–2 other hetero atoms, the nitrogen atoms being either substituted or unsubstituted, and
$B^1$ represents a single bond or a group of the following formula (ii),

wherein $R^1$, $R^2$, and $R^3$ independently represent a hydrogen atom, a substituted or unsubstituted alkyl group having 1–6 carbon atoms, a substituted or unsubstituted alkenyl group having 2–6 carbon atoms, or a substituted or unsubstituted alkynyl group having 2–6 carbon atoms, wherein $R^2$ may bond with $R^1$ or $R^3$ to form a ring;
W represents a substituted or unsubstituted alkylene group having 1–7, preferably 2–5 carbon atoms, a substituted or unsubstituted alkenylene group having 2–7, preferably 2–5 carbon atoms, a substituted or unsubstituted alkynylene group having 2–7, preferably 2–5 carbon atoms, a substituted or unsubstituted, 3–10 member, preferably 5–10 member monocyclic or polycyclic alkylene group, a substituted or unsubstituted, 6–15 member, preferably 6–10 member monocyclic or polycyclic aromatic ring, a substituted or unsubstituted, 6–15 member, preferably 6–10 member, monocyclic or partially saturated polycyclic aromatic ring, a substituted or unsubstituted, 5–15 member, preferably 5–10 member monocyclic or polycyclic heteroaromatic ring, containing 1–3 oxygen atoms, 1–3 sulfur atoms, and/or 1–3 nitrogen atoms, a substituted or unsubstituted, 5–15 member, preferably 5–10 member, monocyclic or partially saturated polycyclic heteroaromatic ring, containing 1–3 oxygen atoms, 1–3 sulfur atoms, and 1–3 nitrogen atoms, or a substituted or unsubstituted, 3–15 member, preferably 5–10 member saturated monocyclic or polycyclic heteroring, containing 1–3 oxygen atoms, 1–3 sulfur atoms, and/or 1–3 nitrogen atoms;
D represents a functional group of the following formula (iii),

wherein $W^1$ represents an oxygen atom, a sulfur atom, or a functional group of the following formula (iv),

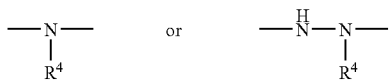

wherein $R^4$ represents a hydrogen atom or a group $-G^{1'}-G^{2'}-W^{2'}-G^{3'}$.

$G^1$ and $G^{1'}$ independently represent a single bond, a substituted or unsubstituted $C_1$ to $C_{10}$, preferably $C_1$ to $C_5$, linear or branched alkylene group, a substituted or unsubstituted $C_2$ to $C_{10}$ linear or branched alkenylene group having 1 or 2 double bonds, a substituted or unsubstituted $C_2$ to $C_{10}$, preferably $C_2$ to $C_5$, linear or branched alkynylene group having 1 or 2 triple bonds, or a functional group of the following formula (v),

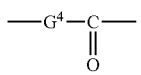

wherein $G^4$ represents a substituted or unsubstituted $C_1$ to $C_3$ alkylene group, $G^2$ and $G^{2'}$ independently represent a single bond, a substituted or unsubstituted $C_3$ to $C_{10}$ monocyclic or polycyclic alkylene group, a substituted or uhsubstituted, 6–15 member, preferably 6–10 member monocyclic or polycyclic aromatic ring, a substituted or unsubstituted, 6–15 member monocyclic or partially saturated polycyclic aromatic ring, a substituted or unsubstituted, 5–15 member, preferably 5–10 member monocyclic or polycyclic heteroaromatic ring, containing 1–3 oxygen atoms, 1–3 sulfur atoms, and/or 1–3 nitrogen atoms, a substituted or unsubstituted, 5–15 member monocyclic or partially saturated polycyclic heteroaromatic ring, containing 1–3 oxygen atoms, 1–3 sulfur atoms, and/or 1–3 nitrogen atoms, or a substituted or unsubstituted, 3–15 member, preferably 5–10 member saturated hetero ring, containing 1–3 oxygen atoms, 1–3 sulfur atoms, and/or 1–3 nitrogen atoms, $W^2$ and $W^{2'}$ independently represent a single bond, an oxygen atom, a sulfur atom, or a functional group of the following formula (vi),

wherein $R^5$ indicates a hydrogen atom, a substituted or unsubstituted $C_1$ to $C_{10}$ linear or branched alkyl group (which may form a ring together with $G^1$ or $G^2$), or a group $G^{3''}$, and $G^3$, $G^{3'}$, and $G^{3''}$ independently represent a hydrogen atom, a substituted or unsubstituted $C_1$ to $C_6$ linear or branched alkyl group, a substituted or unsubstituted $C_2$ to $C_6$ linear or branched alkenyl group having 1 or 2 double bonds, a substituted or unsubstituted $C_2$ to $C_6$ linear or branched alkynyl group having 1 or 2 triple bonds, a substituted or unsubstituted $C_3$ to $C_{10}$ monocyclic or polycyclic alkylene group, a substituted or unsubstituted $C_7$ to $C_{15}$ aralkyl group, a substituted or unsubstituted, 6–15 member, preferably 6–10 member monocyclic or polycyclic aromatic ring, a substituted or unsubstituted, 6–15 member monocyclic or partially saturated polycyclic aromatic ring, a substituted or unsubstituted, 5–15 member, preferably 5–10 member monocyclic or polycyclic heteroaromatic ring, containing 1–3 oxygen atoms, 1–3 sulfur atoms, and/or 1–3 nitrogen atoms, a substituted or unsubstituted, 5–15 member, preferably 5–10 member, monocyclic or partially saturated polycyclic heteroaromatic ring, containing 1–3 oxygen atoms, 1–3 sulfur atoms, and/or 1–3 nitrogen atoms, or a substituted or unsubstituted, 3–15 member, preferably 5–10 member saturated hetero ring, containing 1–3 oxygen atoms, 1–3 sulfur atoms, and/or 1–3 nitrogen atoms;

x represents a functional group of the following formula (vii),

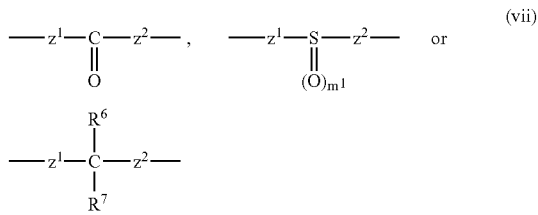

wherein $z^1$ and $z^2$ independently represent a single bond, a methylene group, oxygen atom, sulfur atom, or substituent of the following formula (viii),

$R^6$, $R^7$, and $R^8$ independently represent a hydrogen atom or a substituted or unsubstituted $C_1$ to $C_3$ alkyl group, and $m^1$ is an integer of 0–2; and y represents a functional group of the following formula (ix),

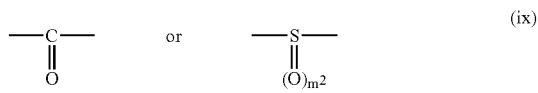

wherein $m^2$ is an integer of 0–2;

when the compound has asymmetric points, the absolute configuration of each asymmetrical point may be R, S, or a mixture thereof.

In addition, in the formula (I) of the present invention, $n^1$ is preferably an integer of 1 or 2, $n^2$ is preferably an integer of 2 or 3, $z^1$ is preferably a single bond, and z preferably represents the following formula (viii'),

wherein $R^8$ preferably represents a hydrogen atom or a substituted or unsubstituted $C_1$ to $C_3$ alkyl group.

In addition, y preferably represents a group of the following formula (ix'),

Furthermore, $W^1$ preferably represents a group of the following formula (iv'),

(iv')

wherein $R^4$ is as defined above.

The compound of the above formula (I), wherein $A^1$ and $A^2$ individually represent a guadinino group or a group of the following formula (ia),

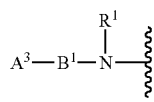

(ia)

wherein $A^3$ is a monocyclic heteroaromatic ring containing 1 or 2 hetero atoms (when the hetero atom is a nitrogen atom, the nitrogen atom is either substituted or unsubstituted), or a dicyclic, partially saturated or unsaturated, heteroaromatic ring containing 1 or 2 hetero atoms (when the hetero atom is a nitrogen atom, the nitrogen atom is either substituted or unsubstituted), and $B^1$ and $R^1$ are as defined above), W is an alkylene group having 2 or 3 carbon atoms, a cycloalkylene group having 5–10 carbon atoms, a monocyclic or dicyclic aromatic ring having 6–10 carbon atoms, or a hetero-aromatic ring having 5–10 carbon atoms, y is a group —C(=O)—, x is a group —$(CH_2)_{n^3}$—(C=O)—NH— (wherein $n^3$ is 0 or 1), and $n^1$, $n^2$, and D are as defined above, or salts thereof are preferable in the present invention.

Another preferable compound of the present invention is a compound of the above formula (I) and formula (iii), wherein $A^1$, $A^2$, W, x, y, $n^1$, and $n^2$ are the same as mentioned above, $W^1$ is —$NR^4$— (wherein $R^4$ represents a hydrogen atom or a linear or branched alkyl group having 1–5 carbon atoms), wherein $G^1$ represents a linear or branched alkylene group having 1–5 carbon atoms, $G^2$ is a single bond, $W^2$ is a single bond, an oxygen atom, or a sulfur atom, and $G^3$ is a substituted or unsubstituted, monocyclic or polycyclic aromatic ring having 6–15 carbon atoms, a substituted or unsubstituted 3–15 member monocyclic or polycyclic heteroaromatic ring containing 1–3 oxygen atoms, 1–3 nitrogen atoms, and/or 1–3 sulfur atoms, or a salt thereof.

In this instance, the substituent D consisting of combinations of $W^1$, $G^1$, $G^2$, $W^2$, and $G^3$ is preferably a substituent shown in the following formulas (x-1) to (x-3).

Formulas (x-1)

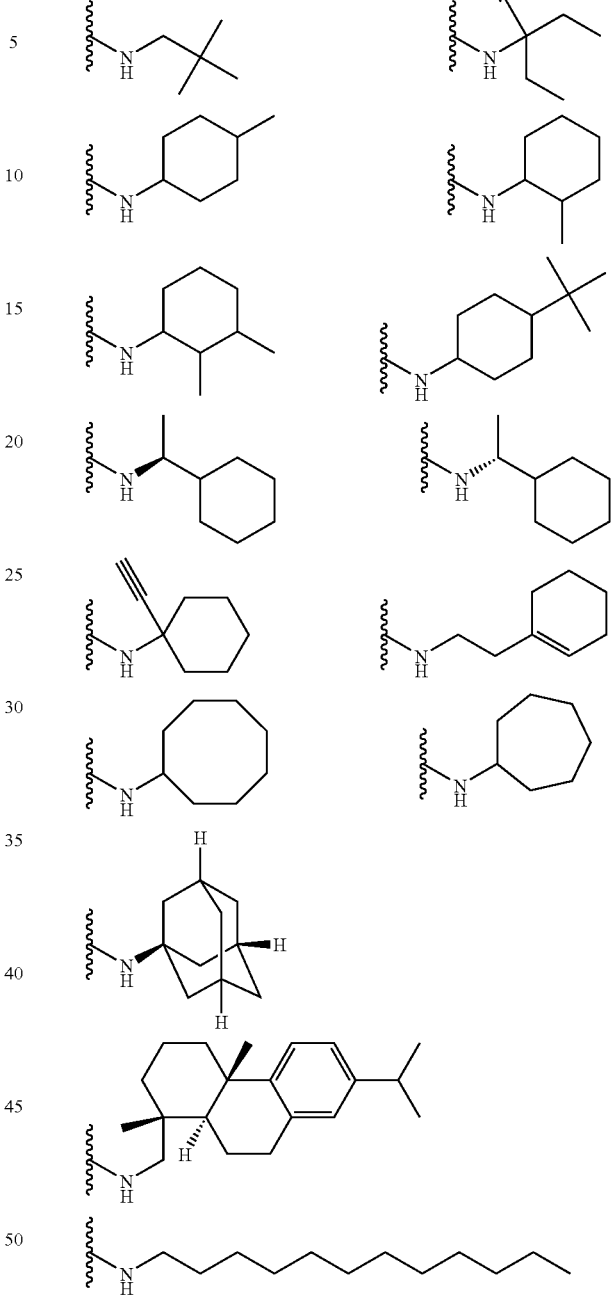
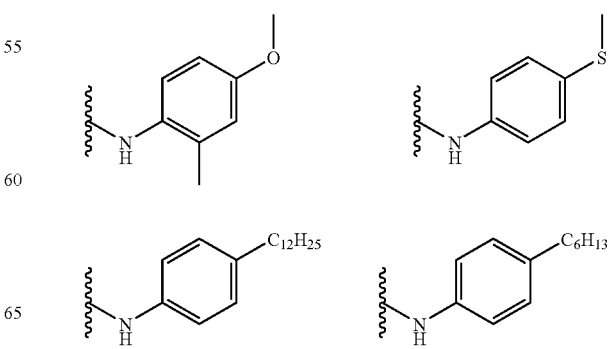

-continued
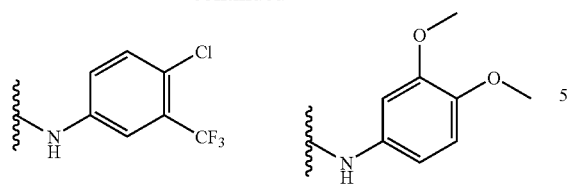
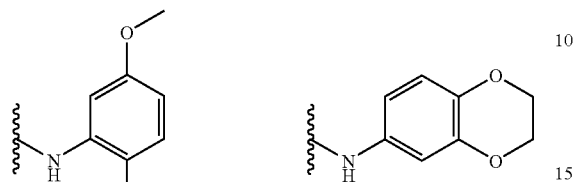
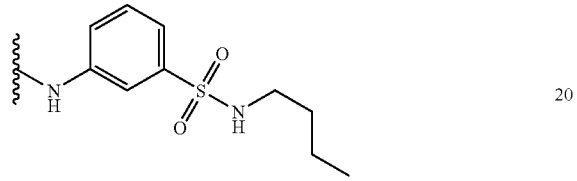
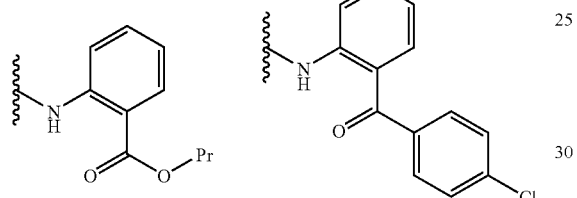
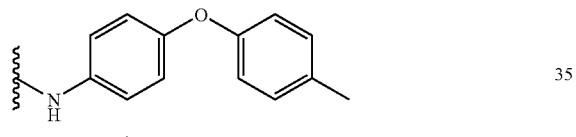
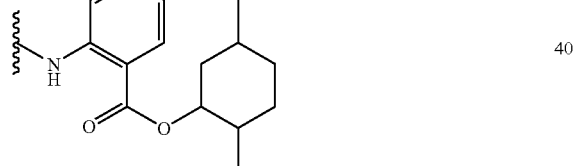
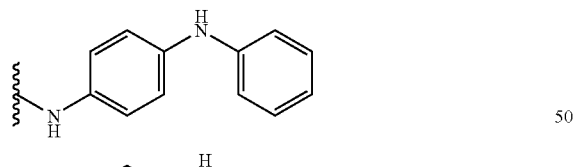
Formulas (x-2)
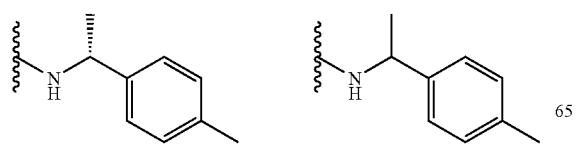
-continued
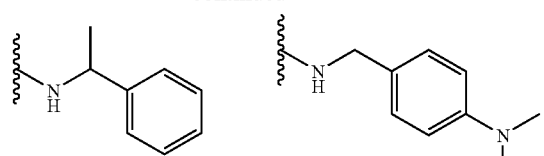
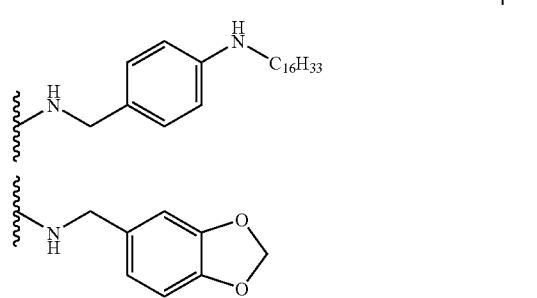
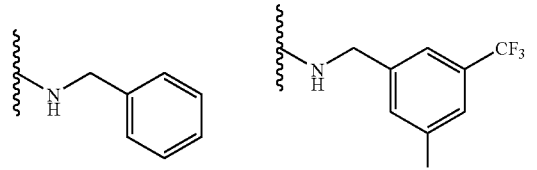
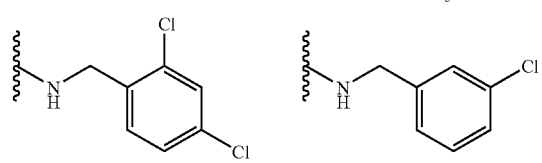
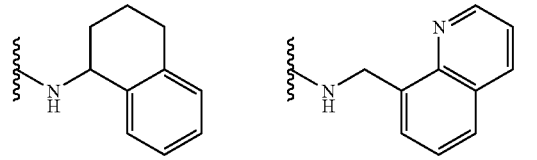
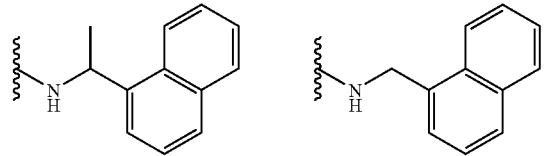
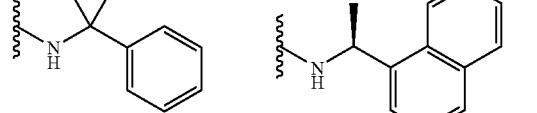
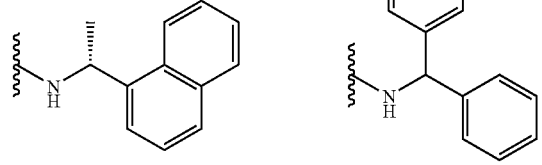

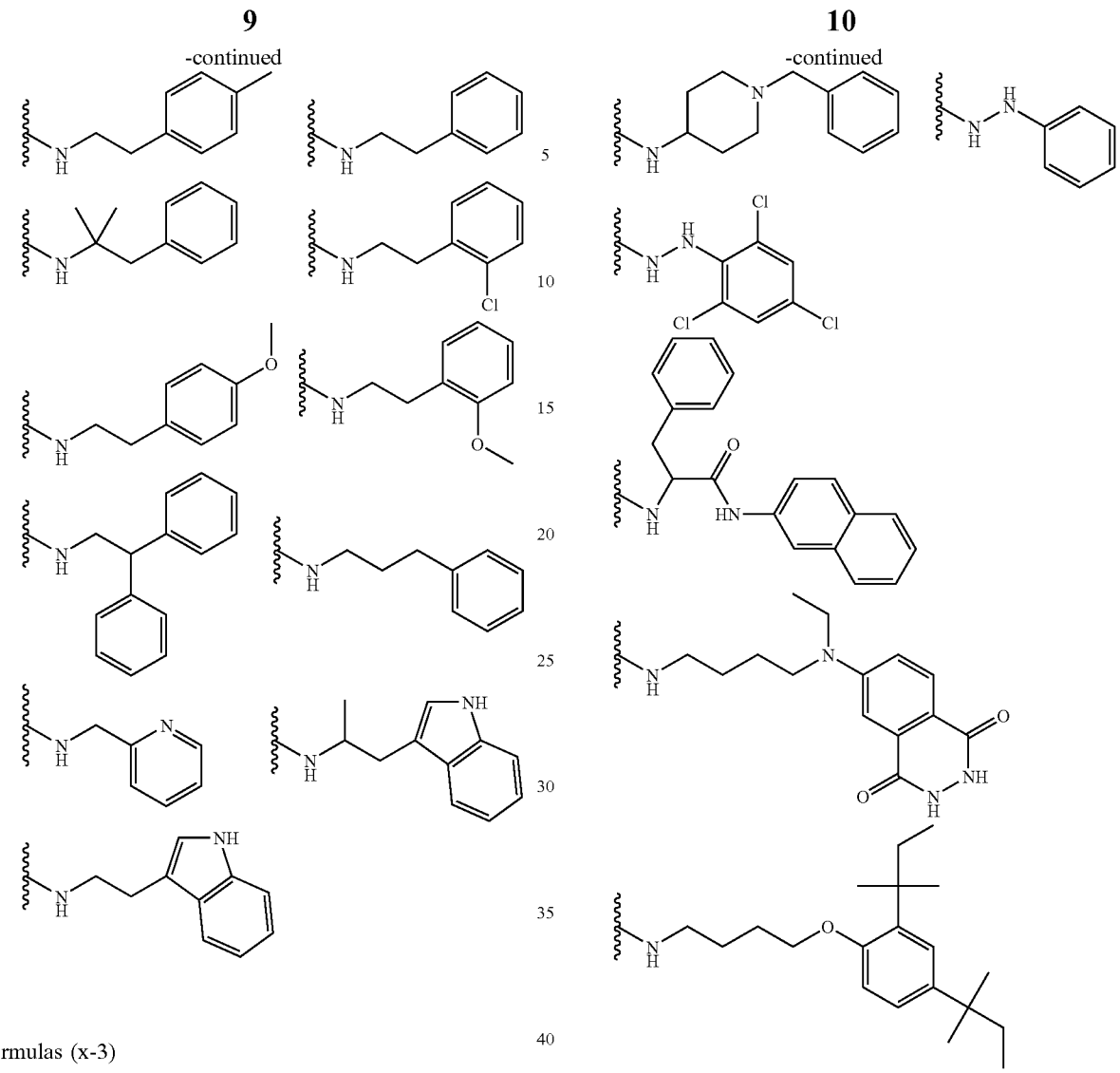

Formulas (x-3)

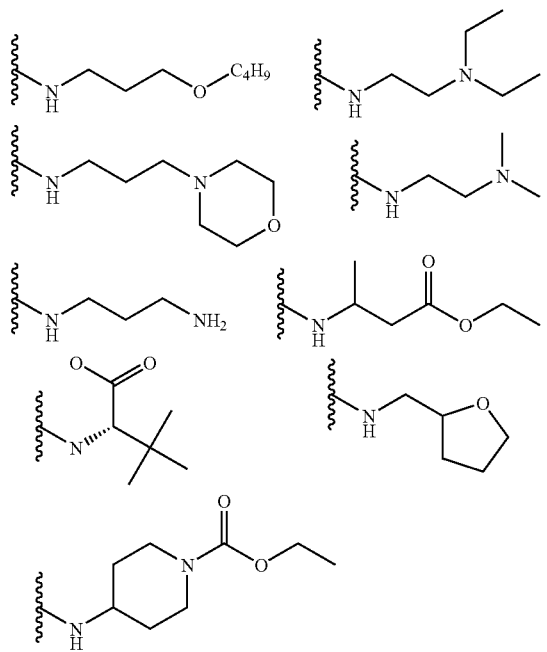

As salts of these compounds, a trifluoroacetate, hydrochloride, acetate, sulfate, nitrate, lactate, maleate, methanesulfonate, oxalate, malonate, succinate, fumarate, proprionate, butyrate, and the like can be given.

Some of the general terms used in this specification can be defined as follows and can be used individually or in combination.

As used in the specification to indicate $A^3$ or $A^4$, "monocyclic heteroaromatic ring containing 1–4 nitrogen atoms and, optionally, 1–2 other hetero atoms" includes a pyrrole ring, imidazole ring, pyrazole ring, oxazole ring, isoxazole ring, thiazole ring, isothiazole ring, triazole ring, thiadiazole ring, oxadiazole ring, pyridine ring, pyrazine ring, pyrimidine ring, pyridazine ring, triazine ring, and the like; "polycyclic heteroaromatic ring containing 1–4 nitrogen atoms and, optionally, 1–2 other hetero atoms" includes a quinoline ring, isoquinoline ring, benzimidazole ring, imidazopyridyl ring, imidazopyrimidyl ring, imidazopyrazinyl ring, benzothiazolyl ring, indole ring, isoindole ring, thiazolyl ring, purine ring, phenanthroline ring, acridine ring, carbazole ring, and the like; and "heteroaromatic ring, either partially saturated or unsaturated and containing 1–3 nitrogen atoms and, optionally, 1–2 other hetero atoms" includes a tetrahydroquinolyl ring, cyclopentenopyridyl ring, cycloheptenopyridyl ring, cyclohexenoimidazolyl ring, tetrahydroindolyl ring, and the like.

The bonding sites on the heterocyclic ring are any positions of carbon atoms on the heterocyclic ring.

As used in the specification to indicate W, the "functional group" is a divalent functional group combining with the groups on the both ends, "cycloalkylene group" includes cyclopropylene group, cyclobutylene group, cyclopentylene group, cyclohexylene group, 2-cyclohexenylene group, and the like; the "monocyclic or polycyclic aromatic ring" includes a benzene ring, naphthalene ring, anthracene ring, phenanthrene ring, indene ring, fluorene ring, and the like; and the "partially saturated aromatic ring" includes tetralin ring, indan ring, dihydroanthracene ring, and the like.

The "monocyclic or polycyclic heteroaromatic ring, partially saturated hetero ring, or saturated monocyclic or polycyclic hetero ring, containing 1–3 oxygen atoms, 1–3 sulfur atoms, and/or 1–3 nitrogen atoms" includes a thiophene ring, furan ring, pyridine ring, pyrimidine ring, pyridazine ring, pyrazine ring, indole ring, isoindole ring, pyrrole ring, isoquinoline ring, isobenzthiophene ring, quinoline ring, benzthiophene ring, and the like.

When W is a cyclic compound, the bonding sites on the ring may be any positions. For example, when W is a phenyl group or naphthyl group, 1 and 4 positions are preferable, and when W is a pyridyl group, 2 and 5 positions are preferable, but the bonding positions are not limited to these.

The "alkyl group" indicated by $R^1$, $R^2$, $R^3$, $R^6$, $R^7$, $R^8$, $G^3$, $G^{3'}$, or $G^{3''}$ in the specification is a monovalent, linear, branched, or cyclic, saturated hydrocarbon group. As examples, a methyl group, ethyl group, propyl group, isopropyl group, butyl group, isobutyl group, tert-butyl group, pentyl group, hexyl group, cyclopropyl group, cyclobutyl group, cyclopentyl group, cyclohexyl group, 2-methylcyclohexyl group, decalinyl group, and the like can be given. In the same way, the "alkenyl group" is a monovalent, linear, branched, or cyclic hydrocarbon group containing at least one ethylenic group. Examples include a vinyl group, allyl group, 2-butylenyl group, 1,3-butadienyl group, isoprenyl group, 3-pentenyl group, cyclohexa-2-ene group, cyclohexadienyl group, tetralinyl group, and the like. The "alkynyl group" is a monovalent, linear, branched, or cyclic hydrocarbon group containing at least one acetylenic group. Ethynyl group, 2-propynyl group, 3-pentynyl group, and the like can be given as examples.

The "alkylene group" indicated by W, $G^1$, $G^{1'}$, or $R^5$ in the specification is a divalent, linear, branched, or cyclic, saturated hydrocarbon group. As examples, a methylene group, ethylene group, propylene group, isopropylene group, butylene group, isobutylene group, tert-butylene group, hexylene group, heptylene group, cyclopropylene group, cyclobutylene group, cyclopentylene group, cyclohexylene group, decalinylene group, and the like can be given. The "alkenylene group" is a divalent, linear, branched, or cyclic hydrocarbon group containing at least one ethylenic group. Examples include a ethylenyl group, propenylene group, 2-butenylene group, 2-methyl-2-butenylene group, 2-ethyl-2-butenylene group, butadienylene group, cyclopentenylene group, cyclohexenylene group, cyclohexadienylene group, and the like. The "alkynylene group" is a divalent, linear, branched, or cyclic hydrocarbon group containing at least one acetylenic group. As examples, an acetynylene group, propynylene group, 2-butynylene group, 1-methyl-2-butynylene group, and the like can be given.

The "aralkyl group" indicated by $G^3$, $G^{3'}$, or $G^{3''}$ in the specification is a group consisting of the above-described alkyl group and an aromatic ring such as, for example, a benzyl group, 1-phenethyl group, 2-phenethyl group, 1-phenylpropyl group, 2-phenylbutyl group, 1-naphthylmethyl group, 2-naphthylmethyl group, 1-(1-naphthyl)ethyl group, and 2-(1-naphthyl)ethyl group and the like. The "monocyclic or polycyclic aromatic ring" is a benzene ring, naphthalene ring, anthracene ring, and the like. The "monocyclic or polycyclic heteroaromatic ring containing 1–3 oxygen atoms, 1–3 sulfur atoms, and/or 1–3 nitrogen atoms" are an imidazole ring, furan ring, thiophene ring, pyridine ring, pyrimidine ring, pyrazine ring, indole ring, indazole ring, benzimidazole ring, pyridinopyrrole ring, and the like. The monocyclic or partially saturated polycyclic heteroaromatic ring "containing 1–3 oxygen atoms, 1–3 sulfur atoms, and/or 1–3 nitrogen atoms" indicates a tetrahydroquinoline ring, cyclopentapyridine ring, and the like. The "saturated monocyclic or polycyclic heterocyclic ring containing 1–3 oxygen atoms, 1–3 sulfur atoms, and 1–3 nitrogen atoms" indicates a tetrahydrofuran ring, pyrrolidine ring, imidazoline ring, and the like.

The term "substituted group" as used in the expression of substituents includes a halogen group, nitro group, hydroxyl group, thiol group, carbonyl group, carboxyl group, sulfenyl group, sulfone group, amino group, amide group, cyano group, carbamoyl group, alkoxy group, alkoxycarbonyl group, alkylamino group, dialkylamino group, aminocarbonyl group, alkylaminocarbonyl group, dialkylaminocarbonyl group, alkanoylamino group, alkanoylalkylamino group, alkylthio group, alkylsulfenyl group, alkylsulfone group, phenyl group, and the like.

The "alkyl" included in these substituents is the same as the alkyl group mentioned above, and the "alkoxy" means an "alkyl-oxy" consisting of the above alkyl group and an oxygen atom bonding at one end of the alkyl group. The "alkanoyl" means a substituent formed by the above alkyl group via a carbonyl group.

DETAILED DESCRIPTION OF THE INVENTION AND PREFERRED EMBODIMENT

The compound of the present invention is prepared by commonly used organic chemical reactions. Some examples of the manufacturing process are described below. However, the processes are not limited to these.

Manufacturing Process 1

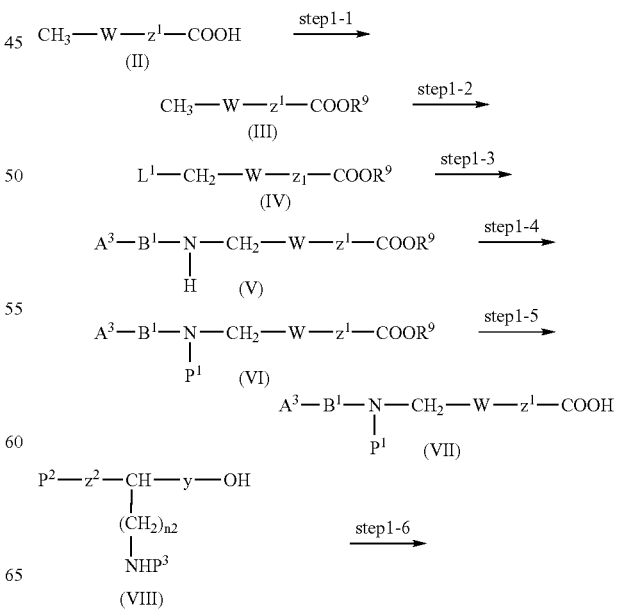

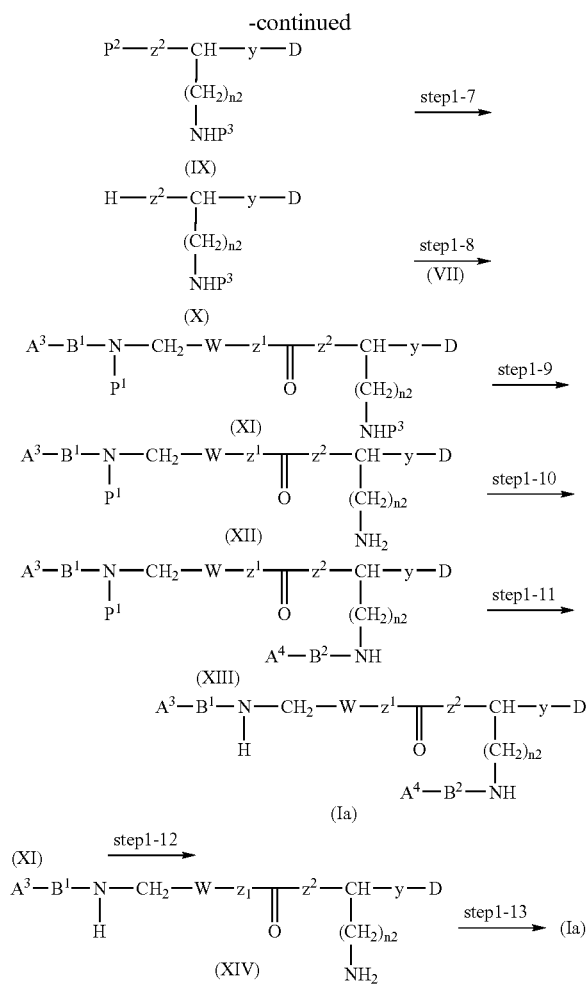

Step 1-1

A readily available known compound (II), $CH_3$—$W$—$z^1$—COOH ($W$ and $z^1$ are as defined above) is dissolved in an alcohol solvent, $R^9$—OH ($R^9$ is a methyl group, ethyl group, benzyl group, etc.) and reacted at −20° C. to 100° C. for 0.5–24 hours while introducing hydrochloric acid gas into the solution to obtain the target compound (III).

Step 1-2

The compound (III) is dissolved in an organic solvent such as carbontetrachloride, chloroform, or benzene. After the addition of a halogenation agent such as N-bromosuccinimide, N-chlorosuccinimide, or the like and, optionally, a radical generator such as azoisobutylonitrile, the mixture is reacted at 0–100° C. to obtain the target compound (IV) ($L^1$ is a halogen atom such as chlorine or bromine).

Step 1-3

The compound (IV) is dissolved in an organic solvent such as tetrahydrofuran (hereinafter referred to as "THF") or dimethylformamide (hereinafter referred to as "DMF"). After the addition of a primary amine, $A^3$-$B^1$—$NH_2$ ($A^3$ and $B^1$ are as defined above), and a base such as potassium carbonate or triethylamine, the mixture is reacted at a temperature from room temperature to 100° C. to obtain the target compound (V).

Step 1-4

The compound (V) is dissolved in an organic solvent such as THF or DMF. After the addition of a protective agent such as a compound represented by $P^1$–$L^1$, $P^1{_2}O$ ($P^1$ is a protective group such as butoxycarbonyl or benzyloxycarbonyl) and a base such as triethylamine or an aqueous solution of sodium hydroxide, the mixture is reacted at a temperature from −10° C. to 100° C. to obtain the target compound (VI).

It is possible to omit the step 1-3, in which case the compound (IV) and $A^3$-$B^1$—$NHP^1$ ($A^3$, $B^1$, and $P^1$ are as defined above) are reacted together with a base such as sodium hydride and powdery potassium hydroxide in an organic solvent such as DMF or THF at a temperature from room temperature to 120° C. to obtain the target compound (VI).

Step 1-5

The compound (VI) is dissolved in one or two organic solvents selected from DMF, THF, methanol, ethanol, and the like, a basic aqueous solution such as an aqueous solution of sodium hydroxide is added, and the mixture is reacted at 0–100° C. to obtain the target compound (VII).

Step 1-6

A readily available known compound (VIII) ($z^2$, y, and $n^2$ are the same as defined above, $P^2$ and $P^3$ independently represent a protective group such as 9-fluorenylmethylcarbonyl (Fmoc), t-butoxycarbonyl (Boc), benzyloxycarbonyl (Cbz), and the like) is dissolved in an organic solvent such as DMF. A compound of the formula H–D (D is as defined above) is added. Then, a condensing agent such as N-ethyl-N-(3-dimethylaminopropyl) carbodiimide (WSC I) hydrochloride, benzotriazole-1-yloxy-tris(dimethylamino)phosphonium hexafluorophosphate (BOP), 2-ethoxy-1-ethoxycarbonyl-1,2-dihydroquinoline (EEDQ), and the like and, as required, a catalyst such as 1-hydroxybenzotriazole (HOBt), 4-dimethylaminopyridine (DMAP), or the like are added, and the mixture is reacted at a temperature from −20° C. to 80° C. to obtain the target compound (IX).

Step 1-7

The group $P^2$ in the compound (IX) is selectively removed to obtain the target compound. (X). For example, when the-group $P^2$ is Fmoc, the compound (IX) is dissolved in an organic solvent such as DMF and reacted together with an organic base such as diethylamine or morpholine at a temperature from room temperature to 100° C. to obtain the target compound (X).

Step 1-8

The compound (X) is dissolved in an organic solvent such as DMF. After the addition of the above-mentioned compound (VII) and a condensing agent such as WSCI hydrochloride, BOP, or EEDQ, and, optionally, a catalyst such as HOBt or DMAP, the mixture is reacted at a temperature from −20° C. to 80° C. to obtain the target compound (XI).

Step 1-9

The group $P^3$, which is a protective group of the compound (XI), is selectively removed to obtain the target compound (XII). For example, when the group $P^3$ is Cbz, the compound (XI) is dissolved in ethanol, methanol, or hydrated dioxane and reacted in the presence of a hydrogenation catalyst such as palladium-carbon in a hydrogen gas atmosphere at room temperature to obtain the target compound (XII).

Step 1-10

The compound (XII) is dissolved in an organic solvent such as methanol, ethanol or acetonitril. $A^4$CHO or $A^4$=O ($A^4$ is as defined above and $A^4$=O is a compound in which the carbon atom at any optional position in $A^4$ is a ketone, for example, 2-acetylpyridine, tetrahydroquinolin-8-one, and the like) and a reducing agent such as sodium borohydride, sodium cyanoborohydride, are added into the solution, and after adjusting pH of the solution as required, the mixture is reacted at a temperature from −20° C. to 60° C. to obtain the target compound (XIII).

Step 1-11

The group $P^1$, which is a protective group of the compound (XIII), is removed to obtain the target compound (Ia), which indicates a compound included in the compounds of the above-described formula (I).

For example, when the group $P^1$ is Boc, the compound (XIII) is dissolved in an organic solvent such as methanol, dioxane, or the like. Then, a mineral acid such as hydrochloric acid or a strong organic acid such as trifluoroacetic acid is added to obtain the target compound (Ia).

Step 1-12

The groups $P^1$ and $P^3$, which are protective groups of the compound (XI), are simultaneously removed to obtain the target compound (XIV). For example, when the groups $P^1$ and $P^3$ are a combination of Boc and Cbz, the compound (XI) is dissolved in an organic solvent such as chloroform and reacted by adding cresol.thioanisole.rifluoroacetic acid at a temperature from room temperature to 80° C. to obtain the target compound (XIV).

Step 1-13

The compound (XIV) is dissolved in an organic solvent such as methanol, ethanol or acetonitril. $A^4$CHO or $A^4$=O ($A^4$ is as defined above and $A^4$=O is a compound in which the carbon atom at any optional position in $A^4$ is a ketone, for example, 2-acetylpyridine, tetrahydroquinolin-8-one, and the like) and a reducing agent such as sodium borohydride or sodium cyanoborohydride, are added into the solution, and after adjusting pH of the solution as required, the mixture is reacted at a temperature from −20° C. to 60° C. to obtain the target compound (Ia), which indicates a compound included in the compounds of the above-described formula (I).

Manufacturing Process 2

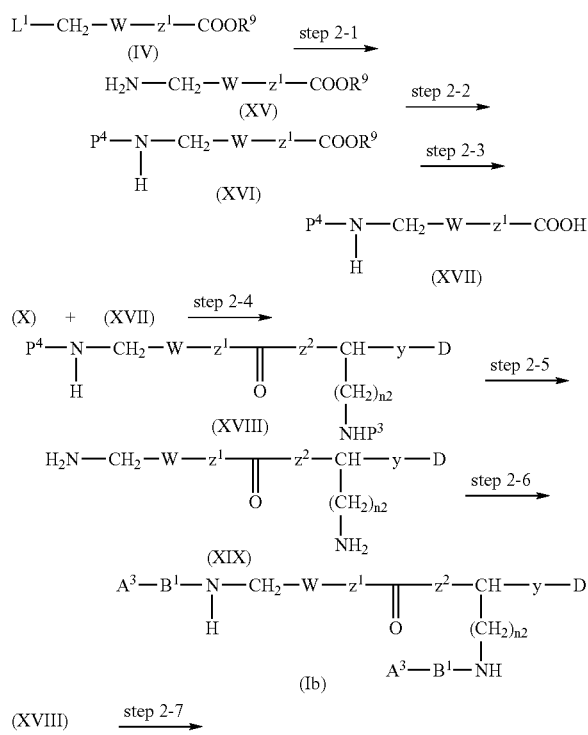

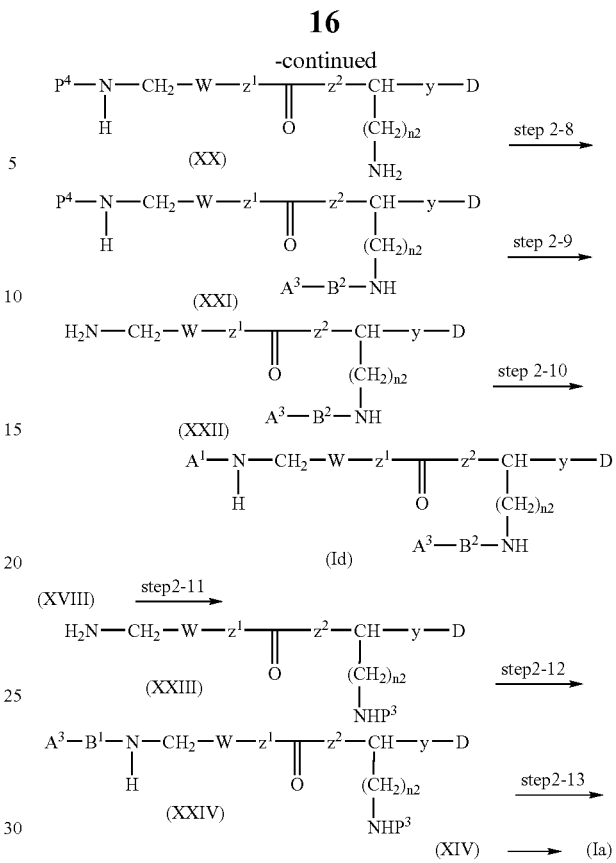

Step 2-1

The compound (IV) previously described in the Manufacturing Process 1 is dissolved in an organic solvent such as DMF and reacted with potassium phthalimide to obtain an intermediate. The intermediate is reacted with hydrazine hydrate in an organic solvent such as ethanol, methanol, or the like to obtain the target compound (XV).

Step 2-2

The compound (XV) is dissolved in an organic solvent such as THF or DMF, and a protective agent such as a compound represented by $P^4$-$L^1$, $P^4_2$O ($P^4$ is a protective group such as Boc, Cbz, or the like) and a base such as triethylamine or an aqueous solution of sodium hydroxide are added into the solution. The mixture is reacted at a temperature from −20° C. to 80° C. to obtain the target compound (XVI).

Step 2-3

The compound (XVI) is dissolved in one or two organic solvents selected from DMF, THF, methanol, ethanol, and the like, and a basic aqueous solution such as an aqueous solution of sodium hydroxide are added into the solution. The mixture is reacted at 0–100° C. to obtain the target compound (XVII).

Step 2-4

The compound (X) is dissolved in an organic solvent such as DMF, and the above-mentioned compound (XVII), a condensing agent such as WSCI hydrochloride, BOP, or EEDQ, and, optionally, a catalyst such as HOBt or DMAP are added into the solution. The mixture is reacted at a temperature from −20° C. to 80° C. to obtain the target compound (XVIII).

Step 2-5

The groups $P^3$ and $P^4$, which are protective groups of the compound (XVIII), are removed to obtain the target compound (XIX). For example, when the both groups $P^3$ and $P^4$ are Bocs, the compound (XVIII) is dissolved in an organic solvent such as methanol, dioxane. Then, a mineral acid such as hydrochloric acid or a strong organic acid such as trifluoroacetic acid is added into the solution to obtain the target compound (XIX).

Step 2-6

The compound (XIX) is dissolved in an organic solvent such as methanol, ethanol or acetonitril. $A^3CHO$ or $A^3=O$ ($A^3$ is as defined above and $A^3=O$ is a compound in which the carbon atom at any optional position in $A^3$ is a ketone, for example, 2-acetylpyridine, tetrahydroquinolin-8-one, and the like) and a reducing agent such as sodium borohydride or sodium cyanoborohydride, are added into the solution, and after adjusting pH of the solution as required, the mixture is reacted at a temperature from $-20°$ C. to $60°$ C. to obtain the target compound (Ib), which indicates a compound included in the compounds of the above-described formula (I).

Step 2-7

The group $P^4$, which is a protective group of the compound (XVIII), is selectively removed to obtain the target compound (XX). For example, when the group $P^3$ is Cbz and $P^4$ is Boc, the compound (XVIII) is dissolved in a solvent such as ethanol, methanol, or hydrated dioxane and reacted in the presence of a hydrogenation catalyst such as palladium-carbon in a hydrogen gas atmosphere at room temperature to obtain the target compound (XX).

Step 2-8

The compound (XX) is dissolved in an organic solvent such as methanol, ethanol or acetonitril. $A^3CHO$ or $A^3=O$ ($A^3$ is as defined above and $A^3=O$ is a compound in which the carbon atom at any optional position in $A^3$ is a ketone, for example, 2-acetylpyridine, tetrahydroquinolin-8-one, and the like) and a reducing agent such as sodium borohydride, sodium or cyanoborohydride, are added into the solution, and after adjusting pH of the solution as required, the mixture is reacted at a temperature from $-20°$ C. to $60°$ C. to obtain the target compound (XXI).

Step 2-9

The group $P^3$, which is a protective group of the compound (XXI), is removed to obtain the target compound (XXII). For example, when the group $P^3$ is Boc, the compound (XXI) is dissolved in an organic solvent such as methanol, dioxane, or the like. Then, a mineral acid such as hydrochloric acid or a strong organic acid such as trifluoroacetic acid is added into the solition to obtain the target compound (XXII).

Step 2-10

The compound (XXII) is dissolved in an organic solvent such as methanol, ethanol or acetonitril. $A^3CHO$ or $A^3=O$ ($A^3$ is as defined above and $A^3=O$ is a compound in which the carbon atom at any optional position in $A^3$ is a ketone, for example, 2-acetylpyridine, tetrahydroquinolin-8-one, and the like) and a reducing agent such as sodium borohydride or sodium cyanoborohydride, are added into the solution, and after adjusting pH of the solution as required, the mixture is reacted at a temperature from $-20°$ C. to $60°$ C. to obtain the target compound (Id), which indicates a compound included in the compounds of the above-described formula (I).

Alternatively, the compound (XXII) is reacted with a guanidinization reagent such as pyrazolecarboxamide in the presence of a suitable base in an organic solvent such as methanol or DMF at a temperature from $0°$ C. to $100°$ C. to obtain the target compound (Id).

Step 2-11

The group $P^4$, which is a protective group of the compound (XVIII), is selectively removed to obtain the target compound (XXIII). For example, when the group $P^3$ is Cbz and $P^4$ is Boc, the target compound (XXIII) can be obtained by causing the compound (XVIII) to coexist with trifluoroacetic acid in chloroform or with hydrochloric acid in a mixed solvent of dioxane and methanol.

Step 2-12

The compound (XXIII) is dissolved in an organic solvent such as methanol, ethanol or acetonitril. $A^3CHO$ or $A^3=O$ ($A$ is as defined above and $A^3=O$ is a compound in which the carbon atom at any optional position in $A^3$ is a ketone, for example, 2-acetylpyridine, tetrahydroquinolin-8-one, and the like) and a reducing agent such as sodium borohydride or sodium cyanoborohydride, are added into the solution, and after adjusting pH of the solution as required, the mixture is reacted at a temperature from $-20°$ C. to $60°$ C. to obtain the target compound (XXIV)

Step 2-13

The group $P^3$, which is a protective group of the compound (XXIV), is removed to obtain the target compound (XXV). For example, when the group $P^3$ is Cbz, the compound (XXIV) is dissolved in ethanol, methanol, or hydrated dioxane and reacted in the presence of a hydrogenation catalyst such as palladium-carbon in a hydrogen gas atmosphere at room temperature to obtain the target compound (XIV). The compound (XIV) is converted into the compound (Ia) in the same manner as in Step 1-13 of Manufacturing Process 1.

Manufacturing Process 3

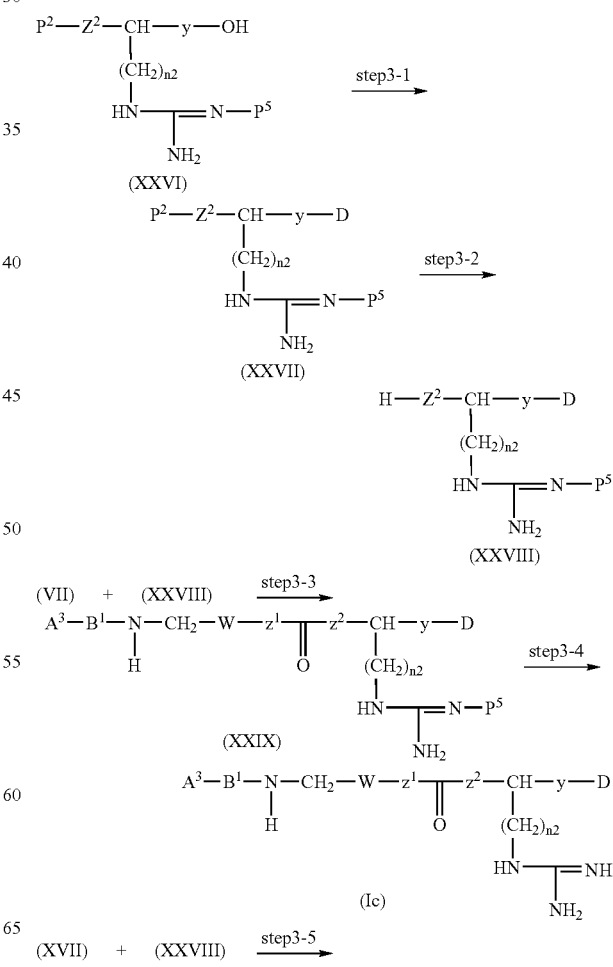

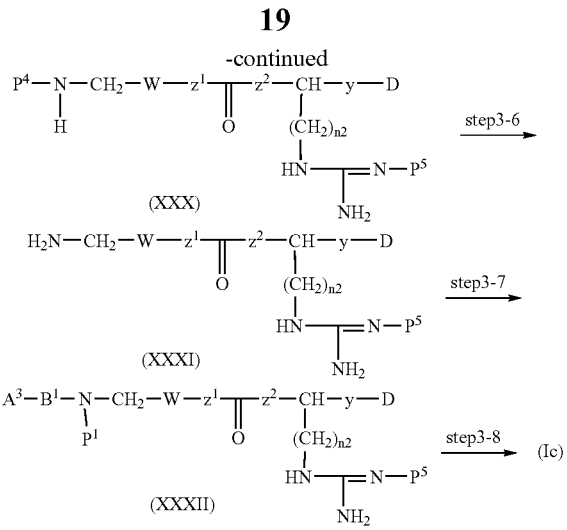

Step 3-1

A readily available known compound (XXVI) ($z^2$, y, and $n^2$ are as defined above, $P^2$ indicates a protective group such as Fmoc, Boc, Cbz, or the like, and $P^5$ is a protective group of guanidine such as a pentamethylchromansulfonyl group or toluenesulfonyl group) is dissolved in an organic solvent such as DMF. After the addition of a compound of the formula H-D (D is as defined above) and a condensing agent such as WSCI hydrochloride, BOP, or EEDQ, and, optionally, a catalyst such as HOBt or DMAP, the mixture is reacted at a temperature from −20° C. to 80° C. to obtain the target compound (XXVII).

Step 3-2

The group $P^2$ in the compound (XXVII) is selectively removed to obtain the target compound (XXVIII). For example, when the group $P^2$ is Fmoc, the compound (XXVII) is dissolved in an organic solvent such as DMF and reacted together with an organic base such as diethylamine or morpholine at a temperature from room temperature to 100° C. to obtain the target compound (XXVIII).

Step 3-3

The compound (XXVIII) is dissolved in an organic solvent such as DMF. After the addition of the above-mentioned compound (VII) and a condensing agent such as WSCI hydrochloride, BOP, or EEDQ, and, optionally, a catalyst such as HOBt or DMAP, the mixture is reacted at a temperature from −20° C. to 80° C. to obtain the target compound (XXIX).

Step 3-4

The compound (XXIV) is dissolved in an organic solvent such as chloroform and methylene chloride. After the addition of trifluoroacetic acid, the mixture is stirred at a temperature from −20° C. to 60° C. to obtain the target compound (Ic), which indicates a compound included in the compounds of the above-described formula (I).

Step 3-5

The compound (XXVIII) is dissolved in an organic solvent such as DMF. After the addition of the above-mentioned compound (XVII) and a condensing agent such as WSCI hydrochloride, BOP, or EEDQ, and, optionally, a catalyst such as HOBt or DMAP, the mixture is reacted at a temperature from −20° C. to 80° C. to obtain the target compound (XXX).

Step 3-6

The group $P^4$, which is a protective group of the compound (XXX), is selectively removed to obtain the target compound (XXXI). For example, when the group $P^4$ is Cbz, the compound (XXX) is dissolved in ethanol, methanol, or hydrated dioxane and reacted in the presence of a hydrogenation catalyst such as palladium-carbon in a hydrogen gas atmosphere at room temperature to obtain the target compound (XXXI).

Step 3-7

The compound (XIV) is dissolved in an organic solvent such as methanol, ethanol or acetonitril. $A^4$CHO or $A^4$=O ($A^4$ is as defined above and $A^4$=O is a compound in which the carbon atom at any optional position in $A^4$ is a ketone, for example, 2-acetylpyridine, tetrahydroquinolin-8-one, and the like) and a reducing agent such as sodium borohydride or sodium cyanoborohydride, are added into the solution, and after adjusting pH of the solution as required, the mixture is reacted at a temperature from −20° C. to 60° C. to obtain the target compound (XXXII).

Step 3-8

The compound (XXXII) is dissolved in an organic solvent such as chloroform and methylene chloride. After the addition of trifluoroacetic acid, the mixture is stirred at a temperature from −20° C. to 60° C. to obtain the target compound (Ic), which indicates a compound included in the compounds of the above-described formula (I).

Manufacturing Process 4

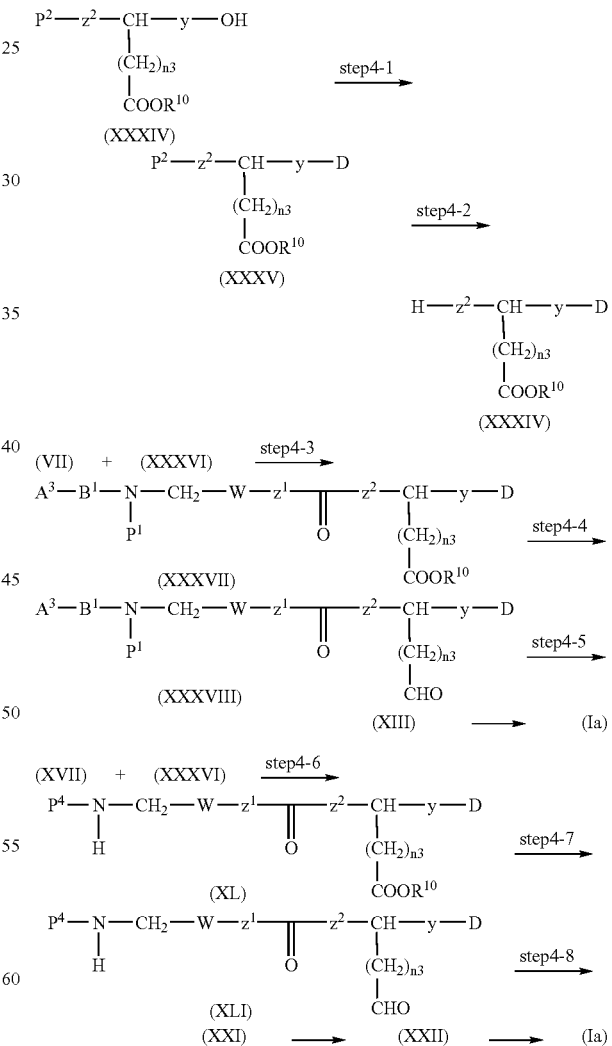

Step 4-1

A readily available known compound (XXXIV) ($z^2$ is as defined above, $n^3$ indicates an integer of 1–3, $R^{10}$ represents a methyl group, ethyl group, benzyl group, and the like, and $P^2$ indicates a protective group such as Fmoc, Boc, Cbz, or the like) is dissolved in an organic solvent such as DMF. After the addition of the compound of the formula H-D (D is as defined above) and a condensing agent such as WSCI hydrochloride, BOP, or EEDQ, and, optionally, a catalyst such as HOBt or DMAP, the mixture is reacted at a temperature from −20° C. to 80° C. to obtain the target compound (XXXV).

Step 4-2

The group $P^2$, which is a protective group of the compound (XXXV), is selectively removed to obtain the target compound (XXXVI). For example, when the group $P^2$ is Boc, the compound (XXXV) is dissolved in an organic solvent such as methanol, ethanol, or the like. Then, hydrogen chloride gas is introduced into the solution to obtain the target compound (XXXVI).

Step 4-3

The compound (XXXVI) is dissolved in an organic solvent such as DMF. After the addition of the above-mentioned compound (VII) and a condensing agent such as WSCI hydrochloride, BOP, or EEDQ, and, optionally, a catalyst such as HOBt or DMAP, the mixture is reacted at a temperature from −20° C. to 80° C. to obtain the target compound (XXXVII).

Step 4-4

The group $COOR^{10}$ in the compound (XXXVII) is converted into CHO to obtain the target compound (XXXVIII). For example, an intermediate (an alcoholic compound) is synthesized from the compound (XXXVII) using a reducing agent such as lithium aluminum hydride in an organic solvent such as THF. Then, the intermediate is oxidized using dimethylsulfoxide-oxalyl chloride, pyridinium dichlorochromate, or the like to obtain the target compound (XXXVIII).

Step 4-5

The compound (XXXVIII) is dissolved in an organic solvent such as methanol, ethanol or acetonitril. $A^4$-$B^2$—$NH_2$ ($A^4$ and $B^2$ are as defined above) and a reducing agent such as sodium borohydride or sodium cyanoborohydride, are added into the solution, and after adjusting pH of the solution as required, the mixture is reacted at a temperature from −20° C. to 60° C. to obtain the target compound (XIII).

The compound (XIII) is converted into the compound (Ia) in the same manner as in Step 1-11 of Manufacturing Process 1.

Step 4-6

The compound (XXXVI) is dissolved in an organic solvent such as DMF. After the addition of the above-mentioned compound (XVII) and a condensing agent such as WSCI hydrochloride, BOP, or EEDQ, and, optionally, a catalyst such as HOBt or DMAP, the mixture is reacted at a temperature from −20° C. to 80° C. to obtain the target compound (XL).

Step 4-7

The group $COOR^{10}$ in the compound (XL) is converted into CHO to obtain the target compound (XLI). For example, an intermediate (an alcoholic compound) is synthesized from the compound (XL) using a reducing agent such as lithium aluminum hydride in an organic solvent such as THF. Then, the intermediate is oxidized using dimethylsulfoxide-oxalyl chloride, pyridinium dichlorochromate, or the like to obtain the target compound (XLI).

Step 4-8

The compound (XXXVIII) is dissolved in an organic solvent such as methanol, ethanol or acetonitril. $A^4$-$B^2$—$NH_2$ ($A^4$ and $B^2$ are as defined above) and a reducing agent such as sodium borohydride or sodium cyanoborohydride, are added into the solution, and a reducing agent such as sodium borohydride or sodium cyanoborohydride, and, after adjusting pH of the solution, as required, the mixture is reacted at a temperature from −20° C. to 60° C. to obtain the target compound (XXI).

The compound (XXI) is converted into the compound (Ib) in the same manner as described in Step 2-9 and Step 2-10 of Manufacturing Process 2.

Manufacturing Process 5

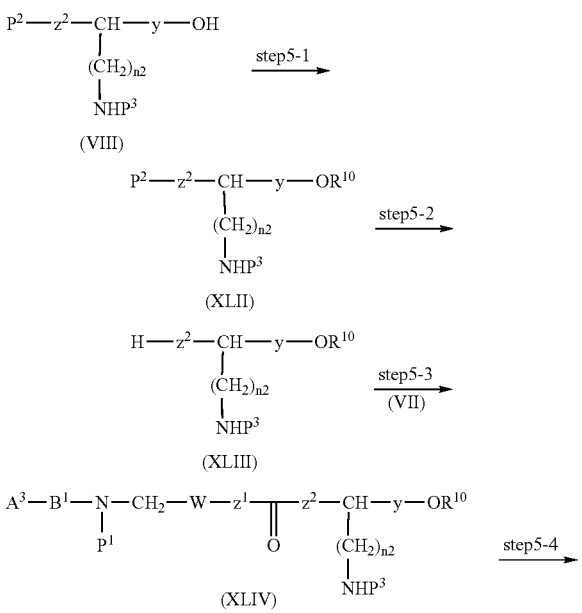

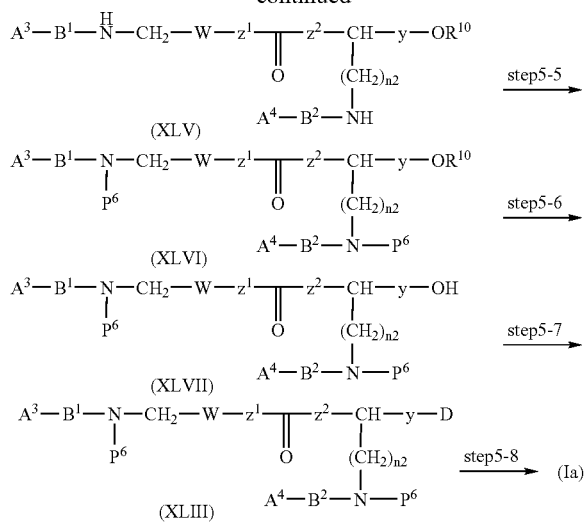

Step 5-1

A readily available known compound (VIII) (each substituent is as defined above) is dissolved in an alcohol solvent, $R^9$—OH ($R^9$ is a methyl group, ethyl group, benzyl group, etc.) and, after the addition of a condensing agent such as WSCI hydrochloride, BOP, or EEDQ and, optionally, a catalyst such as HOBt or DMAP, the compound is reacted at $-20°$ C. to $80°$ C. to obtain the target compound (XLII).

Step 5-2

The group $P^2$ in the compound (XLII) is selectively removed to obtain the target compound (XLIII).

For example, when the group $P^2$ is Fmoc, the compound (XLI) is dissolved in an organic solvent such as DMF and reacted together with an organic base such as diethylamine or morpholine at a temperature from room temperature to $100°$ C. to obtain the target compound (XLIII).

Step 5-3

The compound (XLIII) is dissolved in an organic solvent such as DMF. After the addition of the above-mentioned compound (VII) and a condensing agent such as WSCI hydrochloride, BOP, or EEDQ, and, optionally, a catalyst such as HOBt or DMAP, the mixture is reacted at a temperature from $-20°$ C. to $80°$ C. to obtain the target compound (XLIV).

Step 5-4

The groups $P^1$ and $P^3$, which are protective groups of the compound (XLIV) are removed from the compound (XLIV) (for example, when $P^1$ and $P^3$ are Boc, such protective groups can be removed by dissolving the compound (XLIV) in a solvent such as methanol or dioxane, and adding a mineral acid such as hydrochloric acid or a strong organic acid such as trifluoroacetic acid). The resultant compound is dissolved in an organic solvent such as methanol, ethanol, or acetonitrile, and to the solution are added $A^4$CHO or $A^4$=O ($A^4$ is as defined above and $A^4$=O is a compound in which the carbon atom at any optional position in $A^4$ is a ketone, for example, 2-acetylpyridine, tetrahydroquinolin-8-one, and the like) and a reducing agent such as sodium borohydride or sodium cyanoborohydride, and, after adjusting pH of the solution, as required, the mixture is reacted at a temperature from $-20°$ C. to $60°$ C. to obtain the target compound (XLV).

Step 5-5

The compound (XLV) is dissolved in an organic solvent such as THF or DMF. After the addition of a protective agent such as a compound represented by $P^6$-$L^1$, $P^6_2$O ($P^6$ is a protective group such as butoxycarbonyl or benzyloxycarbonyl) and a base such as triethylamine or an aqueous solution of sodium hydroxide, the mixture is reacted at a temperature from $-10°$ C. to $100°$ C. to obtain the target compound (XLVI).

Step 5-6

The compound (XLVI) is dissolved in one or two organic solvents selected from DMF, THF, methanol, ethanol, and the like, a basic aqueous solution such as an aqueous solution of sodium hydroxide is added, and the mixture is reacted at $0–100°$ C. to obtain the target compound (XLVII).

Step 5-7

The compound (XLVII) is dissolved in an organic solvent such as DMF. After the addition of H-D (D is as defined above) and a condensing agent such as WSCI hydrochloride, BOP, or EEDQ, and, optionally, a catalyst such as HOBt or DMAP, the mixture is reacted at a temperature from $-20°$ C. to $80°$ C. to obtain the target compound (XLVIII).

Step 5-8

The group $P^6$, which is a protective group of the compound (XLVIII), is removed from the compound to obtain the target compound (Ia). For example, when the group $P^6$ is-Boc, the compound (XLVIII) is dissolved in a solvent such as methanol, dioxane, or the like. Then, a mineral acid such as hydrochloric acid or a strong organic acid such as trifluoroacetic acid is added to obtain the target compound (Ia).

The following compounds can be given as examples of the nitrogen-containing compounds of the present invention.

(S)-2-(4-(N-2-picolylaminomethyl)benzoylamino)-5-((imidazol-2-ylmethyl)amino)valeric acid 1-naphthalenemethylamide [Compound No. 1]

(S)-2-(4-(N-2-picolylaminomethyl)benzoylamino)-5-((pyrrol-2-ylmethyl)amino)valeric acid 1-naphthalenemethylamide [Compound No. 2]

(S)-2-(4-(N-2-picolylaminomethyl)benzoylamino)-5-((1-methylimidazol-2-ylmethyl)amino)valeric acid 1-naphthalenemethylamide [Compound No. 3]

(S)-2-(4-(N-2-picolylaminomethyl)benzoylamino)-5-((imidazol-4-ylmethyl)amino)valeric acid 1-naphthalenemethylamide [Compound No. 4]

(S)-2-(4-(N-2-picolylaminomethyl)benzoylamino)-5-((1-methylpyrrol-2-ylmethyl)amino)valeric acid 1-naphthalenemethylamide [Compound No. 5]

(S)-2-(4-(N-2-picolylaminomethyl)benzoylamino)-5-((1-methylimidazol-2-ylmethyl)amino)valeric acid 1-naphthalenemethylamide [Compound No. 6]

(S)-2-(4-(N-2-picolylaminomethyl)benzoylamino)-5-((quinolin-2-ylmethyl)amino)valeric acid 1-naphthalenemethylamide [Compound No. 7]

(2S)-2-((4-(N-2-picolylaminomethyl)phenylacetyl)amino)-5-(5,6,7,8-tetrahydroquinolin-8-yl)aminovaleric acid 1-naphthalenemethylamide [Compound No. 8]

(2S)-2-(4-(2-(N-2-picolylamino)ethyl)benzoylamino)-5-(5,6,7,8-tetrahydroquinolin-8-yl)aminovaleric acid 1-naphthalenemethylamide [Compound No. 9]

(S)-2-(4-(2-(N-2-picolylamino)ethyl)benzoylamino)-5-(N-2-picolylamino)valeric acid 1-naphthalenemethylamide [Compound No. 10]

(S)-2-(5-(N-2-picolylaminomethyl)furan-2-ylcarbonyl)amino-5-(5,6,7,8-tetrahydroquinolin-8-yl)aminovaleric acid 1-naphthalenemethylamide [Compound No. 11]

(2S)-2-(2-(N-2-picolylaminomethyl)pyridin-5-ylcarbonyl)amino-5-((5,6,7,8-tetrahydroquinolin-8-yl)amino)valeric acid 1-naphthalenemethylamide [Compound No. 12]

(2S)-2-(5-(N-2-picolylaminomethyl)pyrazine-2-carbonylamino)-5-(5,6,7,8-tetrahydroquinolin-8-ylamino)valeric acid 1-naphthalenemethylamide [Compound No. 13]

(2S)-2-(5-(N-2-picolylaminomethyl)thiophene-2-carbonylamino)-5-(5,6,7,8-tetrahydroquinolin-8-ylamino)valeric acid 1-naphthalenemethylamide [Compound No. 14]

(2S)-2-(5-(N-(imidazol-2-ylmethyl)aminomethyl)thiophene-2-carbonylamino)-5-picolylaminovaleric acid 1-naphthalenemethylamide [Compound No. 15]

(2S)-2-(5-(N-(imidazol-2-ylmethyl)aminomethyl)thiophene-2-carbonylamino)-5-(5,6,7,8-tetrahydroquinolin-8-yl)aminovaleric acid 1-naphthalenemethylamide [Compound No. 16]

(S)-2-(4-(8-quinolylaminomethyl)benzoylamino)-5-(2-picolylamino)valeric acid 1-naphthalenemethylamide [Compound No. 17]

(2S)-2-(4-((N-imidazol-2-ylmethyl)aminomethyl)naphthoylamino)-5-(2-picolylamino)valeric acid 2-(3-indolyl)ethylamide [Compound No. 18]

(2S)-2-(4-((N-(imidazol-2-ylmethyl)aminomethyl)naphthoylamino)-5-(5,6,7,8-tetrahydroquinolin-8-ylamino)valeric acid 2-(3-indolyl)ethylamide [Compound No. 19]

(S)-2-(4-((imidazol-4-ylmethyl)aminomethyl)benzoylamino)-5-((imidazol-4-ylmethyl)amino)valeric acid 1-naphthalenemethylamide [Compound No. 20]

(S)-2-(4-((imidazol-2-ylmethyl)aminomethyl)benzoylamino)-5-((imidazol-2-ylmethyl)amino)valeric acid 1-naphthalenemethylamide [Compound No. 21]

(S)-2-(4-((1-methylpyrrol-2-ylmethyl)aminomethyl)benzoylamino)-5-((1-methylpyrrol-2-ylmethyl)amino)valeric acid 1-naphthalenemethylamide [Compound No. 22]

(S)-2-(4-((1-methylimidazol-2-ylmethyl)aminomethyl)benzoylamino)-5-((1-methylimidazol-2-ylmethyl)amino)valeric acid 1-naphthalenemethylamide [Compound No. 23]

(S)-2-(4-(N-2-picolylamino)butyrylamino)-5-(2-picolylamino)valeric acid 1-naphthalenemethylamide [Compound No. 24]

(2S)-2-(trans-(4-(5,6,7,8-tetrahydroquinolin-8-yl)aminomethyl)cyclohexylcarbonyl)amino-5-(5,6,7,8-tetrahydroquinolin-8-ylamino)valeric acid 1-naphthalenemethylamide [Compound No. 25]

(2S)-2-(4-(5,6,7,8-tetrahydroquinolin-8-ylaminomethyl)naphthoyl)amino-5-(5,6,7,8-tetrahydroquinolin-8-ylamino)valeric acid 1-naphthalenemethylamide [Compound No. 26]

(S)-2-(4-(N-2-picolylaminomethyl)naphthoylamino)-5-(2-picolylamino)valeric acid 1-naphthalenemethylamide [Compound No. 27]

(S)-2-(4-((imidazol-2-ylmethyl)aminomethyl)naphthoylamino)-5-((imidazol-2-ylmethyl)amino)valeric acid 1-naphthalenemethylamide [Compound No. 28]

(S)-2-(4-((1-methylimidazol-2-ylmethyl)aminomethyl)naphthoylamino)-5-((1-methylimidazol-2-ylmethyl)amino)valeric acid 1-naphthalenemethylamide [Compound No. 29]

(S)-2-(4-((1-methylimidazol-2-ylmethyl)aminomethyl)benzoylamino)-5-((1-methylpyrrol-2-ylmethyl)amino)valeric acid 1-naphthalenemethylamide [Compound No. 30]

(S)-2-(4-((imidazol-2-ylmethyl)aminomethyl)benzoylamino)-5-((1-methylpyrrol-2-ylmethyl)amino)valeric acid 1-naphthalenemethylamide [Compound No. 31]

(S)-2-(4-((pyrazol-3-ylmethyl)aminomethyl)benzoylamino)-5-((1-methylpyrrol-2-ylmethyl)amino)valeric acid 1-naphthalenemethylamide [Compound No. 32]

(S)-2-(4-((1-methylbenzimidazol-2-ylmethyl)aminomethyl)benzoylamino)-5-((1-methylbenzimidazol-2-yl)methylamino)valeric acid 1-naphthalenemethylamide [Compound No. 33]

(S)-2-(4-((1-methylbenzimidazol-2-ylmethyl)aminomethyl)benzoylamino)-5-((1-methylpyrrol-2-ylmethyl)amino)valeric acid 1-naphthalenemethylamide [Compound No. 34]

(S)-2-(4-((thiazol-2-ylmethyl)aminomethyl)benzoylamino)-5-((1-methylpyrrol-2-ylmethyl)amino)valeric acid 1-naphthalenemethylamide [Compound No. 35]

(S)-2-(4-((1-methylimidazol-2-ylmethyl)aminomethyl)benzoylamino)-5-((imidazole-2-ylmethyl)amino)valeric acid 1-naphthalenemethylamide [Compound No. 36]

(S)-2-(4-((imidazol-2-ylmethyl)aminomethyl)benzoylamino)-5-((1-methylimidazol-2-ylmethyl)amino)valeric acid 1-naphthalenemethylamide [Compound No. 37]

(2S)-2-(4-(N-2-picolylaminomethyl)naphthoylamino)-5-(5,6,7,8-tetrahydroquinolin-8-ylamino)valeric acid 1-naphthalenemethylamide [Compound No. 38]

(2S)-2-(4-((N-imidazol-2-ylmethyl)aminomethyl)benzoylamino)-5-(5,6,7,8-tetrahydroquinolin-8-ylamino)valeric acid 1-naphthalenemethylamide [Compound No. 39]

(S)-2-(4-((N-imidazol-2-ylmethyl)aminomethyl)naphthoylamino)-5-(2-picolylamino)valeric acid 1-naphthalenemethylamide [Compound No. 40]

(2S)-2-(4-((N-imidazol-2-ylmethyl)aminomethyl)naphthoylamino)-5-(5,6,7,8-tetrahydroquinolin-8-ylamino)valeric acid 1-naphthalenemethylamide [Compound No. 41]

(S)-2-((4-guanidinomethyl)benzoyl)-5-(N-2-picolylamino)-valeric acid 1-naphthalenemethylamide [Compound No. 42]

$N^\alpha$-(4-(N-2-picolylaminomethyl)benzoyl)-L-arginine 1-naphthalenemethylamide [Compound No. 43]

$N^\alpha$-(4-(N-2-picolylaminomethyl)naphthoyl)-L-arginine 1-naphthalenemethylamide [Compound No. 44]

$N^\alpha$-(4-(imidazol-2-ylmethyl)aminomethylnaphthoyl)-L-arginine 1-naphthalenemethylamide [Compound No. 45]

N$^\alpha$-(2-(N-2-picolylaminomethyl)pyridin-5-ylcarbonyl)-L-arginine 1-naphthalenemethylamide [Compound No. 46]

N$^\alpha$-(5-(N-2-picolylaminomethyl)thiophen-2-ylcarbonyl)-L-arginine 1-naphthalenemethylamide [Compound No. 47]

N$^\alpha$-(4-(imidazole-2-ylmethyl)aminomethylnaphthoyl)-L-arginine 2-(3-indolyl)ethylamide [Compound No. 48]

N$^\alpha$-(4-(imidazol-2-ylmethyl)aminomethylnaphthoyl)-L-arginine(1'S)-(1'-(1-naphthyl)ethyl)amide [Compound No. 49]

N$^\alpha$-(4-(imidazol-2-ylmethyl)aminomethylnaphthoyl)-L-arginine(1'R)-(1'-(1-naphthyl)ethyl)amide [Compound No. 50]

N$^\alpha$-(4-(imidazol-2-ylmethyl)aminomethylnaphthoyl)-L-arginine 4-hexadecylaminobenzylamide [Compound No. 51]

N$^\alpha$-(4-(5,6,7,8-tetrahydroquinoline-8-ylaminomethyl)benzoyl)-L-arginine 1-naphthalenemethylamide [Compound No. 52]

N$^\alpha$-(4-(imidazol-2-ylmethyl)aminomethylbenzoyl)-L-arginine 1-naphthalenemethylamide [Compound No. 53]

(S)-2-(4-(N-2-picolylaminomethyl)benzoylamino)-5-(quinolin-8-ylamino)valeric acid 1-naphthalenemethylamide [Compound No. 54]

(2S)-2-(4-(N-2-picolylaminomethyl)naphthoylamino)-5-((8R)-5,6,7,8-tetrahydroquinolin-8-ylamino)valeric acid 1-naphthalenemethylamide [Compound No. 55]

(S)-2-(4-(imidazol-2-ylmethyl)aminomethyl)naphthoylamino)-5-(2-picolylamino)valeric acid (1'S)-(1'-(1-naphthyl)ethyl)amide [Compound No. 56]

(S)-2-(4-(imidazol-2-ylmethyl)aminomethyl)naphthoylamino)-5-(5,6,7,8-tetrahydroquinolin-8-ylamino)valeric acid (1'S)-(1'-(1-naphthyl)ethyl)amide [Compound No. 57]

(S)-2-(4-(1-methylimidazol-2-ylmethyl)aminomethyl)naphthoylamino)-5-(N-2-picolylamino)valeric acid (1'R)-(1'-(1-naphthyl)ethyl)amide [Compound No. 58]

(S)-2-(4-(imidazol-2-ylmethyl)aminomethyl)naphthoylamino)-5-(5,6,7,8-tetrahydroquinolin-8-ylamino)valeric acid (1'R)-(1'-(1-naphthyl)ethyl)amide [Compound No. 59]

(S)-2-(4-(N-2-picolylaminomethyl)benzoylamino)-5-(N-2-picolylamino)valeric acid 1-naphthalenemethylamide [Compound No. 60]

(S)-2-(4-(N-2-picolylaminomethyl)methylbenzoylamino)-4-(N-2-picolylamino)butyric acid 1-naphthalenemethylamide [Compound No. 61]

(S)-2-(4-(N-2-picolylaminomethyl)methylbenzoylamino)-3-(N-2-picolylamino)propionic acid 1-naphthalenemethylamide [Compound No. 62]

(S)-2-(4-(N-2-picolylaminomethyl)benzoylamino)-5-(N-2-picolylamino)capric acid 1-naphthalenemethylamide [Compound No. 63]

(2S)-2-(4-((5,6,7,8-tetrahydroquinolin-8-yl)aminomethyl)benzoylamino)-5-((5,6,7,8-tetrahydroquinolin-8-yl)amino)valeric acid 1-naphthalenemethylamide [Compound No. 64]

(2S)-2-(4-(N-2-picolylaminomethyl)benzoylamino)-5-((5,6,7,8-tetrahydroquinolin-8-yl)amino)valeric acid 1-naphthalenemethylamide [Compound No. 65]

(S)-2-(4-(3-picolylaminomethyl)benzoylamino)-5-(3-picolylamino)valeric acid 1-naphthalenemethylamide [Compound No. 66]

(S)-2-(4-(N-2-picolylaminomethyl)benzoylamino)-5-(N-2-picolylamino)valeric acid 3-(n-butoxy)propylamide [Compound No. 67]

(S)-2-(4-(N-2-picolylaminomethyl)benzoylamino)-5-(N-2-picolylamino)valeric acid tetrahydrofurfurylamide [Compound No. 68]

(S)-2-(4-(N-2-picolylaminomethyl)benzoylamino)-5-(N-2-picolylamino)valeric acid phenylhydrazide [Compound No. 69]

(S)-2-(4-(N-2-picolylaminomethyl)benzoylamino)-5-(N-2-picolylamino)valeric acid 2-(3-indolyl)ethylamide [Compound No. 70]

(S)-2-(4-(N-2-picolylaminomethyl)benzoylamino)-5-(N-2-picolylamino)valeric acid (1-benzylpiperazin-4-yl)amide [Compound No. 71]

(2S)-2-(4-(N-2-picolylaminomethyl)benzoylamino)-5-(N-2-picolylamino)valeric acid (1'S)-1'-(2-naphthyl)aminocarbonylphenethylamide [Compound No. 72]

(S)-2-(4-(N-2-picolylaminomethyl)benzoylamino)-5-(N-2-picolylamino)valeric acid 4-hexadecylaminobenzylamide [Compound No. 73]

(S)-2-(4-(N-2-picolylaminomethyl)benzoylamino)-5-(N-2-picolylamino)valeric acid 4-(N-(1,2,3,4-tetrahydro-1,4-dicarbonyl-phthalazin-6-yl)-N-ethylamino)butylamide [Compound No. 74]

(S)-2-(4-(N-2-picolylaminomethyl)benzoylamino)-5-(N-2-picolylamino)valeric acid 2,4,6-trichlorophenylhydrazide [Compound No. 75]

(S)-2-(4-(N-2-picolylaminomethyl)benzoylamino)-5-(N-2-picolylamino)valeric acid 2-picolylamide [Compound No. 76]

(S)-2-(4-(N-2-picolylaminomethyl)benzoylamino)-5-(N-2-picolylamino)valeric acid 2-(N,N-diethylamino)ethylamide [Compound No. 77]

(S)-2-(4-(N-2-picolylaminomethyl)benzoylamino)-5-(N-2-picolylamino)valeric acid 3-(morpholin-1-yl)propylamide [Compound No. 78]

(S)-2-(4-(N-2-picolylaminomethyl)benzoylamino)-5-(N-2-picolylamino)valeric acid 2-(N,N-methylamino)ethylamide [Compound No. 79]

(S)-2-(4-(N-2-picolylaminomethyl)benzoylamino)-5-(N-2-picolylamino)valeric acid 4-(2,4-di-t-amylphenoxy)butylamide [Compound No. 80]

(S)-2-(4-(N-2-picolylaminomethyl)benzoylamino)-5-(N-2-picolylamino)valeric acid 3-aminopropylamide [Compound No. 81]

(S)-2-(4-(N-2-picolylaminomethyl)benzoylamino)-5-(N-2-picolylamino)valeric acid 5-indazoleamide [Compound No. 82]

(2S)-2-(2-(N-2-picolylaminomethyl)pyridin-5-ylcarbonyl)amino-5-(5,6,7,8-tetrahydroquinolin-8-yl)aminovaleric acid (1'S)-1'-(1-naphthyl)ethylamide [Compound No. 83]

(2S)-2-(2-(N-2-picolylaminomethyl)pyridin-5-ylcarbonyl)amino-5((1-methyl-imidazol-2-yl)methylamino)aminovaleric acid (1'S)-1'-(1-naphthyl)ethylamide [Compound No. 84]

(2S)-2-(4-(N-2-picolylaminomethyl)naphthoyl)amino-5-(5,6,7,8-tetrahydroquinolin-8-yl)aminovaleric acid (1'S)-1'-(1-naphthyl)ethylamide [Compound No. 85]

N$^\alpha$-(4-(N-2-picolylaminomethyl)benzoyl)-L-arginine (1'S)-1'-(1-naphthyl)ethylamide [Compound No. 86]

(2S)-2-(4-((1-methylimidazol-2-ylmethyl)aminomethyl)naphthoylamino-5-((1-methylimidazol-2-ylmethyl)amino)valeric acid (1'S)-1'-(1-naphthyl)ethylamide [Compound No. 87]

(2S)-2-(2-(N-2-picolylaminomethyl)pyridin-5-ylcarbonyl)amino-5-(N-methylpyrrol-2-ylmethyl)aminovaleric acid (1'S)-1'-(1-naphthyl)ethylamide [Compound No. 88]

N$^\alpha$-(4-(N-(1-methylimidazol-2-yl)methylaminomethyl)-1-naphthalenecarbonyl)-L-arginine 2-(1-naphthyl)isopropylamide [Compound No. 89]

N$^\alpha$-(2-(N-2-picolylaminomethyl)pyridin-5-ylcarbonyl)-L-arginine (1'S)-1'-(1-naphthyl)ethylamide [Compound No. 90]

(2S)-2-(4-(N-2-picolylaminomethyl)benzoyl)amino-5-(5,6,7,8-tetrahydroquinolin-8-yl)aminovaleric acid (1'S)-1'-(1-naphthyl)ethylamide [Compound No. 91]

(2S)-2-(4-(N-2-picolylaminomethyl)naphthoyl)amino-5-(5,6,7,8-tetrahydroquinolin-8-yl)aminovaleric acid 2-(3-indolyl)ethylamide [Compound No. 92]

N$^{\alpha}$-4-(N-2-picolylaminomethyl)benzoyl-N$^{G}$-nitroarginine (1'S)-1'-(1-naphthyl)ethylamide [Compound No. 93]

(2R)-2-(4-(N-(imidazol-2-ylmethyl)aminomethyl)benzoyl) amino-5-(5,6,7,8-tetrahydroquinolin-8-yl)aminovaleric acid (1'S)-1'-(1-naphthyl)ethylamide [Compound No. 94]

N$^{\alpha}$-4-(N-2-(imidazol-2-ylmethyl)aminomethyl)benzoyl-L-arginine (1'S)-1'-(1-naphthyl)ethylamide [Compound No. 95]

(2S)-2-((1-methylimidazol-2-ylmethyl)aminomethyl)benzoylamino-5-(5,6,7,8-tetrahydroquinolyl-8-yl)aminovaleric acid 1-naphthalenemethyleneamide [Compound No. 96]

N$^{\alpha}$-(4-((N-(1-methylimidazole-2-ylmethyl)amino)methyl)naphthalene-1-carbonyl)-L-arginine (1'S)-1'-(1-naphthyl)ethylamide [Compound No. 97]

N$^{\alpha}$-(4-((imidazol-2-ylmethyl)amino)methyl)naphthalene-1-carbonyl)L-arginine(1'S)-N-methyl-N-(1'-(1-naphthyl)ethyl)amide [Compound No. 98]

N$^{\alpha}$-(4-(N-2-picolylaminomethyl)naphthoyl)-L-arginine (1'S)-1'-(1-naphthyl)ethylamide [Compound No. 99]

N$^{\alpha}$-(4-(N-2-picolylaminomethyl)naphthalene-1-carbonyl)-L-arginine-D-3-(1-naphthyl)alanine methyl ester [Compound No. 100]

N$^{\alpha}$-(4-(N-2-picolylaminomethyl)naphthalene-1-carbonyl)-L-arginine-D-3-(1-naphthyl)alanine [Compound No. 101]

(2S)-2-(8-2-picolylaminomethylquinoline-5-carbonyl)amino-5-(5,6,7,8-tetrahydroquinolin-8-yl)aminovaleric acid (1'S)-1'-(1-naphthyl)ethylamide [Compound No. 102]

N$^{\alpha}$-(4-((imidazol-2-ylmethyl)amino)methyl)naphthalene-1-carbonyl)L-arginine N-methyl-1-naphthylmethylamide [Compound No. 103]

(2S)-2-(4-(2-pyridyl)aminomethylnaphthalene-1-carbonyl)amino-5-(5,6,7,8-tetrahydroquinolin-8-yl)aminovaleric acid 1-naphthylmethylamide [Compound No. 104]

(2S)-2-(4-(N-2-picolylaminomethyl)naphthalene-1-carbonyl)amino-5-((8S)-5,6,7,8-tetrahydroquinolin-8-yl)aminovaleric acid 1-naphthylmethylamide [Compound No. 105]

(2S)-2-(4-((N-imidazol-2-ylmethyl)aminomethyl)benzoylamino-5-(5,6,7,8-tetrahydroquinolin-8-yl)aminovaleric acid (1'S)-1'-(1-naphthyl)ethylamide [Compound No. 106]

(2S)-2-(4-((N-1-methylimidazol-2-ylmethyl)aminomethyl)benzoylamino-5-(5,6,7,8-tetrahydroquinolin-8-yl)aminovaleric acid (1'S)-1'-(1-naphthyl)ethylamide [Compound No. 107]

(2S)-2-(4-(2-picolylaminomethyl)benzoyl-5-(imidazol-2-yl)aminovaleric acid (1'S)-1'-(1-naphthyl)ethylamide [Compound No. 108]

(2S)-2-(4-2-picolylaminomethyl)benzoyl-5-(pyridin-2-yl)aminovaleric acid (1'S)-1'-(1-naphthyl)ethylamide [Compound No. 109]

(S)-2-(4-((N-imidazol-2-ylmethyl)aminomethyl)benzoyl) amino-5-(4,5-dihydroimidazol-2-yl)aminovaleric acid (1'S)-1'-(1-naphthyl)ethylamide [Compound No. 110]

(S)-2-(4-((N-(imidazol-2-ylmethyl)aminomethyl)benzoyl) amino-5-(pyrimidin-2-yl)aminovaleric acid (1'S)-1'-(1-naphthyl)ethylamide [Compound No. 111]

(S)-2-(4-((N-imidazol-2-ylmethyl)aminomethyl)benzoyl) amino-5-(3,4,5,6-tetrahydropyrimidine-2-yl)aminovaleric acid (1'S)-1'-(1-naphthyl)ethylamide [Compound No. 112]

(S)-2-(4-(N-2-picolylaminomethyl)benzoyl)amino-5-(4,5-dihydroimidazol-2-yl)aminovaleric acid (1'S)-1'-(1-naphthyl)ethylamide [Compound No. 113]

(S)-2-(4-(N-2-picolyl)aminomethyl)benzoyl)amino-5-(pyrimidin-2-yl)aminovaleric acid (1'S)-1'-(1-naphthyl)ethylamide [Compound No. 114]

(S)-2-(4-(N-2-picolylaminomethyl)benzoyl)amino-5-(3,4,5,6-tetrahydropyrimidin-2-yl)aminovaleric acid (1'S)-1'-(1-naphthyl)ethylamide [Compound No. 115]

(S)-2-(4-(2-picolylaminomethyl)benzoyl)-5-(2-picolylamino)valeric acid 1'-(1-naphthyl)ethylamide [Compound No. 116]

(S)-2-(4-(2-picolylaminomethyl)benzoyl)-5-(2-picolylamino)valeric acid N-dodecylamide [Compound No. 117]

(S)-2-(4-(2-picolylaminomethyl)benzoyl)-5-(2-picolylamino)valeric acid 3,5-ditrifluoromethylbenzylamide [Compound No. 118]

(S)-2-(4-(2-picolylaminomethyl)benzoyl)-5-(2-picolylamino)valeric acid (+)-dehydroabietylamide [Compound No. 119]

(S)-2-(4-(2-picolylaminomethyl)benzoyl)-5-(2-picolylamino)valeric acid 2,3-dichlorobenzylamide [Compound No. 120]

(S)-2-(4-(2-picolylaminomethyl)benzoyl)-5-(2-picolylamino)valeric acid 2-octylamide [Compound No. 121]

(S)-2-(4-(2-picolylaminomethyl)benzoyl)-5-(2-picolylamino)valeric acid 3-(3-indolyl)-2-propylamide [Compound No. 122]

(S)-2-(4-(2-picolylaminomethyl)benzoyl)-5-(2-picolylamino)valeric acid 2,2-diphenylethylamide [Compound No. 123]

(S)-2-(4-(2-picolylaminomethyl)benzoyl)-5-(2-picolylamino)valeric acid 4-t-butylcyclohexylamide [Compound No. 124]

(S)-2-(4-(2-picolylaminomethyl)benzoyl)-5-(2-picolylamino)valeric acid 2,4-dichlorobenzylamide [Compound No. 125]

(S)-2-(4-(2-picolylaminomethyl)benzoyl)-5-(2-picolylamino)valeric acid benzhydrylamide [Compound No. 126]

(S)-2-(4-(2-picolylaminomethyl)benzoyl)-5-(2-picolylamino)valeric acid 3-chlorobenzylamide [Compound No. 127]

(S)-2-(4-(2-picolylaminomethyl)benzoyl)-5-(2-picolylamino)valeric acid 2-(4-methoxyphenyl)ethylamide [Compound No. 128]

(S)-2-(4-(2-picolylaminomethyl)benzoyl)-5-(2-picolylamino)valeric acid (4-(4-methylphenyl)oxy)phenylamide [Compound No. 129]

(S)-2-(4-(2-picolylaminomethyl)benzoyl)-5-(2-picolylamino)valeric acid 1-(1,2,3,4-tetrahydronaphthyl)amide [Compound No. 130]

The present invention relates to an antiviral drug comprising the above-described compound or a pharmaceutically acceptable salt thereof as an effective component.

The antiviral drug or the salt thereof of the present invention is used for treatment or preventing viral diseases such as AIDS.

The antiviral drug or the salt thereof of the present invention induced no death when intraperitoneally administered to ICR mice (50 mg/kg) twice a day for four consecutive days. Based on this finding, the drug and the salt are judged to have no acute toxicity.

A dose is 0.1–500 mg/kg/day, preferably 1–100 mg/kg/day, which is administered one time or several times a day. Although oral administration is desirable, the route of administration is not limited to this. As a parenteral route, injection, percutaneous administration, enteral administration, or the like is suitably selected. The above-mentioned dose may be appropriately altered according to the symptom of the patient.

The dosage forms for oral administration include powders, tablets, granules, capsules, suppositories, injection solutions, and peroral fluids, in which the antiviral drug or the salt of the present invention and one or more pharmaceutically acceptable additives are formulated. As examples of additives, magnesium stearate, talc, lactose, dextrin, starches, methyl cellulose, fatty acid glycerides, water, propylene glycol, macrogols, alcohol, crystalline cellulose, hydroxypropyl cellulose, low-substituted hydroxypropyl cellulose, carboxymethylcellulose, popidon, polyvinyl alcohol, calcium stearate, and the like can be given. Other additives such as a coloring agent, stabilizer, preservative, pH modifier, isotonizing agent, solubilizer, soothing agent, and the like may be added as required. Granules, tablets, and capsules may be coated with a coating agent such as hydroxypropyl methylcellulose, hydroxypropyl methylcellulose phthalate, and the like. It is desirable that 0.1–500 mg, preferably 1–100 mg, of the antiviral drug of the present invention be included in a single dosage.

The method of preparing the antiviral drug of the present invention will be specifically described by way of examples.

EXAMPLE 1

Preparation of (S)-2-(4-(N-2-picolylaminomethyl)benzoylamino)-5-((imidazol-2-ylmethyl)amino) valeric acid 1-naphthalenemethylamide [Compound No. 1]

Example 1-1

Synthesis of methyl 4-(N-Boc-N-2-picolylaminomethyl)benzoate (Compound VI-1)

A commercially available 2-picolylamine (1.08 g) was dissolved in DMF (22.5 ml). After the addition of triethylamine (1.55 ml), the mixture was cooled to 0° C. A solution of di-t-butyl dicarbonate (2.52 ml) in DMF (7.5 ml) was added dropwise to the solution over 10 minutes. The mixture was allowed to become room temperature and stirred for two hours, followed by solvent evaporation under reduced pressure. The residue was purified by silica gel column chromatography (30 g, chloroform) to obtain a pale yellow liquid (1.71 g).

1.199 g of the pale yellow liquid was dissolved in THF (6 ml). Sodium hydride (60% paraffin mixture, 46.1 mg) was suspended in the solution. After the suspension was stirred for 15 minutes, a commercially available methyl 4-bromomethylbenzoate (241 mg) was added thereto, and the mixture was stirred for two days at room temperature. After the completion of the reaction, aqueous solution of hydrochloric acid (1 mol/l) was added to adjust the pH to 5–7, and concentrated. After the addition of chloroform (40 ml), the mixture was washed with water, followed by concentration. The residue was purified by silica gel column chromatography (6 g, chloroform/ethyl acetate=10/1) to obtain the title compound (2.21 g) as a pale yellow liquid.

MS(Fab,pos.): m/z=357[M+1]$^+$ $^1$H-NMR(500 MHz, CDCl$_3$) δ=1.45(9H,s),3.91(3H,s),4.47(1H,brs), 4.52(1H, brs), 4.60(2H,s),7.17(1H,dd,J=7.6, 4.1 Hz),7.2–7.4 (3H,m), 7.65(1H,t,J=7.6 Hz), 8.52(1H,d,J=4.1 Hz).

Example 1-2

Synthesis of 4-(N-Boc-N-2-picolylaminomethyl)benzoic acid (Compound VII-1)

The compound obtained in Example 1-1 (200.6 mg) was added with methanol (2 ml), THF (2 ml), and 1 mol/l aqueous solution of sodium hydroxide (2 ml), and the mixture was stirred for one day at room temperature. After the completion of the reaction, the solvent was removed by distillation and water (5 ml) was added. Aqueous solution of hydrochloric acid (1 mol/l) was added dropwise to the resulting solution to adjust the pH to 3. The deposited crystals were collected by filtration and dried to obtain the title compound (123.2 mg) as colorless crystals.

MS(Fab,pos.): m/z=343[M+1]$^+$ $^1$H-NMR(500 MHz, DMSO-d$_6$): δ=1.35 and 1.54(9H,brs),4.41(1H,brs), 4.51 (2H,s),4.58(1H,brs),7.2–7.4(4H,m),7.77(1H,td,J=7.6, 1.8 Hz),8.52(1H,dd,J=4.9, 1.7 Hz),12.9(1H,s).

Example 1-3

Synthesis of N$^α$-4-(N-Boc-N-2-picolylaminomethyl)benzoyl-N$^δ$-Cbz-L-ornithine 1-naphthalenemethylamide (Compound XI-1)

A commercially available N$^α$-Fmoc-N$^δ$-Cbz-L-ornithine (3.00 g) was dissolved in DMF (60 ml), and then HOBt (1.24 g), WSCI hydrochloride (1.77 g) and 1-naphthalenemethylamine (1.48 ml) were sequentially added to the solution. The mixture was stirred for 13 hours at room temperature. After the completion of the reaction, the solvent was removed by distillation. The residue was dissolved in chloroform and extracted with 1 mol/l aqueous solution of hydrochloric acid. The organic layer was washed with saturated aqueous solution of sodium hydrogencarbonate. The solvent was removed by distillation to obtain a crude product (4.44 g) as a pale yellowish white solid. The crude product was dissolved in DMF (150 ml) and diethylamine (10 ml) was added. The mixture was stirred for 6 hours at room temperature. After the completion of the reaction, the solvent was removed by distillation and the residue was dried using a vacuum pump to obtain a crude product (4.21 g) as a pale yellowish white solid. The product was dissolved in DMF (140 ml), and was added with WSCI hydrochloride (1.77 g) and the compound obtained in Example 1-2 (2.10 g). The mixture was stirred for 21.5 hours at room temperature. After the completion of the reaction, the solvent was removed by distillation. The residue was purified by silica gel column chromatography (500 g, chloroform/methanol=40/1-15/1) to obtain the title compound (4.25 g) as a pale orange semi-solid.

MS(FAB,Pos.): m/z=730[M+1]$^+$ $^1$H-NMR(500 MHz, DMSO-d$_6$): δ=1.31 and 1.38(9H,2s),1.44–1.54(2H, m),1.73–1.77(2H,m),2.89–3.03(2H,m),4.40(1H,brs), 4.47–4.51 (3H,m),4.56(1H,brs), 4.75(2H,d,J=5.7 Hz),4.98 (2H,s),7.20–7.37(9H,m),7.45–7.47(2H,m),7.51–7.54(2H, m),7.76–7.80(1H,m), 7.83–7.85(1H,m),7.86(2H,d,J=8.3 Hz),7.94–7.95(2H,m),8.05–8.06(1H,m),8.46(1H,d,J=8.1 Hz),8.50–8.52(2H,m).

Example 1–4

Synthesis of N$^α$-4-(N-Boc-N-2-picolylaminomethyl)benzoyl-L-ornithine 1-naphthalenemethylamide (Compound XII-1)

The compound obtained in Example 1-3 (4.25 g) was dissolved in methanol (100 ml). After the addition of 10%

Pd—C (4.25 g), the mixture was stirred for 4.5 hours under normal pressure hydrogen atmosphere. After the completion of the reaction, the catalyst was removed by filtration through celite. The residue was purified by silica gel column chromatography (200 g, chloroform/methanol=12/1-4/1) to obtain the title compound (2.22 g, 64.0%) as white crystals.

MS(FAB,Pos.): m/z=596[M+1]$^+$ $^1$H-NMR(500 MHz, DMSO-d$_6$): δ=1.31 and 1.38(9H,2s),1.59–1.64(2H, m),1.76–1.88(2H,m),2.75–2.79(2H,m),4.40(1H,s),4.49(2H, brs), 4.52–4.57(2H,m),4.77(2H,d,J=5.4 Hz),7.21–7.23(1H, m),7.26–7.36(3H,m),7.46–7.47(2H,m),7.49–7.56(2H,m), 7.77–7.80(3H,m), 7.84–7.86(1H,m),7.90(2H,d,J=8.3 Hz), 7.94–7.96(1H,m),8.05–8.07(1H,m),8.52(1H,m),8.56(1H, m),8.60(1H,t,J=5.6 Hz).

Example 1-5

Synthesis of (S)-2-(4-(N-Boc-N-2-picolylaminomethyl)benzoyl)-5-((imidazol-2-ylmethyl)amino)valeric acid 1-naphthalenemethylamide (Compound XIII-1)

The compound obtained in Example 1-4 (60.0 mg) was dissolved in anhydrous methanol (2.2 ml). After the addition of 2-imidazolecarboxyaldehyde (10.2 mg), the mixture was stirred for 1 hour at room temperature. After evaporation of the solvent, anhydrous methanol (1.2 ml) was added and the mixture was cooled to 0° C. Then, sodium borohydride (7.6 mg) was added and the mixture was stirred for 1.5 hours at room temperature. The residue obtained by concentrating the reaction solution was purified by silica gel column chromatography (6 g, chloroform/methanol=20/1-9/1) to obtain the title compound (46.7 mg) as white crystals.

MS(FAB,Pos.): m/z=676[M+1]$^+$ $^1$H-NMR(500 MHz, CDCl$_3$): δ=1.45 and 1.47(9H,2s),1.92–2.22(4H,m), 2.66–2.74(2H, m),3.71–3.81 (2H,m), 4.46–4.55(2H,m),4.57 (2H, brs),4.68(1H, d,J=4.5 Hz),4.72–4.75 (1H,m), 4.82–4.86(1H, m),4.99–5.03(1H,m),6.88 (2H,s),6.99(2H,s), 7.18–7.26(3H, m),7.29–7.31(1H,m), 7.40–7.53(4H,m), 7.63–7.69 (3H,m), 7.80–7.81(1H,m), 7.85–7.86(1H,m), 7.86–7.88(1H,m), 8.00–8.02(1H,m), 8.12(1H,brs), 8.52(1H, brs).

Example 1-6

Synthesis of (S)-2-(4-(N-2-picolylaminomethyl)benzoylamino)-5-((imidazol-2-ylmethyl)amino) valeric acid 1-naphthalenemethylamide [Compound No. 1]

The compound obtained in Example 1-5 (45.0 mg) was dissolved in methanol (0.9 ml) and added with 4 mol/l hydrochloric acid/dioxane solution (0.9 ml). The mixture was stirred for 4.5 hours at room temperature. The reaction solution was concentrated and the resultant residue was purified by silica gel column chromatography (3.4 g, chloroform/methanol=1/1). The compound obtained was dissolved in 1 mol/l aqueous solution of hydrochloric acid (1.5 ml) and water was removed by distillation to obtain a hydrochloride of the title compound (35.3 mg) as a white solid.

MS(FAB,Pos.): m/z=576[M+1]$^+$ $^1$H-NMR(500 MHz, DMSO-d$_6$): δ=1.75–1.91(4H,m),3.07–3.17(2H,m), 4.30 (4H,brs),4.48(2H,brs),4.55–4.59(1H,m),4.59(2H,d,J=4.9 Hz),7.44–7.47(3H,m),7.52–7.57(3H,m),7.66(2H,d,J=8.6 Hz), 7.72(2H,brs),7.83–7.96(3H,m),8.00(2H,d,J=8.5 Hz), 8.05–8.07 (1H,m),8.65–8.73(3H,m),9.84(2H,brs),10.10(1H, brs).

EXAMPLE 2

Preparation of (S)-2-(4-(N-2-picolylaminomethyl)benzoylamino)-5-((pyrrol-2-ylmethyl)amino)valeric acid 1-naphthalenemethylamide [Compound No. 2]

Example 2-1

Synthesis of (S)-2-(-4-(N-Boc-N-2-picolylaminomethyl)benzoyl)-5-((pyrrol-2-ylmethyl)amino)valeric acid 1-naphthalenemethylamide (Compound XIII-2)

The compound obtained in Example 1-4 (82.4 mg) was dissolved in anhydrous methanol (1.6 ml). After the addition of pyrrole-2-carboxyaldehyde (14.5 mg), the mixture was stirred for 15 hours at room temperature. After the solvent was removed by distillation, anhydrous methanol (1.6 ml) was added and the mixture was cooled to 0° C. Then, sodium borohydride (10.5 mg) was added and the mixture was stirred for 2 hours at room temperature. The reaction solution was concentrated and the residue was purified by silica gel column chromatography (10 g, chloroform/methanol=8/1) to obtain the title compound (55.6 mg) as white crystals.

MS(FAB,Pos.): m/z=675[M+1]$^+$ $^1$H-NMR(500 MHz, CDCl$_3$): δ=1.44 and 1.47(9H,2s),1.57–2.00(4H,m), 2.70–2.78(2H,m),3.66–3.81(2H,m),4.45–4.49(2H,m),4.57 (2H,brs),4.74–4.75(1H,m),4.83–4.87(1H,m),4.99–5.02(1H, m), 4.99–5.02(1H,m),6.00(1H,brs),6.05–6.07(1H,m),6.67 (1H,brs), 7.17–7.24(3H,m),7.28–7.36(3H,m),7.41–7.54(5H, m),7.64–7.68(3H,m),7.80–8.82(1H,m),7.87–7.88(1H,m), 7.98(1H,m),8.01–8.03(1H,m),8.52–8.53 (1H,m).

Example 2-2

Synthesis of (S)-2-(4-(N-2-picolylaminomethyl)benzoylamino)-5-((pyrrol-2-ylmethyl)amino)valeric acid 1-naphthalenemethylamide [Compound No. 2]

The compound obtained in Example 2-1 (55.6 mg) was dissolved in methanol (1.1 ml) and 4 mol/l hydrochloric acid/dioxane solution (1.1 ml) was added. The mixture was stirred for 3.5 hours at room temperature. The reaction solution was concentrated and a rasultant crude product obtained was purified by silica gel column chromatography (8 g, chloroform/methanol=1/1). The compound obtained was dissolved in 1 mol/l aqueous solution of hydrochloric acid (1.1 ml) and water was removed by distillation to obtain a hydrochloride of the title compound (49.8 mg) as a pale orange solid.

MS(FAB,Pos.): m/z=575[M+1]$^+$ $^1$H-NMR(500 MHz, DMSO-d$_6$): δ=1.70–1.91(4H,m),2.83–2.86(2H,m) 4.04–4.06(2H,m),4.29(4H,m),4.52–4.56(1H,m),4.75–4.77 (2H,d, J=4.9 Hz),6.01–6.02(1H,m),6.17–6.18(1H,m), 6.81–6.83(1H,m), 7.44–7.49 (3H,m), 7.52–5.58(3H,m), 7.66–7.68(2H,m), 7.84–8.07(6H,m), 8.65–8.73(3H,m), 9.20 (1H,brs), 9.91(1H,brs), 11.08(1H,s).

EXAMPLE 3

Preparation of (S)-2-(4-(N-2-picolylaminomethyl)benzoylamino)-5-((1-methylimidazol-2-ylmethyl)amino)valeric acid 1-naphthalenemethylamide [Compound No. 3]

Example 3-1

Synthesis of (S)-2-(4-(N-Boc-N-2-picolylaminomethyl)benzoyl)-5-((1-methylimidazol-2-ylmethyl)amino)valeric acid 1-naphthalenemethylamide (Compound XIII-3)

The compound synthesized in Example 1-4 (100 mg) was dissolved in anhydrous methanol (2 ml). After the addition of 1-methyl-2-imidazolecarboxyaldehyde (20.3 mg), The mixture was stirred for 5 hours at room temperature. The solvent was removed by distillation, anhydrous methanol (2 ml) was added and the mixture was cooled to 0° C. Then, sodium borohydride (12.7 mg) was added and the mixture was stirred for 3 hours at room temperature. The reaction solution was concentrated and the residue obtained was purified by silica gel column chromatography (10 g, chloroform/methanol=12/1) to obtain the title compound (77.4 mg) as a white solid.

MS(FAB,Pos.): m/z=690[M+1]$^+$ $^1$H-NMR(500 MHz, DMSO-d$_6$): δ=1.31 and 1.38(9H,2s),1.43–1.52 (2H,m), 1.74–1.81 (2H,m),3.38(3H,s),4.40(1H,m),4.45–4.56(6H, m),4.74–4.47(2H,m),5.23(1H,m),6.71–6.75(2H,m), 7.01–7.07(2H, m),7.22–7.46(4H,m),7.51–7.55(2H,m), 7.76–7.80(1H,m),7.83–7.88(3H,m),7.93–7.95(1H,m), 8.05–8.07(1H,m), 8.50–8.56(3H, m).

Example 3-2

Synthesis of (S)-2-(4-(N-2-picolylaminomethyl) benzoylamino)-5-((1-methylimidazol-2-ylmethyl) amino)valeric acid 1-naphthalenemethylamide [Compound No. 3]

The compound obtained in Example 3-1 (75.9 mg) was dissolved in methanol (1.5 ml) and added with 4 mol/l hydrochloric acid/dioxane solution (1.5 ml). The mixture was stirred for 9 hours at room temperature and then concentrated. The residue obtained was purified by silica gel column chromatography (10 g, chloroform/methanol=1/1).

The compound obtained was dissolved in 1 mol/l aqueous solution of hydrochloric acid (1.5 ml) and water was removed by distillation to obtain a hydrochloride of the title compound (19.6 mg) as a white solid.

MS(FAB,Pos.): m/z=590[M+1]$^+$ $^1$H-NMR(500 MHz, DMSO-d$_6$): δ=1.77–1.91(4H,m),3.09–3.17(2H, m),3.95 (3H,s),4.29(4H,br),4.52–4.59(3H,m),4.76–4.77(2H,m), 7.44–7.48(3H,m),7.52–7.57(3H,m),7.65–7.67(2H,m), 7.71–7.74(2H,m),7.83–8.08(6H,m),8.65–8.66(1H,m), 8.70–8.75(2H,m),9.88(1H,br),10.09(1H,br).

EXAMPLE 4

Preparation of (S)-2-(4-(N-2-picolylaminomethyl) benzoylamino)-5-((imidazol-4-ylmethyl)amino) valeric acid 1-naphthalenemethylamide [Compound No. 4]

Example 4-1

Synthesis of 2-(4-(N-Boc-N-2-picolylaminomethyl) benzoyl)-5-((imidazol-4-ylmethyl)amino)valeric acid 1-naphthalenemethylamide (Compound XIII-4)

The compound synthesized in Example 1-4 (100 mg) was dissolved in anhydrous methanol (2 ml), and added with 4 (5)-imidazolecarboxyaldehyde (17.7 mg). The mixture was stirred for 5 hours at room temperature. The solvent was removed by distillation, anhydrous methanol (2 ml) was added and the mixture cooled to 0° C. Then, sodium borohydride (12.7 mg) was added and the mixture stirred for 3 hours at room temperature. The reaction solution was concentrated and the residue obtained was purified by silica gel column chromatography (10 g, chloroform/methanol=3/1) to obtain the title compound (86.6 mg) as a white solid.

MS(FAB,Pos.): m/z=676[M+1]$^+$ $^1$H-NMR(500 MHz, DMSO-d$_6$): δ=1.31 and 1.38(9H,2s),1.51–1.55(2H,m), 1.77–1.81(2H,m),2.64–2.65(2H,m),3.32(2H,m),3.65(2H, br), 4.40–4.56(5H,m),4.75–4.76(2H,m),7.20–7.35(4H,m), 7.44–7.55 (5H,m),7.76–7.80(1H,m),7.83–7.88(3H,m), 7.91–7.95(1H,m), 8.05–8.07(1H,m),8.52(1H, d,J=4.1 Hz), 8.56 (2H,br).

Example 4-2

Synthesis of (S)-2-(4-(N-2-picolylaminomethyl) benzoylamino)-5-((imidazol-4-ylmethyl)amino) valeric acid 1-naphthalenemethylamide [Compound No. 4]

The compound obtained in Example 4-1 (84.6 mg) was dissolved in methanol (1.7 ml) and added with 4 mol/l hydrochloric acid/dioxane solution (1.7 ml). The mixture was stirred for 9 hours at room temperature. The reaction solution was concentrated and the crude product obtained was purified by silica gel column chromatography (7 g, chloroform/methanol=1/1). The compound obtained was dissolved in 1 mol/l aqueous solution of hydrochloric acid (1.7 ml) and water was removed by distillation to obtain a hydrochloride of the title compound (52.8 mg) as a white solid.

MS(FAB,Pos.): m/z=576[M+1]$^+$ $^1$H-NMR(500 MHz, DMSO-d$_6$): δ=1.74–1.91(5H,m), 2.95(2H,br),4.25–4.30 (6H,m),4.54–4.19(3H,m),4.76–4.77(2H,d,J=5.6 Hz), 7.45–7.48(3H,m),7.49–7.60(4H,m),7.66–7.68(2H,m), 7.82–8.08(7H,m), 8.65–8.76(3H,m), 9.14(1H,m), 9.82–9.92 (2H,m).

EXAMPLE 5

Preparation of (S)-2-(4-(N-2-picolylaminomethyl) benzoylamino)-5-((1-methylpyrrol-2-ylmethyl) amino)valeric acid 1-naphthalenemethylamide [Compound No. 5]

Example 5-1

Synthesis of (S)-2-(4-(N-Boc-N-2-picolylaminomethyl)benzoyl)-5-((1-methylpyrrol-2-ylmethyl)amino)valeric acid 1-naphthalenemethylamide (Compound XIII-5)

The compound synthesized in Example 1-4 (100 mg) was dissolved in anhydrous methanol (2 ml). After the addition of 1-methyl-2-pyrrolecarboxyaldehyde (20.4 μl), the mixture was stirred for 13.5 hours at room temperature. The solvent was moved by distillation, anhydrous methanol (2 ml) was added and the mixture was cooled to 0° C. Then, sodium borohydride (12.7 mg) was added and the mixture was stirred for 3 hours at room temperature. The reaction solution was concentrated and the residue obtained was purified by silica gel column chromatography (10 g, chloroform/methanol=8/1) to obtain the title compound (38.3 mg, 33.1%) as a white solid.

MS(FAB,Pos.): m/z=576[M+1]$^+$ $^1$H-NMR(500 MHz, DMSO-d$_6$): δ=1.31 and 1.38(9H,2s),1.49–1.55(2H,m) 1.73–1.91(2H,m),3.54(3H,s),3.64(2H,br),4.36–4.56(4H,m), 4.71–4.80(2H,m),5.86–5.89(2H,m),6.62(1H,br),7.29–7.35 (4H,m), 7.44–7.55(4H,m), 7.76–7.80(1H,m), 7.83–7.88(4H, m), 7.94–7.96(1H,m), 8.06–8.07(1H,m), 8.50–8.54(3H,m).

Example 5-2

Synthesis of (S)-2-(4-(N-2-picolylaminomethyl) benzoylamino)-5-((1-methylpyrrol-2-ylmethyl) amino)valeric acid 1-naphthalenemethylamide [Compound No. 5]

The compound obtained in Example 5-1 (36.3 mg) was dissolved in methanol (1 ml) and 4 mol/l hydrochloric acid/dioxane solution (1 ml) was added. The mixture was stirred for 2 hours at room temperature, and concentrated, and the residue obtained was purified by silica gel column chromatography (5 g, chloroform/methanol=3/1). The compound obtained was dissolved in 1 mol/l aqueous solution of hydrochloric acid (1 ml) and water was removed by distillation to obtain a hydrochloride of the title compound (41.1 mg) as a white solid.

$^1$H-NMR(500 MHz,DMSO-d$_6$): δ=1.73–1.88 (4H,m), 2.91 (2H,m),3.65 (3H, s),4.07–4.09 (2H,m),4.29 (4H,br), 4.53–4.57 (1H,m),4.76 (2H,d,J=5.8 Hz),5.97–5.99 (1H,m), 6.23–6.24 (1H,m),6.78 (1H,m),7.44–7.45 (3H,m),7.46–7.59 (5H,m),7.67 (2H,d,J=8.3 Hz),7.84–8.08 (6H,m), 8.65–8.75 (3H,m), 9.08 (1H,m), 9.93 (1H,br).

EXAMPLE 6

Preparation of (S)-2-(4-(N-2-picolylaminomethyl)benzoylamino)-5-((1-methylbenzimidazol-2-ylmethyl)amino)valeric acid 1-naphthalenemethylamide [Compound No. 6]

Example 6-1

Synthesis of 2-(4-(N-Boc-N-2-picolylaminomethyl)benzoyl)-5-((1-methylbenzimidazol-2-ylmethyl)amino)valeric acid 1-naphthalenemethylamide (Compound XIII-6)

The compound synthesized in Example 1-4 (50.3 mg) was dissolved in anhydrous methanol (1 ml). After the addition of 1-methyl-2-formylbenzimidazole (16.1 mg), the mixture was stirred for 1.5 hours at room temperature. The solvent was removed by distillation, anhydrous methanol (1 ml) and acetic acid (one drop) were added and the mixture was cooled to 0° C. Then, sodium borohydride (14.2 mg) was added and the mixture was stirred for 0.5 hours at room temperature. The reaction solution was concentrated and the residue obtained was purified by silica gel column chromatography (2.5 g, chloroform/methanol=15/1) to obtain the title compound (31.3 mg) as a white solid.

Example 6-2

Synthesis of (S)-2-(4-(N-2-picolylaminomethyl)benzoylamino)-5-((1-methylbenzimidazol-2-ylmethyl)amino)valeric acid 1-naphthalenemethylamide [Compound No. 6]

The compound obtained in Example 6-1 (28.7 mg) was dissolved in methanol (0.3 ml) and 4 mol/l hydrochloric acid/dioxane solution (0.5 ml) was added. The mixture was stirred for 2.5 hours at room temperature. The reaction solution was concentrated and the residue obtained was reprecipitated from chloroform/methanol to obtain a hydrochloride of the title compound (19.0 mg) as a pale yellow solid.

EXAMPLE 7

Preparation of (S)-2-(4-(N-2-picolylaminomethyl)benzoylamino)-5-((quinolin-2-ylmethyl)amino)valeric acid 1-naphthalenemethylamide [Compound No. 7]

Example 7-1

Synthesis of 2-(4-(N-Boc-N-2-picolylaminomethyl)benzoyl)-5-((quinolin-2-ylmethyl)amino)valeric acid 1-naphthalenemethylamide (Compound XIII-7)

The compound synthesized in Example 1-4 (50.3 mg) was dissolved in anhydrous methanol (1 ml). After the addition of 2-quinoline aldehyde (15.8 mg), the mixture was stirred for 1.5 hours at room temperature. After the solvent was removed by distillation, anhydrous methanol (1 ml) and acetic acid (one drop) were added and the mixture was cooled to 0° C. Then, sodium borohydride (14.2 mg) was added and the mixture was stirred for 0.5 hours at room temperature. The reaction solution was concentrated and the residue obtained was purified by silica gel column chromatography (2.5 g, chloroform/methanol=15/1) to obtain the title compound (12.9 mg) as pale yellow foam.

MS(FAB,Pos.): m/z=737[M+1]$^+$ $^1$H-NMR(500 MHz, CDCl$_3$): δ=1.42(9H,s),1.61–1.73(1H,m),1.73–1.83 (1H,m), 1.79–1.89(1H,m),2.16–2.22(1H,m),2.68–2.77(1H,m), 2.78–2.84(1H,m),3.74(1H,d,J=15.1 Hz),3.79(1H,d,J=15.1 Hz), 4.37 and 4.38(2H,2s),4.46 and 4.50(2H,2s),4.77–4.81 (1H,m), 4.88(1H,dd,J=14.5, 5.2 Hz),4.94(1H,dd,J=14.5,5.4 Hz),7.00–7.20 (4H,m),7.21–7.28(1H,m),7.30(1H,d,J=6.6 Hz),7.43–7.49(3H,m), 7.57–7.66(4H,m),7.69(1H,d,J=8.3 Hz),7.73(1H,d,J=7.8 Hz),7.77–7.82(1H,m),7.86(1H,d,J=8.3 Hz),7.97(1H,d; J=8.1 Hz),8.00–8.02(1H,m),8.38–8.44(1H,m),8.53(1H,ddd,J=4.9,2.0,1.0 Hz).

Example 7-2

Synthesis of (S)-2-(4-(N-2-picolylaminomethyl)benzoylamino)-5-((quinolin-2-ylmethyl)amino)valeric acid 1-naphthalenemethylamide [Compound No. 7]

The compound obtained in Example 7-1 (10.6 mg) was dissolved in methanol (0.2 ml) and 4 mol/l hydrochloric acid/dioxane solution (0.2 ml) was added. The mixture was stirred for 1.5 hours at room temperature. The reaction solution was concentrated and the residue obtained was azeotropically distilled with methanol to remove excessive hydrochloric acid, thereby obtaining a hydrochloride of the title compound (10.7 mg) as a pale yellow solid.

MS(FAB,Pos.): m/z=637[M+1]$^+$ $^1$H-NMR(500 MHz, DMSO-d$_6$): δ=1.79–1.97(4H,m),3.07–3.15(2H,m), 4.31 (4H,brs),4.49–4.56(2H,m),4.57–4.65(1H,m),4.77(1H,d,J= 5.6 Hz),7.42–7.58(5H,m),7.64–7.75(5H,m),7.82–7.89(2H, m), 7.93–7.98(2H,m),8.01(2H,d,J=8.1 Hz),8.03–8.10(3H, m),8.48(1H, d,J=8.5 Hz),8.68(1H,d,J=4.9 Hz),8.74–8.76 (2H,m),9.54(2H,brs), 10.05(2H,brs).

EXAMPLE 8

Preparation of (2S)-2-((4-(N-2-picolylaminomethyl)phenylacetyl)amino)-5-(5,6,7,8-tetrahydroquinolin-8-yl)aminovaleric acid 1-naphthalenemethylamide [Compound No. 8]

Example 8-1

Synthesis of methyl 4-bromomethylphenyl acetate (Compound IV-1)

Commercially available 4-bromomethylphenyl acetic acid (505.0 mg) was dissolved in methanol (5 ml) and tetrahydrofuran (5 ml). 2 mol/l trimethylsilyl diazomethane-hexane solution (1.31 ml) was added dropwise to this solution. After the addition, the mixture was stirred for one hour, acetic acid was added dropwise until the pale yellow color of the solution disappeared. The solvent was removed by distillation. The residue was dissolved in chloroform, washed with 1 mol/l hydrochloric acid, 1 mol/l aqueous solution of sodium hydroxide, and saturated brine, and dried over anhydrous sodium sulfate. After evaporating the solvent, the residue was purified by silica gel column chromatography (25 g, hexane/ethyl acetate=5/1) to obtain the title compound (447.7 mg) as a colorless solid.

MS(FAB,Pos.): m/z=243, 245[M+1]$^+$ $^1$H-NMR(500 MHz,CDCl$_3$): δ=3.63(2H,s),3.70(3H,s),4.49(2H,s), 7.25–7.28(2H,m),7.34–7.38(2H,m).

Example 8-2

Synthesis of Methyl 4-(N-2-picolylaminomethyl) phenylacetate (Compound V-1)

A commercially available 2-picolylamine (92.9 mg) was dissolved in DMF (2 ml) and potassium carbonate (56.5 mg) was added. After the addition of the compound obtained in Example 8-1 (100.8 mg), the solution was stirred for 1 hour at room temperature. After the reaction, the reaction solution was concentrated and the residue was dissolved in chloroform. The solution was washed with distilled water and dried over anhydrous sodium sulfate. After the solvent was removed by distillation under reduced pressure, the residue was purified by silica gel column chromatography (5.5 g, chloroform/methanol=15/1) to obtain the title compound (73.2 mg) as colorless oil.

MS(FAB,Pos.): m/z=271[M+1]$^+$ $^1$H-NMR(500 MHz, CDCl$_3$): δ=1.85(2H,brs),3.62(2H,s),3.69(3H,s), 3.83(2H,s), 3.92(2H,s),7.15–7.18(1H,m),7.23–7.27(3H,m),7.30–7.36 (3H,m),7.64(1H,td,J=7.6,1.7 Hz),8.56(1H,ddd,J=5.1,1.7,1.0 Hz).

Example 8-3

Synthesis of methyl 4-(N-Boc-N-2-picolylaminomethyl)phenylacetate (Compound VI-2)

The compound obtained in Example 8-2 (66.5 mg) was dissolved in DMF (1.3 ml). After the addition of triethylamine (14.5 μl) and di-t-butyldicarbonate (84.8 μl), the mixture was stirred for 1 hour at room temperature. After the reaction, the solvent was removed by distillation. The residue was purified by silica gel column compound (86.2 mg) as a colorless liquid.

MS(FAB,Pos.): m/z=371[M+1]$^+$ $^1$H-NMR(500 MHz, CDCl$_3$): δ=1.42 and 1.49(9H,2s),3.61(2H,s),3.70 (3H,s), 4.38, 4.47, 4.48 and 4.57(4H,4s),7.16–7.39(6H,m),7.65 (1H, td,J=7.6,1.7 Hz), 8.53(1H,d,J=4.4 Hz).

Example 8-4

Synthesis of 4-(N-Boc-N-2-picolylaminomethyl) phenylacetic acid (Compound VII-2)

The compound obtained in Example 8-3 (83.2 mg) was dissolved in THF (0.8 ml) and methanol (0.8 ml). After the addition of 1 N aqueous solution of sodium hydroxide (0.8 ml), the mixture was stirred for 35 minutes at room temperature. After the reaction, the solvent was removed by distillation and the residue was dissolved in distilled water. Aqueous solution of hydrochloric acid (1 mol/l) was added to the solution to adjust the pH to 3–4. The settled-down oily product was extracted with chloroform, washed with saturated brine, and dried over anhydrous sodium sulfate. The solvent was removed by distillation and the residue was dried under vacuum to obtain the title compound (78.7 mg) as colorless oil.

MS(FAB,Pos.): m/z=357[M+1]$^+$ $^1$H-NMR(500 MHz, CDCl$_3$): δ=1.42 and 1.49(9H,2s),3.63(2H,s),4.45, 4.53 and 4.55 (4H,4s),7.14–7.28(6H,m),7.71(1H,td,J=7.6,1.7 Hz), 8.58(1H,d, J=4.4 Hz).

Example 8-5

Synthesis of N$^α$-Fmoc-N$^δ$-Cbz-L-ornithine 1-naphthalenemethylamide (Compound IX-1)

A commercially available N$^α$-Fmoc-N$^δ$-Cbz-L-ornithine (501.8 mg) was dissolved in DMF (10 ml). HOBt (177.8 mg) WSCI hydrochloride (311.4 mg), and 1-naphthalenemethylamine (0.165 ml) were added to the solution. The mixture was stirred for 12 hours at room temperature. After the reaction, the solvent was removed by distillation. The residue was dissolved in chloroform and extracted with 1 mol/l aqueous solution of hydrochloric acid. The organic layer was washed with 1 mol/l aqueous solution of sodium hydroxide. The solvent was removed by distillation to obtain the title compound (620 mg) as a white solid.

MS(FAB,Pos.): m/z=628[M+1]$^+$ $^1$H-NMR(500 MHz, CDCl$_3$): δ=1.35–1.57(2H,m),1.39(9H,s),1.68–1.95 (2H,m), 2.96–3.07(2H,m),4.17(2H,d,J=6.1 Hz),4.48(1H,td,J=8.3, 5.1 Hz),4.75(2H,d,J=5.6 Hz), 4.98(2H,s),7.23–7.39(8H,m), 7.40–7.51(3H,m),7.51–7.59(2H,m),7.80–7.92(3H,m), 7.92–7.98(1H,m), 8.01–8.06(1H,m),8.43(1H,d,J=7.8 Hz), 8.51(1H,t,J=5.6 Hz).

Example 8-6

Synthesis of N$^δ$-Cbz-L-ornithine 1-naphthalenemethylamide (Compound X-1)

The compound obtained in Example 8-5 (122.8 mg) was dissolved in DMF (2.6 ml). After the addition of diethylamine (0.26 ml), the mixture was stirred for 2 hours at room temperature. After the reaction, the solvent was removed by distillation under reduced pressure and the residue was dried under vacuum to obtain the title compound (133.5 mg).

MS(FAB,Pos.): m/z=406[M+1]$^+$

Example 8-7

Synthesis of N$^α$-4-(N-Boc-N-2-picolylaminomethyl) phenylacetyl-N$^δ$-Cbz-L-ornithine 1-naphthalenemethylamide (Compound XI-2)

The compound obtained in Example 8-6 (133.5 mg) was dissolved in DMF (1.36 ml). After the addition of WSCI hydrochloride (54.6 mg), HOBt (28.2 mg), and the compound obtained in Example 8-4 (68.0 mg), the mixture was stirred for 17 hours at room temperature. After the reaction, the solvent was removed by distillation. The residue was dissolved in chloroform and washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (3.5 g, chloroform/ methanol=25/1) to obtain the title compound (112.3 mg) as a white solid.

MS(FAB,Pos.): m/z=744[M+1]$^+$ $^1$H-NMR(500 MHz, DMSO-d$_6$): δ=1.2–1.5(2H,m),1.30 and 1.40(9H,2s), 1.50–1.57 (1H,m),1.63–1.70(1H,m),2.94–2.98(2H,m),3.47 (2H,s), 4.28–4.32(1H,m),4.35, 4.38, 4.42 and 4.46(4H,4s), 4.71(1H,dd, J=15.2,5.9 Hz),4.76(1H,dd,J=15.2,5.9 Hz),4.99 (2H,s),7.13–7.21 (5H,m),7.25–7.39(7H,m),7.40–7.44(2H, m),7.50–7.55(2H,m),7.77 (1H,td,J=7.8,2.0 Hz),7.82–7.86 (1H,m),7.91–7.96(1H,m),8.01–8.04(1H,m.),8.30–8.33(1H, m),8.49–8.55(2H,m).

Example 8-8

Synthesis of (2S)-2-(4-(N-Boc-N-2-picolylaminomethyl)phenylacetyl)amino-5-(5,6,7,8-tetrahydroquinolin-8-yl)aminovaleric acid 1-naphthalenemethylamide (Compound XIII-8)

The compound obtained in Example 8-7 (34.9 mg) was dissolved in dioxane/water (8/2) solution (1.75 ml). After the addition of 10% Pd—C (37.9 mg), the mixture was stirred for 2.5 hours under hydrogen atmosphere at room temperature. After the reaction, the catalyst was removed by filtration through celite and the solvent was removed by distillation under reduced pressure. The residue was dissolved in methanol (0.6 ml). Then, 5,6,7,8-tetrahydroquinolin-8-one (13.6 mg), prepared by the method described in Journal of Medicinal Chemistry, vol. 20, No. 10, pp 1351–1354 (1977), and sodium cyanoborohydride (6.6 mg) were added. Acetic acid was added to adjust the pH of the mixture to 4–5. After the reaction for two days while stirring at room temperature, the solvent was removed by distillation. The residue was purified by silica gel column chromatography (3 g, chloroform/methanol=10/1) to obtain the title compound (21.4 mg) as white foam.

MS(FAB,Pos.): m/z=741[M+1]$^+$ $^1$H-NMR(500 MHz, DMSO-d$_6$): δ=1.30 and 1.40(9H,2s),1.48–1.80(6H,m), 1.90–2.00(1H,m),2.05–2.15(1H,m),2.70–3.00(4H,m),3.48 (2H,s), 4.0–4.2(1H,br),4.30–4.52(5H,m),4.69–4.80(2H,m), 7.14–7.24(5H, m),7.27–7.30(2H,m),7.41–7.45(2H,m), 7.51–7.55(2H,m),7.58–7.63(2H,m),7.77(1H,td,J=7.6,1.7 Hz),7.83–7.86(1H,m),7.92–7.96(1H,m),8.02–8.05(1H,m), 8.38(1H,d,J=6.1 Hz),8.44(1H,brs), 8.51 (1H,d,J=4.9 Hz), 8.57(1H,t,J=5.6 Hz).

Example 8-9

Synthesis of (2S)-2-((4-(N-2-picolylaminomethyl)phenylacetyl)amino)-5-(5,6,7,8-tetrahydroquinolin-8-yl)aminovaleric acid 1-naphthalenemethylamide [Compound No. 8]

The compound obtained in Example 8-8 (18.0 mg) was dissolved in methanol (0.2 ml) and 4 mol/l hydrochloric acid/dioxane solution was added. The mixture was stirred for 1.5 hours at room temperature. After the reaction, the solvent was removed by distillation. The residue was purified by silica gel column chromatography (1.0 g, chloroform/methanol/water=7/3/0.5). The obtained product was added with an aqueous solution of hydrochloric acid, concentrated and then azeotropically distilled with water. The resulting solid was washed with ether to obtain a hydrochloride of the title compound (14.4 mg) as a white solid.

MS(FAB,Pos.): m/z=641[M+1]$^+$ $^1$H-NMR(500 MHz, DMSO-d$_6$): δ=1.55–1.82(5H,m),1.82–1.93(1H,m), 1.97–2.02 (1H,m),2.24–2.32(1H,m),2.78–2.83(2H,m), 2.85–2.97(1H,m),3.01–3.13(1H,m),3.55(1H,d,J=14.7 Hz), 3.58(1H,d, J=14.7 Hz), 4.20(2H,s), 4.29(2H,s),4.29–4.40 (2H,m),4.68–4.78(2H,m),7.32(2H,d, J=8.1 Hz),7.37–7.40 (4H,m),7.52–7.57 (3H,m),7.68(1H,d,J=7.8 Hz),7.84(1H,d, J=7.6 Hz),7.90(1H,td, J=7.6,1.7 Hz), 7.92(1H,d,J=8.1 Hz), 8.03–8.07 (1H,m),8.47–8.53 (2H,m),8.64–8.69(2H,m),9.12 (2H,brs),9.72(2H,brs).

EXAMPLE 9

Preparation of (2S)-2-(4-(2-(N-2-picolylamino)ethyl)benzoyl)amino-5-(5,6,7,8-tetrahydroquinolin-8-yl)aminovaleric acid 1-naphthalenemethylamide [Compound No. 9]

Example 9-1

Synthesis of methyl 4-bromoethylbenzoate (Compound IV-2)

Commercially available 4-bromoethylbenzoic acid (997.9 mg) was dissolved in methanol (30 ml). After the addition of WSCI hydrochloride (1.2527 g) and HOBt (598.5 mg), the solution was stirred for 24 hours at 60° C. After the reaction, the solvent was removed by distillation. The residue was dissolved in chloroform, washed with 1 mol/l hydrochloric acid, 1 mol/l aqueous solution of sodium hydroxide, and saturated brine, and dried over anhydrous sodium sulfate. The solvent was removed by distillation and the residue was purified by silica gel column chromatography to obtain the title compound (829.5 mg) as a colorless solid.

MS(FAB,Pos.): m/z=243, 245[M+1]$^+$ $^1$H-NMR(60 MHz, CDCl$_3$): δ=3.0–3.5(2H,m),3.5–3.9(2H,m),3.91(3H, s),7.1–7.4(2H,m),7.8–8.1(2H,m).

Example 9-2

Synthesis of Methyl 4-(2-(2-picolylamino)ethyl)benzoate (Compound V-2)

Commercially available 2-picolylamine (0.625 ml) was dissolved in toluene (15 ml) and diisopropylethylamine (0.715 ml) was added. After the addition of the compound obtained in Example 9-1 (499.7 mg), the mixture was stirred for two days at 80° C. After the reaction, toluene was added. The solution was washed with distilled water and saturated brine, and dried over anhydrous sodium sulfate. The solvent was removed by istillation under reduced pressure, and the residue was purified by silica gel column chromatography (25 g, chloroform/methanol=25/1) to obtain the title compound (400.1 mg) as light brown oil.

MS(FAB,Pos.): m/z=271[M+1]$^+$ $^1$H-NMR(500 MHz, CDCl$_3$): δ=2.88–2.97(4H,m),3.91(3H,s) 3.93(2H, s),7.16 (1H,ddd, J=7.6,4.9, 1.2 Hz),7.24–7.30(3H,m),7.63(1H, td,J= 7.6,1.7 Hz),8.54(1H,ddd,J=4.9,1.7,1.0 Hz).

Example 9-3

Synthesis of Methyl 4-(2-(N-Boc-N-2-picolylamino)ethyl)benzoate (Compound VI-3)

The compound obtained in Example 9-2 (59.5 mg) was dissolved in DMF (1.2 ml). After the addition of triethylamine (30.9 μl) and di-t-butyldicarbonate (50.5 μl), the mixture was stirred for 100 minutes at room temperature. After the reaction, the solvent was removed by distillation. The residue was purified by silica gel column chromatography (3 g, chloroform/ethyl acetate=1/1) to obtain the title compound (60.6 mg) as colorless oil.

MS(FAB,Pos.): m/z=371[M+1]$^+$ $^1$H-NMR(500 MHz, CDCl$_3$): δ=1.40 and 1.46(9H,2s),2.85 and 2.93(2H,2t, J=7.4 Hz),3.48 and 3.56(2H,2t,J=7.4 Hz),3.90(3H,s),4.43 and 4.54 (2H, 2s),7.16–7.24(2H,m),7.26(2H,brs),7.64(1H,td,J=7.8, 1.7 Hz), 7.94(2H,d, 8.5 Hz),8.53(1H,ddd, J=4.9,1.7,1.0 Hz).

Example 9-4

Synthesis of 4-(2-(N-Boc-2-picolylamino)ethyl)benzoic acid (Compound VII-3)

The compound obtained in Example 9-3 (446.1 mg) was dissolved in THF (4.5 ml) and methanol (4.5 ml) After the addition of 1 mol/l aqueous solution of sodium hydroxide (4.5 ml), the mixture was stirred for 5 hours at room temperature. After the reaction, the solvent was removed by distillation and the residue was dissolved in distilled water. Aqueous solution of hydrochloric acid (1 mol/l) was added to the solution to adjust the pH to 3–4. The settled-down oily product was extracted with chloroform. The organic layer was washed with saturated brine, and dried over anhydrous sodium sulfate. The solvent was removed by distillation and the residue was dried under vacuum to obtain the title compound (432.2 mg) as a white solid.

MS(FAB,Pos.): m/z=357[M+1]$^+$ $^1$H-NMR(500 MHz, CDCl$_3$): δ=1.26 and 1.32(9H,2s),2.82–2.90(2H,m), 3.43–3.53(2H,m),4.39 and 4.44(2H,2s),7.20(1H,d,J=7.9 Hz),7.24–7.35(3H,m),7.76(1H,td,J=7.6,1.8 Hz),7.86(2H,d, J=8.1 Hz),8.51(1H,brs),12.85(1H,brs).

Example 9-5

Synthesis of N$^α$-4-(2-(N-Boc-N-2-picolylamino) ethyl)benzoyl-N$^δ$-Cbz-L-ornithine 1-naphthalenemethylamide (Compound XI-3)

The compound obtained in Example 8-6 (200 mg) was dissolved in DMF (4 ml). After the addition of WSCI hydrochloride (92.4 mg), HOBt (48.3 mg), and the compound obtained in Example 9-4 (114.9 mg), the mixture was stirred for 17 hours at room temperature.

After the reaction, the solvent was removed by distillation. The residue was dissolved in chloroform and washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (15 g, chloroform/methanol=30/1) to obtain the title compound (187.6 mg) as a white solid.

MS(FAB,Pos.): m/z=744[M+]$^+$ $^1$H-NMR(500 MHz, DMSO-d$_6$): δ=1.26 and 1.36(9H,2s),1.39–1.60(2H,m), 1.68–1.85(2H,m),2.80–2.90(2H,m),2.92–3.06(2H,m), 3.38–3.53 (2H,m),4.38 and 4.42(2H,2s),4.47–4.52(1H,m), 4.75(2H,d,J=5.9 Hz),4.98(2H,s),7.19(1H,d, J=8.1 Hz), 7.23–7.38(9H,m),7.43–7.49(1H,m),7.50–7.56(1H,m),7.77 (1H,t,J=7.8 Hz),7.84(2H,d, J=8.1 Hz),7.92–7.95(1H,m), 8.03–8.06(1H,m),8.41(1H,br),8.51 (2H,brs).

Example 9-6

Synthesis of N$^α$-4-(2-(N-Boc-N-2-picolylamino) ethyl)benzoyl-N$^δ$-L-ornithine 1-naphthalenemethylamide (Compound XII-2)

The compound obtained in Example 9-5 (76.0 mg) was dissolved in a dioxane/water (8/2) solution (5 ml). After the addition of 10% Pd—C (78.9 mg), the mixture was stirred for 4.5 hours under hydrogen atmosphere at room temperature. After the reaction, the catalyst was removed by filtration through celite and the solvent was removed by distillation under reduced pressure to obtain the title compound (63.7 mg) as colorless oil.

Example 9-7

Synthesis of (2S)-2-(4-(2-(N-2-picolylamino)ethyl) benzoylamino)-5-(5,6,7,8-tetrahydroquinolin-8-yl) amino)valeric acid 1-naphthalenemethylamide [Compound No. 9]

The compound obtained in Example 9-6 (28.9 mg) was dissolved in methanol (0.6 ml) Then, 5,6,7,8-tetrahydroquinolin-8-one (14.0 mg) and sodium cyanoborohydride (7.1 mg) were added to the solution. Acetic acid was added to adjust the pH of the mixture to about 4. After the reaction for two hours while stirring at room temperature, the solvent was removed by distillation. The residue was purified by silica gel column chromatography. (3 g, chloroform/methanol=10/1) to obtain a compound (21.2 mg) as white foam.

The compound (8.4 mg) was dissolved in methanol (0.2 ml) and 4 mol/l hydrochloric acid/dioxane solution (0.2 ml) was added. The mixture was stirred for 75 minutes at room temperature. After the completion of the reaction, the solvent was removed by distillation. The residue was purified by silica gel column chromatography (0.5 g, chloroform/methanol/water=7/3/0.5). The obtained product was added with an aqueous solution of hydrochloric acid and concentrated and then azeotropically distilled with water. The resulting solid was washed with ether to obtain a hydrochloride of the title compound (5.6 mg) as a white solid.

MS(FAB,Pos.): m/z=641[M+1]$^+$ $^1$H-NMR(500 MHz, DMSO-d$_6$): δ=1.62–1.94(6H,m),1.95–2.01(1H,m), 2.25–2.35 (1H,m),2.78–2.82(2H,m),2.95–3.02(1H,m), 3.05–3.18 (3H,m),3.44(2H,t,J=7.0 Hz),4.38(2H,t,J=5.4 Hz), 4.42(1H,m),4.51–4.61(1H,m),4.76(2H,d,J=5.6 Hz), 7.35–7.38(2H,m),7.44–7.47 (2H,m),7.48–7.60(3H,m),7.66 (1H,d,J=7.6 Hz),7.80–7.84(1H,m), 7.85–7.99(4H,m), 8.02–8.05(1H,m),8.41–8.44(1H,m),8.59(1H,d, J=8.1 Hz), 8.62–8.73(2H,m),9.10(2H,br), 9.53(2H,br).

EXAMPLE 10

Preparation of (S)-2-(4-(2-(N-2-picolylamino)ethyl) benzoylamino)-5-(N-2-picolylamino)valeric acid 1-naphthalenemethylamide [Compound No. 10]

Example 10-1

Synthesis of (S)-2-(4-(N-Boc-2-picolylaminoethyl) benzoyl)amino-5-(2-picolylamino)valeric acid 1-naphthalenemethylamide (Compound XIII-9)

The compound obtained in Example 9-6 (25.0 mg) was dissolved in methanol (0.6 ml). After the addition of 2-pyridinealdehyde (4.6 µl), the mixture was stirred for 2 days at room temperature. After the completion of the reaction, the solvent was removed by distillation. The residue was dried under vacuum, followed by the addition of anhydrous methanol (0.6 ml). Then, the mixture was cooled to 0° C. and sodium borohydride (9.2 mg) was added. The mixture was stirred for 1.5 hours at room temperature. After the completion of the reaction, the solvent was removed by distillation. The residue was purified by silica gel column chromatography (3 g, chloroform/methanol=10/1) to obtain the title compound (15.4 mg) as white foam.

$^1$H-NMR(500 MHz,DMSO-d$_6$): δ=1.26 and 1.36 (9H,2s), 1.40–1.60 (2H,m), 1.71–1.84 (2H,m),2.40–2.60 (2H,m), 2.89–2.91 (2H,m),3.18–3.51 (2H,m),3.73 (2H,s),4.39 and 4.42 (2H,2s),4.48 (1H,dd,J=14.2,8.5 Hz), 4.73 (1H,dd,J= 15.4,5.4 Hz),4.76 (1H,dd,J=15.4,5.4 Hz),7.18–7.32 (5H,m), 7.37 (1H,d,J=7.8 Hz),7.43–7.47 (2H,m),7.50–7.55 (2H, m),7.70 (1H,td,7.5,1.7 Hz), 7.76 (1H,t,J=7.5 Hz),7.83 (2H, d,J=8.1 Hz),7.82–7.85 (1H,m),7.92–7.95 (1H,m),8.04–8.07 (1H,m),8.45 (1H,ddd, J=4.9,1.7,1.0),8.51 (3H,brs).

Example 10-2

Synthesis of (S)-2-(4-(2-(N-2-picolylamino)ethyl) benzoylamino)-5-(N-2-picolylamino)valeric acid 1-naphthalenemethylamide [Compound No. 10]

The compound obtained in Example 10-1 (13.9 mg) was dissolved in methanol (0.28 ml) and 4 mol/l hydrochloric acid/dioxane solution (0.28 ml) was added to the solution. The mixture was stirred for 75 minutes at room temperature. After the completion of the reaction, the solvent was removed by distillation. The residue was purified by silica gel column chromatography (0.5 g, chloroform/methanol/water=7/3/0.5). The obtained product was added with aqueous solution of hydrochloric acid, concentrated and then azeotropically distilled with water. The resulting solid was washed with ether to obtain a hydrochloride of the title compound (13.8 mg) as a white solid.

MS(FAB,Pos.): m/z=601[M+1]$^+$ $^1$H-NMR(500 MHz, DMSO-d$_6$): δ=1.68–1.92(4H,m),2.96–3.03(2H,m), 3.07–3.15(2H,m), 3.20–3.28(2H,m), 4.29(2H,t,J=5.6 Hz), 4.38 (2H,t,J=5.6 Hz), 4.52–4.58(1H,m),4.76(2H,J=5.6 Hz), 7.37(1H, d,J=8.3 Hz),7.43–7.49(4H,m),7.52–7.57(3H,m), 7.59(1H,d,J=8.1 Hz),7.83–7.86(1H,m),7.88–7.96(5H,m), 8.05–8.08(1H,m), 8.59–8.63 (1H,m),8.65–8.70(1H,m),9.33 (2H,brs),9.59(2H,brs).

EXAMPLE 11

Preparation of (S)-2-(5-(N-2-picolylaminomethyl)furan-2-ylcarbonyl)amino-5-(5,6,7,8-tetrahydroquinolin-8-yl)aminovaleric acid 1-naphthalenemethylamide [Compound No. 11]

Example 11-1

Synthesis of ethyl 5-(N-2-picolylaminomethylfuran)-2-carboxylate (Compound V-3)

Commercially available ethyl 5-chloromethyl-2-furan carboxylate (100.6 mg) was dissolved in DMF (2.0 ml). Potassium carbonate (75.1 mg) and 2-picolylamine (0.167 ml) were added to the solution. The mixture was stirred for 3 hours at room temperature. After the reaction, the solvent was removed by distillation. The residue was dissolved in chloroform, washed with distilled water, and dried over anhydrous sodium sulfate. The solvent was removed by distillation, and the resultant residue was purified by silica gel column chromatography (4.5 g, chloroform/methanol=25/1) to obtain the title compound (103.2 mg) as a pale yellow oil.

MS(FAB,Pos.): m/z=261[M+1]$^+$ $^1$H-NMR(500 MHz, CDCl$_3$): δ=1.37(3H,t,J=7.1 Hz),3.91(2H,s),3.94 (2H, s),4.35 (2H,q,J=7.1 Hz),6.36(d,J=3.4 Hz),7.17(1H,ddt,J=7.5,4.9,1.0 Hz),7.31(1H,dt,J=7.5,1.0 Hz),7.65(1H,td,J=7.5,1.7 Hz),8.47 (1H,ddd,J=4.9,1.7,1.0 Hz).

Example 11-2

Synthesis of ethyl 5-(N-Boc-N-2-picolylaminomethylfuran)-2-carboxylate (Compound VI-4)

The compound obtained in Example 11-1 (96.1 mg) was dissolved in DMF (2.0 ml). After the addition of triethylamine (62.3 μl) and di-t-butyldicarbonate (84.8 μl), the mixture was stirred for 4 hours at room temperature. After the reaction, the solvent was removed by distillation. The residue was purified by silica gel column chromatography (chloroform/ethyl acetate=1/1) to obtain the title compound (131.0 mg) as pale yellow oil.

MS(FAB,Pos.): m/z=361[M+1]$^+$ $^1$H-NMR(500 MHz, CDCl$_3$): δ=1.36(3H,t,J=7.1 Hz),1.41 and 1.51(9H, 2s),4.34 (2H,q,J=7.1 Hz),4.49, 4.58, 4.61 and 4.64(4H,4s),6.21 and 6.35(1H, 2brs),7.07 (1H,brs),7.17(1H,dd,J=7.5,4.9 Hz), 7.23–7.27(1H,m), 7.64(1H,td,J=7.5,1.7 Hz),8.53(1H,dd,J= 4.9,1.7 Hz).

Example 11-3

Synthesis of 5-(N-Boc-N-2-picolylaminomethylfuran)-2-carboxylic acid (Compound VII-4)

The compound obtained in Example 11-2 (122.8 mg) was dissolved in methanol (1.2 ml) and THF (1.2 ml). After the addition of 1 mol/l aqueous solution of sodium hydroxide (1.2 ml), the mixture was stirred for 5 hours at room temperature. After the reaction, the solvent was removed by distillation. The residue was dissolved in distilled water (1.2 ml) and aqueous solution of hydrochloric acid (1 mol/l) was added to adjust the pH to 4. The mixture was extracted with chloroform. The organic layer was dried over anhydrous sodium sulfate. The solvent was removed by distillation to obtain the target compound (113.3 mg) as pale yellow oil.

MS(FAB,Pos.): m/z=333[M+1]$^+$ $^1$H-NMR(500 MHz, CDCl$_3$): δ=1.27 and 1.42(9H,2s),4.44, 4.47, 4.50 and 4.57 (4H,4s),6.37 and 6.45(1H,2brs),7.09(1H,brs),7.18(1H,m), 7.27(1H,d,J=7.1 Hz), 7.75(1H,t,J=7.1 Hz),8.50(1H,d,J=4.4 Hz).

Example 11-4

Synthesis of N-(5-(N$^α$-Boc-N-2-picolylaminomethyl)furan-2-ylcarbonyl)-N$^δ$-Cbz-L-ornithine 1-naphthalenemethylamide (Compound XI-4)

The compound obtained in Example 8-6 (152.6 mg) was dissolved in DMF (3 ml). After the addition of WSCI hydrochloride (73.3 mg), HOBt (30.8 mg), and the compound obtained in Example 11-3 (85.5 mg), the mixture was stirred for 19 hours at room temperature. After the reaction, the solvent was removed by distillation. The residue was dissolved in chloroform and washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (7 g, chloroform/methanol=25/1) to obtain the title compound (137.3 mg) as white foam.

MS(FAB,Pos.): m/z=720[M+1]$^+$

Example 11-5

Synthesis of (2S)-2-(5-(N-Boc-N-2-picolylaminomethyl)furan-2-ylcarbonyl)amino-5-(5,6,7,8-tetrahydroquinolin-8-yl)aminovaleric acid 1-naphthalenemethylamide (Compound XIII-10)

The compound obtained in Example 11-4 (135.9 mg) was dissolved in a dioxane/water (8/2) solution (6.5 ml). After the addition of 10% Pd—C (138.5 mg), the mixture was stirred for 4.5 hours under hydrogen atmosphere at room temperature. After the reaction, the catalyst was removed by filtration through celite and the solvent was removed by distillation under reduced pressure to obtain a crude product (107.6 mg). 75.1 mg of this crude product was dissolved in methanol (2.25 ml). Then, 5,6,7,8-tetrahydroquinolin-8-one (27.2 mg) and sodium cyanoborohydride (10.4 mg, 0.165 mml) were added. 40 drops of acetic acid was added to adjust the pH of the mixture to about 4. After the reaction for 14 hours while stirring at room temperature, the solvent was removed by distillation. The residue was purified by silica gel column chromatography (5 g, chloroform/methanol=10/1) to obtain the title compound (38.7 mg) as white foam.

MS(FAB,Pos.): m/z=717[M+1]$^+$ $^1$H-NMR(500 MHz, DMSO-d$_6$): δ=1.28 and 1.42(9H,2s),1.49–1.92(6H,m), 2.00–2.20(1H,m),2.65–2.95(5H,m),4.40–4.60(6H,m),4.76 (2H,d, J=5.6 Hz),6.38, 6.42 and 6.44(1H,brs),7.12 and 7.14 (1H,brs),7.18–7.22(3H,m),7.40–7.48(2H,m),7.49–7.62(3H, m),7.77(1H,td,J=7.8, 1.0 Hz),7.80–7.85(1H,m),7.87–7.91 (1H,m),8.02–8.08(1H,m), 8.30–8.49(1H,m),8.50(1H,d,J= 4.9 Hz),8.60–8.75(1H,br).

Example 11-6

Synthesis of (2S)-2-(5-(N-2-picolylaminomethyl) furan-2-ylcarbonyl)amino-5-(5,6,7,8-tetrahydroquinolin-8-yl)aminovaleric acid 1-naphthalenemethylamide [Compound No. 11]

The compound obtained in Example 11-5 (30.6 mg) was dissolved in methanol (0.7 ml), and 4 mol/l hydrochloric acid/dioxane solution (0.7 ml) was added. The mixture was stirred for 3 hours at room temperature. After the reaction, the solvent was removed by distillation. The residue was purified by silica gel column chromatography (1 g, chloroform/methanol/water=7/3/0.5). The obtained product was added with an aqueous solution of hydrochloric acid, concentrated and then azeotropically distilled with water. The resulting solid was washed with ether to obtain a hydrochloride of the title compound (22.7 mg) as a white solid.

MS(FAB,Pos.): m/z=617[M+1]$^+$ $^1$H-NMR(500 MHz, DMSO-$d_6$): δ=1.68–2.02(7H,m),2.23–2.35(1H,m) 2.77–3.05(2H,m),2.88–3.01(1H,m),3.02–3.18(1H,m),4.36 (2H,s), 4.39(2H,s),4.37–4.43(1H,m),4.51–4.59(1H,m),4.76 (1H,d,J=5.6 Hz),6.79(1H,d,J=3.4 Hz),7.29(1H,d,J=3.4 Hz), 7.38(1H,dd,J=7.5, 4.9 Hz),7.43–7.49(3H,m),7.51–7.57(2H, m),7.59(1H,brs), 7.67(1H,d,J=7.6 Hz),7.83–7.87(1H,m), 7.88–7.92(1H,m),7.93–7.96(1H,m),8.05–8.08(1H,m),8.46 (2H,brs),8.64(1H,d,J=4.9 Hz), 8.51(1H, brs),9.19(2H,brs), 10.09(2H,brs).

EXAMPLE 12

Preparation of (2S)-2-(2-(N-2-picolylaminomethyl) pyridin-5-ylcarbonyl)amino-5-((5,6,7,8-tetrahydroquinolin-8-yl)amino)valeric acid 1-naphthalenemethylamide [Compound No. 12]

Example 12-1

Synthesis of methyl 6-(N-2-picolylaminomethyl) nicotinate (Compound V-4)

Commercially available methyl 6-methylnicotinate (2.5116 g) was dissolved in chloroform (50 ml), and N-bromosuccinimide (3.5682 g) and azoisobutylonitrile (290.4 mg) were added to the solution. The mixture was stirred for 22 hours at 70° C. After the reaction, the solvent was removed by distillation. The residue was purified by silica gel column chromatography (100 g, hexane/ethyl acetate=4/1) to obtain a crude product (1.0883 g) as a pale yellow solid. 280.7 mg of the solid (280.7 mg) was dissolved in DMF (5.6 ml), and potassium carbonate (168.5 mg) and 2-picolylamine (0.370 ml) were added. The mixture was stirred for 12 hours at room temperature. After the reaction, the solvent was removed by distillation. The residue was dissolved in chloroform, washed with distilled water, and dried over anhydrous sodium sulfate. The solvent was removed by distillation, and then the residue was purified by silica gel column chromatography (25 g, chloroform/methanol 25/1) to obtain the title compound (298.3 mg) as a pale yellow oil.

MS(FAB,Pos.): m/z=258[M+1]$^+$ $^1$H-NMR(500 MHz, CDCl$_3$): δ=3.97(3H,s),3.99(2H,s),4.03(2H,s),7.18 (1H,dd, J=7.5,4.9 Hz),7.34(1H,d,J=7.5 Hz),7.47(1H,d,J=7.5 Hz), 7.65(1H,t,J=7.5 Hz),8.28(1H,d,J=7.5 Hz),8.56(1H,d,J=4.9 Hz),9.17(1H,s).

Example 12-2

Synthesis of methyl 6-(N-Boc-N-2-picolylaminomethyl)nicotinate (Compound VI-5)

The compound obtained in Example 12-1 (292.7 mg) was dissolved in DMF (6 ml). After the addition of triethylamine (0.192 ml) and di-t-butyldicarbonate (0.288 ml), the mixture was stirred for 1.5 hours at room temperature. After the reaction, the solvent was removed by distillation. The residue was purified by silica gel column chromatography (chloroform/ethyl acetate=1/1) to obtain the title compound (352.2 mg) as pale yellow oil.

MS(FAB,Pos.): m/z=358[M+1]$^+$ $^1$H-NMR(500 MHz, CDCl$_3$): δ=1.39 and 1.44(9H,s),3.95(3H,s),4.61, 4.64, 4.71 and 4.74(4H,4s),7.17(1H,ddd,J=4.9,1.7. 1.0 Hz),7.20–7.26 (1H,m),7.31–7.41(1H,m),7.67(1H,t,J=7.6 Hz),8.25(1H,d, J=8.1 Hz),8.51(1H,m), 9.11(1H,s).

Example 12-3

Synthesis of 6-(N-Boc-N-2-picolylaminomethyl) nicotinic acid (Compound VII-5)

The compound obtained in Example 12-2 (351.3 mg) was dissolved in methanol (3.5 ml) and THF (3.5 ml). After the addition of 1 mol/l aqueous solution of sodium hydroxide (3.5 ml), the mixture was stirred for 2 hours at room temperature. After the reaction, the solvent was removed by distillation. The residue was dissolved in distilled water (1.2 ml) and aqueous solution of hydrochloric acid (1 mol/l) was added to adjust the pH to 4. The mixture was extracted with chloroform. The organic layer was dried over anhydrous sodium sulfate. The solvent was removed by distillation to obtain the target compound (277.9 mg) as a white solid.

MS(FAB,Pos.): m/z=344[M+1]$^+$ $^1$H-NMR(500 MHz, CDCl$_3$): δ=1.46 and 1.55(9H,s),4.54, 4.63, 4.77 and 4.84 (4H,4s),7.20–7.30(1H,m),7.30–7.40(1H,m),7.42–7.63(1H, m), 7.87(1H,td,J=7.6,1.7 Hz),8.16–19(1H,m),8.51(1H,dd,J= 4.1, 1.7 Hz),8.86(1H,s).

Example 12-4

Synthesis of N$^α$-(2-(N-Boc-N-2-picolylaminomethyl)pyridin-5-ylcarbonyl)-N$^δ$-Cbz-L-ornithine 1-naphthalenemethylamide (Compound XI-5)

The compound obtained in Example 8-6 (165.3 mg) was dissolved in DMF (3 ml). After the addition of WSCI hydrochloride (78.5 mg), HOBt (40.1 mg), and the compound obtained in Example 12-3 (90.4 mg), the mixture was stirred for 23 hours at room temperature. After the reaction, the solvent was removed by distillation. The residue was dissolved in chloroform and washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (10 g, chloroform/methanol=20/1) to obtain the title compound (167.6 mg) as white foam.

MS(FAB,Pos.): m/z=731[M+1]$^+$ $^1$H-NMR(500 MHz, DMSO-$d_6$): δ=1.41 and 1.43(9H,2s),1.45–1.58(1H,m), 1.60–1.73(1H,m),1.77–1.81(1H,m),1.82–1.94(1H,m), 3.03–3.17 (1H,m),3.49–3.62(1H,m),4.40–4.49(1H,m), 4.55–4.80(7H,m), 4.85–5.02(3H,m),7.10–7.20(4H,m), 7.21–7.40(7H,m),7.41–7.55 (3H,m),7.66(1H,t,J=7.6 Hz), 7.75(1H,d,J=8.1 Hz),7.83(1H,d,J=8.1 Hz),7.98(1H,d,J=8.5 Hz),8.05(1H,dd,J=8.1,2.0 Hz),8.52(1H,brs, 8.95(1H,brs).

Example 12-5

Synthesis of (2S)-2-(2-(N-Boc-N-2-picolylaminomethyl)pyridin-5-ylcarbonyl)amino-5-(5,6,7,8-tetrahydroquinolin-8-yl)aminovaleric acid 1-naphthalenemethylamide (Compound XIII-11)

The compound obtained in Example 12-4 (149.9 mg) was dissolved in a dioxane/water (8/2) solution (7.5 ml). After the addition of 10% Pd—C (154.6 mg), the mixture was stirred for 4.5 hours under hydrogen atmosphere at room temperature. After the reaction, the catalyst was removed by filtration through celite and the solvent was removed by distillation under reduced pressure to obtain a crude product (100.2 mg). 75.4 mg of the crude product was dissolved in methanol (1.5 ml). Then, 5,6,7,8-tetrahydroquinolin-8-one (53.6 mg) and sodium cyanoborohydride (43.2 mg) were added. 25 drops of acetic acid was added to adjust the pH of the mixture to about 5. The mixture was stirred for 22 hours at room temperature. After the reaction, the solvent was removed by distillation. The residue was purified by silica gel column chromatography (5 g, chloroform/methanol=10/1) to obtain the title compound (30.6 mg) as white foam.

MS(FAB,Pos.): m/z=728[M+1]$^+$ $^1$H-NMR(500 MHz, DMSO-d$_6$): δ=1.31(9H,s),1.60–2.00(5H,m),2.15–2.35(1H, m),2.70–2.85(2H,m),2.86–3.05(2H,m),4.50–4.62(2H,m), 4.52, 4.56, 4.60 and 4.65(4H,4s),4.77(2H,d,J=5.9 Hz), 7.20–7.41 (4H,m),7.47 (2H,d,J=4.1 Hz),7.52–7.55(2H,m), 7.64(1H,d,J=6.4 Hz),7.79(1H,td,J=7.8,1.7 Hz),7.84–7.86 (1H,m),7.93–7.96(1H,m), 8.03–8.08(1H,m),8.22(1H,d,J= 8.1 Hz),8.42–8.48(1H,m),8.51 (1H,dd,J=5.6,1.5 Hz),8.61 (1H,brs),8.75–8.88(1H,m),9.00(1H,s).

Example 12-6

Synthesis of (2S)-2-(2-(N-2-picolylaminomethyl)pyridin-5-ylcarbonyl)amino-5-((5,6,7,8-tetrahydroquinolin-8-yl)amino)valeric acid 1-naphthalenemethylamide [Compound No. 12]

The compound obtained in Example 12-5 (26.8 mg) was dissolved in methanol (0.5 ml), and 4 mol/l hydrochloric acid/dioxane solution (0.5 ml) was added. The mixture was stirred for 4.5 hours at room temperature. After the reaction, the solvent was removed by distillation. The residue was purified by silica gel column chromatography (1 g, chloroform/methanol/water=7/3/0.5). The obtained product was added with an aqueous solution of hydrochloric acid and concebtrated, and then azeotropically distilled with water. The resulting solid was washed with ether to obtain a hydrochloride of the title compound (25.8 mg) as a white solid.

MS(FAB,Pos.): m/z=628[M+1]$^+$ $^1$H-NMR(500 MHz, DMSO-d$_6$): δ=1.63–2.05(7H,m),2.25–2.38(1H,m), 2.77–2.82 (2H,m),2.88–3.01(1H,m),3.01–3.17(1H,m), 4.40–4.43 (1H,m),4.44(2H,s), 4.49(2H,s),4.50–4.61(1H,m), 4.77(2H,d, J=5.9 Hz),7.37(1H,dd,J=7.5,4.9 Hz), 7.44–7.52 (3H,m),7.52–7.59 (2H,m),7.60(1H,d,J=7.8 Hz),7.66–7.69 (1H,m),7.67(1H,d, J=5.9 Hz),7.83–7.87(1H,m),7.88–7.97 (2H,m),8.06–8.09(1H,m), 8.39(1H,dt, 8.1,2.0 Hz),8.46(1H, td,J=4.6,1.5 Hz),8.67(1H,ddd,J=4.9,1.7,1.0 Hz),8.79(1H,t, J=5.9 Hz),9.24(1H,d,J=8.1H),9.14(1H,d,J=2.0 Hz).

EXAMPLE 13

Preparation of (2S)-2-(5-(N-2-picolylaminomethyl)pyrazine-2-carbonylamino)-5-(5,6,7,8-tetrahydroquinolin-8-ylamino)valeric acid 1-naphthalenemethylamide [Compound No. 13]

Example 13-1

Synthesis of 2-methoxycarbonyl-5-methylpyrazine (Compound III-1)

Commercially available 5-methylpyrazine 2-carboxylic acid (2.05 g) was dissolved in methanol (0.6 ml) and chlorine gas was blown into the solution for 5 minutes. After four hours, the reaction solution was concentrated and 1 mol/l aqueous solution of sodium hydroxide was added, followed by extraction with chloroform. The organic layer was washed with saturated brine, dried over anhydrous sodium sulfate, and concentrated. The resulting solid was recrystallized from hexane/ethyl acetate. The deposited crystals were collected by filtration and dried under reduced pressure to obtain the title compound (1.44 g) as light brown scale-like crystals.

MS(EI,Pos.): m/z=152[M+1]$^+$ $^1$H-NMR(500 MHz, DMSO-d$_6$): δ=2.68(3H,s),4.04(3H,s),8.59(1H,d, J=1.0 Hz), 9.20(1H,1.0 Hz).

Example 13-2

Synthesis of 5-bromomethyl-2-methoxycarbonylpyrazine (Compound IV-3)

The compound obtained in Example 13-1 (500 mg) was dissolved in carbontetrachloride (10 ml) and N-bromosuccinimido (585 mg) and azobisisobutylonitrile (54 mg) were added. After stirring for 20 hours over an oil bath at 70° C., the reaction mixture was filtered and the filtrate was concentrated. The residue was purified by silica gel column chromatography (14 g, chloroform/ethyl acetate=2/1) to obtain the title compound (328.7 mg) as pale yellow syrup.

MS(EI,Pos.): m/z=229, 231[M+1]$^+$ $^1$H-NMR(500 MHz, DMSO-d$_6$): δ=4.06(3H,s) 4.62(2H,s),8.83(1H,d, J=1.5 Hz), 9.26(1H,d,J=1.5 Hz).

Example 13-3

Synthesis of 5-(N-Boc-N-2-picolylaminomethyl)pyrazine-2-carboxylic acid (Compound VII-6)

The compound obtained in Example 13-2 (320 mg) was dissolved in DMF (6.4 ml) and potassium carbonate (383 mg) and 2-picolylamine (286 μl) were added. After the reaction for 17 hours, the reaction solution was concentrated, and added with water, followed by extraction with chloroform. The organic layer was washed with saturated brine, dried over anhydrous sodium sulfate, and concentrated to obtain a crude product of the title compound (444.1 mg) as brown syrup. The crude product was dissolved in dioxane (4 ml), and di-t-butyldicarbonate (0.35 ml) and 1 mol/l aqueous solution of sodium hydroxide (4 ml) were added. After the reaction for 2 hours, the reaction solution was concentrated. After the addition of dilute hydrochloric acid, the residue was extracted with chloroform. The organic layer was washed with saturated brine, dried over anhydrous sodium sulfate, and concentrated to obtain the title compound (158.8 mg) as a light brown solid.

MS(FAB,Pos.): m/z=345[M+1]$^+$

Example 13-4

Synthesis of N$^α$-(5-(N-Boc-N-2-picolylaminomethyl)pyrazine-2-carbonyl)-N$^δ$-Cbz-L-ornithine 1-naphthalenemethylamide (Compound XI-6)

The compound obtained in Example 8-6 (160 mg) was dissolved in DMF (3.2 ml) and diethylamine (0.32 ml) was added. After one hour, the reaction solution was concebtrated and the residue obtained was dissolved in DMF (1 ml). Then, WSCI hydrochloride (73 mg), DMAP (31 mg), and a solution of the compound obtained in Example 13-3 in DMF (1 ml) were sequentially added. After 15 hours, the reaction solution was concentrated. After the addition of chloroform and 1 mol/l hydrochloric acid, the residue was extracted with chloroform. The organic layer was washed with saturated brine and dried over anhydrous sodium sulfate. The residue was crude-purified by silica gel column chromatography (4 g, chloroform/ethyl acetate=1/2) to obtain the title compound (95.2 mg) as colorless syrup.

MS(FAB,Pos.): m/z=732[M+1]$^+$

Example 13-5

Synthesis of (2S)-2-(5-(N-Boc-N-2-picolylaminomethyl)pyrazine-2-carbonylamino-5-(5,6,7,8-tetrahydroquinolin-8-ylamino)valeric acid 1-naphthalenemethylamide (Compound XIII-12)

The compound obtained in Example 13-4 (95.2 mg) was dissolved in dioxane (4 ml) and water (1 ml), and 5% Pd—C was added. Hydrogen gas was introduced into the reaction solution. After 16 hours, the reaction solution was filtered through a glass filter G4 and the filtrate was concentrated. The residue was dissolved in methanol (2.4 ml), and acetic acid (0.24 ml), 5,6,7,8-tetrahydroquinolin-8-one (57 mg), and sodium cyanoborohydride (24 mg) were added. After 21 hours, the reaction solution was concentrated. The residue was purified by silica gel column chromatography (10 g, chloroform/methanol=10/1) to obtain the title compound (58.4 mg) as colorless syrup.

MS(FAB,Pos.): m/z=729[M+1]$^+$ $^1$H-NMR(500 MHz, CDCl$_3$): δ=1.41, 1.42, 1.43 and 1.44(9H,4s),1.70–2.97(10H,m),3.03–3.11(0.5H,m),3.28–3.34(0.5H,m),3.90–4.00 (0.5H,m),4.19–4.26(0.5H,m),4.60–5.02(8H,m),7.06–7.54(10H,m),7.67(1H,t,J=7.1 Hz),7.72–7.79(1H,m),7.84(1H,t,J=9.5 Hz), 8.03(1H,t,J=9.8 Hz),8.28(1H,d,J=3.2 Hz),8.38–8.57 (2H,m),9.19(1H,d,J=3.4 Hz).

Example 13-6

Synthesis of (2S)-2-(5-(N-2-picolylaminomethyl)pyrazine-2-carbonylamino)-5-(5,6,7,8-tetrahydroquinolin-8-ylamino)valeric acid 1-naphthalenemethylamide [Compound No. 13]

The compound obtained in Example 13-5 (57.2 mg) was dissolved in methanol (0.6 ml) and 4 mol/l hydrochloric acid/dioxane solution (0.6 ml) was added. After 4 hours, the reaction solution was concentrated. The residue was purified by silica gel column chromatography (1 g, chloroform/methanol=5/1). After the addition of 1 mol/l hydrochloric acid, the residue was concentrated and dried under reduced pressure to obtain a hydrochloride of the title compound (29.3 mg) as a light brown solid.

MS(FAB,Pos.): m/z=629[M+1]$^+$ $^1$H-NMR(500 MHz, DMSO-d$_6$): δ=1.68–2.02(7H,m),2.25–2.31(1H,m), 2.79 (2H,t,J=6.3 Hz),2.90–3.00(1H,m),3.00–3.14(1H,m), 4.38–4.42(1H,m),4.47(2H,s),4.61(2H,s),4.60–4.67(1H,m), 4.78(2H,d, J=5.6 Hz),7.35–7.39(1H,m),7.43–7.58(8H,m), 7.67(1H,d,J=7.8 Hz), 7.93–7.97(3H,m),8.03–8.07(1H,m), 8.45(1H,d,J=3.9 Hz),8.63–8.67(1H,m),8.81(1H,s),8.89(1H,d,J=8.5 Hz),8.95(1H,s),8.97–9.17(2H,br),10.00–10.11(2H,br).

EXAMPLE 14

Preparation of (2S)-2-(5-(N-2-picolylaminomethyl)thiophene-2-carbonylamino)-5-(5,6,7,8-tetrahydroquinolin-8-ylamino)valeric acid 1-naphthalenemethylamide [Compound No. 14]

Example 14-1

Synthesis of 2-bromomethyl-5-methoxycarbonylthiophene (Compound IV-4)

Commercially available 5-methylthiophene carboxylic acid (2.05 g) was dissolved in methanol (60 ml) and chlorine gas was blown into the solution for 5 minutes. After 23 hours, the reaction solution was concentrated and 1 mol/l aqueous solution of sodium hydroxide was added, followed by extraction with chloroform. The organic layer was washed with saturated brine, dried over anhydrous sodium sulfate and concentrated. 500 mg of the resultant residue was dissolved in carbontetrachloride (10 ml) and N-bromosuccinimido (570 mg) and azobisisobutylonitrile (53 mg) were added. After stirring for 20 hours over an oil bath at 70° C., the reaction mixture was filtered and the filtrate was concentrated. The residue was purified by silica gel column chromatography (15 g, hexane/ethyl acetate=8/1) to obtain the title compound (516.1 mg) as pale yellow syrup.

MS(EI,Pos.): m/z=233, 235[M+1]$^+$ $^1$H-NMR(500 MHz, CDCl$_3$): δ=3.89(3H,s),4.68(2H,s),7.10(1H,d,J=3.7 Hz),7.64 (1H,d,J=3.7 Hz).

Example 14-2

Synthesis of 5-(N-Boc-N-2-picolylaminomethyl)thiophene-2-carboxylic acid (Compound VII-7)

The compound obtained in Example 14-1 (513 mg) was dissolved in DMF (10 ml) and potassium carbonate (603 mg) and 2-picolylamine (0.45 ml) were added. After 17 hours, the reaction solution was concentrated. After the addition of water, the residue was extracted with chloroform. The organic layer was washed with saturated brine, dried over anhydrous sodium sulfate, and concentrated. The residue was dissolved in dioxane (6 ml), and di-t-butyldicarbonate (0.55 ml) and 1 mol/l aqueous solution of sodium hydroxide (6 ml) were added. After 6 hours, 1 mol/l aqueous solution of sodium hydroxide (about 2 ml) was added to the reaction solution. The mixture was stirred for a further four hours. The reaction solution was concentrated. The residue was made weakly acidic with the addition of water and 1 mol/l hydrochloric acid and extracted with chloroform. The organic layer was dried over anhydrous magnesium sulfate and concentrated. The residue obtained was dissolved in methanol (12 ml), and 1 mol/l aqueous solution of sodium hydroxide (12 ml) was added. After 16 hours, the reaction solution was concentrated and the residue was dissolved in water. 1 mol/l hydrochloric acid was gradually added to the solution to adjust the pH to 4–5. The mixture was allowed to stand still overnight. The deposited solid was collected by filtration and dried under reduced pressure to obtain the title compound (523.3 mg) as a white solid.

MS(FAB,Pos.): m/z=349[M+1]$^+$ $^1$H-NMR(500 MHz, CDCl$_3$): δ=1.50 and 1.55(9H,2s),4.52, 4.60, 4.64 and 4.69 (4H,4s),6.93 and 6.97(1H,2d,J=3.7 Hz),7.33(1H,dd, J=5.6, 7.1 Hz),7.37 and 7.50(1H,2d,J=7.6 Hz),7.67(1H,d,J=3.7 Hz), 7.80(1H,t,J=7.3 Hz), 8.69(1H,brs).

Example 14-3

Synthesis of N$^α$-(5-(N-Boc-N-2-picolylaminomethyl)thiophene-2-carbonyl)-N$^δ$-Cbz-L-ornithine 1-naphthalenemethylamide (Compound XI-7)

The compound obtained in Example 8-6 (283 mg) was dissolved in DMF (5.6 ml) and diethylamine (0.56 ml) was added. After one hour, the reaction solution was concentrated. 146 mg of the resulting residue was dissolved in DMF, and WSCI hydrochloride (104 mg), DMAP (66 mg), and the compound obtained in Example 14-2 (138 mg) were added. After 14 hours, chloroform and 1 mol/l hydrochloric acid were added to the reaction solution, and the mixture was extracted with chloroform. The organic layer was washed with saturated brine and concentrated. The residue was purified by silica gel column chromatography (10 g, chloroform/ethyl acetate=2/1) to obtain the title compound (208.6 mg) as colorless syrup.

MS(FAB,Pos.): m/z=736[M+1]$^+$ $^1$H-NMR(500 MHz, CDCl$_3$): δ=1.43 and. 1.54(9H,2s),1.40–1.55(2H,m), 1.69–1.78(1H,m),1.82–1.90(1H,m),3.05–3.12(1H,m), 3.47–3.56(1H,m),4.44–4.90(6H,m),4.99(1H,dd,J=6.1,14.6 Hz),6.92–7.54 (13H,m),7.64(1H, t,J=7.8 Hz),7.75(1H,d,J=8.3 Hz),7.83(1H,d, J=7.8 Hz),7.97(1H,d,J=8.5 Hz),8.54(1H, d, J=4.2 Hz).

Example 14-4

Synthesis of N$^α$-(5-(N-2-picolylaminomethyl) thiophene-2-carbonyl)-L-ornithine 1-naphthalenemethylamide (Compound XIV-1)

A mixed solution of trifluoroacetic acid (1.4 ml), thioanisole (0.36 ml), and m-cresol (0.32 ml) was added to the compound obtained in Example 14-3 (56.2 mg). After 1.5 hours, the reaction solution was concentrated. Methanol was added to the residue and the mixture was washed with hexane. The methanol layer was concentrated and the residue was crude-purified by silica gel column chromatography (3 g, chloroform/methanol/water=7/3/0.5) to obtain the title compound (18.2 mg) as colorless syrup.

MS(FAB,Pos.): m/z=502[M+1]$^+$

Example 14-5

Synthesis of (2S)-2-(5-(N-2-picolylaminomethyl) thiophene-2-carbonylamino)-5-(5,6,7,8-tetrahydroquinolin-8-ylamino)valeric acid 1-naphthalenemethylamide [Compound No. 14]

The compound obtained in Example 14-4 (18.2 mg) was dissolved in methanol (0.6 ml), and acetic acid (0.06 ml), 5,6,7,8-tetrahydroquinolin-8-one (16 mg), and sodium cyanoborohydride (7 mg) were added. After 3 days, the reaction solution was concentrated. The residue was purified by silica gel column chromatography (1 g, chloroform/methanol=5/1). 1 mol/l hydrochloric acid was added to the resulting colorless syrup, and the mixture was concentrated and dried under reduced pressure to obtain ahydrochloride of the title compound (6.7 mg) as a white solid.

MS(FAB,Pos.): m/z=633[M+1]$^+$ $^1$H-NMR(500 MHz, DMSO-d$_6$): δ=1.65–2.07(7H,m),2.24–2.33(1H,m), 2.79 (2H,t,J=6.3 Hz),2.89–2.99(1H,m),3.03–3.13(1H,m),4.30 (2H, s),4.38–4.55(4H,m),4.76(2H,d,J=5.6 Hz),7.35–7.40 (2H,m),7.42–7.49(3H,m),7.50–7.57(2H,m),7.61(1H,d,J=7.8 Hz),7.67(1H,d,J=7.8 Hz),7.81–7.88(1H,m),7.89–7.97(3H, m),8.02–8.07(1H,m),8.46(1H,dt,J=1.5,4.6 Hz),8.66(1H,d,J= 4.9 Hz),8.77(1H,dd,J=3.9,5.9 Hz),8.87(1H,d,J=8.3 Hz), 9.00–9.38(2H,br),9.98–10.09(2H, br)

EXAMPLE 15

Preparation of (2S)-2-(5-(N-(imidazol-2-ylmethyl) aminomethyl)thiophene-2-carbonylamino)-5-picolylaminovaleric acid 1-naphthalenemethylamide [Compound No. 15] and (2S)-2-(5-(N-(imidazol-2-ylmethyl)aminomethylthiophene-2-carbonylamino)-5-(5,6,7,8-tetrahydroquinolin-8-yl)aminovaleric acid 1-naphthalenemethylamide [Compound No. 16]

Example 15-1

Synthesis of 2-methoxycarbonyl-5-(N-(imidazol-2-ylmethyl)aminomethyl)thiophene (Compound V-5)

The compound obtained in Example 14-1 (2.02 g) was dissolved in DMF (30 ml), and potassium phthalimide (1.92 g) was added. After 3.5 hours, the reaction solution was concentrated. After the addition of water, the residue was extracted with chloroform. The organic layer was dried over anhydrous sodium sulfate and concentrated. The resulting residue was reprecipitated from methanol to obtain the title compound (1.52 g) as a yellow solid.

The compound (714 mg) was dissolved in ethanol (3.6 ml), and hydrazine monohydrate (0.57 ml) was added. After the reaction for 20 hours, the reaction solution was concentrated. The resulting solid was washed with chloroform. The washing solution was concentrated and the resulting residue was dissolved in methanol (14 ml). After the addition of 2-imidazolecarboxyaldehyde (232 mg) and triethylamine (0.34 ml), the mixture was stirred for 20 hours. Sodium borohydride (183 mg) was added to the reaction solution. After two hours, a small amount of silica gel was added and the mixture was concentrated. The residue was purified by silica gel column chromatography (15 g, chloroform/methanol 20/1) to obtain the title compound (105 mg) as yellow syrup.

Example 15-2

Synthesis of 2-methoxycarbonyl-5-(N-(imidazol-2-ylmethyl)-N-Boc-aminomethyl)thiophene (Compound VI-6)

The compound obtained in Example 15-1 (102 mg) was dissolved in DMF (3 ml) and triethylamine (84 μl) and di-t-butyldicarbonate (102 μl) were added. After 18 hours, the reaction solution was concentrated. After the addition of water, the residue was extracted with chloroform. The organic layer was dried over anhydrous sodium sulfate and concentrated. The residue was purified by silica gel column chromatography (4 g, hexane/ethyl acetate=2/1) to obtain the title compound (84 mg) as yellow syrup.

MS(FAB,Pos.): m/z=352[M+1]$^+$ $^1$H-NMR(500 MHz, CDCl$_3$): δ=1.57(9H,s),3.88(3H,s),4.73(2H,s), 4.86(2H,s), 6.87(1H,d,J=3.7 Hz),6.91(1H,d. J=1.7 Hz),7.29(1H,s), 7.61 (1H,d,J=3.7 Hz).

Example 15-3

Synthesis of 5-(N-(imidazol-2-ylmethyl)-N-Boc-aminomethyl)thiophene-2-carboxylic acid (Compound VII-8)

The compound obtained in Example 15-2 (84 mg) was dissolved in methanol (0.8 ml), and 1 mol/l aqueous solution of sodium hydroxide (0.8 ml) and THF (0.8 ml) were added. After 1.5 hours, the reaction solution was concentrated. After the addition of water and 1 mol/l hydrochloric acid, the solvent was removed by distillation to obtain the title compound (a mixture with sodium chloride, 121 mg) as a pale yellow solid.

MS(FAB,Pos.): m/z=338[M+1]$^+$

Example 15-4

Synthesis of (2S)-2-(5-(N-(imidazol-2-ylmethyl) aminomethyl)thiophene-2-carbonylamino)-5-picolylaminovaleric acid 1-naphthalenemethylamide [Compound No. 15] and (2S)-2-(5-(N-(imidazol-2-ylmethyl)aminomethyl)thiophene-2-carbonylamino)-5-(5,6,7,8-tetrahydroquinolin-8-yl)aminovaleric acid 1-naphthalenemethylamide [Compound No. 16]

The compound obtained in Example 8-6 (180 mg) was suspended in DMF (3.6 ml) and diethylamine (0.36 ml) was added. After 30 minutes, the reaction solution was concentrated and dried under reduce pressure. The obtained residue was dissolved in DMF (0.8 ml) and added to a solution of the compound obtained in Example 15-3 (81 mg) in DMF (1.6 ml). In addition, WSCI hydrochloride (69 mg) and DMAP (44 mg) were added. After 5 hours, the reaction solution was concentrated. 1 mol/l hydrochloric acid was added to the residue, and the mixture was extracted with chloroform. The organic layer was washed with saturated brine, dried over anhydrous sodium sulfate, and concentrated. The residue was purified by silica gel column chromatography (4 g, chloroform/methanol 10/1) to obtain a crude product (105 mg) as a yellow syrup. A mixed solution of trifluoroacetic acid (2.5 ml), thioanisole (0.68 ml), and m-cresol (0.61 ml) was added. After 30 minutes, the reaction solution was concentrated. After the addition of 1 mol/l hydrochloric acid, the resulting residue was washed with chloroform, and the water layer was concentrated. The obtained residue was dissolved in methanol (1.6 ml). The solution was used for the following reactions 1) and 2).

1) Pyridine-2-aldehyde (3 μl) and triethylamine (13 μl) were added to the above solution (0.8 ml). After 15 hours, sodium borohydride (3.6 mg) was added to the reaction solution. Then, after 10 minutes, a small amount of silica gel was added and the mixture was concentrated. The residue was purified by silica gel column chromatography (0.5 g, chloroform/methanol/water=7/3/0.5). After the addition of 1 mol/l hydrochloric acid, the residue was concentrated and subjected to azeotropic distillation with methanol to obtain hydrochloride of the title compound (10.0 mg) as a white solid.

MS(FAB,Pos.): m/z=582[M+1]$^+$ $^1$H-NMR(500 MHz, DMSO-d$_6$): δ=1.68–1.90(4H,m),3.00(2H,t,J=7.3 Hz),4.28 (2H,s),4.30(2H,s),4.36(2H,s),4.47–4.52(1H,m), 4.77(2H,d, J=4.9 Hz), 7.26(1H,d,J=3.4 Hz),7.43–7.50(4H,m), 7.54–7.60(4H,m),7.8.5–7.92(3H,m), 7.92–7,99(1H,m), 8.03–8.08(1H,m),8.27(1H,s),8.62(1H,d,J=4.9 Hz), 8.69(1H, t,J=5.7 Hz).

2) 5,6,7,8-tetrahydroquinolin-8-onee (21 mg), acetic acid (0.16 ml), and sodium cyanoborohydride (12 mg) were added to the above solution (0.8 ml). After the reaction for 30 hours, the reaction solution was concentrated. The residue was purified by silica gel column chromatography (0.5 g, chloroform/methanol/water=7/3/0.5). 1 mol/l hydrochloric acid was added to the residue. The mixture was concentrated and subjected to azeotropic distillation with methanol to obtain hydrochloride of the title compound (5.4 mg) as a white solid.

MS(FAB,Pos.): m/z=622[M+1]$^+$ $^1$H-NMR(500 MHz, DMSO-d$_6$): δ=1.70–2.03(7H,m),2.28–2.35(1H,m), 2.78–2.83(2H,m),2.88–3.00(1H,m.),4.39–4.46(1H,m),4.51 (2H,s), 4.55(2H,s),4.76(2H,d,J=5.6 Hz),7.37(1H,dd,J=4.8, 7.7 Hz),7.40(1H,d,J=3.4 Hz),7.46(2H,d,J=4.6 Hz), 7.51–7.58(2H,m),7.67(1H,d, J=7.8 Hz),7.73(2H,s),7.85(1H, t,J=4.7 Hz),7.93–7.98(2H,m), 8.04–8.09(1H,m),8.46(1H,t, J=3.2 Hz),8.75(1H,brt),8.85(1H,d, J=8,3 Hz),9.13(2H,brs), 10.05(2H,brs).

EXAMPLE 16

Preparation of (S)-2-(4-(8-quinolylaminomethyl) benzoyl-amino)-5-(2-picolylamino)valeric acid 1-naphthalenemethylamide [Compound No. 17]

Example 16-1

Synthesis of Methyl 4-(8-quinolylaminomethyl) benzoate (Compound VI-7)

8-Aminoquinoline (1.26 g) was dissolved in DMF (20 ml), and potassium carbonate (1.2 g) and methyl 4-bromomethylbenzoate (1.0 g) were added. After stirring for 20 hours, the reaction solution was concentrated. The resulting residue was diluted with chloroform and water was added. The mixture was extracted with chloroform. The organic layer was washed with saturated brine, dried over anhydrous sodium sulfate, and concentrated to obtain the title compound (2.20 g) as a yellow syrup.

Example 16-2

Synthesis of 4-(8-quinolylaminomethyl)benzoic acid (Compound VII-9)

The compound obtained in Example 16-1 (1 g) was dissolved in methanol (10 ml), and 1 mol/l aqueous solution of sodium hydroxide (10 ml) was added. The reaction solution was dissolved in THF (10 ml). After the reaction for 7 hours, the reaction solution was concentrated. The obtained residue was dissolved in water and 1 mol/l hydrochloric acid was gradually added while stirring to obtain a precipitate. The precipitate was collected by filtration through glass filter G4 and washed with water to obtain the title compound (560.1 mg) as a pale yellow solid.

Example 16-3

Synthesis of N$^α$-(4-(8-quinolylaminomethyl) benzoyl)-N$^δ$-Boc-L-ornithine 1-naphthalenemethylamide (Compound XI-8)

The compound obtained in Example 23-1 (228.1 mg) was dissolved in DMF (4.5 ml) and diethylamine (0.45 ml) was added. After 1 the reaction for one hour, the reaction solution was concentrated. The obtained residue was dissolved in DMF (4 ml), and WSCI hydrochloride (110 mg), DMAP (70 mg), and the compound obtained in Example 16-2 (128 mg) were added. After 15 hours, the reaction solution was concentrated and 0.2 N hydrochloric acid was added. The mixture was extracted with chloroform and the organic layer was washed with saturated brine. The organic layer was dried over anhydrous sodium sulfate and concentrated. The residue was purified by silica gel column chromatography (15 g, chloroform/ethyl acetate=4/1) to obtain the title compound (210 mg) as yellow syrup.

MS(FAB,Pos.): m/z=632[M+1]$^+$ $^1$H-NMR(500 MHz, CDCl$_3$): δ=1.27(9H,s),1.45–1.63(2H,m),1.70–1.80(1H,m), 1.89–1.97(1H,m),3.00–3.17(1H,m),3.35–3.42(1H, m),4.62 (2H,d,J=5.6 Hz),4.65–4.70(1H,brt),4.80–4.95(3H,m), 6.55 (1H,d,J=7.8 Hz),6.70(1H,t,J=6.0 Hz),7.08(2H,d,J=8.3 Hz), 7.17(1H,d,J=7.8 Hz),7.23–7.50(8H,m),7.70–7.80 (3H,m), 7.84 (1H, d,J=7.6 Hz),7.97(1H,d,J=8.1 Hz),8.08(1H,dd,J= 8.3 Hz, 1.7 Hz), 8.75(1H,dd,J=4.1 Hz, 1.7 Hz).

Example 16-4

Synthesis of (S)-2-(4-(8-quinolylaminomethyl) benzoylamino)-5-(2-picolylamino)valeric acid 1-naphthalenemethylamide [Compound No. 17]

The compound obtained in Example 16-3 (122.6 mg) was dissolved in methanol (1.2 ml) and 4 mol/l hydrochloric acid/dioxane solution (1.2 ml) was added. After the reaction for 1 hour, the reaction solution was concentrated and dried under reduced pressure. The resulting residue was dissolved in methanol (2 ml), and pyridine-2-aldehyde (18 μl) and triethylamine (27 μl) were added. After 15 hours, the reaction solution was concentrated and dried under reduced pressure. The residue was again dissolved in methanol (2 ml) and sodium borohydride (22 mg) was added. After the reaction for 1 hour, the reaction solution was concentrated. The residue was purified by silica gel column chromatography (4 g, chloroform/methanol/water=7/3/0.5) to obtain the title compound (114.0 mg) as an orange solid.

MS(FAB,Pos.): m/z=623[M+1]$^+$ $^1$H-NMR(500 MHz, DMSO-d$_6$): δ=1.69–1.90(4H,m),2.90–3.00(2H,br) 4.44–4.50 (1H,m),4.63(2H,s),4.74(2H,d,J=5.9 Hz),4.91(2H, s), 6.61(1H,d,J=7.6 Hz),7.13(1H,d,J=7.8 Hz),7.33(1H,t,J= 7.9 Hz), 7.40–7.63(7H,m),7.80–7.97(5H,m),8.00–8.09(2H, m),8.37(1H,d, J=8.1 Hz),8.51–8.62(3H,m),8.79(1H,d,J=4.9 Hz),8.85(1H,dd,J=1.7 Hz, 4.1 Hz),9.28(2H,br).

EXAMPLE 17

Preparation of (2S)-2-(4-((N-(imidazol-2-ylmethyl) aminomethyl)naphthoylamino)-5-(2-picolylamino) valeric acid 2-(3-indolyl)ethylamide [Compound No. 18]

Example 17-1

Synthesis of Methyl 4-methyl-1-naphthalene Carboxylate (Compound III-2)

Commercially available 4-methyl-1-naphthalenecarboxylic acid (250.6 mg) was dissolved in methanol (7.5 ml). Hydrogen chloride gas was blown into the solution for five minutes while cooling with ice. Then, the mixture was stirred for 19 hours at room temperature and the solvent was removed by distillation. The residue was dissolved in chloroform, washed with 1 mol/l aqueous solution of sodium hydroxide, and dried over anhydrous sodium sulfate. The solvent was removed by distillation. The residue was dried under reduced pressure to obtain the target compound (269.9 mg) as colorless oil.

MS(FAB,Pos.): m/z=200[M+], 201[M+1]$^+$ $^1$H-NMR(500 MHz,CDCl$_3$): δ=2.73(3H,s),3.98(3H,s),7.33(1H,d,J=7.3 Hz),7.61(1H,dd,J=8+0.5,6.8 Hz),7.56(1H,dd,J=8.3,6.8 Hz), 8.04(1H,d,J=8.3 Hz),8.08(1H,d,J=7.3 Hz),8.97(1H,d,J=8.5 Hz).

Example 17-2

Synthesis of Methyl 4-bromomethyl-1-naphthalene Carboxylate (Compound IV-5)

The compound obtained in Example 17-1 (269.9 mg) was dissolved in carbontetrachloride (8 ml), and N-bromosuccinimide (252.6 mg) and azobisisobutylonitrile (22.1 mg) were added to the solution. The mixture was stirred for 6 hours at 70° C. After the completion of the reaction, the solid was removed using a glass filter and the filtrate was concentrated. The residue was dissolved in chloroform and washed with 1 mol/l aqueous solution of sodium hydroxide and saturated brine. The solution was dried over anhydrous sodium sulfate. The solvent was removed by distillation and the residue was dried under reduced pressure to obtain the title compound (363.3 mg) as pale yellow oil.

MS(FAB,Pos.): m/z=279, 281[M+1]$^+$ $^1$H-NMR(60 MHz, CDCl$_3$): δ=3.94(3H,s),4.86(3H,s),7.35–7.68(3H,m), 7.88–8.21(2H,m),8.66–8.89(1H,m).

Example 17-3

Synthesis of Methyl 4-aminomethyl-1-naphthalene Carboxylate (Compound XV-1)

The compound obtained in Example 17-2 (328.1 mg) was dissolved in DMF (7.2 ml). After the addition of potassium phthalimide (359.4 mg), the mixture was stirred for 12 hours at room temperature. After the completion of the reaction, the solvent was removed by distillation. The residue was dissolved in chloroform and washed with distilled water, 1 mol/l aqueous solution of sodium hydroxide, and saturated brine, and dried over anhydrous sodium sulfate. The solvent was removed by distillation and the residue was purified by silica gel column chromatography (15 g, hexane/ethyl acetate=2/1) to obtain a white solid (281.2 mg). 1.50 g of the solid was dissolved in methanol (30 ml). Hydrazine monohydrate (7.5 ml) was added and the mixture was heated to 60° C. Methanol (30 ml) was added, followed by stirring for a further one hour at 60° C. After the reaction, the solvent was removed by distillation and the residue was dissolved in chloroform. The solution was washed with distilled water and saturated brine, and dried over anhydrous sodium sulfate. The solvent was removed by distillation and the residue was dried under vacuum to obtain the title compound (789.1 mg) as a pale yellow solid.

MS(FAB,Pos.): m/z=216[M+1]$^+$ $^1$H-NMR(500 MHz, CDCl$_3$): δ=4.00(3H,s),4.39(2H,s),7.55(1H,d,J=7.6 Hz), 7.57–7.65(2H,m),8.11(1H,d,J=8.3 Hz),8.15(1H,d,J=7.3 Hz),8.97(1H,d,J=8.5 Hz).

Example 17-4

Synthesis of 4-(N-Boc-N-(imidazol-2-ylmethyl) aminomethyl)naphthalene Carboxylic acid (Compound VII-10)

The compound obtained in Example 17-3 (120.9 mg) was dissolved in methanol (4.8 ml). After the addition of triethylamine (51.5 µl) and imidazole-2-carboaldehyde (65.0 mg), the mixture was stirred for 8 hour at room temperature. After the reaction, the reaction solution was concentrated. The residue was dried under reduced pressure and dissolved in anhydrous methanol (8 ml). The mixture was coo-led to 0° C. Sodium borohydride (40.7 mg) was added to the solution and the mixture-was stirred for 0.5 hour at room temperature. After the reaction, the reaction solution was concentrated. The residue was dissolved in chloroform, washed with distilled water and saturated brine, and dried over anhydrous sodium sulfate. The solvent was removed by distillation to obtain a crude product (203.0 mg) as a pale yellow oil. The oil was dissolved in DMF (4 ml). After the addition of triethylamine (94.8 µl) and di-t-butyldicarbonate (142 µl), the mixture was stirred for 15 hours at room temperature.

After the reaction, the reaction solution was concentrated and dried under reduced pressure to obtain a crude product (314.5 mg) as a yellow viscous oil. The yellow viscous oil (314.5 mg) was dissolved in THF (3 ml) and methanol (3 ml). After the addition of 0.1 mol/l aqueous solution of sodium hydroxide (3 ml), the mixture was stirred for 2 hours at room temperature. After the reaction, the solvent was removed by distillation and the residue was neutralized with 1 mol/l aqueous solution of hydrochloric acid. Water was added and the mixture was extracted with chloroform to obtain the title compound (59.9 mg) as colorless oil.

MS(FAB,Pos.): m/z=382[M+1]$^+$ $^1$H-NMR(500 MHz, DMSO-d$_6$+D$_2$O): δ=1.39(9H,s),4.26 and 4.36(2H,2s), 4.92 and 4.95(2H,2s),6.80–7.28(3H,m),7.48–7.52(2H,m),7.58 (1H,d,J=7.3 Hz),8.02(1H,br),8.70(1H,br).

Example 17-5

Synthesis of N$^α$-Fmoc-N$^δ$-Cbz-L-ornithine 2-(3-indolyl)ethylamide (Compound IX-2)

Commercially available N$^α$-Fmoc-N$^δ$-Cbz-L-ornithine (528.0 mg) was dissolved in DMF (10.6 ml), and HOBt (235 mg), WSCI hydrochloride (334 mg), and tryptamine (0.165 ml) were added to the solution. The mixture was stirred for 16 hours at room temperature. After the reaction, the solvent was removed by distillation. The residue was dissolved in chloroform and extracted with 1 mol/l aqueous solution of hydrochloric acid. The organic layer was washed with a saturated aqueous solution of sodium bicarbonate. The solvent was removed by distillation and the residue was purified by silica gel column chromatography (50 g, chloroform/ethyl acetate=1/1) to obtain the title compound (690 mg) as a white solid.

MS(FAB,Pos.): m/z=597[M+1]$^+$ $^1$H-NMR(500 MHz, CDCl$_3$): δ=1.63(9H,s),1.64–1.78(1H,m),2.90–3.04 (3H,m), 3.20–3.28(1H,m),3.48–3.62(3H,m),4.10–4.22(2H,m), 4.28–4.40(2H,m),4.58–4.62(1H,m),5.58–5.62(1H,m). 6.28–6.38(1H,m),7.00(1H, s),7.10(1H,t,J=7.3 Hz),7.17(1H, t,J=7.3 Hz), 7.28–7.38(3H,m),7.40(2H,t,J=7.4 Hz), 7.50–7.62(3H,m),7.77 (2H,d,J=7.5 Hz),8.12–8.20(1H,m).

Example 17-6

Synthesis of N$^α$-(4-(N-Boc-N-imidazol-2-ylmethyl) aminomethylnaphthoyl)-N$^δ$-Boc-L-ornithine 2-(3-indolyl)ethylamide (Compound XI-9)

The compound obtained in Example 17-5 (453.2 mg) was dissolved in DMF (9.1 ml). After the addition of diethylamine (0.91 ml), the mixture was stirred for 1 hour at room temperature. After the reaction, the solvent was removed by distillation under reduced pressure and the residue was dried under vacuum. The compound obtained in Example 17-4 (289.7 mg) and HOBt (153.9 mg) were added to the product. The mixture was dissolved in DMF (5.8 ml) and WSCI hydrochloride (218.4 mg) were added. The mixture was stirred for 19 hours.

The solvent was removed by distillation. 1 mol/l aqueous solution of hydrochloric acid was added to the residue and the mixture was extracted with chloroform. The organic layer was washed with saturated aqueous solution of sodium bicarbonate and dried over anhydrous sodium sulfate. Then, the solvent was removed by distillation.

The residue was purified by silica gel column chromatography (60 g, chloroform/methanol=15/1) to obtain the title compound (233.5 mg) as a pale yellow solid.

MS(FAB,Pos.): m/z=738[M+1]$^+$ $^1$H-NMR(500 MHz, CDCl$_3$): δ=1.63(9H,s),1.90–1.98(1H,m),2.92–3.10 (3H,m), 3.22–3.38(1H,m),3.60–3.72(2H,m),4.22–4.35(2H,m), 4.62–4.84 (2H,m),5.00–5.10 (1H,m),6.48–6.60(1H,m), 6.76–6.82(1H,m),6.84–7.60(13H,m,J=7.3 Hz),7.92–8.04 (1H,m),8.12–8.18(1H,m).

Example 17-7

Synthesis of N$^α$-4-((imidazol-2-ylmethyl) aminomethyl)naphthoyl-L-ornithine 2-(3-indolyl) ethylamide (Compound XIV-2)

The compound obtained in Example 17-6 (233.5 mg) was dissolved in methanol (4.67 ml) and 4 mol/l hydrochloric acid/dioxane solution (4.67 ml) was added. The mixture was stirred for 1 hour at room temperature. After the reaction, the solvent was removed by distillation and the residue was dried under reduced pressure to obtain the title compound (216 mg) as a white solid.

Example 17-8

Synthesis of (2S)-2-(4-((N-imidazol-2-ylmethyl) aminomethyl)naphthoylamino)-5-(2-picolylamino) valeric acid 2-(3-indolyl)ethylamide [Compound No. 18]

The compound obtained in Example 17-7 (107 mg) was dissolved in anhydrous methanol (2.55 ml). After the addition of pyridine-2-aldehyde (20.3 mg) and triethylamine (66.2 µl), the mixture was stirred for 14.5 hours at room temperature. After the reaction, the solvent was removed by distillation. The residue was dried under reduced pressure and dissolved in anhydrous methanol (2.55 ml), followed by the addition of sodium borohydride (12.0 mg). After stirring for one hour, the solvent was removed by distillation. The residue was purified by silica gel column chromatography (15 g, chloroform/methanol/water=7/3/0.5). After the addition of 1 mol/l hydrochloric acid to the resulting compound, the mixture was concentrated to dryness-to obtain hydrochloride of the title compound (65.6 mg) as a light brown solid.

MS(FAB,Pos.): m/z=629[M+1]$^+$ $^1$H-NMR(500 MHz, DMSO-d$_6$): δ=1.65–1.90(4H,m),2.88(2H,t,J=7.32), 2.90–3.04 (3H,m),3.36–3.44(2H,m),4.22–4.36(2H,m), 4.64–4.78 (2H,m),4.82–4.96(2H,m),6.98(1H,t,J=7.4 Hz), 7.06(1H,t,J=7.4 Hz),7.20(1H,s),7.34(1H,d,J=8.1 Hz), 7.40–7.44(1H,m),7.56 (2H,t,J=8.3 Hz),7.60–7.80(5H,m), 7.84(1H,d,J=7.3 Hz),7.91(1H, t,J=7.3 Hz),8.24–8.36(3H, m),8.64(1H,d,J=3.9 Hz),8.77(1H,d,J=7.8 Hz),9.20–9.42 (2H,m).

EXAMPLE 18

Preparation of (2S)-2-(4-((N-imidazol-2-ylmethyl) aminomethyl)naphthoylamino)-5-(5,6,7,8-tetrahydroquinolin-8-ylamino)valeric acid 2-(3-indolyl)ethylamide [Compound No. 19]

The compound obtained in Example 17-7 (107 mg) was dissolved in anhydrous methanol (2.55 ml). After the addition of triethylamine (66.2 µl), 5,6,7,8-tetrahydroquinolin-8-onee (28.0 mg) and sodium cyanoborohydride (19.9 mg) were added. Acetic acid was added to adjust the pH of the mixture to 4 and the mixture was stirred for 15 hours at room temperature. After the reaction, the solvent was removed by distillation. The residue was purified by silica gel column chromatography (5 g, chloroform/methanol/water=7/3/0.5). After the addition of 1 mol/l hydrochloric acid, the residue was concentrated to dryness to obtain the title compound (82.4 mg) as a white solid.

MS(FAB,Pos.): m/z=669[M+1]$^+$ $^1$H-NMR(500 MHz, DMSO-d$_6$): δ=1.65–1.96(4H,m),2.78–2.92(4H,m), 3.36–3.50(2H,m),4.42–4.58(2H,m),4.64–4.78(2H,m), 4.84–4.96 (2H,m),6.98(1H, t,J=7.1 Hz),7.06(1H,t,J=6.1 Hz),7.20(1H,s), 7.34–7.42(2H,m), 7.56(2H,t,J=7.8 Hz), 7.62–7.78(4H,m),7.85(1H,d,J=7.3 Hz),8.24–8.36(3H,m), 8.49(1H,d,J=3.4 Hz),8.77(1H, d,J=7.8 Hz),9.05–9.24(2H, m).

EXAMPLE 19

Preparation of (S)-2-(4-((imidazol-4-ylmethyl) aminomethyl)benzoylamino)-5-((imidazol-4-ylmethyl)amino)valeric acid 1-naphthalenemethylamide [Compound No. 20]

Example 19-1

Synthesis of 4-N-Boc-aminomethylbenzoic Acid (XVII-1)

Commercially available 4-aminomethylbenzoic acid (20.85 g) was dissolved in dioxane (100 ml) After the addition of 1 mol/l sodium hydroxide (100 ml), the mixture was cooled to 0° C. A solution of di-t-butyl dicarbonate (30.71 g) in dioxane (100 ml) was added dropwise to the solution over 30 minutes. The mixture was allowed to become room temperature and stirred for 16 hours, followed by removal of the solvent by distillation under reduced pressure. The residue was dissolved in 0.5 N aqueous solution of sodium hydroxide (276 ml). Then, 1 mol/l aqueous solution of hydrochloric acid was added to obtain a precipitate. The precipitate was dried to obtain the title compound (31.32 g) as a white solid.

MS(FAB,Pos.): m/z=252[M+1]$^+$ $^1$H-NMR(500 MHz, DMSO-d$_6$): δ=1.48(9H,s),4.40(2H,brs),4.96(1H, brs),7.38 (2H,d, J=8.5 Hz),8.07(2H,d,J=8.5 Hz).

Example 19-2

Synthesis of N$^α$-4-(N-Boc-aminomethyl)benzoyl-N$^δ$-Boc-L-ornithine 1-naphthalenemethylamide (Compound XVIII-1)

Commercially available N$^α$-Fmoc-N$^δ$-Boc-ornithine (501.7 mg) was dissolved in DMF (6.0 ml), and WSCI hydrochloride (328.0 mg) and HOBt (166.4 mg) were added to the solution. After the addition of 1-naphthalenemethylamine (195 ml), the mixture was stirred for 20 hours at room temperature. After the reaction, the solvent was removed by distillation. The residue was dissolved in chloroform and washed with 1 mol/l aqueous solution of hydrochloric acid and saturated brine. The organic layer was dried over anhydrous sodium sulfate. The solvent was removed by distillation to obtain a crude product. (631.7 mg) as white foam. 499.9 mg of the crude product was dissolved in DMF (10 ml) and diethylamine (1.0 ml) was added. The mixture was stirred for 180 minutes at room temperature. After the reaction, the solvent was removed by distillation and the residue was dried using a vacuum pump. The product (509.2 mg) was dissolved in DMF (10 ml). WSCI hydrochloride (241.9 mg), HOBt (113.8 mg), and the compound obtained in Example 19-1 (253.9 mg) were added to the solution. The mixture was stirred for 13.5 hours at room temperature. After the reaction, the solvent was removed by distillation. The residue was dissolved in chloroform and washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (25 g, chloroform/methanol=25/1) to obtain the title compound (310.8 mg) as a white solid.

MS(FAB,Pos.): m/z=605[M+1]$^+$ $^1$H-NMR(500 MHz, DMSO-d$_6$): δ=1.36(9H,s),1.39(9H,s),1.35–1.45(2H, m),1.60–1.80(2H,m),2.91(2H,m),4.17(2H,d,J=7.7 Hz),4.48 (1H,m), 4.75(2H,d,J=5.9 Hz), 6.80(1H,t,J=5.6 Hz),7.31(2H, d,J=8.3 Hz), 7.4–7.45(3H,m),7.5–7.6(2H,m),7.8–7.9(3H, m),7.95(1H,m),8.06(1H,m),8.45(1H,d,J=5.9 Hz), 8.51(1H, d,J=5.4 Hz).

Example 19-3

Synthesis of N$^α$-(4-aminomethylbenzoyl)-L-ornithine 1-naphthalenemethylamide (Compound XIX-1)

The compound obtained in Example 19-2 (106.2 mg) was dissolved in methanol (1.0 ml) and 4 mol/l hydrochloric acid/dioxane solution (2.0 ml) was added. The mixture was stirred for 20 hours at room temperature. After the reaction, the solvent was removed by distillation and the residue was dried using a vacuum pump to obtain the title compound (98.1 mg) as a white solid.

MS(FAB,Pos.): m/z=405[M+1]$^+$

Example 19-4

Synthesis of (S)-2(4-((imidazol-4-ylmethyl) aminomethyl)benzoylamino)-5-((imidazol-4-ylmethyl)amino)valeric acid 1-naphthalenemethylamide [Compound No. 20]

The compound obtained in Example 19-3 (77.2 mg) was dissolved in anhydrous methanol (1.5 ml). After the addition of triethylamine (54.1 μl) and 1-methyl-2-imidazole carboxyaldehyde (32.7 mg), the mixture was stirred for 2.5 hours at room temperature. After the reaction, the solvent was removed by distillation and anhydrous methanol (1.5 ml) was added to the residue. Then, the mixture was cooled to 0° C. Sodium borohydride (18.4 mg) was added to the solution and the mixture was stirred for 1 hour, while allowing gradually to become room temperature. After the reaction, the solvent was removed by distillation. The residue was purified by silica gel column chromatography (6 g, chloroform/methanol/water=7/3/0.5). The compound was dissolved in 1 mol/l hydrochloric acid (2 ml) and water was removed by distillation to obtain hydrochloride of the title compound (96.0 mg) as a white solid.

MS(FAB,Pos.): m/z=[M+1]$^+$ $^1$H-NMR(500 MHz,DMSO-d$_6$): δ=1.47–1.94(4H,m),2.78–3.00(2H,m), 4.26(4H,s),4.32 (2H,s),4.51–4.60(1H,m),4.77(2H,d,J=5.9 Hz), 7.44–7.49 (2H,m),7.52–7.60(2H,m),7.69(2H,d,J=8.3 Hz),7.80(1H, s),7.81–7.85(1H,m),7.85(1H,s),7.93–7.95(1H,m),8.00(2H, d,J=8.3 Hz),8.05(1H,m),8.70(1H,d,J=8.1 Hz),8.74(1H,t,J= 5.9 Hz),9.09(1H,s),9.11(1H,s),9.77(2H,br),10.34(1H,br).

EXAMPLE 20

Preparation of (S)-2(4-((imidazol-2-ylmethyl) aminomethyl)benzoylamino)-5-((imidazol-2-ylmethyl)amino)valeric acid 1-naphthalenemethylamide [Compound No. 21]

The compound obtained in Example 19-3 (16.8 mg) was dissolved in methanol (0.6 ml). After the addition of triethylamine (7.1 mg) and 2-imidazole carboxyaldehyde (7.1 mg), the mixture was stirred for 2 hours at room temperature. After the solvent was removed by distillatio, anhydrous methanol (0.6 ml) was added and the mixture was cooled to 0° C. Sodium borohydride (8.0 mg) was added to the solution and the mixture was stirred for 30 minutes, while allowing gradually to become room temperature. After the reaction, the solvent was removed by distillation. The residue was purified by silica gel column chromatography (0.8 g, chloroform/methanol/water=7/3/0.5). The obtained product was dissolved in 1 mol/l aqueous solution of hydrochloric acid and water was removed by distillation to obtain hydrochloride of the title compound (15.9 mg) as a white solid.

MS(FAB,Pos): m/z=595[M+1]$^+$ $^1$H-NMR(500 Mz,DMSO-d$_6$): δ=1.71–1.90(4H,m),3.05–3.17(2H,m), 4.34 (2H,m),4.43(2H,m),4.55(1H,m),4.77(2H,d,J=2.2 Hz),7.47 (2H, m),7.56(2H,m),7.64(6H,m),7.86(1H,m),7.96(1H,m), 7.98(1H,m), 8.06(1H,m),8.70(2H,m),9.94(1H,brs).

EXAMPLE 21

Preparation of (S)-2(4-((1-methylpyrrol-2-ylmethyl) aminomethyl)benzoylamino)-5-((1-methylpyrrol-2-ylmethyl)amino)valeric acid 1-naphthalenemethylamide [Compound No. 22]

The compound obtained in Example 19-2 (100 mg) was dissolved in methanol (2 ml) and 4 mol/l hydrochloric acid/dioxane (2 ml) was added. The mixture was stirred for 2 hours at room temperature. After the reaction, the solvent was removed by distillation. The residue was dissolved in anhydrous methanol (2 ml). After the addition of triethylamine (55.3 μl) and 1-methyl-2-pyrrole carboxyaldehyde (41.8 μl), the mixture was stirred for 4 hours at room temperature. After the reaction, the solvent was removed by distillation and anhydrous methanol (2 ml) was added to the residue. Then, the mixture was cooled to 0° C. Sodium borohydride (18.8 mg) was added to the solution and the mixture was stirred for 12 hours, while allowing gradually to become room temperature.

After the reaction, the solvent was removed by distillation. The residue was purified by silica gel column chromatography (10 g, chloroform/methanol=10/1).

The compound was dissolved in 1 mol/l aqueous solution of hydrochloric acid (2 ml) and water was removed by distillation to obtain hydrochloride of the title compound (83.7 mg) as a white solid.

MS(FAB,Pos.): m/z=591[M+1]$^+$ $^1$H-NMR(500 MHz, DMSO-d$_6$): δ=1.70–1.91(4H,m),2.93(2H,br),3.63 (6H,2s), 4.10–4.22(6H,m),4.53–4.57(1H,m),4.76–4.77(2H,m), 5.98–6.02(2H,m),6.21–6.27(2H,m),6.79–6.82(2H,m), 7.45–7.56 (4H,m),7.64(2H,d,J=7.8 Hz),7.84–7.86(1H,m), 7.94–7.99(3H,m), 8.05–8.08(1H,m),8.67–8.70(2H,m),8.82 (1H,br),9.42(1H,br).

EXAMPLE 22

Preparation of (S)-2(4-((1-methylimidazol-2-ylmethyl)aminomethyl)benzoylamino)-5-((1-methylimidazol-2-ylmethyl)amino)valeric acid 1-naphthalenemethylamide [Compound No. 23]

The compound obtained in Example 19-2 (100 mg) was dissolved in methanol (2 ml) and 4 mol/l hydrochloric acid/dioxane (2 ml) was added. The mixture was stirred for 3 hours at room temperature. After the reaction, the solvent was removed by distillation. The residue was dissolved in anhydrous methanol (2 ml). After the addition of triethylamine (55.3 μl) and 1-methyl-2-imidazole carboxyaldehyde (38.2 mg), the mixture was stirred for 3 hours at room temperature. After the reaction, the solvent was removed by distillation and anhydrous methanol (2 ml) was added to the residue. Then, the mixture was cooled to 0° C. Sodium borohydride (18.8 mg) was added to the solution and the mixture was stirred for 25 hours, while allowing gradually to become room temperature. After the reaction, the solvent was removed by distillation. The residue was purified by silica gel column chromatography (10 g, chloroform/methanol=4/1). The compound was dissolved in 1 mol/l aqueous solution of hydrochloric acid (2 ml) and water was removed by distillation to obtain hydrochloride of the title compound (89.2 mg) as a white solid.

MS(FAB,Pos.): m/z=593[M+1]$^+$ $^1$H-NMR(500 MHz, DMSO-d$_6$): δ=1.77–1.91(4H,m), 3.04–3.09(3H,m), 3.95 (3H,s),3.96(3H,s),4.40(2H,br),4.52(2H,br),4.55–4.58(3H, m),4.76–4.77(2H,m),7.45–7.50(2H,m),7.52–7.57(2H,m), 7.71–7.75 (6H, m),7.84–7.86 (1H,m),7.93–7.96(1H,m), 8.00–8.04(2H, m), 8.06–8.08(1H,m), 8.72–8.75(2H,m), 10.07(1H,br).

EXAMPLE 23

Preparation of (S)-2-(4-(N-2-picolylamino) butyrylamino)-5-(2-picolylamino)valeric acid 1-naphthalenemethylamide [Compound No. 24]

Example 23-1

Synthesis of N$^\alpha$-Fmoc-N$^\delta$-Boc-L-ornithine 1-naphthalenemethylamide (Compound IX-3)

Commercially available N$^\alpha$-Fmoc-N$^\delta$-Boc-L-ornithine (501.7 mg) was dissolved in DMF (10 ml), and HOBt (166.4 mg), WSCI hydrochloride (328.0 mg), and 1-naphthalenemethylamine (0.195 ml) were added to the solution. The mixture was stirred for 12 hours at room temperature. After the reaction, the solvent was removed by distillation. The residue was dissolved in chloroform and the solution was extracted with 1 mol/l aqueous solution of hydrochloric acid. The organic layer was washed with a saturated aqueous solution of sodium hydrogencarbonate. The solvent was removed by distillation to obtain the title compound (631.7 mg) as a white solid.

MS(FAB,Pos.): m/z=594[M+1]$^+$

Example 23-2

Synthesis of N$^\delta$-Boc-L-ornithine 1-naphthalenemethylamide (Compound X-2)

The compound obtained in Example 23-1 (250.8 mg) was dissolved in DMF (5 ml). After the addition of diethylamine. (0.5 ml), the mixture was stirred for 2 hours at room temperature. After the reaction, the solvent was removed by distillation under reduced pressure and the residue was dried under vacuum to obtain the title compound (269.1 mg).

MS(FAB,Pos.): m/z=372[M+1]$^+$

Example 23-3

Synthesis of N$^\alpha$-(4-N-Boc-aminobutyryl)-N$^\delta$-Boc-L-ornithine 1-naphthalenemethylamide (Compound XVIII-2)

The compound obtained in Example 23-2 (216.2 mg) was dissolved in DMF (4 ml). After the addition of WSCI hydrochloride (102.0 mg), HOBt (50.2 mg), and commercially available 4-N-Boc-aminovaleric acid (76.5 mg), the mixture was stirred for 16 hours at room temperature. After the reaction, the solvent was removed by distillation. The residue was dissolved in chloroform and washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (10 g, chloroform/methanol=30/1) to obtain the title compound (148.9 mg) as a white solid.

MS(FAB,Pos.): m/z=557[M+1]$^+$ $^1$H-NMR(500 MHz, DMSO-d$_6$): δ=1.36(9H,s),1.37(9H,s),1.41–1.57(1H, m), 1.58–1.70(3H,m),2.13(2H,t,J=7.4 Hz),2.84–2.97(2H,m), 4.27(1H,m),4.73(2H,d,J=4.4 Hz),6.77(1H,d,J=5.7 Hz),6.81 (1H,t,J=5.7 Hz),7.41–7.49(2H,m),7.53–7.58(2H,m),7.845 (1H,d,J=8.1 Hz), 7.92–7.97(1H,m),8.01–8.05(2H,m),8.47 (1H,d,J=5.7 Hz).

Example 23-4

Synthesis of (S)-2-(4-(N-2-picolylamino) butyrylamino)-5-(2-picolylamino)valeric acid 1-naphthalenemethylamide [Compound No. 24]

The compound obtained in Example 23-3 (102.7 mg) was dissolved in methanol (1.0 ml), and 4 mol/l hydrochloric acid/dioxane solution (1.0 ml) was added. The mixture was stirred for 2 hours at room temperature. After the reaction, the solvent was removed by distillation and the residue was dried using a vacuum pump. 50.7 mg of the product (50.7 mg) was dissolved in methanol (1.0 ml). After the addition of triethylamine (39.1 μl) and 2-picolylamine (23.1 μl), the mixture was stirred for 2 hours at room temperature. After the reaction, the solvent was removed by distillation. After the addition of anhydrous methanol (1.0 ml), the residue was cooled to 0° C. and sodium borohydride (35.3 mg) was added. The mixture was stirred for one hour. After the reaction, the solvent was removed by distillation. The residue was purified by silica gel column chromatography (4 g, chloroform/methanol/water=7/3/0.5). The compound was dissolved in 1 mol/l aqueous solution of hydrochloric acid and water was removed by distillation to obtain hydrochloride of the title compound (44.2 mg) as a white solid.

MS(FAB,Pos.): m/z=539[M+1]$^+$ $^1$H-NMR(500 MHz, DMSO-$d_6$): δ=1.57–1.62(1H,m) 1.62–1.71(3H,m) 1.85–2.00(2H,m),2.90–3.05(2H,m),4.30(2H,s),4.29–4.35 (1H,m), 4.34(2H,s),4.73(2H,d,J=5.6 Hz),7.40–7.60(6H,m), 7.67(2H,dd, J=10.9, 7.8 Hz),7.84(1H,d, 7.8 Hz),7.90–8.01 (3H,m),8.05(1H,d,J=7.3 Hz),8.31(1H,d,J=8.1 Hz), 8.63–8.75(3H,m),9.40–9.68(4H,br).

EXAMPLE 24

Preparation of (2S)-2-(trans-(4-(5,6,7,8-tetrahydroquinolin-8-yl)aminomethyl) cyclohexylcarbonyl)amino-5-(5,6,7,8-tetrahydroquinolin-8-ylamino)valeric acid 1-naphthalenemethylamide [Compound No. 25]

Example 24-1

Synthesis of N-Boc-tranexamic acid (Compound XVII-2)

Tranexamic acid (3.14 g) was dissolved in dioxane (63 ml). After the addition of di-t-butyl-di-carbonate (4.59 ml) and 1 mol/l aqueous solution of sodium hydroxide (20 ml), the mixture was stirred for 3.5 hours at room temperature. After the reaction, the solvent was removed by distillation. The residue was dissolved in 1 mol/l aqueous solution of sodium hydroxide (20 ml) and distilled water (10 ml). 1 mol/l aqueous solution of hydrochloric acid was added to produce crystals. The crystals were collected by filtration, dissolved in chloroform, washed with saturated brine, and dried over anhydrous sodium sulfate. The solvent was removed by distillation to obtain the target compound (4.88 g) as a white solid.

MS(FAB,Pos.): m/z=258[M+1]$^+$ $^1$H-NMR(500 MHz, DMSO-$d_6$): δ=0.95(2H,qd,J=12.8, 3.0 Hz),1.20–1.58 (12H, m),1.83(2H,d,J=11.5 Hz),2.04(2H,dd,J=13.9., 3.0 Hz),2.25 (1H, tt,J=12.2, 3.0 Hz),2.99(2H,t,J=6.3 Hz),4.66(1H,brs).

Example 24-2

Synthesis of N$^α$-(4-trans-(N-Boc-aminomethylcyclohexyl)carbonyl)-N$^δ$-Boc-L-ornithine 1-naphthalenemethylamide (Compound XVIII-3)

The compound obtained in Example 23-2 (328.2 mg) was dissolved in DMF (6 ml). After the addition of WSCI hydrochloride (146.3 mg), HOBt (75.4 mg), and the compound obtained in Example 24-1 (156.3 mg), the mixture was stirred for 5.5 hours at room temperature. After the reaction, the solvent was removed by distillation. The residue was dissolved in chloroform and washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (25 g, chloroform/methanol=25/1) to obtain the title compound (213.0 mg) as a white solid.

MS(FAB,Pos.): m/z=611[M+1]$^+$ $^1$H-NMR(500 MHz, DMSO-$d_6$): δ=0.76–0.90(2H,m),1.20–1.40(4H,m), 1.36 (9H,s),137(9H,s),1.40–1.55(1H,m),1.58–1.77(6H,m),2.13 (1H,t,J=11.9 Hz),2.75(2H,dd,J=12.5, 6.3 Hz),2.81–2.93(2H, m), 4.25(1H,dd,J=14.0,8.5 Hz),4.72(2H,d,J=5.6 Hz), 6.77–6.83(2H,m), 7.41(1H,d,J=6.6 Hz),7.45(t,J=7.5 Hz), 7.52–7.57(2H,m),7.83–7.87(2H,m),7.92–7.96(1H,m), 8.01–8.04(1H,m),8.38(1H,t,J=5.6 Hz).

Example 24-3

Synthesis of (2S)-2-(trans-(4-(5,6,7,8-tetrahydroquinolin-8-yl)aminomethyl) cyclohexylcarbonyl)amino-5-(5,6,7,8-tetrahydroquinolin-8-ylamino)valeric acid 1-naphthalenemethylamide [Compound No. 25]

The compound obtained in Example 24-2 (108.3 mg) was dissolved in methanol (1.0 ml) and 4 mol/l hydrochloric acid/dioxane solution (1.0 ml) was added. The mixture was stirred for 90 minutes at room temperature. After the reaction, the solvent was removed by distillation and the residue was dried using a vacuum pump to obtain a crude product (111.5 mg) as a white solid. 39.1 mg of the crude product was dissolved in methanol (0.8 ml). Triethylamine (3 drops) was added to adjust the pH to 7–8. Then, 5,6,7, 8-tetrahydroquinolin-8-one (72.4 mg) was added. Sodium cyanoborohydride (41.6 mg) and acetic acid (30 drops) were added to the solution. The mixture was stirred for 22 hours at room temperature. After the reaction, the solvent was removed by distillation. The residue was purified by silica gel column chromatography (2 g, chloroform/methanol/water=7/3/0.5). The compound was dissolved in 1 mol/l aqueous solution of hydrochloric acid and water was removed by distillation to obtain hydrochloride of the title compound (23.3 mg) as a white solid.

MS(FAB,Pos.): m/z=673[M+1]$^+$ $^1$H-NMR(500 MHz, DMSO-$d_6$): δ=0.90–1.07(2H,m),1.23–1.42(2H,m), 1.55–1.95(14H,m),1.97–2.08(2H,m),2.20(1H,d,J=11.8 Hz), 2.27–2.36(2H,m), 2.65–2.72(2H,m),2.75–2.85(4H,m), 2.87–3.00(1H, m),3.01–3.11(1H,m),4.28–4.35(1H,m), 4.37–4.42(1H,m),4.42–4.52(1H,m),4.73(1H,dd,J=15.8,5.6 Hz),4.75(1H,dd,J=15.8,5.6 Hz), 7.36–7.45(3H,m),7.46(1H, d,J=7.1 Hz),7.53–7.56(2H,m),7.68 (2H,d,J=7.8 Hz),7.85 (1H,d,J=7.8 Hz),7.94–7.96 (1H,m), 8.03–8.06(1H,m),8.49 (1H,d,J=3.9 Hz),8.45–8.60(2H,brs),8.96(2H, brs),9.04(2H, brs).

EXAMPLE 25

Preparation of (2S)-2-(4-(5,6,7,8-tetrahydroquinolin-8-ylaminomethyl)naphthoyl) amino-5-(5,6,7,8-tetrahydroquinolin-8-ylamino) valeric acid 1-naphthalenemethylamide [Compound No. 26]

Example 25-1

Synthesis of methyl 4-Boc-aminomethyl-1-naphthalene carboxylate (Compound XVI-1)

The compound obtained in Example 17-3 (209.9 mg) was dissolved in DMF (4 ml). After the addition of di-t-butyldicarbonate (322 µl) and triethylamine (262 µl), the mixture was stirred for 18 hours at room temperature. After the reaction, the solvent was removed by distillation. The residue was purified by silica gel column chromatography (6 g, chloroform) to obtain the title compound (288.9 mg) as pale yellow oil.

MS(FAB,Pos.): m/z=316[M+1]$^+$ $^1$H-NMR(500 MHz, CDCl$_3$): δ=1.47(9H,s),4.00(3H,s),4.82(2H,d,J=5.6 Hz),4.89 (1H,brs),7.48(1H,d,J=7.6 Hz),7.58–7.66(2H,m),8.09(1H,d, J=8.3 Hz), 8.11(1H,d,J=7.6 Hz),8.94(1H,d,J=8.1 Hz).

Example 25-2

Synthesis of 4-Boc-aminomethyl-1-naphthalene carboxylic acid (Compound XVII-3)

The compound obtained in Example 25-1 (266.6 mg) was dissolved in THF (2.7 ml) and methanol (2.7 ml). After the addition of 1 mol/l aqueous solution of sodium hydroxide (2.7 ml), the mixture was stirred for 5 hours at room temperature. After the reaction, the solvent was removed by distillation. The residue was dissolved in distilled water and 1 mol/l aqueous solution of hydrochloric acid was added to produce a precipitate. The precipitate was collected by filtration and dried to obtain the title compound (233.5 mg) as a white solid.

MS(FAB,Pos.): m/z=302[M+1]$^+$ $^1$H-NMR(500 MHz, CDCl$_3$): δ=1.41(9H,s),4.64(2H,d,J=5.8 Hz),4.89(1H,brs), 7.46(1H,d,J=7.5 Hz),7.57(1H,t,J=5.8 Hz),7.58–7.68(2H, m),8.10(1H,d,J=7.5 Hz),8.19(1H,d,J=8.2 Hz),8.90(1H,d,J= 7.5 Hz).

Example 25-3

Synthesis of N$^α$-4-(N-Boc-aminomethyl)naphthoyl-N$^δ$-Boc-ornithine 1-naphthalenemethylamide (Compound XVIII-4)

The compound obtained in Example 23-2 (170.3 mg) was dissolved in DMF (3 ml). After the addition of WSCI hydrochloride (73.6 mg), HOBt (42.9 mg), and the compound obtained in Example 25-2 (78.6 mg), the mixture was stirred for 14 hours at room temperature. After the reaction, the solvent was removed by distillation. The residue was dissolved in chloroform, washed with 1 mol/l hydrochloric acid, 1 mol/l aqueous solution of sodium hydroxide, and saturated brine, and dried over anhydrous sodium sulfate. After the solvent was removed by distillation, the residue was purified by silica gel column chromatography (10 g, chloroform/methanol=30/1) to obtain the title compound (84.0 mg) as a white solid.

MS(FAB,Pos.): m/z=655[M+1]$^+$

Example 25-4

Synthesis of (2S)-2-(4-(5,6,7,8-tetrahydroquinolin-8-ylaminomethyl)naphthoylamino)-5-(5,6,7,8-tetrahydroquinolin-8-ylamino)valeric acid 1-naphthalenemethylamide [Compound No. 26]

The compound obtained in Example 25-3 (50.4 mg) was dissolved in methanol (0.5 ml) and 4 mol/l hydrochloric acid/dioxane solution (0.5 ml) was added. The mixture was stirred for 2 hours at room temperature. After the reaction, the reaction solution was concentrated and dried under reduced pressure. 50.5 mg of the compound was dissolved in methanol (1 ml). Triethylamine (26.9 µl), 5,6,7,8-tetrahydroquinolin-8-one (28.3 mg), and sodium cyanoborohydride (15.0 mg) were added. 10 drops of acetic acid was added to adjust the pH of the mixture to about 4–5. Then, the mixture was stirred for 19 hours at room temperature. After the reaction, the reaction mixture was concentrated. The residue was purified by silica gel column chromatography (3.5 g, chloroform/methanol=10/1.5) and treated with 1 mol/l aqueous solution of hydrochloric acid to obtain hydrochloride of the title compound (52.8 mg) as a pale yellow solid.

MS(FAB,Pos.): m/z=717[M+1]$^+$ $^1$H-NMR(500 MHz, DMSO-d$_6$): δ=1.75–2.11(10H,m),2.13–2.21(1H,m), 2.31–2.40 (1H,m),2.79–2.84(2H,m),2.85–2.91(2H,m), 2.95–3.03 (1H,m),3.04–3.20(1H,m),4.41–4.48(1H,m), 4.58–4.71(3H,m), 4.79–4.89(2H,m),4.95–5.05(1H,m),7.39 (1H,dd,J=7.8, 4.8 Hz), 7.43–7.47(1H,m), 7.49(1H,d,J=8.1 Hz),7.53–7.59(3H,m),7.60–7.64(1h,m),7.69(1H,d,J=8.1 Hz), 7.69–7.75(3H,m),7.87(2H,t,J=7.1 Hz),7.95–7.99(1H, m),8.10–8.13(1H,m),8.29(1H,d,J=8.5 Hz), 8.37(1H,d,J=6.8 Hz),8.48(1H,d,J=3.7 Hz),8.61(1H,d,J=3.9 Hz),8.78(1H,t,J= 5.6 Hz),8.87(1H,d,J=8.1 Hz),9.26(2H,br),9.74(2H,br).

EXAMPLE 26

Preparation of (S)-2-(4-(N-2-picolylaminomethyl) naphthoylamino)-5-(2-picolylamino)valeric acid 1-naphthalenemethylamide [Compound No. 27]

The compound obtained in Example 25-3 (26.9 mg) was dissolved in methanol (0.56 ml) and 4 mol/l hydrochloric acid/dioxane solution (0.56 ml) was added. The mixture was stirred for 2 hours at room temperature. After the reaction, the reaction solution was concentrated and dried under reduced pressure. 50.5 mg of the product was dissolved in methanol (0.56 ml). After the addition of triethylamine (13.9 µl) and 2-pyridine aldehyde (8.2 mg), the mixture was stirred for 19 hours at room temperature. After the reaction, the reaction solution was concentrated. The residue was dried under reduced pressure and dissolved in anhydrous methanol (0.56 ml). The mixture was cooled to 0° C. Sodium borohydride (10.3 mg) was added to the solution and the mixture was stirred for 7 hours at room temperature. After the reaction, the reaction mixture was concentrated. The residue was purified by silica gel column chromatography (1.5 g, chloroform/methanol/water=7/3/0.5) and treated with 1 mol/l aqueous solution of hydrochloric acid to obtain hydrochloride of the title compound (21.8 mg) as a white solid.

MS(FAB,Pos.): m/z=637[M+1]$^+$ $^1$H-NMR(500 MHz, DMSO-d$_6$): δ=1.78–1.97(4H,m),2.96–3.10(2H,m), 4.31 (2H,s),4.47(2H,s),4.58–4.65(1H,m),4.72–4.88(3H,m), 7.44–7.51(3H,m),7.54–7.64(6H,m),7.68–7.70(2H,m),7.88 (1H,d, J=8.3 Hz),7.90(1H,d,J=5.9 Hz),7.91–8.00(3H,m), 8.10–8.13(1H, m),8.28(1H,d,J=8.8 Hz),8.30(1H,d,J=8.5 Hz),8.63(1H,ddd,J=4.9, 1.7,1.0 Hz),8.71(1H,d,J=4.9 Hz), 8.75(1H,d,J=5.4 Hz),8.86(1H,d, J=8.1 Hz),9.30(2H,br),9.83 (2H,br).

EXAMPLE 27

Preparation of (S)-2-(4-((imidazol-2-ylmethyl) aminomethyl)naphthoylamino)-5-((imidazol-2-ylmethyl)amino)valeric acid 1-naphthalenemethylamide [Compound No. 28]

The compound obtained in Example 25-3 (100.0 mg) was dissolved in methanol (2 ml) and 4 mol/l hydrochloric acid/dioxane solution (2 ml) was added. The mixture was stirred for 1.5 hours at room temperature. After the reaction, the reaction solution was concentrated and dried under reduced pressure. 108.2 mg of the crude product was dissolved in methanol (2 ml). After the addition of triethylamine (51.5 µl) and 2-imidazole carboaldehyde (30.9 mg), the mixture was stirred for 24 hours at room temperature. After the reaction, the reaction solution was concentrated. The residue was dried under reduced pressure and dissolved in anhydrous methanol (2 ml). The mixture was cooled to 0° C. Sodium borohydride (26.3 mg) was added to the solution and the mixture was stirred for 0.5 hour at room temperature. After the reaction, the reaction mixture was concentrated. The residue was purified by silica gel column chromatography (1.5 g, chloroform/methanol/water=7/3/0.5) and treated with 1 mol/l aqueous solution of hydrochloric acid to obtain of the title compound (64.2 mg) as a white solid.

MS(FAB,Pos.): m/z=614[M+1]$^+$ $^1$H-NMR(500 MHz, DMSO-d$_6$+D$_2$O): δ=1.70–1.96(4H,m),3.02–3.15(2H, m),4.47(2H,s),4.60–4.65(1H,m),4.65(2H,s),4.75–4.91(3H, m), 7.48–7.52(1H,m),7.54–7.68(8H,m),7.70–7.74(2H,m), 7.77(1H,d, J=7.6 Hz),7.89(1H,d,J=8.1 Hz),7.97–7.99(1H, m),8.09–8.12(1H,m), 8.23–8.28(2H,m).

EXAMPLE 28

Preparation of (S)-2-(4-((1-methylimidazol-2-ylmethyl)aminomethyl)naphthoylamino)-5-((1-methylimidazol-2-ylmethyl)amino)valeric acid 1-naphthalenemethylamide [Compound No. 29]

The compound obtained in Example 25-3 (100.3 mg) was dissolved in methanol (2 ml) and 4 mol/l hydrochloric acid/dioxane solution (2 ml) was added. The mixture was stirred for 4 hours at room temperature. After the reaction, the reaction solution was concentrated and dried under reduced pressure. The residue was dissolved in methanol (2 ml). After the addition of triethylamine (51.5 μl) and 1-methyl-2-imidazole carboaldehyde (37.4 mg), the mixture was stirred for 24 hours at room temperature. After the reaction, the reaction solution was concentrated. The residue was dried under reduced pressure and dissolved in anhydrous methanol (2 ml). The mixture was cooled to 0° C. Sodium borohydride (33.1 mg) was added to the solution and the mixture was stirred for 0.5 hour at room temperature. After the reaction, the reaction mixture was concentrated. The residue was purified by silica gel column chromatography (1.5 g, chloroform/methanol/water=7/3/0.5) and treated with 1 mol/l aqueous solution of hydrochloric acid to obtain hydrochloride of the title compound (75.4 mg) as a white solid.

MS(FAB,Pos.): m/z=643[M+1]$^+$ $^1$H-NMR(500 MHz, DMSO-d$_6$): δ=1.80–1.97(4H,m) 3.02–3.17(2H,m), 3.98(3H, s), 4.01(3H,s),4.55(2H,s),4.60–4.66(1H,m),4.80(2H, s),4.81 (1H,dd,J=15.6,5.6 Hz),4.85(1H,dd,J=15.6,5.6 Hz),4.92(2H, s),7.47–7.51(1H,m),7.54–7.60(3H,m),7.63(1H,t,J=7.1 Hz), 7.69(1H,t,J=7.1 Hz),7.74(1H,d,J=7.3 Hz),7.76–7.79(4H,m), 7.86-7.89(2H,m),7.96–7.98(1H,m),8.10–8.12(1H,m),8.29 (1H,d,J=8.3 Hz),8.37(1H,d, J, 8.5 Hz),8.78(1H,t,J=5.6 Hz), 8.89(1H,d,J=7.8 Hz),10.21(2H,brs).

EXAMPLE 29

Preparation of (S)-2-(4-((1-methylimidazole-2-ylmethyl)aminomethyl)benzoylamino)-5-((1-methylpyrrol-2-ylmethyl)amino)valeric acid 1-naphthalenemethylamide [Compound No. 30]

Example 29-1

Synthesis of N$^α$-4-(N-Boc-aminomethyl)benzoyl-N$^δ$-Cbz-L-ornithine 1-naphthalenemethylamide (Compound XVIII-5)

The compound obtained in Example 8-6 (5.12 g) was dissolved in DMF (100 ml). After the addition of WSCI hydrochloride (2.94 g), DMAP (1.88 g), and the compound obtained in Example 19-1 (2.572 g), the mixture was stirred for 16 hours at room temperature. After the reaction, the solvent was removed by distillation. Chloroform was added and the mixture was washed with 1 mol/l aqueous solution of hydrochloric acid. The solvent was removed by distillation. The resulting solid was washed with a 1:1 mixed solution of hexane and ethyl acetate to obtain the title compound (6.21 g) as a white solid.

MS(FAB,Pos.): m/z=639[M+1]$^+$

Example 29-2

Synthesis of (S)-2-(4-(N-Boc-aminomethyl) benzoylamino)-5-((1-methylpyrrol-2-ylmethyl) amino)valeric acid 1-naphthalenemethylamide (Compound XXI-1)

The compound obtained in Example 29-1 (209.5 mg) was dissolved in methanol (8 ml). After the addition of 10% Pd—C (209.5 mg), the mixture was stirred for 140 minutes under normal pressure hydrogen atmosphere. After the reaction, the catalyst was removed by filtration through celite and the solvent was removed by distillation from the reaction solution. The residue obtained was dissolved in anhydrous methanol (5 ml). After the addition of 1-methyl-2-pyrrolecarboxyaldehyde (49.7 μl), the pH of the solution was adjusted to about 5 with the addition of acetic acid. Then, sodium cyanoborohydride (61.8 mg) was added and the mixture was stirred for 25 hours at room temperature. After the reaction, the solvent was removed by distillation. The residue was purified by silica gel column chromatography (12 g, chloroform/methanol=15/1) to obtain the title compound (101.8 mg) as a white solid.

MS(FAB,Pos.): m/z=598[M+1]$^+$ $^1$H-NMR(500 MHz, DMSO-d$_6$): δ=1.39(9H,s),1.63–1.90(4H,m),2.64-2.77(2H, m),3.57(3H,s),3.92(2H,m),4.17(2H,d,J=6.2 Hz),4.49-4.54 (1H,m),4.76(2H,d,J=5.6 Hz),5.94(1H,m),6.06(1H,m),6.72 (1H, m),7.31(2H,d,J=8.3 Hz),7.44–7.55(5H,m), 7.83–7.87 (3H,m), 7.93–7.96(1H,m),8.04–8.08(1H,m),8.49–8.51(1H, m),8.55–8.57(1H,m).

Example 29-3

Synthesis of (S)-2-(4-((1-methylimidazole-2-ylmethyl)aminomethyl)benzoylamino)-5-((1-methylpyrrol-2-ylmethyl)amino)valeric acid 1-naphthalenemethylamide [Compound No. 30]

The compound obtained in Example 29-2 (100 mg) was dissolved in methanol (2 ml) and 4 mol/l hydrochloric acid/dioxane (2 ml) was added. The mixture was stirred for 2 hours at room temperature. After the reaction, the solvent was removed by distillation. The residue was dissolved in anhydrous methanol (4 ml). After the addition of triethylamine (83.9 μl) and 1-methyl-2-imidazole carboxyaldehyde (22.1 mg), the mixture was stirred for 3 hours at room temperature. After the solvent was removed by distillation, anhydrous methanol (2 ml) was added and the mixture was cooled to 0° C. Sodium borohydride (12.7 mg) was added to the solution and the mixture was stirred for 62 hours, while allowing gradually to become room temperature. After the reaction, the solvent was removed by distillation. The residue was purified by silica gel column chromatography (10 g, chloroform/methanol=2/1). The compound was dissolved in 1 mol/l aqueous solution of hydrochloric acid (2 ml) and water was removed by distillation to obtain hydrochloride of the title compound (71.7 mg) as a light reddish solid.

MS(FAB,Pos.): m/z=592[M+1]$^+$ $^1$H-NMR(500 MHz, DMSO-d$_6$): δ=1.72–1.87(4H,m),2.91(2H,m),3.95(3H, s),4.08–4.09(2H,m),4.39(2H,m),4.53–4.56(3H,m),4.76(2H, d,J=5.7 Hz),5.98–5.99(1H,m), 6.22–6.24(1H,m),6.78–6.79 (1H,m), 7.45–7.49(2H,m),7.53–7.56(2H,m),7.71–7.73(4H, m),7.83–7.86(1H,m),7.93–7.95(1H,m),7.96–8.01(2H,m), 8.06–8.08(1H,m), 8.71–8.73(2H,m),9.00(2H,br).

EXAMPLE 30

Preparation of (S)-2-(4-((imidazol-2-ylmethyl) aminomethyl)benzoylamino)-5-((1-methylpyrrole-2-ylmethyl)amino)valeric acid 1-naphthalenemethylamide [Compound No. 31]

The compound obtained in Example 29-2 (106.1 mg) was dissolved in methanol (2 ml) and 4 mol/l hydrochloric acid/dioxane (2 ml) was added. The mixture was stirred for 3 hours at room temperature. After the reaction, the solvent was removed by distillation. The residue was dissolved in anhydrous methanol (8 ml) After the addition of triethylamine (89.0 µl) and 2-imidazole carboxyaldehyde (25.6 mg), the mixture was stirred for 2 hours at room temperature. After the solvent was removed by distillation, anhydrous methanol (4 ml) was added and the mixture was cooled to 0° C. Sodium borohydride (13.4 mg) was added to the solution and the mixture was stirred for 24 hours, while allowing gradually to become room temperature. After the reaction, the solvent was removed by distillation. The residue was purified by silica gel column chromatography (10 g, chloroform/methanol 3/1). The compound was dissolved in 1 mol/l aqueous solution of hydrochloric acid (2 ml) and water was removed by distillation to obtain hydrochloride of the title compound (75.0 mg) as a light reddish solid.

MS(FAB,Pos.): m/z=578[M+1]$^+$ $^1$H-NMR(500 MHz, DMSO-d$_6$): =1.72–1.91(4H,m),2.91(2H,m),4.07–4.10(2H, m),4.39(2H,s),4.53–4.57(3H,m),4.75–4.77(2H,m), 5.98–5.99(1H,m),6.22–6.24(1H,m),6.78–6.79(1H,m), 7.45–7.48(2H,m), 7.53–7.56(2H,m),7.69–7.73(4H,m), 7.83–7.86(1H,m),7.93–7.99 (3H,m),8.01–8.08(1H,m), 8.71–8.72(2H,m),8.98(2H,brs).

EXAMPLE 31

Preparation of (S)-2-(4-((pyrazol-3-ylmethyl) aminomethyl)benzoylamino)-5-((1-methylpyrrole-2-ylmethyl)amino)valeric acid 1-naphthalenemethylamide [Compound No. 32]

The compound obtained in Example 29-2 (110.0 mg) was dissolved in methanol (2 ml) and 4 mol/l hydrochloric acid/dioxane (2 ml) was added. The mixture was stirred for 3 hours at room temperature. After the reaction, the solvent was removed by distillation. The residue was dissolved in anhydrous methanol (4 ml) After the addition of triethylamine (92.2 µl) and pyrazole-3-carboxyaldehyde (21.2 mg), the mixture was stirred for 16 hours at room temperature. After the solvent was removed by distillation, anhydrous methanol (4 ml) was added and the mixture was cooled to 0° C. Sodium borohydride (13.9 mg) was added to the solution and the mixture was stirred for 25 minutes, while allowing gradually to become room temperature. After the reaction, the solvent was removed by distillation. The residue was purified by silica gel column chromatography (10 g, chloroform/methanol=5/1). The compound was dissolved in 1 mol/l aqueous solution of hydrochloric acid (2 ml) and water was removed by distillation to obtain hydrochloride of the title compound (55.6 mg) as a pale orange solid.

MS(FAB,Pos.): m/z=578[M+1]$^+$ $^1$H-NMR(500 MHz, DMSO-d$_6$): δ=1.72–1.91(4H,m),2.91(2H,br),3.64 (3H,s), 4.07–4.22(6H,m),4.53–4.57(1H,m), 4.76–4.77(2H,m), 5.98–5.99(1H,m),6.22–6.23(1H,m),6.45–6.51(1H,m), 6.78–6.79(1H,m),7.45–7.49(2H,m),7.52–7.57(2H,m), 7.63–7.65(2H,m), 7.79–7.80(1H,m),7.83–7.86(1H,m), 7.93–8.00(3H,m),8.06–8.08(1H,m),8.70–8.83(2H,m),9.00 (2H,br), 9.76(2H,br). g

EXAMPLE 32

Synthesis of (S)-2-(4-((1-methylbenzimidazol-2-ylmethyl)aminomethyl)benzoylamino)-5-((1-methylbenzimidazol-2-yl)methylamino)valeric acid 1-naphthalenemethylamide [Compound No. 33]

The compound obtained in Example 19-2 (100.4 mg) was dissolved in methanol (1 ml) and 4 mol/l hydrochloric acid/dioxane solution (1 ml) was added. The mixture was stirred for 3 hours at room temperature. After the reaction, the solvent was removed by distillation. The residue was dissolved in methanol. The solution was neutralized with Amberlite IRA-410, and then the solvent was removed by distillation. The residue was dissolved in anhydrous methanol (1 ml). After the addition of 1-methyl-2-formylbenzimidazole (53.8 mg), the mixture was reacted for 1.5 hours at room temperature. The reaction solution was concentrated, dried under reduced pressure, and again dissolved in methanol (2 ml) After the addition of sodium borohydride (25.6 mg), the mixture was reacted for 0.5 hour at room temperature. After the reaction, the solvent was removed by distillation. The residue was dissolved in chloroform, washed with distilled water and saturated brine, and dried over anhydrous sodium sulfate. The solvent was concentrated and the residue was purified by silica gel column chromatography (5 g, chloroform/methanol/water= 7/3/0.5). After the addition of 1 mol/l hydrochloric acid, the residue was concentrated and azeotropically distilled to obtain hydrochloride of the title compound (28.2 mg) as a white solid.

MS(Fab,pos.): m/z=693[M+H]$^+$ $^1$H-NMR(500 MHz, DMSO-d$_6$): δ=1.87–1.97(4H,m),3.93(3H,s),3.97(3H, s),4.46(2H,s),4.55–4.62(1H,m),4.64(2H,s),4.67(2H,s),4.76 (2H, d,J=5.6 Hz),7.36–7.58(6H,m),7.71–7.79(7H,m), 7.93–7.95(1H,m), 8.01(2H,d,J=8.5 Hz),8.05–8.08(1H,m), 8.73–8.76(2H,m),9.94(2H, brs).

EXAMPLE 33

Preparation of (S)-2-(4-((1-methylbenzimidazole-2-ylmethyl)aminomethyl)benzoylamino)-5-((1-methylpyrrol-2-ylmethyl)amino)valeric acid 1-naphthalenemethylamide [Compound No. 34]

The compound obtained in Example 29-2 (156.3 mg) was dissolved in methanol (2 ml) and 4 mol/l hydrochloric acid/dioxane (2 ml) was added. The mixture was stirred for 165 minutes at room temperature. After the reaction, the solvent was removed by distillation. The residue was dissolved in anhydrous methanol (4 ml). After the addition of triethylamine (131.1 µl) and 1-methyl-2-formylbenzimidazole (62.8 mg), the mixture was stirred for 12 hours at room temperature. After the solvent was removed by distillation, anhydrous methanol (4 ml) was added and the mixture was cooled to 0° C. Sodium borohydride (19.8 mg) was added to the solution and the mixture was stirred for 30 minutes, while allowing gradually to become room temperature. After the reaction, the solvent was removed by distillation. The residue was purified by silica gel column chromatography (10 g, chloroform/methanol=10/1). The compound was dissolved in 1 mol/l aqueous solution of hydrochloric acid (2 ml) and water was removed by distillation to obtain hydrochloride of the title compound (44.1 mg) as a reddish white solid.

MS(FAB,Pos.): m/z=642[M+1]$^1$ $^1$H-NMR(500 MHz, DMSO-d$_6$): δ=1.73–1.91(4H,m),2.09(2H,br),3.64 (3H,s), 3.85(3H,s),4.08–4.12(2H,m),4.38–4.43(2H,m),4.47–4.59 (3H,m),4.76–4.77(2H,m),5.98–5.99(1H,m),6.22–6.23(1H, m), 6.79–6.80(1H,m),7.29–7.59(6H,m),7.60–7.73(2H,m), 7.84–7.86(1H,m),7.94–8.08(4H,m), 8.70–8.72(2H,m),8.96 (2H,br).

EXAMPLE 34

Preparation of (S)-2-(4-((thiazol-2-ylmethyl) aminomethyl)benzoylamino)-5-((1-methylpyrrole-2-ylmethyl)amino)valeric acid 1-naphthalenemethylamide [Compound No. 35]

The compound obtained in Example 29-2 (161.1 mg) was dissolved in methanol (2 ml), and 4 mol/l hydrochloric acid/dioxane (2 ml) was added. The mixture was stirred for 12 hours at room temperature. After the reaction, the solvent was removed by distillation. The residue was dissolved in anhydrous methanol (4 ml). After the addition of triethylamine (135.1 μl) and 2-formylthiazole (28.1 μl), the mixture was stirred for 2.5 hours at room temperature. After the solvent was removed by distillation, anhydrous methanol (4 ml) was added and the mixture was cooled to 0° C. Sodium borohydride (20.4 mg) was added to the solution and the mixture was stirred for 20 minutes, while allowing gradually to become room temperature. After the reaction, the solvent was removed by distillation. The residue was purified by silica gel column chromatography (10 g, chloroform/methanol=10/1). The compound was dissolved in 1 mol/l aqueous solution of hydrochloric acid (2 ml) and water was removed by distillation to obtain hydrochloride of the title compound (81.4 mg) as a pale orange solid.

MS(FAB,Pos.): m/z=595[M+1]$^+$ $^1$H-NMR(500 MHz, DMSO-d$_6$): δ=1.72–1.91(4H,m),2.91(2H,br),3.65(3H,s), 4.17–4.32(2H,m),4.53–4.57(3H,m),4.76–4.77(2H,m), 5.98–5.99(1H,m),6.23–6.24(1H,m),6.78–6.79(1H,m), 7.45–7.52(2H,m),7.53–7.56(2H,m),7.65–7.70(2H,m), 7.83–7.86(2H,m), 7.88–7.99(4H,m),8.00–8.08(1H,m), 8.70–8.74(2H,m),9.02(2H, br),10.14(2H,br).

EXAMPLE 35

Preparation of (S)-2-(4-((1-methylimidazole-2-ylmethyl)aminomethyl)benzoylamino)-5-((imidazol-2-ylmethyl)amino)valeric acid 1-naphthalenemethylamide [Compound No. 36]

Example 35-1

Synthesis of (S)-2-((N-Boc-aminomethyl) benzoylamino)-5-((imidazol-2-ylmethyl)amino)-L-ornithine 1-naphthalenemethylamide (Compound XXI-2)

The compound obtained in Example 29-1 (233.5 mg) was dissolved in methanol (8 ml). After the addition of 10% Pd—C (233.5 mg), the mixture was stirred for 140 minutes under normal pressure hydrogen atmosphere. After the reaction, the catalyst was removed by filtration through celite and the solvent was removed by distillation from the reaction solution. The residue obtained was dissolved in anhydrous methanol (5 ml). After the addition of 2-imidazole carboxyaldehyde (42.2 mg), the mixture was cooled to 0° C. Then, sodium borohydride (27.7 mg) was added. The mixture was stirred for 30 minutes at 0° C. and one hour at room temperature. After the reaction, the solvent was removed by distillation. The residue was purified by silica gel column chromatography (12 g, chloroform/methanol=10/1) to obtain the title compound (108.11 mg) as a white solid.

$^1$H-NMR(500 MHz,DMSO-d$_6$): δ=1.39(9H,s),1.42–1.56 (2H,m),1.72–1.82(2H,m), 3.68(2H,s),4.12–4.17(2H,m), 4.43–4.51(5H,m), 4.75–4.76(2H,m),5.29–5.31 (2H,m), 7.30–7.31(2H,m),7.44–7.55 (5H,m),7.83–7.86(3H,m), 7.92–7.95(1H,m), 8.04–8.06(1H,m), 8.48–8.56(2H,m).

Example 35-2

Synthesis of (S)-2-(4-((1-methylimidazole-2-ylmethyl)aminomethyl)benzoylamino)-5-((imidazol-2-ylmethyl)amino)valeric acid 1-naphthalenemethylamide [Compound No. 36]

The compound obtained in Example 35-1 (104.2 mg) was dissolved in methanol (2 ml) and 4 mol/l hydrochloric acid/dioxane (2 ml) was added. The mixture was stirred for 2 hours at room temperature. After the reaction, the solvent was removed by distillation. The residue was dissolved in anhydrous methanol (4 ml). After the addition of triethylamine (89.3 μl) and 1-methyl-2-imidazole carboxyaldehyde (29.4 mg), the mixture was stirred for 12 hours at room temperature. After the solvent was removed by distillation, anhydrous methanol (4 ml) was added and the mixture was cooled to 0° C. Sodium borohydride (13.5 mg) was added to the solution and the mixture was stirred for 85 minutes, while allowing gradually to become room temperature. After the reaction, the solvent was removed by distillation. The residue was purified by silica gel column chromatography (10 g, chloroform/methanol=1/1). The compound was dissolved in 1 mol/l aqueous solution of hydrochloric acid (2 ml) and water was removed by distillation to obtain hydrochloride of the title compound (34.7 mg) as a white solid.

MS(FAB,Pos.): m/z=579[M+1]$^+$ $^1$H-NMR(500 MHz, DMSO-d$_6$): δ=1.74–1.91(4H,m),3.91(3H,s),4.37–4.59 (8H, m), 4.73–4.77(2H,m),7.44–7.71(10H,m),7.84–7.86(1H, m),7.94–8.08(4H,m), 8.69–8.72(2H,m).

EXAMPLE 36

Preparation of (S)-2-(4-((imidazol-2-ylmethyl) aminomethyl)benzoylamino)-5-((1-methylimidazol-2-ylmethyl)amino)valeric acid 1-naphthalenemethylamide [Compound No. 37]

Example 36-1

Synthesis of (S)-2-(4-(N-Boc-aminomethyl) benzoylamino)-5-((1-methylimidazol-2-ylmethyl) amino)valeric acid 1-naphthalenemethylamide (Compound XXI-3)

The compound obtained in Example 29-1 (255.2 mg) was dissolved in methanol (10 ml). After the addition of 10% Pd—C (170 mg), the mixture was stirred for 120 minutes under normal pressure hydrogen atmosphere. After the reaction, the catalyst was removed by filtration through celite and the solvent was removed by distillation from the reaction solution. The residue obtained was dissolved in anhydrous methanol (8 ml). After the addition of 1-methyl-2-imidazole carboxyaldehyde (52.8 mg), the mixture was cooled to 0° C. Then, sodium borohydride (30.2 mg) was added. The mixture was stirred for 5 minutes at 0° C. and 45 minutes at room temperature. After the reaction, the solvent was removed by distillation. The residue was purified by silica gel column chromatography (13 g, chloroform/methanol=10/1) to obtain the title compound (117.4 mg) as a white solid.

MS(FAB,Pos.): m/z=598[M+1]$^+$ $^1$H-NMR(500 MHz, DMSO-d$_6$): δ=1.39(9H,s),1.73–1.81(2H,m),3.57 (3H,s), 4.16–4.17(2H,m),4.45–4.49(3H,m), 0.71–4.79(2H,m),5.22 (1H,t,J=5.6 Hz),6.70(1H,d,J=1.0 Hz),6.75(1H,d,J=1.0 Hz), 7.00(1H,d,J=1.0 Hz),7.06(1H,d,J=1.0 Hz), 7.29–7.31(2H, m),7.44–7.49 (3H,m),7.82–7.85(3H,m), 7.92–7.96(2H,m), 8.04–8.07(2H,m), 8.46–8.48(1H,m),8.53–8.56(1H,m).

Example 36-2

Synthesis of (S)-2-(4-((imidazole-2-ylmethyl) aminomethyl)benzoylamino)-5-((1-methylimidazol-2-ylmethyl)amino)valeric acid 1-naphthalenemethylamide [Compound No. 37]

The compound obtained in Example 36-1 (114.4 mg) was dissolved in methanol (2 ml), and 4 mol/l hydrochloric acid/dioxane (2 ml) was added. The mixture was stirred for 2 hours at room temperature. After the reaction, the solvent was removed by distillation. The residue was dissolved in anhydrous methanol (4 ml). After the addition of triethylamine (95.8 μl) and 2-imidazole carboxyaldehyde (22.0 mg), the mixture was stirred for 16 hours at room temperature. After the solvent was removed by distillation, anhydrous methanol (4 ml) was added and the mixture was cooled to 0° C. Sodium borohydride (14.5 mg) was added to the solution and the mixture was stirred for 4.5 hours, while allowing gradually to become room temperature. After the reaction, the solvent was removed by distillation. The residue was purified by silica gel column chromatography (10 g, chloroform/methanol=2/1). The compound was dissolved in 1 mol/l aqueous solution of hydrochloric acid (2 ml) and water was removed by distillation to obtain hydrochloride of the title compound (81.3 mg) as a pale yellow solid.

MS(FAB,Pos.): m/z=579[M+1]$^+$ $^1$H-NMR(500 MHz, DMSO-d$_6$): δ=1.77–1.91(4H,m),3.93(3H,s),4.37–4.38 (2H, m),4.50–4.59(5H,m),4.73–4.77(2H,m),7.44–7.70(10H, m),7.82–7.88(1H,m),7.92–8.01(3H,m),8.06–8.08(1H,m), 8.62–8.75(2H,m),10.05–10.15 (2H,m).

EXAMPLE 37

Preparation of (2S)-2-(4-(N-2-picolylaminomethyl) naphthoylamino)-5-(5,6,7,8-tetrahydroquinolin-8-ylamino)valeric acid 1-naphthalenemethylamide [Compound No. 38]

Example 37-1

Synthesis of N$^α$-4-(N-Boc-aminomethyl)naphthoyl-N$^δ$-Cbz-L-ornithine 1-naphthalenemethylamide (Compound XVIII-6)

The compound obtained in Example 8-6 (209.1 mg) was dissolved in DMF (4 ml). After the addition of WSCI hydrochloride (91.5 mg), HOBt (54.0 mg), and the compound obtained in Example 25-2 (85.5 mg), the mixture was stirred for 19 hours at room temperature. After the reaction, the solvent was removed by distillation. The residue was dissolved in chloroform, washed with methanol, and filtered to obtain the title compound (155.1 mg) as white foam.

MS(FAB,Pos.): m/z=689[M+1]$^+$ $^1$H-NMR(500 MHz, DMSO-d$_6$): δ=1.41(9H,s), 1.48–1.62(2H,m),1.63–1.82 (2H, m), 2.99–3.10(2H,m),4.52–4.61(1H,m),4.62(2H,d,J=5.9 Hz),4.81(2H,d,J=5.9 Hz), 5.00(2H,s),7.28–7.39(6H,m),7.40 (1H,d,J=7.3 Hz),7.45–7.49(1H,m),7.49–7.61(7H,m),7.86 (1H,d,J=8. Hz),7.95–7.98(1H,m),8.07(1H,d,J=7.1 Hz),8.15 (1H,d,J=8.1 Hz), 8.24(1H,d,J=8.1 Hz),8.59(1H,br),8.67(1H, d,J=7.8 Hz).

Example 37-2

Synthesis of N$^α$-4-(N-2-picolylaminomethyl) naphthoyl-N$^δ$-Cbz-L-ornithine 1-naphthalenemethylamide (Compound XXIV-1)

The compound obtained in Example 37-1 (149.6 mg) was dissolved in methanol (1.5 ml), and 4 mol/l hydrochloric acid/dioxane (1.5 ml) was added. The mixture was stirred for 2.5 hours at room temperature. After the reaction, the reaction solution was concentrated and dried under reduced pressure. 70.0 mg of the product was dissolved in methanol (2.8 ml). After the addition of triethylamine (48.0 μl) and 2-pyridine aldehyde (12.0 μl), the mixture was stirred for one hour at room temperature. After the reaction, the solvent was removed by distillation and the residue was dried under reduced pressure. Anhydrous methanol (6.5 ml) was added to the residue and the mixture was cooled to 0° C. Sodium borohydride (22.8 mg) was added to the solution and the mixture was stirred for 15 minutes at room temperature. After the reaction, the reaction solution was concentrated. The residue was purified by silica gel column chromatography (3.5 g, chloroform/methanol=20/1) to obtain the title compound (40.4 mg) as white foam.

MS(FAB,Pos.): m/z=680[M+1]$^+$ $^1$H-NMR(500 MHz, DMSO-d$_6$): δ=1.52–1.58(2H,m),1.70–1.78(2H,m), 3.02 (2H,m),3.89(2H,s),4.21(2H,s),4.53–4.59(1H,m),4.81(2H,d, J=4.9 Hz),4.99(2H,s), 7.21–7.40(7H,m),7.44–7.52(3H,m), 7.52–7.61(6H,m),7.78(1H,td,J=7.6,1.7 Hz),7.86(1H,d,J=8.1 Hz),7.95–7.98(1H,m),8.09(1H,d,J=7.1 Hz),8.21(1H,d,J=8.3 Hz),8.23(1H,d, J=8.5 Hz),8.47(1H,d,J=5.6 Hz),8.56(1H,t,J= 5.6 Hz),8.64(1H,d,J=7.8 Hz).

Example 37-3

Synthesis of (2S)-2-(4-(N-2-picolylaminomethyl) naphthoylamino)-5-(5,6,7,8-tetrahydroquinolin-8-ylamino)valeric acid 1-naphthalenemethylamide [Compound No. 38]

The compound obtained in Example 37-2 (32.7 mg) was dissolved in a dioxane/water (8/2) solution (1.5 ml). After the addition of 10% Pd—C (32.4 mg), the mixture was stirred for 24 hours under hydrogen atmosphere at room temperature. After the reaction, the catalyst was removed by filtration through celite and the solvent was removed by distillation under reduced pressure to obtain a crude product (24.9 mg). The crude product was dissolved in methanol (0.5 ml). Then, 5,6,7,8-tetrahydroquinolin-8-one (7.9 mg) and sodium cyanoborohydride (4.7 mg) were added. 7 drops of acetic acid was added to adjust the pH of the mixture to about 4–5. The mixture was stirred for 15.5 hours at room temperature. After the completion of the reaction, the solvent was removed by distillation. The residue was purified by silica gel column chromatography (5 g, chloroform/methanol=10/2). After the addition of 1 mol/l hydrochloric acid, the residue was concentrated and dried under reduced pressure to obtain the title compound (9.7 mg) as a white solid.

MS(FAB,Pos.): m/z=677[M+1]$^+$ $^1$H-NMR(500 MHz, DMSO-d$_6$): δ=1.62–2.01(7H,m),2.30–2.40(1H,m), 2.78–2.88(2H,m),2.95–3.03(1H,m),3.04–3.22(1H,m),4.47 (3H,m), 4.61–4.70(1H,m),4.79(2H,s),4.83(1H,d,J=15.6,5.6 Hz),4.85(1H, dd,J=15.6,5.6 Hz),7.37–7.42(1H,m), 7.47–7.51(2H,m),7.52–7.64 (5H,m),7.67–7.73(3H,m),7.80 (1H,d,J=7.1 Hz),7.88(1H,d,J=8.1 Hz),7.93(1H,td,J=7.6,1.7 Hz),8.07–8.13(1H,m),8.26–8.33(2H, m), 8.49(1H,d,J=4.6 Hz),8.71(1H,d,J=4.8 Hz),8.76(1H,brs),8.87(1H,d,J=7.8 Hz), 9.10(2H,br),9.80(2H,br).

EXAMPLE 38

Preparation of (2S)-2-(4-((N-imidazol-2-ylmethyl) aminomethyl)naphthoylamino)-5-(5,6,7,8-tetrahydroquinolin-8-ylamino)valeric acid 1-naphthalenemethylamide [Compound No. 39]

Example 38-1

Preparation of $N^\alpha$-4-(aminomethyl)benzoylamino-$N^\delta$-Cbz-L-ornithine 1-naphthalenemethylamide [Compound XXIII-1]

The compound obtained in Example 29-1 (351.2 mg) was dissolved in chloroform (5 ml), and trifluoroacetic acid (5 ml) was added. After 15 minutes, the reaction solution was concentrated. The residue was purified by silica gel column chromatography (10 g, chloroform/methanol=5/1) to obtain the title compound (363.7 mg) as a light brown solid.

MS(FAB,Pos.): m/z=539[M+1]$^+$ $^1$H-NMR(500 MHz, CDCl$_3$): δ=1.42–1.56(2H,m),1.70–1.84(2H,m), 2.96–3.06 (2H,m),4.08–4.13(2H,m),4.48–4.53(1H,m),4.74–4.79 (2H, m),4.98(2H,s), 7.26–7.37(6H,m),7.45–7.50(2H,m), 7.51–7.58(4H,m),7.84–7.88(1H,m), 7.92–7.98(3H,m), 8.05–8.09(1H, m),8.20(2H,br),8.52–8.59(2H,m).

Example 38-2

Synthesis of $N^\alpha$-(4-(N-(imidazol-2-ylmethyl) aminomethyl)benzoyl)-$N^\delta$-Cbz-L-ornithine 1-naphthalenemethylamide (Compound XXIV-2)

The compound obtained in Example. 38-1 (107.2 mg) was dissolved in methanol (5 ml). After the addition of triethylamine (28 μl) and 2-imidazole carboxyaldehyde (19 mg), the mixture was stirred for 2 days. Then, sodium borohydride (23 mg) was added. After 20 minutes, the reaction solution was concentrated with the addition of a small amount of silica gel. The obtained residue was purified by silica gel column chromatography (5 g, chloroform/methanol=5/1) to obtain the title compound (72.2 mg) as a pale yellow solid.

MS(FAB,Pos.): m/z=619[M+1]$^+$ $^1$H-NMR(500 MHz, DMSO-d$_6$): δ=1.41–1.58(2H,m),1.70–1.84(2H,m) 2.97–3.05 (2H,m),4.48–4.53(1H,m),4.75(2H,d,J=5.6 Hz), 4.98(2H, s),6.79(1H,s), 7.02(1H,s),7.26–7.38(6H,m), 7.42–7.48(4H,m), 7.51–7.57(2H,m),7.82–7.90 (3H,m), 7.93–7.96(1H,m),8.04–8.08(1H,m),8.44(1H,d,J=8.1 Hz), 8.51(1H,t, J=5.7 Hz).

Example 38-3

Synthesis of (2S)-2-(4-((N-imidazol-2-ylmethyl) aminomethyl)benzoylamino)-5-(5,6,7,8-tetrahydroquinolin-8-ylamino)valeric acid 1-naphthalenemethylamide [Compound No. 39]

The compound obtained in Example 38-2 (71.1 mg) was dissolved in dioxane (2.8 ml) and water (0.7 ml), and 5% Pd—C (35 mg) was added. Hydrogen gas was introduced into the reaction solution. After 22 hours, the reaction solution was filtered through a glass filter G4 and the filtrate was concentrated. The resulting residue was dissolved in methanol (3.2 ml), and 5,6,7,8-tetrahydroquinolin-8-one (21 mg) and triethylamine (28 μl) were added. After 19 hours, sodium borohydride. (15 mg) was added to the reaction solution. After 15 minutes, the reaction solution was concentrated with the addition of a small amount of silica gel. The residue was purified by silica gel column chromatography (2.5 g, chloroform/methanol/water=7/3/0.5). The crude product was dissolved in methanol and activated carbon was added to the solution. After removal of the activated carbon by filtration, the filtrate was concentrated to obtain yellow syrup. 1 mol/l hydrochloric acid was added to the syrup, and the mixture was azeotropically distilled with methanol and dried under reduced pressure to obtain hydrochloride of the title compound (21.7 mg) as a yellow solid.

MS(FAB,Pos.): m/z=616[M+1]$^+$ $^1$H-NMR(500 MHz, CDCl$_3$): δ=1.68–2.03(5H,m),2.29–2.36(1H,m), 2.50–2.63 (2H,m),2.92–3.17(2H,m),4.36–4.47(3H,m),4.48–4.60(3H, m),4.76(2H,d,J=5.4 Hz),7.34–7.40(1H,m),7.42–7.48(2H, m), 7.50–7.56(3H,m),7.65–7.75 (5H,m),7.82–7.89(1H,m), 7.93–8.08(4H,m),8.46(1H,t,J=4.6 Hz),8.59–8.72(2H,m), 9.06(1H,br).

EXAMPLE 39

Preparation of (S)-2-(4-((N-imidazol-2-ylmethyl) aminomethyl)naphthoylamino)-5-(2-picolylamino) valeric acid 1-naphthalenemethylamide [Compound No. 40]

Example 39-1

Synthesis of $N^\alpha$-4-(aminomethyl)naphthoylamino-$N^\delta$-Cbz-L-ornithine 1-naphthalenemethylamide (Compound XXIII-2)

The compound obtained in Example 37-1 (291.0 mg) was dissolved in chloroform (4.4 ml), and trifluoroacetic acid (4.4 ml) was added. After 1 hour, the reaction solution was concentrated, azeotropically distilled with methanol, and dried under reduced pressure. The resulting residue was purified by silica gel column chromatography (10 g, chloroform/methanol=10/1) to obtain the title compound (306.2 mg) as a white solid.

MS(FAB,Pos.): m/z=589[M+1]$^+$ $^1$H-NMR(500 MHz, CDCl$_3$): δ=1.49–1.64(2H,m),1.67–1.83(2H,m), 3.00–3.10 (2H,m),4.57–4.63(3H,m),4.79–4.86(2H,m),5.00 (2H,s), 7.28–7.39(5H,m), 7.48 (1H,dd,J=7.1, 8.1 Hz),7.52–7.71 (6H,m),7.87(1H,d,J=8.1 Hz),7.95–8.00(1H,m), 8.08–8.13 (1H,m), 8.18(1H,d,J=8.5 Hz),8.27(1H,d,J=8.5 Hz), 8.30–8.40(2H,br), 8.62(1H,t,J=5.8 Hz),8.77(1H,d,J=7.8 Hz).

Example 39-2

Synthesis of $N^\alpha$-4-(imidazol-2-ylmethylaminomethyl)naphthoylamino-$N^\delta$-Cbz-L-ornithine 1-naphthalenemethylamide (Compound XXIV-3)

The compound obtained in Example 39-1 (304.0 mg) was dissolved in methanol (9 ml). After the addition of 2-imidazole carboxyaldehyde (55 mg), the mixture was stirred for 3 days. Then, sodium borohydride (59 mg) was added. After one hour, the reaction solution was concentrated with the addition of a small amount of silica gel. The obtained residue was purified by silica gel column chromatography. (10 g, chloroform/methanol=10/1) to obtain the title compound (204.4 mg) as a pale yellow solid.

Example 39-3

Synthesis of N$^\alpha$-4-(imidazol-2-ylmethylaminomethyl)naphthoylamino-L-ornithine 1-naphthalenemethylamide (Compound XXV-1)

A mixed solution of trifluoroacetic acid (1.75 ml), thioanisole (0.49 ml), and m-cresol (0.44 ml) was added to the compound obtained in Example 39-2 (70.0 mg). After the reaction for 30 minutes, the reaction solution was concentrated and water was added. The mixture was made acidic with the addition of a small amount of hydrochloric acid. The aqueous solution was washed with chloroform and the water layer was concentrated to obtain the title compound (112.5 mg) as a white solid.

Example 39-4

Synthesis of (S)-2-(4-((N-imidazol-2-ylmethyl)aminomethyl)naphthoylamino)-5-(2-picolylamino) valeric acid 1-naphthalenemethylamide [Compound No. 40]

The compound obtained in Example 39-3 (56 mg) was dissolved in methanol (1.4 ml). After the addition of pyridine-2-aldehyde (7 µl) and triethylamine (11 µl), the mixture was stirred for 17.5 hours. Then, sodium borohydride (6 mg) was added to the reaction solution. After stirring for 2 hours, the reaction solution was concentrated with the addition of a small amount of silica gel. The residue was purified by silica gel column chromatography (1 g, chloroform/methanol/water=7/3/0.5). After the addition of 1 mol/l hydrochloric acid to the resulting compound, the mixture was concentrated to dryness to obtain hydrochloride of the title compound (8.3 mg) as a light brown solid.

MS(FAB,Pos.): m/z=626[M+1]$^+$ $^1$H-NMR(500 MHz, CDCl$_3$): d=1.78–1.97(4H,m),2.47–2.60(4H,m) 3.00–3.12 (2H,m),4.31(2H,t,J=5.6 Hz),), 4.57–4.67(3H,m),4.78–4.90 (3H,m),7.44–7.78 (12H,m),7.74–8.00(4H,m),8.10–8.14(1H, m),8.28(1H,d,J=9.3 Hz),8.33(1H,d,J=8.5 Hz),8.64(1H,d,J= 4.9 Hz), 8.73(1H,t,J=5.6 Hz),8.88(1H,d,J=8.1 Hz), 9.29(2H, br).

EXAMPLE 40

Preparation of (2S)-2-(4-((N-imidazol-2-ylmethyl) aminomethyl)naphthoylamino)-5-(5,6,7,8-tetrahydroquinolin-8-ylamino)valeric acid 1-naphthalenemethylamide [Compound No. 41]

The compound obtained in Example 39-4 (13.7 mg) was dissolved in methanol (0.69 ml), and 5,6,7,8-tetrahydroquinolin-8-one (5.7 mg), acetic acid (69 µl), and sodium cyanoborohydride (4.8 mg) were added. After two days, the reaction solution was concentrated. The residue was purified by silica gel column chromatography (0.5 g, chloroform/methanol/water=7/3/0.5). After the addition of 1 mol/l hydrochloric acid, the residue was concentrated to dryness to obtain the title compound (8.2 mg) as a white solid.

MS(FAB,Pos.): m/z=666[M+1]$^+$ $^1$H-NMR(500 MHz, DMSO-d$_6$): δ=1.74–2.08(8H,m),2.79–2.88(2H,m) 2.94–3.19(2H,m),4.43–4.50(1H,m),4.57–4.69(3H,m), 4.79–4.90(4H,m),7.37–7.77(12H,m),7.79–7.91(2H,m), 7.96–8.00(1H,m), 8.09–8.13(1H,m),8.28–8.34(2H,m),8.49 (1H,d,J=4.6 Hz),8.70–8.77(1H,m),8.87(1H,d,J=7.1 Hz), 9.08(2H,brs).

EXAMPLE 41

Preparation of (S)-2-((4-guanidinomethyl)benzoyl)-5-(N-2-picolylamino)-valeric acid 1-naphthalenemethylamide [Compound No. 42]

Example 41-1

Synthesis of 4-(N-Cbz aminomethyl)benzoic acid (Compound XVII-4)

Commercially available 4-aminomethylbenzoic acid (5 g) was dissolved in 1 mol/l aqueous solution of sodium hydroxide (33 ml). Benzylchloroformate (5.2 ml) and 1 mol/l aqueous solution sodium hydroxide (40 ml) were gradually and simultaneously added while stirring at room temperature. After 3 hours, 1 mol/l hydrochloric acid was added to the reaction solution to adjust the pH to 3, and the deposited precipitate was collected by filtration through glass filter G4. The precipitate was washed with water and hexane, and dried under reduced pressure to obtain the title compound (8.162 g) as a white solid.

$^1$H-NMR(500 MHz,DMSO-d$_6$): δ=4.26(2H,d,J=6.3 Hz), 5.05(2H,s), 7.30–7.40(7H,m),7.88(2H,d,J=8.3 Hz),7.91(1H, t,J=6.3 Hz).

Example 41-2

Synthesis of N$^\alpha$-(4-(N-Cbz)aminomethylbenzoyl)-L-ornithine 1-naphthalenemethylamide (Compound XX-1)

The compound obtained in Example 23-2 (350 mg) was dissolved in DMF (7 ml). After the addition of WSCI hydrochloride (265.0 g), DMAP (169 mg), and the compound obtained in Example 41-1 (276.0 mg), the mixture was stirred for 24 hours at room temperature. After the reaction, the solvent was removed by distillation. The residue was dissolved in chloroform, washed with 1 mol/l aqueous solution of hydrochloric acid and saturated aqueous solution of sodium hydrogencarbonate, and dried over sodium hydrogensulfate. The solvent was removed by distillation and the residue was purified by silica gel column chromatography (20 g, chloroform/methanol=10/1). 130 mg of the obtained product was dissolved in methanol (2.6 ml) and 4 mol/l hydrochloric acid/dioxane solution (2.6 ml) was added. The mixture was stirred for 70 minutes at room temperature. After the reaction, the solvent was removed by distillation and the residue was dried under vacuum to obtain hydrochloride of the title compound (147 mg) as a white solid.

Example 41-3

Synthesis of (S)-2((4-(N-Cbz)aminomethylbenzoyl) amino)-5-(2-picolylamino)valeric acid 1-naphthalenemethylamide (Compound XXI-4-1)

The compound obtained in Example 41-2 (0.15 g) was dissolved in methanol (3.0 ml), and 2-pyridine aldehyde (0.02 g), sodium cyanoborohydride (0.04 g), and triethylamine (0.02 g) were added. The reaction solution was adjusted to pH about 5 using acetic acid and stirred for 48 hours at room temperature. The resulting reaction solution was concentrated and dried. The residue was purified by silica gel column chromatography (15 g, chloroform/methanol=10/1) to obtain the title compound (0.05 g) as a colorless solid.

MS(FAB,Pos): m/z=630[M+1]$^+$ $^1$H-NMR(500 Mz,DMSO-d$_6$): δ=1.52–1.62(2H,m),1.78–1.85(2H,m), 2.64

(2H,m),3.90(2H,brs),4.26(2H,d), 4.49(1H,m),4.75(2H,m), 5.05(2H,s),7.27(2H,m),7.33(2H,d), 7.36(4H,m),7.38(1H,m), 7.46(2H,m),7.53(2H,m),7.75(1H,m),7.84(3H,m),8.05(1H,m),8.50(1H,m),8.53(2H,m).

Example 41-4

Synthesis of (S)-2((4-(N-Cbz)aminomethylbenzoyl) amino)-5-(N-Boc-2-picolylaminomethyl)valeric acid 1-naphthalenemethylamide (Compound XXI-4-2)

The compound obtained in Example 41-3 (0.05 g) was dissolved in DMF (1.0 ml) and triethylamine (0.01 g), and the resulting solution was stirred for 1.5 hours at room temperature. The reaction solution was concentrated and dried. Chloroform was added to the residue and the mixture was washed with saturated aqueous solution of ammonium chloride. The organic layer was concentrated. The residue was dried and purified by silica gel column chromatography (6 g, chloroform/methanol=30/1) to obtain the title compound (0.04 g) as colorless oil.

MS(FAB,Pos): m/z=730[M+1]$^+$ $^1$H-NMR(500 Mz,DMSO-d$_6$): δ=1.24, 1.35(9H,2s) 1.50(1H,m),1.59, m), (1H,m),1.73(2H3.21(1H,m),3.32(1H,brs),4.25(2H,d), 4.36, 4.40(2H,2s),4.48(1H,m),4.73(2H,d), 5.05(2H,s),7.15(1H,d), 7.23(1H, m),7.33(3H,m),7.37(4H,m),7.45(2H,m),7.53(2H,m),7.73(1H,m),7.84 (3H,m),7.93(2H,m),8.47(2H,m),8.53(1H,m).

Example 41-5

Synthesis of (S)-2-((4-aminomethylbenzoyl)amino)-5-(N-Boc-2-picolylaminomethyl)valeric acid 1-naphthalenemethylamide (Compound XXII-1)

The compound obtained in Example 41-4 (0.02 g) was dissolved in methanol (0.5 ml). After the addition of 10% Pd—C (0.02 g), the mixture was stirred for 2 hours under hydrogen atmosphere at room temperature. After the reaction, the catalyst was removed by filtration and solvent was removed by distillation. The residue was dried under vacuum to obtain the title compound (0.01 g) as colorless oil.

Example 41-6

Synthesis of (S)-2-((4-guanidinomethylbenzoyl) amino)-5-(2-picolylaminomethyl)valeric acid 1-naphthalenemethylamide [Compound No. 42]

The compound obtained in Example 41-5 (0.01 g) was dissolved in DMF (0.3 ml). After the addition of dimethylpyrazolecarboxyamidine nitrate (0.01 g), the mixture was adjusted to pH 8 with triethylamine and stirred for 3 days. The reaction solution was concentrated. Chloroform was added to the residue and the mixture was washed with saturated aqueous solution of sodium hydrogencarbonate. The organic layer was concentrated and dried under reduced pressure. The residue was purified by silica gel column chromatography (5 g, chloroform/methanol/water=7/3/0.5) to obtain the title compound (0.01 g) as white foam. The foam was dissolved in methanol (0.3 ml) and 4 mol/l hydrochloric acid/dioxane solution (0.3 ml) was added dropwise. The mixture was stirred for 3 hours at room temperature. The reaction solution was concentrated and dried under reduced pressure to obtain a crude product (0.01 g). The crude product was purified by silica gel column chromatography (0.5 g, chloroform/methanol/water=7/3/0.5) and 1 mol/l hydrochloric acid was added. The mixture was concentrated to obtain hydrochloride of the title compound (0.01 g) as white foam.

MS(FAB,Pos): m/z=538[M+1]$^+$ $^1$H-NMR(500 Mz,DMSO-d$_6$): δ=1.75–1.87(4H,m),2.98(2H,brs),4.29 (2H,s),4.46(2H,d), 4.55(1H,m),4.76(2H,d), 7.40–7.45(5H,m), 7.50–7.59(3H,m),7.84–7.90(2H,m),7.93–7.97(3H,m),8.06(1H,m), 8.61(1H,m),8.66(1H,brs),9.22(2H,brs).

EXAMPLE 42

Preparation of N$^α$-(4-(N-2-picolylaminomethyl) benzoyl)-L-arginine 1-naphthalenemethylamide [Compound No. 43]

Example 42-1

Synthesis of N$^α$-Fmoc-N$^G$-Pmc-L-arginine 1-naphthalenemethylamide (Compound XXVII-1)

Commercially available N$^α$-Fmoc-N$^G$-Pmc-L-arginine (301.4 mg) was dissolved in DMF (6.0 ml), and WSCI hydrochloride (132.1 mg) and HOBt (90.3 mg) were added to the solution. After the addition of 1-naphthalenemethylamine (98.0 μl), the solution was stirred for 20 hours at room temperature. After the reaction, the solvent was removed by distillation. The residue was purified by silica gel column chromatography (30 g, chloroform/methanol=20/1) to obtain the title compound (259.7 mg) as white foam.

MS(Fab,pos.): m/z=788[M+1]$^+$ $^1$H-NMR(500 MHz, CDCl$_3$): δ=1.24(6H,s),1.4–1.5(2H,m),1.6–1.7(3H,m),1.75–1.84(1H,m),2.05(3H,s),2.44(3H,s),2.47(3H,s),2.50 (2H, t,J=6.8 Hz),3.0–3.2 (2H,m),4.00(1H,t,J=7.1 Hz),4.21 (2H,d,J=7.1 Hz),4.2–4.3(1H,m),4.69(1H,dd, J=13.4, 5.3 Hz),4.81(1H,dd, J=13.4, 5.3 Hz),5.9–6.2(3H,brs),6.04(1H,brs), 7.15–7.5(11H,m), 7.65(1H,d,J=8.1 Hz),7.70(2H,d,J= 7.6 Hz),7.91(1H,d,J=7.8 Hz).

Example 42-2

Synthesis of N$^α$-(4-(N-Boc-N-2-picolylaminomethyl)benzoyl)-N$^G$-Pmc-L-arginine 1-naphthalenemethylamide (Compound XXIX-1)

The compound obtained in Example 42-1 (200 mg) was dissolved in DMF (4 ml). After the addition of diethylamine (0.4 ml), the mixture was stirred for 30 minutes at room temperature. After the reaction, the solvent was removed by distillation and the residue was dried using a vacuum pump. The residue was dissolved in DMF (4 ml) and WSCI (86.3 mg), HOBt (51.5 mg), and the compound obtained in Example 1-2 (131.2 mg) were added. The mixture was stirred for 3.5 hours at room temperature. After the reaction, the solvent was removed by distillation. The residue was purified by silica gel column chromatography (5 g, chloroform/methanol=25/1) to obtain the title compound (127.1 mg) as white foam.

MS(Fab,pos.): m/z=904[M+1]$^+$ $^1$H-NMR(500 MHz, CDCl$_3$): δ=1.28(6H,s),1.43 and 1.45(9H,brs),1.4–1.5(2H,m), 1.77(2H,t,J=6.8 Hz),1.8–1.95(2H,m),2.06(3H,s), 2.46 (3H,s),2.47(3H,s),2.56(2H,t,J=6.8 Hz),3.1–3.2(1H,m), 3.3–3.4(1H,m),4.44(1H,brs),4.48(1H,brs),4.56(2H,brs),4.70 (1H,dd, J=15.4, 5.8 Hz),4.88(1H,dd,J=15.4, 5.8 Hz),5.9–6.2 (3H,brs), 7.1–7.35(6H,m),7.35–7.45(4H,m),7.64(1H,td,J= 7.6,1.7 Hz), 7.65–7.75(3H,m),7.8(1H,m),7.95(1H,d,J=5.6 Hz),8.52(1H,brs).

Example 42-3

Synthesis of N$^α$-(4-(N-2-picolylaminomethyl) benzoyl)-L-arginine 1-naphthalenemethylamide [Compound No. 43]

The compound obtained in Example 42-2 (90.2 mg) was dissolved in chloroform (0.45 ml) and trifluoroacetic acid (0.45 ml) was added. The mixture was stirred over night at room temperature. After the reaction, the solvent was removed by distillation. The residue was purified by silica gel column chromatography (10 g, chloroform/methanol/water=7/3/0.5). After the addition of 1 mol/l aqueous solution of hydrochloric acid, the product was azeotropically distilled with water to obtain the hydrochloride of the title compound (16.4 mg) as a white solid.

MS(Fab,pos.): m/z=538[M+1]$^+$ $^1$H-NMR(500 MHz, DMSO-d$_6$): δ=1.4–1.6(2H,m),1.7–1.8(1H,m),1.8–1.9(1H, m), 3.1–3.2(2H,m),4.31(2H,s),4.54(2H,dd,J=14.0, 5.6 Hz), 4.77(2H,d,J=5.6 Hz), 7.4–7.7(11H,m),7.8–8.1(7H,m), 8.4–8.55(3H,m),9.5–9.7 (2H,brs).

EXAMPLE 43

Preparation of N$^α$-(4-(N-2-picolylaminomethyl) naphthoyl)-L-arginine 1-naphthalenemethylamide [Compound No. 44]

Example 43-1

Synthesis of methyl 4-(N-Boc-N-2-picolylaminomethyl)-1-naphthalene carboxylic acid (Compound VI-8)

The compound obtained in Example 17-3 (1.500 g) was dissolved in DMF (30 ml). After the addition of potassium carbonate (750.9 mg) and 2-picolylamine (1.63 ml), the mixture was stirred for 12 hours at room temperature. After the reaction, the solvent was removed by distillation. The residue was dissolved in chloroform. The solution was washed with distilled water, and dried over anhydrous sodium sulfate. The solvent was removed by distillation and the residue was dried under reduced pressure to obtain a crude product (1.87 g) as orange oil. The oil was dissolved in DMF (30 ml). After the addition of triethylamine (1.5 ml) and di-t-butyldicarbonate (1.85 ml, 8.06 mmol), the mixture was stirred for 22 hours at room temperature. After the reaction, the reaction solution was concentrated and the residue was purified by silica gel column chromatography (100 g, hexane/ethyl acetate=3/2) to obtain the title compound (1.60 g) as yellow viscous oil.

MS(FAB,Pos.): m/z=407[M+1]$^+$ $^1$H-NMR(500 MHz, CDCl$_3$): δ=1.45(9H,s),4.00(3H,s),4.43 and 4.61(2H, 2s), 5.04 and 5.11(2H,2s),7.10–7.33(2H,m),7.34–7.40(1H,m), 7.52–7.65(3H,m), 8.00–8.23(2H,m),8.51(1H,d,J=4.4 Hz), 8.91–8.96(1H,m).

Example 43-2

Synthesis of 4-(N-Boc-N-2-picolylaminomethyl)-1-naphthalene carboxylic acid (Compound VII-11)

The compound obtained in Example 43-1 (1.60 g) was dissolved in THF (16 ml) and methanol (16 ml). After the addition of 1 mol/l aqueous solution of sodium hydroxide (16 ml), the mixture was stirred for 16 hours at room temperature. After the reaction, the solvent was removed by distillation. The residue was dissolved in distilled water and 1 mol/l aqueous solution of hydrochloric acid was added to produce a precipitate. The precipitate was collected by filtration and dried to obtain the title compound (1.3537 g) as a white solid.

MS(FAB,Pos.): m/z=393[M+1]$^+$ $^1$H-NMR(500 MHz, DMSO-d$_6$): δ=1.33 and 1.37(9H,2s),4.41 and 4.51 (2H, 2s),5.02 and 5.07(2H,2s),7.19–7.28(2H,m),7.36–7.45(1H, m), 7.62(1H,td,J=6.9, 1.4 Hz),7.67(1H,td,J=6.9, 1.4 Hz), 7.75(1H,td, J=7.6,1.8 Hz),8.09–8.23(2H,m),8.51(1H,brs), 8.91(1H,d,J=7.8 Hz).

Example 43-3

Synthesis of N$^α$-(4-(N-Boc-N-2-picolylaminomethyl)naphthoyl)-N$^G$-Pmc-L-arginine 1-naphthalenemethylamide (Compound XXIX-2)

The compound obtained in Example 42-1 (253.4 mg) was dissolved in DMF (5 ml). After the addition of diethylamine (0.5 ml), the mixture was stirred for 4 hours at room temperature. After the reaction, the solvent was removed by distillation and the residue was dried under vacuum. The product was dissolved in DMF (5 ml) and WSCI hydrochloride (91.8 mg), HOBt (54.1 mg), and the compound obtained in Example 43-2 (141.2 mg) were added. The mixture was stirred for 17 hours at room temperature. After the reaction, the solvent was removed by distillation. The residue was dissolved in chloroform. The solution was washed with 1 mol/l aqueous solution of hydrochloric acid, 1 mol/l aqueous solution of sodium hydroxide, and saturated brine, and dried over anhydrous sodium sulfate. The solution was concentrated under reduced pressure and the residue was purified by silica gel column chromatography (15 g, chloroform/methanol=30/1) to obtain the title compound (252.5 mg) as yellow viscous oil.

MS(FAB,Pos.): m/z=954[M+1]$^+$ $^1$H-NMR(500 MHz, CDCl$_3$): δ=1.28(6H,s),1.44 and 1.49(9H,2s),1.52–1.65(2H, m),1.70–1.82(3H,m),1.83–1.98(1H,m),2.05(3H,s),2.44 and 2.45(6H,2s), 2.54(2H,t,J=6.6 Hz),3.10–3.33(2H,m),4.37 and 4.51(2H,2s),4.69–4.91(3H,m),4.96 and 5.00(2H,2s), 6.14(3H,br),7.08–7.16(2H,m),7.20–7.35(3H,m),7.37–7.57 (6H,m), 7.58–7.61(1H,m),7.69(1H,d,J=8.1 Hz),7.77–7.82 (1H,m),7.97(1H, br),8.10–8.21(2H,m),8.49(1H,br).

Example 43-4

Synthesis of N$^α$-(4-(N-2-picolylaminomethyl) naphthoyl)-L-arginine 1-naphthalenemethylamide [Compound No. 44]

The compound obtained in Example 43-3 (119.7 mg) was dissolved in chloroform (1.2 ml). After the solution was cooled to 0° C., trifluoroacetic acid (1.2 ml) was added. The mixture was stirred for 4 hours at room temperature. After the reaction, the solvent was removed by distillation. The residue was dried using a vacuum pump and purified by silica gel column chromatography (5 g, chloroform/methanol/water=7/3/0.5). Fractions obtained were concentrated. The concentrated fractions were dissolved in 1 mol/l aqueous solution of hydrochloric acid. The solution was concentrated, azeotropically distilled with water, and washed with ether to obtain the title compound (25.5 mg) as a white solid.

MS(FAB,Pos.): m/z=588[M+1]$^+$ $^1$H-NMR(500 MHz, DMSO-d$_6$): δ=1.53–1.70(2H,m),1.70–1.80(1H,m), 1.80–1.92(1H,m),3.09–3.20(2H,m),4.47(2H,s),4.55–4.70 (1H,m), 4.78(2H,s),4.80–4.95(2H,m),6.8(1H,br),7.40(2H, br),7.46–7.50(2H,m),7.54–7.64(5H,m),7.67–7.72(2H,m), 7.80(2H,d,J=7.3 Hz), 7.87(1H,d,J=8.3 Hz),7.93(1H,td,J= 7.8,1.7 Hz),7.96–7.99(1H,m), 8.11–8.13(1H,m),8.26(1H,d, J=8.5 Hz),8.30(1H,d,J=8.5 Hz),8.71(1H,d,J=4.9 Hz),8.74 (1H,t,J=5.9 Hz),8.85(1H,d,J=7.8 Hz),9.84(2H,br).

EXAMPLE 44

Preparation of N$^α$-(4-(imidazol-2-ylmethyl) aminomethylnaphthoyl)-L-arginine 1-naphthalenemethylamide [Compound No. 45]

Example 44-1

Synthesis of N$^α$-(4-((N-Boc-N-imidazol-2-ylmethyl) aminomethyl)naphthoyl)-N$^G$-Pmc-L-arginine 1-naphthalenemethylamide (Compound XXIX-3)

The compound obtained in Example 42-1 (110.0 mg) was dissolved in DMF (2.2 ml). After the addition of diethylamine (0.22 ml), the mixture was stirred for 2 hours at room temperature. After the reaction, the solvent was removed by distillation and the residue was dried under vacuum. The product was dissolved in DMF (2 ml) and WSCI hydrochloride (40.0 mg), HOBt (22.5 mg), and the compound obtained in Example 17-4 (53.3 mg) were added. The mixture was stirred for 17 hours at room temperature. After the reaction, the solvent was removed by distillation. The residue was dissolved in chloroform, washed with 1 mol/l aqueous solution of hydrochloric acid, 1 mol/l aqueous solution of sodium hydroxide, and saturated brine, and dried over anhydrous sodium sulfate. The solution was concentrated under reduced pressure and the residue obtained was purified by silica gel column chromatography (7 g, chloroform/methanol=25/1) to obtain the title compound (59.7 mg) as yellow viscous oil.

MS(FAB,Pos.): m/z=943[M+1]$^+$ $^1$H-NMR(500 MHz, CDCl$_3$): δ=1.28(6H,s),1.49(9H,s),1.50–1.70(2H, m),1.76 (2H,t,J=6.8 Hz),1.70–1.81(1H,m),1.83–1.97(1H,m),2.06 (3H,s),2.45 and 2.46(6H, 2s),2.55(2H,t,J=6.6 Hz),3.08–3.30 (2H, m),4.25(2H,s),4.70–4.80(2H,m), 4.81–4.95(3H,m), 6.17(3H,br), 6.87(2H,s),7.18(1H,d,J=7.3 Hz),7.31(1H,tJ= 7.8 Hz), 7.36–7.51 (7H,m),7.65–7.78(1H,m),7.71(1H,d,J= 8.1 Hz),7.80–7.83(1H,m), 7.93–8.00(1H,m),8.13(1H,d,J= 8.5 Hz).

Example 44-2

Synthesis of N$^α$-(4-((N-imidazol-2-ylmethyl)aminomethyl)naphthoyl)-L-arginine 1-naphthalenemethylamide [Compound No. 45]

The compound obtained in Example 44-1 (53.7 mg) was dissolved in chloroform. (1 ml). After the solution was cooled to 0° C., trifluoroacetic acid (1 ml) was added. The mixture was stirred for 5 hours at room temperature. After the reaction, the solvent was removed by distillation. The residue was dried using a vacuum pump and purified by silica gel column chromatography (2.5 g, chloroform/methanol/water=7/3/0.5). Fractions were concentrated. The concentrated fractions were dissolved in 1 mol/l aqueous solution of hydrochloric acid. The solution was concentrated, azeotropically distilled with water, and washed with ether to obtain the title compound (6.0 mg) as a white solid.

MS(FAB,Pos.): m/z=577[M+1]$^+$ $^1$H-NMR(500 MHz, DMSO-d$_6$+D$_2$O): δ=1.53–1.70(2H,m),1.70–1.80 (1H, m),1.80–1.90(1H,m),3.08–3.20(2H,m),4.55–4.62(3H,m), 4.77–4.95(4H,m),7.47–7.51(1H,m),7.54–7.65(5H,m),7.66 (1H,d, J=7.3 Hz),7.71(1H,t,J=7.1 Hz),7.75(1H,d, 7.3 Hz), 7.89(1H,d,J=8.1 Hz),7.97–8.00(1H,m),8.09–8.12(1H,m), 8.22(1H,d,J=8.5 Hz), 8.26(1H,d,J=8.5 Hz).

EXAMPLE 45

Preparation of N$^α$-(2-(N-2-picolylaminomethyl)pyridin-5-ylcarbonyl)-L-arginine 1-naphthalenemethylamide [Compound No. 46]

Example 45-1

Synthesis of N$^α$-(2-(N-Boc-N-2-picolylaminomethyl)pyridin-5-ylcarbonyl)-N$^G$-Pmc-L-arginine 1-naphthalenemethylamide (Compound XXIX-4)

The compound obtained in Example 42-1 (116.8 mg) was dissolved in DMF (2 ml). After the addition of diethylamine (0.2 ml), the mixture was stirred for 2 hours at room temperature. After the reaction, the solvent was removed by distillation and the residue was dried under vacuum. The product was dissolved in DMF (2 ml) and WSCI hydrochloride (44.5 mg), HOBt (24.4 mg), and the compound obtained in Example 12-3 (50.1 mg) were added. The mixture was stirred for 17 hours at room temperature. After the reaction, the solvent was removed by distillation. The residue was dissolved in chloroform. The solution was washed with 1 mol/l aqueous solution of hydrochloric acid, 1 mol/l aqueous solution of sodium hydroxide, and saturated brine, and dried over anhydrous sodium sulfate. The solution was concentrated under reduced pressure and purified by silica gel column chromatography (10 g, chloroform/methanol=15/1) to obtain the title compound (118.0 mg) as yellow viscous oil.

MS(FAB,Pos.): m/z=905[M+1]$^+$ $^1$H-NMR(500 MHz, DMSO-d$_6$): δ=1.23(6H,s),1.31(9H,s),1.49–1.68(2H, m),1.73(2H,t,J=6.8 Hz),1.69–1.79(1H,m),1.79–1.90(1H,m), 2.00(3H,s),2.45 and 2.46(6H,2s),2.55(2H,t,J=6.6 Hz), 2.99–3.12(2H, m),4.47–4.55(1H,m),4.52, 4.56, 4.60 and 4.65(4H,4s),4.73(1H, dd,J=15.2,5.6 Hz),4.78(1H,dd,J=15.2, 5.6 Hz),6.37(2H,br),6.67(1H,br),7.25–7.40(3H,m), 7.45–7.47(2H,m),7.50–7.56(2H,m),7.78(1H,td,J=7.6,1.7 Hz),7.82–7.86(1H,m),7.92–7.96(1H,m),8.03–8.06(1H,m), 8.21(1H,dd,J=8.3,2.0 Hz),8.51(1H,d,J=4.9 Hz),8.58(1H,br), 8.73(1H,d, J=7.1 Hz),8.98–8.99(1H,m).

Example 45-2

Synthesis of N$^α$-(2-(N-2-picolylaminomethyl)pyridin-5-ylcarbonyl)-L-arginine 1-naphthalenemethylamide [Compound No. 46]

The compound obtained in Example 45-1 (45.0 mg) was dissolved in chloroform (0.5 ml). After the solution was cooled to 0° C., trifluoroacetic acid (0.5 ml) was added. The mixture was stirred for 5 hours at room temperature. After the reaction, the solvent was removed by distillation. The residue was dried using a vacuum pump and purified by silica gel column chromatography (2 g, chloroform/methanol/water=7/3/0.5). Fractions were concentrated. The concentrated fractions were dissolved in 1 mol/l aqueous solution of hydrochloric acid. The solution was concentrated, azeotropically distilled with water, and washed with ether to obtain the title compound (10.1 mg) as a white solid.

MS(FAB,Pos.): m/z=539[M+1]$^+$ $^1$H-NMR(500 MHz, DMSO-d$_6$): δ=1.48–1.64(2H,m),1.78–1.95(2H,m), 3.09–3.19 (2H,m),4.43(2H,s),4.49(2H,s),4.50–4.58(1H,m), 4.77(1H,d,J=5.6 Hz),6.90(2H,br),7.40(1H,br),7.45–7.50 (3H,m), 7.52–7.57(3H,m),7.64(1H,d,J=8.1 Hz),7.78–7.88 (2H,m),7.91(1H, td,J=7.6,1.7 Hz),7.92–7.98(1H,m), 8.05–8.10(1H,m),8.39(1H,d, J=7.1 Hz),8.66(1H,d,J=4.9 Hz),8.98(1H,br),9.14(1H,br),9.83(2H, br).

EXAMPLE 46

Preparation of N$^α$-(5-(N-2-picolyl-aminomethyl)thiophene-2-ylcarbonyl)-L-arginine 1-naphthalenemethylamide [Compound No. 47]

Example 46-1

Synthesis of N$^α$-(5-(N-Boc-N-2-picolyl)aminomethylthiophen-2-ylcarbonyl)-N$^G$-Pmc-L-arginine 1-naphthalenemethylamide (Compound XXIX-5)

The compound obtained in Example 42-1 (199.5 mg) was dissolved in DMF (4 ml). After the addition of diethylamine (0.4 ml), the mixture was stirred for 4 hours at room temperature. After the reaction, the solvent was removed by distillation and the residue was dried under vacuum. The product was dissolved in DMF (2 ml) and WSCI hydrochloride (72.9 mg), HOBt (40.4 mg), and the compound obtained in Example 14-2 (93.0 mg) were added. The mixture was stirred for 17 hours at room temperature. After the reaction, the solvent was removed by distillation. The residue was dissolved in chloroform. The solution was washed with 0.1 mol/l aqueous solution of hydrochloric acid, 1 mol/l aqueous solution of sodium hydroxide, and saturated brine, and dried over anhydrous sodium sulfate. The solution was concentrated under reduced pressure and the resultant residue was purified by silica gel column chromatography (10 g, chloroform/methanol=30/1) to obtain the title compound (142.1 mg) as pale yellow foam.

MS(FAB,Pos.): m/z=910[M+1]$^+$ $^1$H-NMR(500 MHz, DMSO-d$_6$): δ=1.2–1.6(2H,m),1.23(6H,s),1.30 and 1.47(9H, 2s), 1.63–1.82(2H,m), 1.73(2H,t,J=6.8 Hz),2.00(3H,s),2.45 (3H,s),2.46(3H,s),2.54(2H, t,J=6.8 Hz),2.99–3.10(2H,m), 4.38–4.45(3H,m),4.58 and 4.65(2H,2s),4.73(1H,dd,J=15.1, 5.4 Hz),4.76(1H,dd,J=15.1,5.4 Hz),6.39(2H,brs),6.68(1H, brs),7.00(1H,d,J=12.9 Hz),7.18–7.24(1H, m),7.18–7.24(1H, m),7.44–7.48(2H,m),7.50–7.55(2H,m),7.74(1H, m),7.77 (1H,td,J=7.6,1.7 Hz),7.83–7.86(1H,m), 7.92–7.96(1H, m),8.02–8.05(1H,m),8.51–8.58(3H,m).

Example 46-2

Synthesis of N$^α$-(5-(N-2-picolylaminomethyl) thiophen-2-ylcarbonyl)-L-arginine 1-naphthalenemethylamide [Compound No. 47]

The compound obtained in Example 46-1 (121.6 mg) was dissolved in chloroform (1 ml). After the solution was cooled to 0° C., trifluoroacetic acid (1 ml) was added. The mixture was stirred for 7 hours at room temperature. After the reaction, the solvent was removed by distillation. The residue was dried using a vacuum pump and purified by silica gel column chromatography (4 g, chloroform/methanol/water=7/3/0.5). Fractions were concentrated. The concentrated fractions were dissolved in 1 mol/l aqueous solution of hydrochloric acid. The solution was concentrated, azeotropically distilled with water, and the solid obtained was washed with ether to obtain the title compound (51.6 mg) as a white solid.

MS(FAB,Pos.): m/z=544[M+1]$^+$ $^1$H-NMR(500 MHz, DMSO-d$_6$): δ=1.42–1.61(2H,m),1.74–1.90(2H,m), 3.05–3.19(2H,m),4.30(2H,s),4.43–4.51(3H,m),4.75(2H,d, J=5.9 Hz),6.80–7.10(2H,brs), 7.32–7.60(1H,brs),7.36(1H,d, J=3.7 Hz),7.43–7.52(4H,m),7.52–7.57(2H,m),7.58(1H,d,J= 8.1 Hz), 7.82–7.89(2H,m),7.92(1H,td,J=7.8,2.0 Hz), 7.93–7.96(1H,m), 7.99(1H,d,J=3.7 Hz),8.05–8.08(1H,m), 8.66(1H,dd,J=4.9,1.7 Hz), 8.73(1H,d,J=5.9 Hz),8.81(1H,d, J=8.1 Hz),9.94(2H,brs).

EXAMPLE 47

Preparation of N$^α$-(4-(imidazol-2-ylmethyl) aminomethylnaphthoyl)-L-arginine 2-(3-indolyl) ethylamide [Compound No. 48]

Example 47-1

Synthesis of N$^α$-Fmoc-N$^G$-Pmc-L-arginine 2-(3-indolyl)ethylamide (Compound XXVII-2)

WSCI hydrochloride (0.954 g) was added to a solution of commercially available N$^α$-Fmoc-N$^G$-Pmc-L-arginine (2,000 g), tryptamine (0.798 g), and HOBt (0.673 g) in anhydrous DMF (20 ml). The mixture was stirred for 16 hours at room temperature. The solvent was removed by distillation. The residue was dissolved in chloroform (20 ml). The solution was washed sequentially with 1 mol/l aqueous solution of hydrochloric acid (30 ml) and saturated aqueous solution of sodium hydrogencarbonate (30 ml), and dried over anhydrous magnesium sulfate. The solvent was removed by distillation and the residue was purified by silica gel column chromatography (75 g, 2% methanol/ chloroform) to obtain the title compound (1.606 g) as a pale yellow solid.

$^1$H-NMR(500 MHz,CDCl$_3$): δ=1.26(6H,s),1.24–1.29(2H, m),1.42–1.52(1H,m), 1.55–1.65(1H,m),1.74(2H,t,J=6.8 Hz),2.09(3H,s),2.55(3H,s),2.55–2.58(2H, m),2.58(3H,s), 2.91(3H,m),3.00–3.18(2H, m),3.42–3.52(1H,m),3.60–3.70 (1H,m),4.00–4.08(1H,m),4.08(1H,t,J=6.8 Hz),4.25–4.32 (2H,m),5.8–5.9(1H,bs),6.0–6.1(2H, bs),6.6–6.7(1H,bs),6.95 (1H,s),7.01(1H,t,J=7.3 Hz),7.10(1H, t,J=8.1 Hz),7.21–7.32 (4H,m),7.35–7.40(2H,m),7.50(2H,d,J=8.3 Hz),7.52(1H,d, J=7.6 Hz),7.73(2H,d,J=7.6 Hz),8.64(1H,s).

Example 47-2

Synthesis of N$^{α-}$(4-(N-Boc-N-imidazol-2-ylmethyl) aminomethylnaphthoyl)-N$^G$-Pmc-L-arginine 2-(3-indolyl)ethylamide (Compound XXIX-6)

The compound obtained in Example 47-1 (0.322 g) was dissolved in anhydrous DMF (10 ml). After the addition of diethylamine (0.059 g), the mixture was stirred for 2.5 hours at room temperature and the solvent was removed by distillation. The compound obtained in Example 17-4 (0.153 g) and HOBt (0.0595 g) were added to the residue. The mixture was dissolved in anhydrous DMF (10 ml) and WSCI hydrochloride (0.084 g) was added. The mixture was stirred for 12 hours at room temperature. After the addition of water (0.5 ml), the reaction solution was concentrated. Chloroform (5 ml) was added to the residue. The mixture was washed with 0.25 mol/l aqueous solution of hydrochloric acid (4 ml) and saturated aqueous solution of sodium hydrogencarbonate (4 ml), and processed through a diatomaceous column to remove the solvent by distillation. The resulting mixture was purified by silica gel column chromatography (5 g, 0–6% methanol/chloroform) to obtain the title compound (0.0579 g) as a white foam.

$^1$H-NMR(500 MHz,CDCl$_3$): δ=1.23–1.38(1H,m),1.29 (6H,s),1.45–1.75(2H,m),1.52(9H,s),1.78(2H,t,J=6.6 Hz), 1.78–1.88(1H,m),2.09(3H,s),2.55(3H,s),2.56(3H,s),2.60 (2H,t,J=6.8 Hz),2.90–3.00(2H,m),3.10–3.30(2H,m), 3.44–3.54(1H,m),3.60–3.70(1H,m),4.27(2H,s),4.58–4.65 (1H,m),4.85(1H,m),4.93(1H,d,J=15.9 Hz),6.05–6.12(1H, bs),6.12–6.20(1H,bs),6.80–6.96(2H,bs),6.99(1H,s), 7.05 (1H,dt, 1.5 Hz, 9.3 Hz),7.13(1H,t,J=7.3 Hz),7.21(1H,d,J= 6.3Hz), 7.34(2H,d,J=7.8 Hz),7.44–7.52(2H,m),7.56(1H,d, J=7.3 Hz), 7.97(1H,d,J=7.3 Hz),8.23(1H,d,J=7.6 Hz).

Example 47-3

Synthesis of N$^α$-(4-(imidazol-2-ylmethyl) aminomethylnaphthoyl)-L-arginine 2-(3-indolyl) ethylamide [Compound No. 48]

The compound obtained in Example 47-2 (0.0499 g) was dissolved in chloroform (1 ml). After the solution was cooled with ice, trifluoroacetic acid (0.5 ml) was added dropwise. After the solution was stirred for 5 hours at room temperature, the solvent was removed by distillation. 1 mol/l hydrochloric acid (3 ml) and chloroform (2 ml) were added to the residue. The water layer was removed, followed by washing with chloroform (2 ml) and removal of solvent by distillation. After the addition of 1 mol/l methanol solution of hydrochloric acid to the obtained residue, the solvent was removed by distillation. The solid obtained by the addition of water (0.25 ml) and acetone (5 ml) was collected and purified by silica gel column chromatography (1.5 g, chloroform/methanol/32% acetic acid aqueous solution=7/3/0.5) The resulting oily substance was dissolved in 1 mol/l aqueous solution of hydrochloric acid (1 ml). The solvent was removed by distillation and the residue was dissolved in methanol. Ethyl acetate was added to the solution to cause a solid to precipitate. After the solvent was removed by distillation, the residue was dried under vacuum to obtain hydrochloride of the title compound (0.0040 g) as a white solid.

MS(FAB,Pos.): m/z=580[M+1]$^+$

EXAMPLE 48

Preparation of N$^\alpha$-(4-(imidazol-2-ylmethyl)aminomethylnaphthoyl)-L-arginine(1'S)-(1'-(1-naphthyl)ethyl)amide [Compound No. 49]

Example 48-1

Synthesis of N$^\alpha$-Fmoc-N$^G$-Pmc-L-arginine (1'S)-(1'-(1-naphthyl)ethyl)amide (Compound XXVII-3)

WSCI hydrochloride (0.636 g) was added to a solution of commercially available N$^\alpha$-Fmoc-N$^G$-Pmc-L-arginine (1.334 g), (S)-1-(1-naphthyl)ethylamine (0.568 g), and HOBt (0.449 g) in anhydrous DMF (13 ml). The mixture was stirred for 16 hours at room temperature. The solvent was removed by distillation. The residue was dissolved in chloroform (20 ml). The solution was washed sequentially with 1 mol/l aqueous solution of hydrochloric acid (30 ml) and saturated aqueous solution of sodium hydrogencarbonate (30 ml), and dried over anhydrous magnesium sulfate. The residue obtained by evaporating the solvent was purified by silica gel column chromatography (50 g, 2% methanol/chloroform) to obtain the title compound (1.949 g) as colorless oil.

$^1$H-NMR(500 MHz,CDCl$_3$): δ=1.26(3H,s),1.27(3H,s, Hz),1.26–1.42(2H,m),1.43–1.55(1H,m),1.58(3H,d,J=6.8 Hz),1.75(2H,t,J=6.6 Hz),2.07(3H,s), 2.51(3H,s,), 2.52(3H, s,), 2.57(2H,t,J=6.8 Hz),3.00–3.10(2H,m),4.10(1H,t,J=7.3 Hz),4.25–4.55(3H,m), 5.65–5.70(1H,bs),5.70–5.80(1H,bs), 5.91(1H,d, J=8.5 Hz),7.23–7.26(2H,m),7.35–7.45(5H,m), 7.28–7.45(3H,m),7.70(1H,d,J=8.3 Hz),7.74(2H,d,J=7.6 Hz),7.80(1H,d,J=8.3 Hz),7.88–7.98(1H, bs).

Example 48-2

Synthesis of N$^\alpha$-(4-(N-Boc-N-imidazol-2-ylmethyl)aminomethylnaphthoyl)-N$^G$-Pmc-L-arginine (1'S)-(1'-(1-naphthyl)ethyl)amide (Compound XXIX-7)

The compound obtained in Example 48-1 (0.326 g) was dissolved in anhydrous DMF (10 ml). After the addition of diethylamine (0.0604 g), the mixture was stirred for 2.5 hours at room temperature and the solvent was removed by distillation. The compound obtained in Example 17-4 (0.157 g) and HOBt (0.0610 g) were added to the residue. The mixture was dissolved in anhydrous DMF (10 ml) and WSCI hydrochloride (0.0861 g) was added. The mixture was stirred for 12 hours at room temperature. After the addition of water (0.5 ml), the reaction solution was concentrated. Chloroform (5 ml) was added to the residue. The mixture was washed with 0.25 mol/l aqueous solution of hydrochloric acid (4 ml) and saturated aqueous solution of sodium hydrogencarbonate (4 ml), and processed through a diatomaceous column to evaporate the solvent. The resulting mixture was purified by silica gel column chromatography (5 g, 0–6% methanol/chloroform) to obtain the title compound (0.0672 g) as white foam.

$^1$H-NMR(500 MHz,CDCl$_3$): δ=1.25–1.36(1H,m),1.29 (6H,s),1.48(9H, s),1.60(3H,d,J=6.8 Hz),1.77(2H,t,J=6.6 Hz),2.07(3H,s),2.49(6H, s),2.58(2H,t,J=6.6 Hz),3.00–3.30 (2H,m),4.20–4.35(2H,m), 4.72–4.82(1H,m),4.85–4.95(2H, m),5.80–5.90(1H,m),6.05–6.15(1H,bs),6.15–6.25(2H,bs), 6.82–7.00(2H,m),7.21(1H,d,J=7.3 Hz),7.38(2H,t,J=7.8 Hz), 7.30–7.60(5H,m),7.74(1H,d,J=8.3 Hz), 7.83(1H,d,J=6.8 Hz),7.94–8.06(2H,m),8.22(1H,d,J=7.6 Hz).

Example 48-3

Synthesis of N$^\alpha$-(4-(imidazol-2-ylmethyl)aminomethylnaphthoyl)-L-arginine(1'S)-(1'-(1-naphthyl)ethyl)amide [Compound No. 49]

The compound obtained in Example 48-2 (0.172 g) was dissolved in chloroform (1.7 ml). After the solution was cooled with ice, trifluoroacetic acid (1.7 ml) was added. The mixture was stirred for 5 hours at room temperature, followed by evaporation of the solvent. 1 mol/l hydrochloric acid (5 ml) and chloroform (3 ml) were added to the residue. The water layer was removed, followed by washing with chloroform (3 ml) and the solvent was removed by distillation. 1 mol/l hydrochloric acid methanol solution was added and the solvent was removed by distillation. The resulting oily substance was dissolved in water (0.5 ml). A solid obtained by the addition of acetone (5 ml) was separated by centrifugation, the supernatant was removed, and the solvent was removed by distillation. The resulting solid was dissolved in 1 mol/l aqueous solution of hydrochloric acid (1 ml). The solvent was removed by distillation and the residue was dissolved in methanol. Ethyl acetate was added to the solution to cause a solid to precipitate. The solvent was removed by distillation to obtain hydrochloride of the title compound (0.0891 g) as a white solid.

MS(FAB,Pos.): m/z=591[M+1]$^+$ $^1$H-NMR(500 MHz, DMSO-d$_6$): δ=1.50–1.63(2H,m)1.56(3H,d,J=6.8 Hz), 1.64–1.76(1H,m)1.78–1.86(1H,m) 3.08–3.18(2H,m) 4.58–4.65(3H, m),4.82(2H,s),5.78(1H,quint,J=7.3 Hz), 7.28–7.71(9H,m) 7.74(1H, t,J=5.4 Hz),7.79(1H,d,J=7.3 Hz), 7.85(1H,d,J=8.3 Hz),7.96(1H,d, J=8.1 Hz),8.15(1H,d,J=8.8 Hz),8.26(1H,d,J=7.6 Hz),8.30(1H,d,J=8.5 Hz),8.72(1H,d,J= 8.1 Hz),8.80(1H,d,J=7.8 Hz).

EXAMPLE 49

Preparation of N$^\alpha$-(4-(imidazol-2-ylmethyl)aminomethylnaphthoyl)-L-arginine(1'R)-(1'-(1-naphthyl)ethyl)amide [Compound No. 50]

Example 49-1

Synthesis of N$^\alpha$-Fmoc-N$^G$-Pmc-L-arginine (1'R)-(1'-(1-naphthyl)ethyl)amide (Compound XXVII-4)

WSCI hydrochloride (0.954 g) was added to a solution of commercially available N$^\alpha$-Fmoc-N$^G$-Pmc-L-arginine (2.00 g), (R)-1-(1-naphthyl)ethylamine (0.853 g), and HOBt (0.674 g) in anhydrous DMF (20 ml). The mixture was stirred for 16 hours at room temperature. The solvent was removed by distillation. The residue was dissolved in chloroform (20 ml). The solution was washed sequentially with 1 mol/l aqueous solution of hydrochloric acid (30 ml) and saturated aqueous solution of sodium hydrogencarbonate (30 ml), and dried over anhydrous sodium sulfate. The residue obtained by evaporating the solvent was purified by silica gel column chromatography (50 g, 2% methanol/chloroform) to obtain the title compound (1.122 g) as colorless oil.

$^1$H-NMR(500 MHz,CDCl$_3$): δ=1.26(3H,s),1.26(3H,s), 1.45–1.78(3H, m),1.56(3H,d,J=6.8 Hz),1.75(2H,t,J=6.8 Hz),1.80–1.90(1H,m), 2.08(3H,s),2.52(3H,s), 2.55(3H,s), 2.52–2.57(2H,m),3.1–3.2(1H,m),3.2–3.3(1H,m), 4.04(1H,t, J=7.1 Hz),4.18–4.28(3H,m), 5.81(1H,t,J=7.3 Hz),5.9–6.0 (1H,bs), 6.0–6.1(2H,bs), 7.18–7.55(10H,m),7.67(1H,d,J= 8.3 Hz),7.72(2H,d,J=7.6 Hz),7.77(1H,d, J=8.1 Hz),8.04(1H, d,J=8.3 Hz).

Example 49-2

Synthesis of N$^α$-(4-(N-Boc-N-imidazol-2-ylmethyl) aminomethylnaphthoyl)-N$^G$-Pmc-L-arginine (1'R)- (1'-(1-naphthyl)ethyl)amide (Compound XXIX-8)

The compound obtained in Example 49-1 (0.326 g) was dissolved in anhydrous DMF (10 ml). After the addition of diethylamine (0.0604 g), the mixture was stirred for 2.5 hours at room temperature and the solvent was removed by distillation. The compound obtained in Example 17-4 (0.157 g) and HOBt (0.0610 g) were added to the residue. The mixture was dissolved in anhydrous DMF (10 ml) and WSCI hydrochloride (0.0861 g) was added. The mixture was stirred for 12 hours at room temperature. After the addition of water (0.5 ml), the reaction solution was concentrated. Chloroform (5 ml) was added to the residue. The mixture was washed with 0.25 mol/l aqueous solution of hydrochloric acid (4 ml) and saturated aqueous solution of sodium hydrogencarbonate (4 ml), and processed through a diatomaceous column to remove the solvent by distillation. The resulting mixture was purified by silica gel column chromatography (5 g, 0–6% methanol/chloroform) to obtain the title compound (0.0780 g) as white foam.

$^1$H-NMR(500 MHz,CDCl$_3$): δ=1.22–1.32(1H,m),1.29 (3H,s),1.48(9H, s),1.40–1.70(2H,m),1.60(3H,d,J=6.8 Hz), 1.77(2H,t,J=6.8 Hz), 1.85–2.00(1H,m), 2.08(3H,s),2.50(3H, s),2.52(3H,s),2.57(2H,t, J=6.8 Hz),3.06–3.26(2H,m),4.23 (2H,s),4.62–4.72(2H,m),4.80–4.95(2H,m),5.80–5.90(1H, m),6.08–6.18(1H,bs),6.80–6.98(2H, bs),7.12(1H,d,J=7.1 Hz),7.29(1H,t,J=7.8 Hz),7.30–7.46(5H,m), 7.52(1H,d,J=7.3 Hz),7.67(1H,d,J=8.3 Hz),7.79(1H,d,J=7.6 Hz),7.94 (1H,d, J=9 Hz),8.02–8.12(2H,m).

Example 49-3

Synthesis of N$^α$-(4-(imidazol-2-ylmethyl) aminomethylnaphthoyl)-L-arginine(1'R)-(1'-(1-naphthyl)ethyl)amide [Compound No. 50]

The compound obtained in Example 49-2 (0.1328 g) was dissolved in chloroform (1.3 ml). After the solution was cooled with ice, trifluoroacetic acid (1.3 ml) was added. The mixture was stirred for 5 hours at room temperature, followed by evaporation of the solvent. 1 mol/l hydrochloric acid (5 ml) and chloroform (3 ml) were added to the residue. The water layer was removed, followed by washing with chloroform (3 ml) and evaporation of the solvent. 1 mol/l hydrochloric acid methanol solution was added and the solvent was removed by distillation. The resulting oily substance was dissolved in water (0.25 ml). A solid obtained by the addition of acetone (5 ml) was separated by centrifugation, the supernatant was removed, and the solvent was removed by distillation. The resulting solid was dissolved in 1 mol/l aqueous solution of hydrochloric acid (1 ml). The solvent was removed by distillation and the residue was dissolved in methanol. Ethyl acetate was added to the solution to cause a solid to precipitate. The solvent was removed by distillation to obtain hydrochloride of the title compound (0.0891 g) as a white solid.

MS(FAB,Pos.): m/z=591[M+1]$^+$ $^1$H-NMR(500 MHz, DMSO-d$_6$): δ=1.55(3H,d,J=6.8 Hz),1.50–1.70(2H,m), 1.70–1.80(1H,m),1.80–1.90(1H,m),3.18(2H,q,J=6.3 Hz), 4.58–4.64(3H,m),4.83(2H,s), 5.75(1H,quint.,J=7.1 Hz), 7.46–7.72(9H, m),7.78(2H,d,J=7.1 Hz),7.86(1H,d,J=8.1 Hz),7.94–7.97(1H,m) 8.14–8.17(1H,m)8.19(1H,d,J=8.5 Hz),8.29(1H,d,J=8.8 Hz),8.80(2H,d,J=8.1 Hz).

EXAMPLE 50

Preparation of N$^α$-(4-(imidazol-2-ylmethyl) aminomethylnaphthoyl)-L-arginine 4-hexadecylaminobenzylamide [Compound No. 51]

Example 50-1

Synthesis of N$^α$-Fmoc-N$^G$-Pmc-L-arginine 4-hexadecylaminobenzylamide (Compound XXVII-5)

WSCI hydrochloride (1.040 g) was added to a solution of commercially available N$^α$-Fmoc-N$^G$-Pmc-L-arginine (2.18 g), 4-hexadecylaminobenzylamine (1.883 g), and HOBt (0.735 g) in anhydrous DMF (20 ml). The mixture was stirred for 16 hours at room temperature. The solvent was removed by distillation. The residue was dissolved in chloroform (20 ml). The solution was washed sequentially with 1 mol/l aqueous solution of hydrochloric acid (30 ml) and saturated aqueous solution of sodium hydrogencarbonate (30 ml), and dried over anhydrous magnesium sulfate. The residue obtained by removal of the solvent by distillation was purified by silica gel column chromatography (50 g, 2% methanol/chloroform) to obtain the title compound (1.321 g) as colorless oil.

$^1$H-NMR(500 MHz,CDCl$_3$): δ=0.88(3H,t,J=6.8 Hz), 1.20–1.40(34H,m), 1.45–1.60 (4H,m),1.76(2H,t,J=6.8 Hz), 2.08(3H,s),2.53(3H,s), 2.55(3H,s),2.58(2H,t,J=6.8 Hz),2.99 (2H,t,J=7.1 Hz),3.10–3.20(1H,bs),3.20–3.30(1H,bs),4.10 (1H,t, J=7.1 Hz),4.15–4.25(3H, m),4.31(2H,d,J=7.3 Hz), 5.90–6.00(1H,bs),6.05–6.15(2H,bs), 6.46(2H,d,J=8.3 Hz), 7.04(2H,d,J=7.1 Hz),7.23–7.26(2H,m),7.36(2H,t,J=7.8 Hz), 7.54(2H,d,J=7.6 Hz),7.55(2H,d,J=7.3 Hz).

Example 50-2

Synthesis of N$^α$-(4-(N-Boc-N-imidazol-2-ylmethyl) aminomethylnaphthoyl)-N$^G$-Pmc-L-arginine 4-hexadecylaminobenzylamide (Compound XXIX-9)

The compound obtained in Example 50-1 (0.397 g) was dissolved in anhydrous DMF (10 ml). After the addition of diethylamine (0.0604 g), the mixture was stirred for 2.5 hours at room temperature and the solvent was removed by distillation. The compound obtained in Example 17-4 (0.157 g) and HOBt (0.0610 g) were added to the residue. The mixture was dissolved in anhydrous DMF (10 ml), and. WSCI hydrochloride (0.0861 g) was added. The mixture was stirred for. 12 hours at room temperature. After the addition of water (0.5 ml), the reaction solution was concentrated. Chloroform (5 ml) was added to the residue. The mixture was washed with 0.25 mol/l aqueous solution of hydrochloric acid (4 ml) and saturated aqueous solution of sodium hydrogencarbonate (4 ml), and processed through a diatomaceous column to remove the solvent by distillation. The resulting mixture was purified by silica gel column chromatography (5 g, 0–6% methanol/chloroform) to obtain the title compound (0.164 g) as a colorless viscous substance.

$^1$H-NMR(500 MHz,CDCl$_3$): δ=0.88(3H,t,J=6.8 Hz), 1.20–1.40(34H,m), 1.49(9H,s),1.45–1.70(3H,m),1.78(1H, 6.6 Hz),2.08(3H,s),2.51(3H,s),2.52(3H,s),2.59(2H,t,J=6.8 Hz),3.03(2H,t,J=7.1 Hz),3.10–3.25(1H,m),3.25–3.35(1H, m), 4.20–4.35(4H,m),4.65–4.75(1H, m),4.93(2H,s), 6.16–6.26(2H,bs),6.49(2H,d,J=8.5 Hz),6.85–6.95 (2H,bs), 7.06(2H,d,J=8.3 Hz),7.20(1H,d,J=7.3 Hz),7.30–7.50(3H, m),7.98(1H,d,J=7.8 Hz),8.20(1H,d,J=8.1 Hz).

Example 50-3

Synthesis of N$^α$-(4-(imidazol-2-ylmethyl) aminomethylnaphthoyl)-L-arginine 4-hexadecylaminobenzylamide [Compound No. 51]

The compound obtained in Example 50-2 (0.139 g) was dissolved in chloroform (1.4 ml). After the solution was cooled with ice, trifluoroacetic acid (1.4 ml) was added. The mixture was stirred for 5.5 hours at room temperature, followed by removal of the solvent. 1 mol/l hydrochloric acid (5 ml) and chloroform (3 ml) were added to the residue. The water layer was removed, followed by washing with chloroform (3 ml) and evaporation of the solvent. The resulting oily substance was dissolved in 1 mol/l methanol solution of hydrochloric acid. The solvent was removed by distillation and the residue was dissolved in water (0.25 ml). Acetone (5 ml) was added to the solution to cause a solid to precipitate, which was separated by centrifugation. After removal of the supernatant, the solid was dried under vacuum to obtain hydrochloride of the title compound (0.0846 g) as a white solid.

MS(FAB,Pos.): m/z=766[M+1]$^+$ $^1$H-NMR(500 MHz, DMSO-d$_6$) 0.85(3H,t,J=6.6 Hz),1.18–1.40(26H, m),1.52–1.70(4H,m),1.70–1.80(1H,m),1.80–1.90(1H,m), 3.10–3.20(4H,m),4.33(2H,s),4.54(1H,dd,J=13.2, 7.6 Hz), 4.66(2H,s),4.86(2H,s),6.8–7.6(6H,m),7.32(2H,bs), 7.62–7.75(4H,m),7.78(1H,t,J=5.6 Hz),7.82(1H,d,J=7.3 Hz), 8.28(1H,dd, 8.6 Hz, 1.0 Hz), 8.31(1H,d,J=7.8 Hz),8.68(1H, bs),8.84(1H,d,J=7.6 Hz).

EXAMPLE 51

Preparation of N$^α$-(4-(5,6,7,8-tetrahydroquinolin-8-ylaminomethyl)benzoyl)-L-arginine 1-naphthalenemethylamide [Compound No. 52]

Example 51-1

Synthesis of N$^α$-(4-(N-Cbz-aminomethyl)benzoyl)-N$^G$-Pmc-L-arginine 1-naphthalenemethylamide (Compound XXX-1)

The compound obtained in Example 42-1 (2.187 g), WSCI (0.95 g), and HOBt (0.67 g) were dissolved in DMF (33 ml). After the addition of 1-naphthalenemethylamine (0.51 ml), the mixture was reacted for 18 hours. The reaction solution was concentrated and 1 mol/l hydrochloric acid was added, followed by extraction with chloroform. Saturated aqueous solution of sodium bicarbonate was added to the organic layer, and the mixture was extracted with chloroform. The organic layer was washed with saturated brine, dried over anhydrous sodium sulfate, and concentrated. The resulting residue was dissolved in DMF (50 ml), and diethylamine (5 ml) was added. After one hour, the residue obtained by concentrating the reaction solution was suspended in DMF (40 ml). WSCI (0.95 g), DMAP (0.60 g), and the compound obtained in Example 41-1 (0.75 g) were added to the suspension. After three days, the reaction solution was concentrated and 1 mol/l hydrochloric acid was added. The mixture was extracted with chloroform and the organic layer was washed with saturated brine. The organic layer was dried over anhydrous sodium sulfate and concentrated. The residue was purified by silica gel column chromatography (80 g, chloroform/methanol=20/1) to obtain the title compound (2.47 g) as a pale yellow solid.

Example 51-2

Synthesis of N$^α$-(4-(aminomethyl)benzoyl)-N$^G$-Pmc-L-arginine 1-naphthalenemethylamide (Compound XXXI-1)

The compound obtained in Example 51-1 (407.3 mg) was dissolved in ethanol (20 ml) and 10% Pd—C (41 mg) was added. After hydrogenation for 3 days, the reaction solution was filtered through a glass filter. The filtrate was concentrated and the obtained residue was purified by silica gel column chromatography (12 g, chloroform/methanol=5/1) to obtain the title compound (113.4 mg) as a white solid.

MS(FAB,Pos.): m/z=713[M+1]$^+$ $^1$H-NMR(500 MHz, CDCl$_3$): δ=1.28(6H,s),1.45–1.95(2H,m),2.05(3H, s),2.44 (3H,s),2.45(3H,s),2.50–2.60(2H,m),3.08–3.19(1H,m), 3.23–3.32(1H,m),3.85(2H,s),4.60–4.73(2H,m),4.83–4.92 (1H,m), 6.14–6.32(2H,br),7.20–7.47(6H,m),7.61–7.82(4H, m),7.92–7.99(1H,m).

Example 51-3

Synthesis of N$^α$-(4-(5,6,7,8-tetrahydroquinolin-8-ylaminomethyl)benzoyl)-N$^G$-(2,2,6,7,8-pentamethylchroman-6-ylsulfonyl)-L-arginine 1-naphthalenemethylamide (Compound XXXII-1)

The compound obtained in Example 51-2 (109.8 mg) was dissolved in methanol (2 ml). 5,6,7,8-tetrahydroquinolin-8-one (34 mg) and triethylamine (21 μl) were added to the solution. After 4 hours, the reaction solution was concentrated and dissolved again in methanol (2 ml). Sodium borohydride (18 mg) was added to the solution. After the reaction for 2 hours, a small amount of water was added. The mixture was concentrated. The obtained residue was purified by silica gel column chromatography (5 g, chloroform/methanol=10/1) to obtain the title compound (61.8 mg) as a brown solid.

MS(FAB,Pos.): m/z=844[M+1]$^+$ $^1$H-NMR(500 MHz, DMSO-d$_6$): δ=1.23(6H,s),1.38–2.09(9H,m),2.00 (3H,s), 2.45(3H,s),2.46(3H,s),2.50–2.56(2H,m),2.67–2.82(2H, m),2.99–3.10(2H,m),3.17(2H,d,J=4.4 Hz),3.90(2H,dd,J= 14.2, 23.4 Hz),4.08–4.12(1H,m),4.43–4.50(1H,m),4.75(2H, d,J=4.9 Hz), 7.17–7.21(1H,m),7.40–7.55(7H,m),7.83(1H,t, J=4.7 Hz),7.87(2H, d,J=8.1 Hz),7.90–7.95(1H,m),8.00–8.06 (1H,m),8.36(1H,dd,J=1.7, 2.9 Hz),8.45(1H,d,J=7.8 Hz),8.53 (1H,t,J=5.7 Hz).

Example 51-4

Synthesis of N$^α$-(4-(5,6,7,8-tetrahydroquinolin-8-ylaminomethyl)benzoyl)-L-arginine 1-naphthalenemethylamide [Compound No. 52]

The compound obtained in Example 51-3 (41.7 mg) was dissolved in chloroform (0.4 ml) and trifluoroacetic acid (0.4 ml) was added. After the reaction for 5 hours, the reaction solution was concentrated. The residue was purified by silica gel column chromatography (1.5 g, chloroform/methanol/water=7/3/0.5). Activated carbon was added to the obtained title compound. The mixture was filtered. After the addition of an excessive amount of 1 mol/l hydrochloric acid, the filtrate was concentrated. Hydrochloride of the title compound (3.5 mg) was obtained as a pale yellow solid.

MS(FAB,Pos.): m/z=578[M+1]$^+$ $^1$H-NMR(500 MHz, DMSO-d$_6$): δ=1.45–1.63(2H,m),1.71(3H,m),1.95 (2H,m), 2.34(1H,m),2.77–2.85(2H,m),3.08–3.15(2H,m),4.28–4.43 (3H,m),4.49–4.56(1H,m),4.76(2H,d,J=5.6 Hz),7.40(1H,dd, J=4.7, 7.7 Hz),7.46(2H,d,J=4.9 Hz), 7.51–7.57(2H,m), 7.66–7.78(4H,m), 7.84(1H,t,J=4.8 Hz),7.95(1H,t,J=4.8 Hz), 8.01(2H,d,J=8.3 Hz), 8.07 (1H,t,J=4.8 Hz),8.53(1H,d,J=4.2 Hz),8.66(2H,d,J=7.8 Hz).

EXAMPLE 52

Preparation of N$^α$-(4-(imidazol-2-ylmethyl) aminomethylbenzoyl)-L-arginine 1-naphthalenemethylamide [Compound No. 53]

Example 52-1

Synthesis of N$^α$-(4-((imidazol-2-ylmethyl) aminomethyl)benzoyl)-N$^G$-Pmc-L-arginine 1-naphthalenemethylamide (Compound XXXII-2)

The compound obtained in Example 51-2 (85.5 mg) was dissolved in methanol (1.7 ml). After the addition of 2-imidazolyl carboaldehyde (12.2 mg), the mixture was stirred for 2 days and 15.5 hours at room temperature. After the reaction, the solvent was removed by distillation. The residue was dried under vacuum, followed by the addition of anhydrous methanol (1.7 ml). Then, the mixture was cooled to 0° C. and sodium borohydride (10.7 mg) was added. The mixture was stirred for 3 hours at room temperature. After the reaction, the solvent was removed by distillation. The residue was purified by silica gel column chromatography (5 g, chloroform/methanol=5/1) to obtain the title compound (75.6 mg) as white foam.

MS(FAB,Pos.): m/z=793[M+1]$^+$ $^1$H-NMR(500 MHz, DMSO-d$_6$): δ=1.23(6H,s),1.38–1.58(2H,m),1.65–1.82(2H, m),1.73(2H,t,J=6.8 Hz),2.00(3H,s),2.45(3H,s),2.46(3H, s),2.50–2.58(2H,t,J=6.8 Hz) 3.00–3.08(2H,m),3.66(2H,s), 3.73 (2H,s),4.46–4.55(1H,m),4.75(2H,d,J=5.1 Hz),6.37(1H, brs),6.70(1H,brs),6.79(1H,s),7.02(1H,s),7.41–7.50(4H,m), 7.52–7.58 (2H,m),7.84(1H,t,J=4.6 Hz),7.86(2H,d,J=8.5 Hz),7.93–7.96(1H, m),8.02–8.06(1H,m),8.44(1H,d,J=7.8 Hz),8.53(1H,t,J=5.6 Hz).

Example 52-2

Synthesis of N$^α$-(4-(imidazol-2-ylmethyl) aminomethyl)benzoyl)-L-arginine 1-naphthalenemethylamide [Compound No. 53]

The compound obtained in Example 52-1 (35.7 mg) was dissolved in chloroform (0.7 ml) and trifluoroacetic acid (0.7 ml) was added. The mixture was stirred for 5 hours at room temperature. After the reaction, the solvent was removed by distillation. The residue was dried using a vacuum pump and purified by silica gel column chromatography (1.5 g, chloroform/methanol/water=7/3/0.5). Fractions were concentrated. The concentrated fractions were dissolved in 1 mol/l aqueous solution of hydrochloric acid. The solution was concentrated, azeotropically distilled with water, and the obtained solid was washed with ether to obtain the title compound (9.1 mg) as a white solid.

MS(FAB,Pos.): m/z=527[M+1]$^+$ $^1$H-NMR(500 MHz, DMSO-d$_6$): δ=1.45–1.62(2H,m),1.70–1.90(2H,m), 3.02–3.15 (2H,m),4.36(2H,s),4.49(2H,s),4.45–4.60(1H,m), 4.76 (2H,d,J=5.9 Hz),6.90(2H,br),7.39(1H,br),7.43–7.50 (2H,m), 7.52–7.57(2H,m),7.67(4H,d,J=8.1 Hz),7.77(1H, brs),7.82–7.87(1H,m),7.93–7.97(1H,m),7.99(2H,d,J=8.1 Hz), 8.03–8.09(1H,m), 8.60–8.70(2H,m).

EXAMPLE 53

Preparation of (S)-2-(4-(N-2-picolylaminomethyl) benzoylamino)-5-(quinolin-8-ylamino)valeric acid 1-naphthalenemethylamide [Compound No. 54]

Example 53-1

Synthesis of N$^α$-Boc-L-glutamic acid 1-naphthalenemethylamide γ-benzyl ester (Compound XXXV-1)

Commercially available N$^α$-Boc-L-glutamic acid γ-benzyl ester (3.168 g) was dissolved in DMF (64 ml). WSCI (2.7 g), DMAP (1.7 g), and 1-naphthalenemethylamine (2.06 ml) were added. After 15 hours, the reaction solution was concentrated and 1 mol/l aqueous solution of hydrochloric acid was added, followed by extraction with chloroform. The organic layer was washed with saturated brine. The organic layer was dried over anhydrous sodium sulfate and concentrated to obtain an unpurified target compound (6.087 g) as a pale yellow solid.

Example 53-2

Synthesis of N$^α$-4-(N-Boc-N-2-picolylaminomethylbenzoyl)-L-glutamic acid 1-naphthalenemethylamide γ-methyl ester (XXXVII-1)

The compound obtained in Example 53-1 (1.125 g) was dissolved in methanol (11 ml) and 4 mol/l hydrochloric acid/dioxane solution (5.5 ml) was added. After the reaction for 1.5 hours, the reaction solution was concentrated and the residue was azeotropically distilled with chloroform. The residue (1.13 g) obtained by drying under reduced pressure was dissolved in DMF (23 ml). WSCI (0.50 g), DMAP (0.32 g), and the compound obtained in Example 1-2 (0.65 g) were added to the solution. After 27 hours, the reaction solution was concentrated and 1 mol/l hydrochloric acid was added. The mixture was extracted with chloroform and the organic layer was washed with saturated brine. The organic layer was dried over anhydrous sodium sulfate and concentrated. The residue was purified by silica gel column chromatography (50 g, hexane/ethyl acetate=1/3) to obtain the target compound (678 mg) as yellow syrup.

MS(Fab,pos.): m/z=625[M+1]$^+$ $^1$H-NMR(500 MHz, CDCl$_3$): δ=1.44 and 1.46(9H, 2s),2.05–2.28(2H,m), 2.37–2.44(1H,m),2.57–2.64(1H,m),3.62(3H,s),4.46(1H,s), 4.50(1H,s),4.59(2H,s),4.63–4.70(1H,m),4.86–4.98(2H,m), 6.90(1H, br),7.45–7.20(1H,m),7.23–7.51(8H,m),7.65(1H,t, J=7.5 Hz),7.70 (2H,d,J=5.6 Hz),7.80(1H,d,J=8.1 Hz),7.87 (1H,d,J=7.1 Hz),7.97(1H,d,J=6.8 Hz),8.01(2H,s),8.53(1H,d, J=4.4 Hz).

Example 53-3

Synthesis of (S)-2-(4-(N-Boc-N-2-picolylaminomethyl)benzoylamino)-5-(quinolin-8-ylamino)valeric acid 1-naphthalenemethylamide (XIII-13)

Lithium aluminum hydride (109 mg) was suspended in THF (13 ml). A solution of the compound obtained in Example 53-2 (672.1 mg) in THF (3.5 ml) was added to the suspension while cooling with ice. After the reaction for 1 hour, water was slowly added to the reaction solution, which was then concentrated. Water was further added to the residue, followed by the addition of saturated aqueous solution of potassium sodium tartrate. The mixture was extracted with chloroform. The organic layer was washed with saturated brine, dried over anhydrous sodium sulfate, and concentrated to obtain an intermediate alcohol compound (566.4 mg) as a pale yellow solid.

Methylene chloride (3.3 ml) was added to DMSO (52 μl), then oxalyl chloride (32 μl) was added dropwise at −78° C. After 5 minutes, the solution of the intermediate alcohol compound (110.3 mg) obtained above in methylene chloride (0.6 ml) was added dropwise. In addition, triethylamine (0.21 ml) was added after 25 minutes. The temperature of the mixture was allowed slowly to rise. After 1.5 hours, water was added at a temperature of −15° C. The organic layer was extracted with chloroform, dried over anhydrous sodium sulfate, and concentrated. The resulting residue was dissolved in methanol (2.2 ml). After the addition of 8-aminoquinoline (32 mg) and triethylamine (26 μl), the mixture was allowed to stand over night. The reaction solution was concentrated, dried under reduced pressure, and dissolved again in methanol (2.2 ml). Acetic acid (0.2 ml) and sodium cyanoborohydride (35 mg) were sequentially added to the solution. After the reaction for 7 days, the reaction solution was concentrated. After the addition of water, the residue was extracted with chloroform. The organic layer was dried over anhydrous sodium sulfate and concentrated. The residue was purified by silica gel column chromatography (5 g, hexane/ethyl acetate=1/4) to obtain the title compound (19.9 mg) as a yellow solid.

MS(FAB,Pos.): m/z=723[M+1]$^+$ $^1$H-NMR(500 MHz, CDCl$_3$): δ=1.44 and 1.46(9H, 2s),1.83–1.95(2H,m), 1.95–2.02(1H,m),2.11–2.20(1H,m),3.35(2H,t,J=6.6 Hz), 4.41–4.72(6H,m),4.82–4.96(2H,m),6.49(1H,br),6.63(1H,d, J=7.3 Hz), 6.93(1H,br),7.03(1H,d,J=7.8 Hz), 7.12–7.62(6H, m),7.60–7.68 (3H,m),7.73–7.97(3H,m),8.04(1H,d,J=7.1 Hz),8.53(1H,d,J=4.4 Hz),8.62(1H,dd,J=4.1,1.7 Hz).

Example 53-4

Synthesis of (S)-2-(4-(N-2-picolylaminomethyl) benzoylamino)-5-(quinolin-8-ylamino)valeric acid 1-naphthalenemethylamide [Compound No. 54]

The compound obtained in Example 53-3 (19.0 mg) was dissolved in methanol (0.19 ml) and 4 mol/l hydrochloric acid/dioxane (0.19 ml) was added. After 2.5 hours, the reaction solution was concentrated and azeotropically distilled with methanol. The residue was purified by silica gel column chromatography (1 g, chloroform/methanol/water= 7/3/0.5). The obtained title compound was dissolved in methanol. Activated carbon (4 mg) was added to the solution, followed by filtration and concentration. After the addition of 1 mol/l hydrochloric acid and a small amount of methanol, the residue was concentrated and dried under reduced pressure to obtain hydrochloride of the title compound (17.9 mg) as a yellow solid.

MS(FAB,Pos.): m/z=623[M+1]$^+$ $^1$H-NMR(500 MHz, CDCl$_3$): δ=1.70–1.89(2H,m),1.90–2.00(2H,m),3.30 (2H,t, J=7.6 Hz),4.30(4H,s),4.57–4.63(1H,m),4.71–4.82(2H,m), 6.77(1H,brd,J=5.9 Hz),7.15(1H,d,J=8.1 Hz),7.38–7.60(8H, m), 7.65(2H,d,J=8.5 Hz),7.84(1H,d,J=7.8 Hz),7.86–7.96 (2H,m),7.99 (2H,d,J=8.5 Hz),8.06(1H,d,J=8.5 Hz),8.34(1H,brd,J= 7.3 Hz),8.62–8.70(3H, m),8.77(1H,d,J=2.9 Hz),9.79(2H,s).

EXAMPLE 54

Preparation of (2S)-2-(4-(N-2-picolylaminomethyl) naphthoylamino)-5-((8R)-5,6,7,8-tetrahydroquinolin-8-ylamino)valeric acid 1-naphthalenemethylamide [Compound No. 55]

Example 54-1

Synthesis of 8-amino-5,6,7,8-tetrahydroquinoline.L-tartrate 5,6,7,8-tetrahydroquinolin-8-ol (3.53 g) synthesized by the method described in Journal of Medicinal Chemistry, vol. 20, No. 10, pp 1351–1354 (1977) was dissolved in benzene (18 ml). Phosphine tribromide (6.74 ml) was added to the solution. After one hour, 1 mol/l aqueous solution of sodium hydroxide was added to adjust the pH of the reaction solution to about 10, followed by extraction with chloroform. The organic layer was washed with saturated brine, dried over anhydrous sodium sulfate, and concentrated. The obtained residue was dissolved in DMF (50 ml) and potassium phthalimide (4.38 g) was added. After stirring for 3 days, the reaction solution was concentrated. After the addition of water, the residue was extracted with chloroform. The organic layer was washed with saturated brine and dried over anhydrous sodium sulfate to concentrate the extract. The obtained residue was purified by silica gel column chromatography (60 g, hexane/ethyl acetate=1/1) to obtain an intermediate. Part of the intermediate (500 mg) was suspended in ethanol (2.5 ml). Hydrazine monohydrate (0.44 ml) was added to the suspension. After stirring for 5 hours, water was added to the reaction solution, followed by extraction with ethyl acetate. The organic layer was washed with saturated brine, dried over anhydrous sodium sulfate, and concentrated. Part of the obtained residue (61.7 mg) was dissolved in methanol and L-tartaric acid (62.5 mg) was added. Chloroform was further added to the solution and the mixture was allowed to stand over night. The deposited crystals were collected by filtration and dried to obtain the title compound (102.1 g) as white needle-like crystals.

MS(FAB,Pos.): m/z=149[M+1]$^+$ $^1$H-NMR(500 MHz, CDCl$_3$): δ=1.69–1.85(2H,m),1.87–2.03(1H,m), 2.17–2.24 (1H,m),2.72–2.88(2H,m),3.97–4.03(1H,m),7.07(1H, dd,J= 4.7, 7.6 Hz),7.38(1H,d,J=7.6 Hz),8.42(1H,d,J=4.7 Hz).

Example 54-2

Synthesis of (R)-8-amino-5,6,7,8-tetrahydroquinoline.L-tartrate

The compound obtained in Example 54-1 (99.8 mg) was dissolved again in methanol (5 ml), and chloroform (5 ml) was added. The mixture was allowed to stand for 3 days. The deposited crystals were collected by filtration to obtain a white needle-like crystals (30.1 mg). 18.4 mg of the crystals were dissolved in methanol (1 ml). Crystals deposited by the addition of chloroform (0.18 ml) were collected by filtration to obtain the optically active isomer of the title amine compound (9.8 mg) as white needle-like crystals. The resulting crystals were determined as the R isomer by X-ray structure analysis. [a]D=−25.5° (H2O, c=0.2)

Example 54-3

Synthesis of (2S)-2-(4-(N-2-picolyl-N-Boc aminomethyl)naphthoylamino)-5-((8R)-5,6,7,8-tetrahydroquinolin-8-ylamino)valeric acid 1-naphthalenemethylamide (Compound XIII-14)

The compound obtained in Example 53-1 (669.3 mg) was dissolved in methanol (6.7 ml) and 4 mol/l hydrochloric acid/dioxane solution (3.3 ml) was added. The mixture was stirred for 1 hour at room temperature. After the reaction, the solvent was removed by distillation. The residue was dried under reduced pressure and dissolved in DMF (12 ml). After the addition of WSCI hydrochloride (404 mg), DMAP (257 mg), and the compound obtained in Example 43-2 (606 mg), the mixture was stirred for 11 hours at room temperature. After the reaction, the solvent was removed by distillation. The residue was dissolved in chloroform and the solution was washed with 1 mol/l aqueous solution of hydrochloric acid and saturated brine. After the solution was dried over anhydrous sodium sulfate, the solvent was removed by distillation. The obtained residue was dissolved in THF (20 ml). A solution of lithium hydride (160 mg) in THF (10 ml) was added and the mixture was stirred for 1.5 hours at room temperature. After the reaction, ethyl acetate was added, followed by filtration through celite. The solvent was removed by distillation and the residue was purified by silica gel column chromatography (30 g, chloroform/methanol=10/1) to obtain an intermediate compound (464.7 mg). A solution of the above intermediate compound (58.9 mg) in methylene chloride (0.3 ml) was added dropwise to a solution of DMSO (26 μl) and oxalyl chloride (16 μl) in methylene chloride (1.8 ml) at −78° C. After the solution was stirred for one hour, triethylamine (0.1 ml) was added and the mixture was allowed to become room temperature. After the addition of chloroform, the mixture was washed with water and dried over anhydrous sodium sulfate. Then, the solvent was removed by distillation. The residue was purified by silica gel column chromatography (3 g, ethyl acetate). An intermediate compound obtained was dissolved in methanol (0.79 ml). The compound obtained in Example 54-2 (8.8 mg), acetic acid (0.03 ml), and NaBH$_3$CN (6 mg) were added, and the mixture was reacted for two days. The reaction solution was concentrated. The residue was purified by silica gel column chromatography (0.5 g, chloroform/methanol=10/1) to obtain the title compound (7.9 mg) as colorless syrup.

MS(FAB,Pos.): m/z=777[M+1]$^+$ $^1$H-NMR(500 MHz, CDCl$_3$): δ=1.46 and 1.49(9H, 2s),1.70–2.50(6H,m), 2.80–2.92(2H,m),3.09–3.18(1H,m),3.24–3.31(1H,m), 4.32–4.45 (2H,m),4.52–4.59(1H, m),4.85–5.10(5H,m), 7.08–7.62(15H,m), 7.79(1H,d,J=7.8 Hz),7.86(1H,d,J=8.1 Hz),8.00–8.07(1H,m),8.12(1H,d,J=8.8 Hz),8.17–8.23(1H, m),8.40(1H, brs),8.51(1H,brs).

Example 54-4

Synthesis of (2S)-2-(4-(N-2-picolylaminomethyl) naphthoylamino)-5-((8R)-5,6,7,8-tetrahydroquinolin-8-ylamino)valeric acid 1-naphthalenemethylamide [Compound No. 55]

The compound obtained in Example 54-3 (7.2 mg) was dissolved in methanol (0.15 ml) and 4 mol/l hydrochloric acid/dioxane solution (0.15 ml) was added. After 2 hours, the reaction solution was concentrated. The residue was purified by silica gel column chromatography (chloroform/methanol/water=7/3/0.5). After the addition of 1 mol/l hydrochloric acid, the residue was concentrated and subjected to azeotropic distillation with methanol to obtain hydrochloride of the title compound (6.3 mg) as a white solid.

MS(FAB,Pos.): m/z=677[M+1]$^+$ $^1$H-NMR(500 MHz, DMSO-d$_6$): δ=1.62–2.01(7H,m),2.30–2.40(1H,m), 2.78–2.88(2H,m),2.95–3.03(1H,m),3.04–3.22(1H,m),4.47 (3H,m), 4.61–4.70(1H,m),4.79(2H,s),4.83(1H,d,J=15.6,5.6 Hz),4.85(1H, dd,J=15.6,5.6 Hz),7.37–7.42(1H, m),7.47–7.51(2H,m),7.52–7.64 (5H,m),7.67–7.73(3H,m), 7.80(1H,d,J=7.1 Hz),7.88(1H,d,J=8.1 Hz),7.93(1H,td,J=7.6, 1.7 Hz),8.07–8.13(1H,m),8.26–8.33(2H, m),8.49(1H,d,J= 4.6 Hz),8.71(1H,d,J=4.8 Hz),8.76(1H,brs),8.87(1H,d,J=7.8 Hz),9.10(2H,br),9.80(2H,br).

EXAMPLE 55

Preparation of (S)-2-(4-(imidazol-2-ylmethyl) aminomethyl)naphthoylamino)-5-(2-picolylamino) valeric acid (1'S)-(1'-(1-naphthyl)ethyl)amide [Compound No. 56]

Example 55-1

Synthesis of N$^α$-Boc-L-glutamine acid (1'S)-(1'-(1-naphthyl)ethyl)amide γ-benzyl ester (Compound XXXV-2)

Commercially available N$^α$-Boc-L-glutamine acid γ-benzyl ester (1.05 g) was dissolved in DMF (21.0 ml). Commercially available (S)-1-(1-naphthyl)ethylamine (0.799 g), WSCI hydrochloride (0.894 g), and HOBt (0.631 g) were added to the solution. The mixture was allowed to stand for one day at room temperature. After confirming completion of the reaction with TLC, the reaction mixture was concentrated under reduced pressure as is. 1 N aqueous solution of hydrochloric acid was added to the residue and the resulting solution was extracted with chloroform. The organic layer separated was washed with saturated aqueous solution of sodium bicarbonate, dried over anhydrous sodium sulfate, and concentrated under reduced pressure. The residue was purified by silica gel column chromatography (50 g, chloroform/ethyl acetate=5/1) to obtain the title compound (1.42 g) as a white solid.

MS(FAB,Pos.): m/z=491[M+1]$^+$ $^1$H-NMR(500 MHz, CDCl$_3$): δ=1.40(9H,s),1.63(3H,d,J=6.8 Hz),1.84–1.91(1H, m),2.01–2.10(1H,m),2.32–2.36(1H,m),2.45–2.51(1H,m), 4.05–4.15(1H,m),5.07(2H,s),5.22–5.30(1H,m),5.90(1H,t,J= 7.3 Hz),6.42–6.50(1H,m),7.23–7.53(9H,m),7.78(1H,d,J= 8.1 Hz), 7.84(1H,d, J=7.8 Hz),8.04(1H,d,J=8.5 Hz).

Example 55-2

Synthesis of N$^α$-(4-(N-Boc-aminomethyl) naphthoyl)-L-glutamine acid (1'S)-(1'-(1-naphthyl) ethyl)amide γ-methyl ester (Compound XL-1)

The compound obtained in Example 55-1 (1.01 g) was dissolved in methanol (15.1 ml) and 10% hydrochloric acid/methanol solution (15.1 ml) was added. The mixture was allowed to stand for 1 day at room temperature. After confirming completion of the reaction with TLC, the reaction mixture was concentrated under reduced pressure as is and dried under vacuum. The product was dissolved in DMF (12.9 ml). The compound obtained in Example 25-2 (0.620 g), WSCI hydrochloride (0.592 g), and DMAP (0.752 g) were added to the solution. The mixture was allowed to stand for one day at room temperature. After confirming completion of the reaction with TLC, the reaction mixture was concentrated under reduced pressure as is. Saturated aqueous solution of sodium bicarbonate was added to the residue and the resulting solution was extracted with chloroform. The organic layer separated was dried over anhydrous sodium sulfate and concentrated under reduced pressure. The residue was purified by silica gel column chromatography (50 g, chloroform/methanol=40/1) to obtain the title compound (1.12 g) as a white solid.

MS(FAB,Pos.): m/z=598[M+1]$^+$ $^1$H-NMR(500 MHz, CDCl$_3$): δ=1.47(9H,s),1.69(3H,d, J=6.6 Hz),2.01–2.08(1H, m),2.15–2.22(1H,m),2.35–2.42(1H,m),2.56–2.63(1H,m), 3.62(3H,s),4.74–4.87(3H,m),5.95(1H,quintet,J=7.0 Hz), 6.82–6.90(1H,m),6.96–7.02(1H,m),7.40–7.60(9H,m),7.81 (1H,d, J=8.3 Hz),7.88(1H,d,J=7.8 Hz),8.04–8.10(2H,m), 8.29(1H,d, J=8.1 Hz).

Example 55-3

Synthesis of (S)-2-(4-(N-Boc-aminomethyl) naphthoylamino)-4-formyl-butyric acid (1'S)-(1'-(1-naphthyl)ethyl)amide (Compound XLI-1)

Lithium aluminum hydride (0.213 g) was suspended in anhydrous tetrahydrofuran (11.2 ml). A solution of the compound obtained in Example 55-2 (1.12 g) in anhydrous tetrahydrofuran (22.4 ml) was added to the suspension. The mixture was stirred for 0.5 hour at room temperature. After confirming completion of the reaction with TLC, ethyl acetate, methanol, and 10% aqueous solution of potassium sodium tartrate were sequentially added to the reaction solution. The mixture was stirred for a further one hour. The reaction solution was extracted with chloroform. The organic layer separated was dried over anhydrous sodium sulfate, followed by concentration under reduced pressure. The residue was purified by silica gel column chromatography (80 g, chloroform/methanol=20/1) to obtain an intermediate alcohol compound (1.44 g) as a white solid.

Oxalyl chloride (0.151 ml) and dimethyl sulfoxide (0.251 ml) were added to methylene chloride (20.1 ml) while stirring at −78° C. After stirring for 0.5 hour, a solution of the intermediate alcohol compound (0.670 g) obtained above in methylene chloride. (6.70 ml) was added. After stirring for a further 0.5 hour, triethylamine (0.738 ml) was added. The mixture was stirred for additional 1.5 hours while cooling with ice. After the addition of water, the reaction solution was extracted with chloroform. The organic layer separated was dried over anhydrous sodium sulfate, followed by concentration under reduced pressure. The residue was purified by silica gel column chromatography (50 g, chloroform/methanol=30/1) to obtain the title compound (0.450 g) as a light orange solid.

MS(FAB,Pos.): m/z=568[M+1]$^+$ $^1$H-NMR(500 MHz, CDCl$_3$): δ=1.47(9H,s),1.73(3H,d,J=6.8 Hz),1.82–1.99(2H, m),2.28–2.40(1H,m),3.56–3.62(2H,m),4.62–4.92(4H,m), 5.98(1H,t,J=7.3 Hz),7.08–7.20(2H,m),7.36–7.60(8H,m), 7.79(1H, d,J=8.1 Hz),7.84–7.90(1H,m),8.04–8.16(3H,m).

Example 55-4

Synthesis of (S)-2-(4-(N-Boc-aminomethyl) naphthoylamino)-5-(2-picolylamino)valeric acid (1'S)-(1'-(1-naphthyl)ethyl)amide (Compound XXI-5)

The compound obtained in Example 55-3 (200.0 mg) was dissolved in methanol (6.0 ml), and 2-aminomethylpyridine (44.3 mg) and sodium cyanoborohydride (44.3 mg) were added at room temperature. After adjusting the pH to 4–5 with the addition of acetic acid, the mixture was stirred for two days. After confirming consumption of the raw materials with TLC, the reaction mixture was concentrated under reduced pressure as is. Water was added to the residue and the solution was extracted with chloroform. The organic layer separated was dried over anhydrous sodium sulfate and concentrated under reduced pressure. The residue was purified by silica gel column chromatography (10 g, chloroform/methanol=15/1) to obtain the title compound (91.5 mg) as a pale yellow solid.

MS(FAB,Pos.): m/z=660[M+1]$^+$ $^1$H-NMR(500 MHz, CDCl$_3$): δ=1.47(9H,s),1.67(3H,d,J=6.8 Hz),1.70–1.90(2H, m),1.90–2.04(2H,m),2.88–3.00(2H,m),3.87(2H,s), 4.62–4.75(2H,m),4.82–4.88(2H,m),5.90–6.00(1H,m), 7.00–7.10(2H,m), 7.34(1H,d,J=7.1 Hz),7.40–7.58(7H,m), 7.77(1H,m,J=8.1 Hz),7.87 (1H,d,J=7.6 Hz),7.90–8.02(2H, m),8.12(1H,d,J=8.5 Hz),8.20–8.32 (2H,m).

Example 55-5

Synthesis of (S)-2-(4-(imidazol-2-ylmethyl) aminomethyl)naphthoylamino)-5-(2-picolylamino) valeric acid (1'S)-(1'-(1-naphthyl)ethyl)amide [Compound No. 56]

The compound obtained in Example 55-4 (91.5 mg) was dissolved in methanol (2 ml) and 4 mol/l hydrochloric acid/dioxane solution (2 ml) was added. The mixture was stirred for one hour at room temperature. After the reaction, the solvent was removed by distillation and the residue was dried under vacuum. The residue was dissolved in anhydrous methanol. After the addition of triethylamine (58.0 ml) and 2-imidazole carboaldehyde (16.0 mg), the mixture was stirred for 5 hours at room temperature. After the reaction, the reaction solution was concentrated. The residue was dried under reduced pressure and dissolved in anhydrous methanol (2 ml). The mixture was cooled to 0° C. Sodium borohydride (10.5 mg) was added to the solution and the mixture was stirred for 0.5 hour at room temperature. After the reaction, the reaction mixture was concentrated. The residue was purified by silica gel column chromatography (5 g, chloroform/methanol/water=7/3/0.5) and treated with 1 mol/l aqueous solution of hydrochloric acid to obtain hydrochloride of the title compound (63.5 mg) as a white solid.

MS(FAB,Pos.): m/z=640[M+1]$^+$ $^1$H-NMR(500 MHz, DMSO-d$_6$): δ=1.56(3H,d,J=6.8 Hz),1.66–1.90(4H,m), 2.96–3.08(2H,m),4.26–4.32(2H,m),4.62–4.78(2H,m), 4.82–4.94 (2H,m),5.74–5.82(1H,m),7.40–7.96(14H,m),8.14 (1H,d,J=8.5 Hz), 8.28(1H,d,J=8.5 Hz),8.30–8.36(1H,m), 8.63(1H,d,J=7.1 Hz),8.83(1H,d,J=7.6 Hz),8.80–8.84(1H, m).

EXAMPLE 56

Preparation of (S)-2-(4-(imidazol-2-ylmethyl) aminomethyl)naphthoylamino)-5-(5,6,7,8-tetrahydroquinolin-8-ylamino)valeric acid (1'S)-(1'-(1-naphthyl)ethyl)amide [Compound No. 57]

Example 56-1

Synthesis of (S)-2-(4-(N-Boc-aminomethyl) naphthoylamino)-5-(5,6,7,8-tetrahydroquinolin-8-ylamino)valeric acid (1'S)-(1'-(1-naphthyl)ethyl) amide (Compound XXI-6)

The compound obtained in Example 55-3 (200.0 mg) was dissolved in methanol (6.00 ml), and the amine obtained in Example 54-1 (126.1 mg) and sodium cyanoborohydride (44.3 mg) were added at room temperature. After adjusting the pH to 4–5 with the addition of acetic acid, the mixture was stirred for 23 hours. After confirming consumption of the raw materials with TLC, the reaction mixture was concentrated under reduced pressure as is. Water was added to the residue and the solution was extracted with chloroform. The organic layer separated was dried over anhydrous sodium sulfate and concentrated under reduced pressure. The residue was purified by silica gel column chromatography (10 g, chloroform/methanol=15/1) to obtain the title compound (162.9 mg) as a pale yellow solid.

MS(FAB,Pos.): m/z=700[M+1]+ 1H-NMR(500 MHz, CDCl$_3$); δ=1.47(9H,s),1.68(3H,d,J=6.6 Hz),1.76–2.10(8H, m),2.20–2.40(2H,m),2.60–2.78(2H,m),3.02–3.38(4H,m), 4.62–4.96 (4H,m),5.84–5.96(1H,m),7.00–7.34(8H,m), 7.73–7.90 (2H,m),7.94–8.40(4H,m).

Example 56-2

Synthesis of (S)-2-(4-(imidazol-2-ylmethyl) aminomethyl)naphthoylamino)-5-(5,6,7,8-tetrahydroquinolin-8-ylamino)valeric acid (1'S)-(1'-(1-naphthyl)ethyl)amide [Compound No. 57]

The compound obtained in Example 56-1 (162.9 mg) was dissolved in methanol (2 ml) and 4 mol/l hydrochloric acid/dioxane solution (2 ml) was added. The mixture was stirred for one hour at room temperature. After the reaction, the solvent was removed by distillation and the residue obtained was dried under vacuum. The residue was dissolved in anhydrous methanol. After the addition of triethylamine (97.3 μl) and 2-imidazole carboaldehyde (26.8 mg), the mixture was stirred for 5 hours at room temperature. After the reaction, the reaction solution was concentrated. The residue was dried under reduced pressure and dissolved in anhydrous methanol (2 ml). The mixture was cooled to 0° C. Sodium borohydride (17.6 mg) was added to the solution and the mixture was stirred for 0.5 hour at room temperature. After the reaction, the reaction mixture was concentrated. The residue was purified by silica gel column chromatography (5 g, chloroform/methanol/water=7/3/0.5) and treated with 1 mol/l aqueous solution of hydrochloric acid to obtain hydrochloride of the title compound (102.0 mg) as a white solid.

MS(FAB,Pos.): m/z=680[M+1]+ 1H-NMR(500 MHz, DMSO-d$_6$): δ=1.56(3H,d,J=6.8 Hz),1.70–1.94(6H,m) 2.24–2.36(2H,m),2.78–2.82(1H,m),4.60–4.76(2H,m), 4.82–4.90 (2H,m),5.76–5.80(1H,m),7.36–7.40(1H,m), 7.44–7.66(12H,m), 7.84(1H,d,J=7.8 Hz),7.96(1H,d,J=7.6 Hz),8.14(1H,d,J=8.5 Hz),8.24–8.36(2H,m),8.42–8.46(1H, m),8.68–8.82(2H,m).

EXAMPLE 57

Preparation of (S)-2-(4-(imidazol-2-ylmethyl) aminomethyl)naphthoylamino)-5-(2-picolylamino) valeric acid (1'R)-(1'-(1-naphthyl)ethyl)amide [Compound No. 58]

Example 57-1

Synthesis of N$^α$-Boc-L-glutamine acid (1'R)-(1'-(1-naphthyl)ethyl)amide γ-benzyl ester (Compound XXXV-3)

Commercially available N$^α$-Boc-L-glutamine acid γ-benzyl ester (1.12 g) was dissolved in DMF (21.0 ml). Commercially available (R)-1-(1-naphthyl)ethylamine (0.853 g), WSCI hydrochloride (0.955 g), and HOBt (0.673 g) were added to the solution. The mixture was allowed to stand for one day at room temperature. After confirming completion of the reaction with TLC, the reaction mixture was concentrated under reduced pressure as is. 1 N aqueous solution of hydrochloric acid was added to the residue and the resulting solution was extracted with chloroform. The organic layer separated was washed with saturated aqueous solution of sodium bicarbonate, dried over anhydrous sodium sulfate, and concentrated under reduced pressure. The residue was purified by silica gel column chromatography (50 g, chloroform/ethyl acetate=5/1) to obtain the title compound (1.63 g) as a white solid.

MS(FAB,Pos.): m/z=491[M+1]+ 1H-NMR(500 MHz, CDCl$_3$): δ=1.33(9H,s),1.63(3H,d,J=6.8 Hz),1.88–1.98(1H, m),2.12–2.22(1H,m),2.45(1H,dt,J=6.8, 16.6 Hz),2.50–2.58 (1H,m),4.08–4.20(1H,m),5.11(2H,s),5.04–5.09(1H,m),5.88 (1H,t,J=7.1 Hz),6.48–6.62(1H,m),7.23–7.53(9H,m),7.78 (1H,d, J=7.8 Hz),7.84(1H,d,J=7.8 Hz),8.04(1H,d,J=8.3 Hz).

Example 57-2

Synthesis of N$^α$-(4-(N-Boc-aminomethyl) naphthoyl)-L-glutamine acid (1'R)-(1'-(1-naphthyl) ethyl)amide γ-methyl ester (Compound XL-2)

The compound obtained in Example 57-1 (1.15 g) was dissolved in methanol (17.3 ml) and 10% hydrochloric acid/methanol solution (17.3 ml) was added. The mixture was allowed to stand for one day at room temperature. After confirming completion of the reaction with TLC, the reaction mixture was concentrated under reduced pressure as is and dried under vacuum to obtain the title compound as a white solid. The solid was dissolved in DMF (14.7 ml). The compound obtained in Example 25-2 (0.706 g), WSCI hydrochloride (0.674 g), and DMAP (0.859 g) were added to the solution. The mixture was allowed to stand for one day at room temperature. After confirming completion of the reaction with TLC, the reaction mixture was concentrated under reduced pressure as is. Saturated aqueous solution of sodium bicarbonate was added to the residue and the resulting solution was extracted with chloroform. The organic layer separated was dried over anhydrous sodium sulfate and concentrated under reduced pressure. The residue was purified by silica gel column chromatography (50 g, chloroform/ methanol=40/1) to obtain the title compound (1.03 g) as a pale yellow solid.

MS(FAB,Pos.): m/z=598[M+1]+ 1H-NMR(500 MHz, CDCl$_3$): δ=1.47(9H,s),1.69(d, 3H,J=6.8 Hz),2.11–2.19(1H, m),2.28–2.35(1H,m),2.50–2.56(1H,m),2.66–2.72(1H,m), 3.67(3H,s),4.70–4.84(3H,m),5.95(1H,quintet,J=7.0 Hz), 6.82–6.92(1H,d,J=7.8 Hz),6.99(1H,d,J=8.3 Hz),7.30–7.57 (9H,m), 7.77(1H,d,J=8.1 Hz),7.85(1H,d,J=7.8 Hz),8.03(1H, d,J=8.3 Hz),8.09 (1H,d,J=8.3 Hz),8.15(1H,d,J=8.5 Hz).

Example 57-3

Synthesis of (S)-2-(4-(N-Boc-aminomethyl) naphthoylamino)-4-formyl-butyric acid (1'R)-(1'-(1-naphthyl)ethyl)amide (Compound XLI-2)

Lithium aluminum hydride (0.196 g) was suspended in anhydrous tetrahydrofuran (10.3 ml). A solution of the compound obtained in Example 57-2 (1.03 g) in anhydrous tetrahydrofuran (20.6 ml) was added. The mixture was stirred for 0.5 hour at room temperature. Completion of the reaction was confermed with TLC, and ethyl acetate, methanol, and 10% aqueous solution of potassium sodium tartrate were sequentially added to the reaction solution. The mixture was stirred for a further one hour. The reaction solution was extracted with chloroform and the organic layer separated was dried over anhydrous sodium sulfate, followed by concentration under reduced pressure. The residue was purified by silica gel column chromatography (80 g, chloroform/methanol=15/1) to obtain an intermediate alcohol compound (0.785 g) as a white solid.

Oxalyl chloride (0.177 ml) and dimethyl sulfoxide (0.294 ml) were added to methylene chloride (23.6 ml) while stirring at −78° C. After stirring for 0.5 hour, a solution of the intermediate alcohol compound (0.670 g) obtained above in methylene chloride (6.70 ml) was added. After stirring for a further 0.5 hour, triethylamine (0.864 ml) was added. The mixture was stirred for 1.5 hours while cooling with ice. After the addition of water, the reaction solution was extracted with chloroform and the organic layer separated was dried over anhydrous sodium sulfate, followed by concentration under reduced pressure. The residue was purified by silica gel column chromatography (50 g, chloroform/methanol=30/1) to obtain the title compound (0.446 g) as a light orange solid.

MS(FAB,Pos.): m/z=568[M+1]$^+$ $^1$H-NMR(500 MHz, CDCl$_3$): δ=1.45(9H,s),1.63(3H,d,J=6.8 Hz),1.80–2.42(4H, m),3.37(2H,m),4.40–5.04(4H,m),5.90–5.98(1H,m),7.05 (1H,d,J=7.1 Hz),7.12–7.60(8H,m),7.64–8.16(5H,m).

Example 57-4

Synthesis of (S)-2-(4-(N-Boc-aminomethyl) naphthoylamino)-5-(2-picolylamino)valeric acid (1'R)-(1'-(1-naphthyl)ethyl)amide (Compound XXI-7)

The compound obtained in Example 57-3 (200.0 mg) was dissolved in methanol (6.00 ml), and 2-aminomethylpyridine (44.3 mg) and sodium cyanoborohydride (44.3 mg) were added at room temperature. After adjusting the pH to 4–5 with the addition of acetic acid, the mixture was stirred for 3 days. After confirming consumption of the raw materials with TLC, the reaction mixture was concentrated under reduced pressure as is. Water was added to the residue and the solution was extracted with chloroform. The organic layer separated was dried over anhydrous sodium sulfate and concentrated under reduced pressure. The residue was purified by silica gel column chromatography (10 g, chloroform/methanol=10/1) to obtain the title compound (66.6 mg) as a pale yellow solid.

MS(FAB,Pos.): m/z=660[M+1]$^+$ $^1$H-NMR(500 MHz, CDCl$_3$): δ=1.47(9H,s),1.68(3H,d,J=6.8 Hz),1.90–2.20(4H, m),3.00–3.16(2H,m),3.86–4.00(2H,m),4.64–4.88(4H,m), 5.90–6.00(1H,m),7.00–7.18(2H,m),7.28–7.60(8H,m),7.73 (1H,d, J=8.1 Hz),7.83(1H,d,J=8.1 Hz),7.90–8.02(2H,m), 8.14(1H,d,J=8.3 Hz),8.22(2H,d,J=8.3 Hz).

Example 57-5

Synthesis of (S)-2-(4-(imidazol-2-ylmethyl) aminomethyl)naphthoylamino)-5-(2-picolylamino) valeric acid (1'R)-(1'-(1-naphthyl)ethyl)amide [Compound No. 58]

The compound obtained in Example 57-4 (66.6 mg) was dissolved in methanol (2 ml) and 4 mol/l hydrochloric acid/dioxane solution (2 ml) was added. The mixture was stirred for one hour at room temperature. After the reaction, the solvent was removed by distillation and the residue was dried under vacuum. The residue was dissolved in anhydrous methanol. After the addition of triethylamine (42.2 μl) and 2-imidazole carboaldehyde (11.6 mg), the mixture was stirred for 5 hours at room temperature. After the reaction, the reaction solution was concentrated. The residue was dried under reduced pressure and dissolved in anhydrous methanol (2 ml). The mixture was cooled to 0° C. Sodium borohydride (7.6 mg) was added to the solution and the mixture was stirred for 0.5 hour at room temperature. After the reaction, the reaction mixture was concentrated. The residue was purified by silica gel column chromatography (5 g, chloroform/methanol/water=7/3/0.5) and treated with 1 mol/l aqueous solution of hydrochloric acid to obtain hydrochloride of the title compound (27.6 mg) as a white solid.

MS(FAB,Pos.): m/z=640[M+1]$^+$ $^1$H-NMR(500 MHz, DMSO-d$_6$): δ=1.55(3H,d,J=6.8 Hz),1.78–1.94(4H,m), 3.00–3.08(2H,m),4.34–4.38(2H,m),4.58–4.76(2H,m), 4.80–4.96 (2H,m),5.74(1H, t,J=7.0 Hz),7.40–7.96(14H,m), 8.14(1H,d,J=8.5 Hz),8.20(1H,d,J=8.5 Hz),8.31(1H,d,J=9.0 Hz),8.65(1H,d,J=7.1 Hz),8.78–8.84(2H,m).

EXAMPLE 58

Preparation of (S)-2-(4-(imidazol-2-ylmethyl) aminomethyl)naphthoylamino)-5-(5,6,7,8-tetrahydroquinolin-8-ylamino)valeric acid (1'R)-(1'-(1-naphthyl)ethyl)amide [Compound No. 59]

Example 58-1

Synthesis of (S)-2-(4-(N-Boc-aminomethyl) naphthoylamino)-5-(5,6,7,8-tetrahydroquinolin-8-ylamino)valeric acid (1'R)-(1'-(1-naphthyl)ethyl) amide (Compound XXI-8)

The compound obtained in Example 57-3 (200.0 mg) was dissolved in methanol (6.00 ml), and the amine obtained in Example 54-1 (126.1 mg) and sodium cyanoborohydride (44.3 mg) were added at room temperature. After adjusting the pH to 4–5 with the addition of acetic acid, the mixture was stirred for 3 days. After confirming consumption of the raw materials with TLC, the reaction mixture was concentrated under reduced pressure as is. Water was added to the residue and the solution was extracted with chloroform. The organic layer separated was dried over anhydrous sodium sulfate and concentrated under reduced pressure. The residue was purified by silica gel column chromatography (10 g, chloroform/methanol=15/1) to obtain the title compound (123.3 mg) as a pale yellow solid.

MS(FAB,Pos.): m/z=700[M+1]$^+$ $^1$H-NMR(500 MHz, CDCl$_3$): δ=1.47(9H,s),1.68(3H,d,J=6.8 Hz),1.76–2.40(8H, m),2.60–2.78(2H,m),3.04–3.40(4H,m),4.62–4.90(4H,m), 5.86–5.96 (1H,m),7.04–7.12(1H,m),7.22–7.58(7H,m), 7.73–7.84 (3H,m),7.90–8.04(4H,m),8.08–8.20(1H,m), 8.24–8.36(1H,m).

Example 58-2

Synthesis of (S)-2-(4-(imidazol-2-ylmethyl) aminomethyl)naphthoylamino)-5-(5,6,7,8-tetrahydroquinolin-8-ylamino)valeric acid (1'R)-(1'-(1-naphthyl)ethyl)amide [Compound No. 59]

The compound obtained in Example 58-1 (123.3 mg) was dissolved in methanol (2 ml) and 4 mol/l hydrochloric acid/dioxane solution (2 ml) was added. The mixture was stirred for one hour at room temperature. After the reaction, the solvent was removed by distillation and the residue was dried under vacuum. The residue was dissolved in anhydrous methanol (3.17 ml). After the addition of triethylamine (73.7 μl) and 2-imidazole carboaldehyde (20.3 mg), the mixture was stirred for 5 hours at room temperature. After the reaction, the reaction solution was concentrated. The residue was dried under reduced pressure and dissolved in anhydrous methanol (2 ml). The mixture was cooled to 0° C. Sodium borohydride (13.3 mg) was added to the solution and the mixture was stirred for 0.5 hour at room temperature. After the reaction, the reaction mixture was concentrated. The residue was purified by silica gel column chromatography (5 g, chloroform/methanol/water=7/3/0.5) and treated with 1 mol/l aqueous solution of hydrochloric acid to obtain hydrochloride of the title compound (75.5 mg) as a white solid.

EXAMPLE 59

Preparation of (S)-2-(4-(N-2-picolylaminomethyl)benzoylamino)-5-(2-picolylamino)valeric acid 1-naphthalenemethylamide [Compound No. 60]

The compound obtained in Example 19-3 (48.8 mg) was dissolved in methanol (1.0 ml). After the addition of triethylamine (30.0 µl) and 2-pyridinealdehyde (17.5 µl), the mixture was stirred for 30 minutes at room temperature. After the reaction, the solvent was removed by distillation and anhydrous methanol (1.0 ml) was added to the residue. Then, the mixture was cooled to 0° C. Sodium borohydride (26.6 mg) was added to the solution and the mixture was stirred for 40 minutes, while allowing gradually to become room temperature. After the reaction, the solvent was removed by distillation. The residue was purified by silica gel column chromatography (2 g, chloroform/methanol/water=7/3/0.5). The resulting compound was dissolved in 1 mol/l aqueous solution of hydrochloric acid and water was removed by distillation to obtain hydrochloride of the title compound (24.8 mg) as a white solid.

MS(FAB,Pos.): m/z=587[M+1]$^+$ $^1$H-NMR(500 MHz, DMSO-d$_6$): δ=1.75–1.90(4H,m),2.90–3.10(2H,m), 4.29 and 4.30(6H,s),4.54–4.58(1H,m),4.76(2H,d,J=5.6 Hz), 7.40–7.49(4H,m),7.52–7.61(4H,m),7.67(2H,d,J=8.1 Hz), 7.84–7.86(1H, m),7.91–7.96(3H,m),7.99(2H, d,J=8.1 Hz), 8.05–8.08(1H,m),8.62(1H,d,J=4.9 Hz),8.66(1H,d,J=4.9 Hz), 8.69–8.73(2H,m),9.37(2H, brs),9.95(2H,brs).

EXAMPLE 60

Preparation of (S)-2-(4-(N-2-picolylamino)methylbenzoylamino)-4-(N-2-picolylamino)butyric acid 1-naphthalenemethylamide [Compound No. 61]

Example 60-1

Synthesis of (S)-2-(N-Fmoc-amino)-4-(N-Boc-amino)butyric acid 1-naphthalenemethylamide (Compound X-3)

Commercially available (S)-2-(N-Fmoc-amino)-4-(N-Boc-amino)butyric acid (201.9 mg) was dissolved in DMF (2.0 ml), and WSCI hydrochloride (106.1 mg) and HOBt (71.0 mg) were added to the solution. After the addition of 1-naphthalenemethylamine (67 ml), the solution was stirred for 16 hours at room temperature. After the reaction, the solvent was removed by distillation. The residue was purified by silica gel column chromatography (10 g, chloroform/methanol=30/1) to obtain the title compound (231.8 mg) as a white solid.

MS(FAB,Pos.): m/z=580[M+1]$^+$ $^1$H-NMR(500 MHz, DMSO-d$_6$): δ=1.37(9H,s),1.65–1.73(1H,m),1.78–1.83(1H, m),2.97–3.03(2H,m),4.05–4.10(1H,m),4.20–4.28(3H,m), 4.75(2H,brs),6.75(1H,brs),7.30–7.37(2H,m),7.42(2H,t,J= 7.4 Hz),7.43–7.49(2H,m),7.50–7.57(2H,m),7.64(1H,d,J= 8.3 Hz), 7.74(1H,t,J=6.7 Hz),7.84(1H,d,J=7.3 Hz),7.90(2H, d,J=7.4 Hz), 7.93(1H,m),8.02(1H,d,J=6.3 Hz),8.42(1H,t,J= 5.6 Hz).

Example 60-2

Synthesis of (S)-2-(4-(N-Boc-aminomethyl)benzoylamino)-4-(N-Boc-amino)butyric acid 1-naphthalenemethylamide (Compound XVIII-8)

The compound obtained in Example 60-1 (152.2 mg) was dissolved in DMF (3.0 ml). After the addition of diethylamine (0.3 ml), the mixture was stirred for 50 minutes at room temperature. After the reaction, the solvent was removed by distillation and the residue was dried using a vacuum pump. The obtained compound was used for the next reaction without purification.

The compound (141.7 mg) was dissolved in DMF (3 ml). WSCI hydrochloride (75.6 mg), HOBt (35.5 mg), and the compound obtained in Example 19-1 (79.3 mg) were added to the solution. The mixture was stirred for 22 hours at room temperature. After the reaction, the solvent was removed by distillation. The residue was dissolved in chloroform and the resulting solution was washed with 1 mol/l aqueous solution of hydrochloric acid, 1 mol/l aqueous solution of sodium hydroxide, and saturated brine. The organic layer separated was dried over anhydrous sodium sulfate and the solvent was removed by distillation. The residue was purified by silica gel column chromatography (7.5 g, chloroform/methanol=30/1) to obtain the title compound (109.1 mg) as a white solid.

MS(FAB,Pos.): m/z=591[M+1]$^+$ $^1$H-NMR(500 MHz, DMSO-d$_6$): δ=1.35(9H,s),1.39(9H,s),1.83–1.87(1H, m),1.91–1.95(1H,m),2.98–3.03(2H,m),4.17(2H,d,J=6.3 Hz),4.48–4.52(1H,m),4.75(2H,d,J=5.6 Hz),6.78(1H,t,J=5.3 Hz),7.31(2H,d, J=8.1 Hz),7.44–7.49(3H,m),7.52–7.56(2H, m),7.83–7.86(3H,m), 7.93–7.96(1H,m),8.04–8.06(1H,m), 8.47–8.49(2H,m).

Example 60-3

Synthesis of (S)-2-(4-aminomethylbenzoylamino)-4-aminobutyric acid 1-naphthalenemethylamide (Compound XIX-2)

The compound obtained in Example 60-2 (49.7 mg) was dissolved in methanol (0.5 ml) and 4 mol/l hydrochloric acid/dioxane solution (0.5 ml) was added. The mixture was stirred for 1.5 hours at room temperature. After the reaction, the solvent was removed by distillation and the residue was dried using a vacuum pump to obtain the title compound (52.4 mg) as a white solid.

MS(FAB,Pos.): m/z=391 M+1]$^+$

Example 60-4

Synthesis of (S)-2-(4-(N-2-picolylamino)methylbenzoylamino)-4-(N-2-picolylamino)butyric acid 1-naphthalenemethylamide [Compound No. 61]

The compound obtained in Example 60-3 (45.1 mg) was dissolved in methanol (0.9 ml). After the addition of triethylamine (24.4 µl) and 2-pyridinealdehyde (14.4 µl), the mixture was stirred for 70 minutes at room temperature. After the reaction, the solvent was removed by distillation and anhydrous methanol (1.0 ml) was added to the residue. Then, the mixture was cooled to 0° C. Sodium borohydride (23.4 mg) was added to the solution and the mixture was stirred for 35 minutes, while allowing gradually to become room temperature. After the reaction, the solvent was removed by distillation. The residue was purified by silica gel column chromatography (chloroform/methanol/water= 7/3/0.5). The compound was dissolved in 1 mol/l aqueous solution of hydrochloric acid and water was removed by distillation to obtain hydrochloride of the title compound (28.4 mg) as a white solid.

MS(FAB,Pos.): m/z=573[M+1]$^+$ $^1$H-NMR(500 MHz, DMSO-d$_6$): δ=2.20–2.37(4H,m),3.0–3.15(2H,m), 4.22–4.37 (6H,m),4.61–4.67(1H,m),4.74(1H,dd,J=15.6,5.9 Hz), 4.79

(1H,dd,J=15.6,5.9 Hz),7.44–7.49(4H,m),7.52–7.58(3H,m), 7.61(1H,d,J=7.8 Hz),7.67(2H,d,J=8.5 Hz),7.86(1H,dd,J=7.3,1.9 Hz), 7.89–7.96(3H,m),7.99(2H,d,J=8.5 Hz), 8.06–8.09(1H,m),8.62(1H,dd,J=4.9,1.7 Hz),8.67(1H,dd,J=4.9,1.7 Hz),8.74(1H,t,J=5.6 Hz),8.86(1H,d,J=7.8 Hz),9.46 (2H,brs),9.96(2H,brs).

EXAMPLE 61

Preparation of (S)-2-(4-(N-2-picolylamino) methylbenzoylamino)-3-(N-2-picolylamino) propionic acid 1-naphthalenemethylamide [Compound No. 61]

Example 61-1

Synthesis of (S)-2-(N-Fmoc-amino)-3-(N-Boc-amino)propionic acid 1-naphthalenemethylamide (Compound X-4)

Commercially available (S)-2-(N-Fmoc-amino)-4-(N-Boc-amino)propionic acid (201.6 mg) was dissolved in DMF (2.0 ml), and WSCI hydrochloride (110.0 mg) and HOBt (75.6 mg) were added to the solution. After the addition of 1-naphthalenemethylamine (29 μl), the solution was stirred for 16 hours at room temperature. After the reaction, the solvent was removed by distillation. The residue was purified by silica gel column chromatography (10 g, chloroform/methanol=30/1) to obtain the title compound (226.3 mg) as a white solid.

MS(FAB,Pos.): m/z=566[M+1]$^+$ $^1$H-NMR(500 MHz, DMSO-d$_6$): δ=1.37(9H,s) 3.26–3.29(2H,m),4.10–4.25(2H,m),4.27–4.29(2H,m),4.76(2H,d,J=5.6 Hz),6.80(1H,t,J=5.6 Hz),7.30–7.37(2H,m),7.43(2H,t,J=7.3 Hz),7.44(2H,d,J=5.8 Hz),7.71(2H,d,J=7.7 Hz),7.88(1H,t,J=4.3 Hz),7.90(2H,d,J=7.6 Hz),7.93(1H,m),8.03(1H,d,J=6.8 Hz),8.51(1H,t,J=5.6 Hz).

Example 61-2

Synthesis of (S)-2-(4-(N-Boc-aminomethyl) benzoylamino)-3-(N-Boc-amino)propionic acid 1-naphthalenemethylamide (Compound XVIII-9)

The compound obtained in Example 61-1 (151.6 mg) was dissolved in DMF (3.0 ml). After the addition of diethylamine (0.3 ml), the mixture was stirred for 60 minutes at room temperature. After the reaction, the solvent was removed by distillation and the residue was dried using a vacuum pump. The obtained compound was used for the next reaction without purification.

The compound (136.0 mg) was dissolved in DMF (3 ml). WSCI hydrochloride (76.6 mg), HOBt (35.3 mg), and the compound obtained in Example 19-1 (79.7 mg) were added to the solution. The mixture was stirred for 23 hours at room temperature. After the reaction, the solvent was removed by distillation. The residue was purified by silica gel column chromatography (7.5 g, chloroform/methanol=30/1) to obtain the title compound (46.2 mg) as a white solid.

MS(FAB,Pos.): m/z=577[M+1]$^+$ $^1$H-NMR(500 MHz, DMSO-d$_6$): δ=1.35(9H,s),1.39(9H,s),3.34–3.72(2H, m),4.16(2H,d,J=6.3 Hz),4.54–4.57(1H,m),4.74(1H,dd,J=11.7, 5.6 Hz),4.78(1H,dd,J=11.7,5.6 Hz),7.05(1H,t,J=5.6 Hz),7.31(2H, d,J=8.3 Hz),7.44–7.49(3H,m), 7.51–7.57(2H, m),7.81–7.85(3H,m), 7.93–7.95(1H,m),8.02–8.05(1H,m), 8.33(1H,d,J=7.8 Hz),8.54(1H, t,J=5.6 Hz).

Example 61-3

Synthesis of (S)-2-(4-aminomethylbenzoylamino)-3-aminopropionic acid 1-naphthalenemethylamide (Compound XIX-3)

The compound obtained in Example 3-2 (43.2 mg) was dissolved in methanol (0.86 ml) and 4 mol/l hydrochloric acid/dioxane solution (0.86 ml) was added. The mixture was stirred for 100 minutes at room temperature. After the reaction, the solvent was removed by distillation and the residue was dried using a vacuum pump to obtain the title compound (42.1 mg) as a white solid.

MS(FAB,Pos.): m/z=377[M+1]$^+$

Example 61-4

Synthesis of (S)-2-(4-(N-2-picolylamino) methylbenzoylamino)-3-(N-2-picolylamino) propionic acid 1-naphthalenemethylamide [Compound No. 62]

The compound obtained in Example 61-3 (36.8 mg) was dissolved in methanol (0.8 ml). After the addition of triethylamine (22.1 μl) and 2-pyridinealdehyde (13.0 μl), the mixture was stirred for 70 minutes at room temperature. After the reaction, the solvent was removed by distillation and anhydrous methanol (1.0 ml) was added to the residue. Then, the mixture was cooled to 0° C. Sodium borohydride (20.8 mg) was added to the solution and the mixture was stirred for 35 minutes, while allowing gradually to become room temperature. After the reaction, the solvent was removed by distillation. The residue was purified by silica gel column chromatography. (2 g, chloroform/methanol/water=7/3/0.5). The compound was dissolved in 1 mol/l aqueous solution of hydrochloric acid and water was removed by distillation to obtain hydrochloride of the title compound (25.9 mg) as a white solid.

MS(FAB,Pos.): m/z=559[M+1]$^1$ $^1$H-NMR(500 MHz, DMSO-d$_6$): δ=3.4–3.7(4H,m),4.34(4H,brs),4.42(2H, s), 4.77(1H,d,J=5.9 Hz),5.00–5.05(1H,m),7.43–7.50(4H,m), 7.52–7.56(2H,m),7.58(1H,d,J=7.8 Hz),7.62(1H,d,J=7.8 Hz),769 (2H,d,J=8.3 Hz),7.85(1H,dd,J=7.3,2.0 Hz), 7.90–7.96(3H,m),8.05 (2H,d,J=8.3 Hz),8.05–8.06(1H,m), 8.62(1H,dd,J=4.9,1.7 Hz),8.67 (1H,dd,J=4.9,1.7 Hz),8.85 (1H,t,J=5.6 Hz),9.16(1H,d,J=7.8 Hz),9.58 (2H,brs),9.99 (2H,brs).

EXAMPLE 62

Preparation of (S)-2-(4-(N-2-picolylaminomethyl) benzoyl)-5-(N-2-picolylamino)capric acid 1-naphthalenemethylamide [Compound No. 63]

Example 62-1

Synthesis of N$^\alpha$-4-(N-Fmoc-aminomethyl)benzoyl-N$^\epsilon$-Boc-L-lysin 1-naphthalenemethylamide (Compound X-5)

Commercially available N$^\alpha$-Fmoc-N$^\delta$-Boc-lysin (510.0 mg) was dissolved in DMF (10 ml), and WSCI hydrochloride (255.4 mg) and HOBt (177.6 mg) were added to the solution. After the addition of 1-naphthalenemethylamine (157 μl), the solution was stirred for 2 days at room temperature. After the reaction, the solvent was removed by distillation. The residue was dissolved in chloroform and the resulting solution was washed with 1 N aqueous solution of hydrochloric acid and saturated brine. The organic layer was dried over anhydrous sodium sulfate and the solvent was removed by distillation. The residue was purified by silica gel column chromatography (25 g, chloroform/ethyl acetate=2/1) to obtain the title compound (455.9 mg) as white foam.

MS(FAB,Pos.): m/z=608[M+1]$^+$ $^1$H-NMR(500 MHz, DMSO-d$_6$): δ=1.36(9H,s),1.22–1.40(4H,m),1.55–1.65(2H, m),2.86(2H,d,J=6.1,5.6 Hz),4.02(1H,m),4.20–4.30(3H, m),4.75(2H,m),6.78(1H,t,J=5.6 Hz),7.31–7.35(2H,m),7.41 (2H,t, J=7.6 Hz),7.43–7.47(2H,m),7.50–7.55(3H,m),7.73 (2H,d,J=7.6 Hz), 7.84(1H,m),7.90(2H,d,J=7.6 Hz),7.94(1H, m),7.93(1H,m),8.03(1H, m),8.45(1H,t,J=5.6 Hz).

Example 62-2

Synthesis of $N^\alpha$-4-(N-Boc-aminomethyl)benzoyl-$N^\epsilon$-Boc-L-lysin 1-naphthalenemethylamide (Compound XVIII-10)

The compound obtained in Example 62-1 (301.0 mg) was dissolved in DMF (6 ml). After the addition of diethylamine (0.6 ml), the mixture was stirred for 140 minutes at room temperature. After the reaction, the solvent was removed by distillation and the residue was dried using a vacuum pump and dissolved in DMF (6 ml). WSCI hydrochloride (143.8 mg), HOBt (75.4 mg), and the compound obtained in Example 19-1 (137.0 mg) were added to the solution. The mixture was stirred for 13.5 hours at room temperature. After the reaction, the solvent was removed by distillation. The residue was purified by silica gel column chromatography (15 g, chloroform/ethyl acetate=1/1) to obtain the title compound (125.2 mg) as a white solid.

MS(FAB,Pos.): m/z=619[M+1]$^+$ $^1$H-NMR(500 MHz, DMSO-d$_6$): δ=1.35(9H,s),1.39(9H,s),1.20–1.45(4H,m), 1.70–1.80(2H,m),2.86(2H,m),4.17(2H,d,J=6.1 Hz), 4.46 (1H,m),4.75(2H,m),6.77(1H,t,J=5.6 Hz),7.31(2H,d,J=8.3 Hz), 7.43–7.49(3H,m),7.51–7.56(2H,m), 7.83–7.86(3H,m), 7.93–7.96(1H,m),8.04–8.60(1H,m),8.40(1H,d,J=7.6 Hz), 8.52(1H,t,J=5.6 Hz).

Example 62-3

Synthesis of $N^\alpha$-(4-aminomethylbenzoyl)-L-lysin 1-naphthalenemethylamide (Compound-XIX-4)

The compound obtained in Example 62-2 (53.7 mg) was dissolved in methanol (2.0 ml) and 4 mol/l hydrochloric acid/dioxane solution (2.0 ml) was added. The mixture was stirred for 20 hours at room temperature. After the reaction, the solvent was removed by distillation and the residue was dried using a vacuum pump to obtain the title compound (51.9 mg) as a white solid.

MS(FAB,Pos.): m/z=419[M+1]$^+$

Example 62-4

Synthesis of (S)-2-(4-(2-picolylaminomethyl) benzoyl)-5-(2-picolylamino)capric acid 1-naphthalenemethylamide [Compound No. 63]

The compound obtained in Example 62-3 (51.9 mg) was dissolved in methanol (1.0 ml). After the addition of triethylamine (29.3 μl) and 2-pyridinealdehyde (17.5 μl), the mixture was stirred for 90 minutes at room temperature. After the reaction, the solvent was removed by distillation and anhydrous methanol (1.0 ml) was added to the residue. Then, the mixture was cooled to 0° C. Sodium borohydride (26.6 mg) was added to the solution and the mixture was stirred for 60 minutes, while allowing gradually to become room temperature. After the reaction, the solvent was removed by distillation. The residue was purified by silica gel column chromatography (2.5 g, chloroform/methanol/water=7/3/0.5). The compound was dissolved in 1 N aqueous solution of hydrochloric acid and water was removed by distillation to obtain hydrochloride of the title compound (31.1 mg) as a white solid.

MS(FAB,Pos.): m/z=601[M+1]$^+$ $^1$H-NMR(500 MHz, DMSO-d$_6$): δ=1.30–1.46(2H,m),1.60–1.75(2H,m), 1.80–1.83(2H,m),2.80–3.00(2H,m),4.30(6H,brs),4.52(1H, m), 4.73(1H,dd,J=15.3,5.6 Hz),4.78(1H,dd,J=15.3,5.6 Hz), 7.44–7.49 (3H,m),7.52–7.55(2H,m),7.59(2H,t,J=7.8 Hz), 7.66(2H,d,J=8.5 Hz),7.83–7.86(1H,m),7.91–7.96(3H,m), 7.99(2H,d,J=8.5 Hz), 8.05–8.09(1H,m),8.64–8.68(4H,m), 9.36(2H,brs),9.95(2H,brs).

EXAMPLE 63

Preparation of (2S)-2-(4-((5,6,7,8-tetrahydroquinolin-8-yl)aminomethyl) benzoylamino)-5-((5,6,7,8-tetrahydroquinolin-8-yl) amino)valeric acid 1-naphthalenemethylamide [Compound No. 64]

The compound obtained in Example 19-3 (25.0 mg) was dissolved in methanol (0.5 ml). After the addition of triethylamine (11 mg) and 5,6,7,8-tetrahydroquinolin-8-one (16.0 mg), the mixture was stirred for 120 minutes at room temperature. After the reaction, the solvent was removed by distillation and anhydrous methanol (0.5 ml) was added to the residue. Then, the mixture was cooled to 0° C. Sodium borohydride (12.0 mg) was added to the solution and the mixture was stirred for 40 minutes, while allowing gradually to become room temperature. After the reaction, the solvent was removed by distillation. The residue was purified by silica gel column chromatography (1 g, chloroform/methanol=5/1). The compound was dissolved in 1 mol/l aqueous solution of hydrochloric acid and water was removed by distillation to obtain hydrochloride of the title compound (10.2 mg) as a white solid.

MS(FAB,Pos.): m/z=667[M+1]$^+$ $^1$H-NMR(500 MHz, DMSO-d$_6$): δ=1.76–1.83(4H,m),1.85–1.91(3H,m), 1.98–2.05(3H,m),2.23–2.36(1H,m),2.36–2.41(1H,m), 2.78–2.82 (4H,m),2.90–2.99(1H,m),3.04–3.17(1H,m),4.37 (2H,m),4.41(2H, m),4.54–4.58(1H,m),4.77(2H,m), 7.36–7.41(2H,m),7.47(2H,m), 7.55(2H,m),7.65–7.73(4H, m),7.84(1H,m),7.94(1H,m),8.00(2H,m), 8.06(1H,m),8.45 (1H,m),8.53(1H,m),8.70(2H,m),9.12(2H,m).

EXAMPLE 64

Preparation of (2S)-2-(4-(N-2-picolylaminomethyl) benzoylamino)-5-((5,6,7,8-tetrahydroquinolin-8-yl) amino)valeric acid 1-naphthalenemethylamide [Compound No. 65]

Example 64-1

Synthesis of $N^\alpha$-4-(N-Boc-N-2-picolylaminomethyl) benzoyl-(N$^\delta$-2-chlorobenzyloxycarbonyl)-L-ornithine 1-naphthalenemethylamide (Compound XI-10)

$N^\alpha$-Fmoc-(N$^\delta$-2-chlorobenzyloxycarbonyl)-L-ornithine (2.03 g), WSCI hydrochloride (1.10 g), and HOBt (0.79 g) were dissolved in DMF (40 ml). 1-naphthalenemethylamine (0.63 ml) was added to the solution. After 17 hours, the reaction solution was concentrated. 1 mol/l hydrochloric acid was added to the residue, and the mixture was extracted with chloroform. Saturated aqueous solution of sodium bicarbonate was added to the organic layer. The mixture was extracted with chloroform. The organic layer separated was dried over anhydrous sodium sulfate and concentrated to obtain a crude product (2.47 g) as a pale yellow solid. Part of the crude product (1.12 g) was dissolved in DMF (20 ml) and diethylamine (2 ml) was added. After one hour, the reaction solution was concentrated. Syrup obtained by drying the residue under reduced pressure, WSCI hydrochloride (0.49 g), DMAP (0.31 g), and the compound synthesized in Example 1-2 (0.58 g) were dissolved in DMF (15 ml). After 15 hours, the reaction solution was concentrated and 1 mol/l hydrochloric acid was added. The mixture was extracted with chloroform. The organic layer separated was washed with saturated brine, dried over anhydrous sodium sulfate, and concentrated. The residue was purified by silica gel column chromatography (50 g, chloroform/methanol=20/1) to obtain the target compound (1.24 g) as a yellow solid.

MS(Fab,pos.): m/z=765[M+H]$^+$ $^1$H-NMR(500 MHz, CDCl$_3$): δ=1.44 and 1.46(9H, 2s) 1.48–1.80(3H,m), 1.85–1.93 (1H,m),3.08–3.15(1H,m),3.46–3.57(1H,m),4.45 (1H, s),4.50(1H,s),4.58(2H, s),4.72–4.80(2H,m),4.84–5.00 (3H,m), 7.10–7.52(15H,m),7.65(1H,t,J=7.8 Hz),7.73(3H,d, J=8.1 Hz),7.97 (1H,d,J=8.3 Hz),8.53(1H,d,J=4.2 Hz).

Example 64-2

Synthesis of (2S)-2-(4-(N-Boc-N-2-picolylaminomethyl)benzoyl-5-((5,6,7,8-tetrahydroquinolin-8-yl)amino)valeric acid 1-naphthalenemethylamide (Compound XIII-15)

The compound obtained in Example 64-1 (130 mg) was dissolved in methanol (6 ml) and 10% palladium-carbon (130 mg) was added. The mixture was reacted under a pressure of 3 atm. After the reaction, the palladium-carbon was removed by filtration and the solvent was removed by distillation to obtain a residue (0.15 g) The resulting residue was dissolved in methanol (2 ml), and 5,6,7,8-tetrahydroquinolin-8-one (27.5 mg) was added to the solution. The mixture was stirred for one hour at room temperature. After removal of the solvent, the residue was dissolved in anhydrous methanol (2 ml). Sodium borohydride (20.7 mg) was added at 0° C., then mixture was stirred for 30 minutes, while the temperature was gradually increased to room temperature. After the reaction, the solvent was removed by distillation. The residue was purified by silica gel column chromatography (7 g, chloroform/methanol=20/1) to obtain the title compound (18.4 mg) as a light brown solid.

MS(FAB,Pos.): m/z=727[M+1]$^1$ $^1$H-NMR(500 MHz, DMSO-d$_6$): δ=1.31 and 1.38(9H,s),1.48–1.68(3H,m), 1.85 (3H,m),1.98(1H,m),2.35–2.72(5H,m),4.39(1H,brs),4.47 (4H, brs),4.55(1H,brs), 4.76(2H,brs),7.18–7.29(6H,m), 7.42–7.54 (5H,m),7.77(1H,m),7.85(3H,m),7.94(1H,m),8.06 (1H,m),8.33(1H, m),8.44–8.63(3H,m).

Example 64-3

Synthesis of (2S)-2-(4-(N-2-picolylaminomethyl)benzoylamino)-5-((5,6,7,8-tetrahydroquinolin-8-yl)amino)valeric acid 1-naphthalenemethylamide [Compound No. 65]

The compound obtained in Example 64-2 (18.4 mg) was dissolved in methanol (0.4 ml) and 4 mol/l hydrochloric acid/dioxane solution (0.6 ml) was added. The mixture was stirred for 2 hours at room temperature. After the reaction, the solvent was removed by distillation. The residue was purified by silica gel column chromatography (1 g, chloroform/methanol=1/1) to obtain a product (13.1 mg). The obtained product was treated with 1 mol/l aqueous solution of hydrochloric acid. The hydrochloric acid was removed by distillation to obtain hydrochloride of the title compound (14.0 mg) as a pale yellow solid.

MS(FAB,Pos.): m/z=627[M+1]$^+$ $^1$H-NMR(500 MHz, DMSO-d$_6$): δ=1.84(6H,m),1.98(1H,m),2.39(1H,m), 2.81 (1H,m),2.97(1H,m),3.09(1H,m),4.32(4H,brs),4.42(1H,m), 4.56 (1H,m),4.77(2H,d), 7.37(1H,m),7.47(3H,m),7.51(1H, m),7.55(2 H,m),7.66(3H,m),7.85–7.91(2H,m),7.94(3H,m), 8.05(1H,m),8.46 (1H,m),8.66(1H,m),8.72(2H,m),9.18(2H, brs), 9.98(2H,brs).

EXAMPLE 65

Preparation of (S)-2-(4-(3-picolylaminomethyl)benzoylamino)-5-(3-picolylamino)valeric acid 1-naphthalenemethylamide [Compound No. 66]

Example 65-1

Synthesis of (S)-2-(4-(3-picolylaminomethyl)benzoylamino)-5-(3-picolylamino)valeric acid 1-naphthalenemethylamide [Compound No. 66]

The compound obtained in Example 19-2 (98.2 mg) was dissolved in methanol (1 ml) and 4 mol/l hydrochloric acid/dioxane solution (1 ml) was added. The mixture was stirred for 2 hours at room temperature. After the reaction, the solvent was removed by distillation. The residue was dissolved in methanol. The solution was neutralized with Amberlite IRA-410, then, the solvent was removed by distillation. The residue was dissolved in anhydrous methanol (1 ml). After the addition of 3-pyridinealdehyde (34.2 μl), the mixture was stirred for 4.5 hours at room temperature. The reaction solution was concentrated, dried under reduced pressure, and again dissolved in methanol (1.4 ml). After the addition of sodium borohydride (25 mg), the mixture was stirred for one hour at room temperature. After the reaction, the solvent was removed by distillation. The residue was dissolved in chloroform and the resulting solution was washed with saturated brine, and dried over anhydrous sodium sulfate. The solvent was removed by distillation and the residue was purified by silica gel column chromatography (4 g, chloroform/methanol/water=7/3/0.5). After the addition of 1 mol/l hydrochloric acid, the residue was concentrated and azeotropically distilled to obtain hydrochloride of the title compound (33.6 mg) as a white solid.

MS(Fab,pos.): m/z=587[M+H]$^+$ $^1$H-NMR(500 MHz, DMSO-d$_6$): δ=1.72–1.95(4H,m),2.90–3.02(2H,m), 4.28 (2H,s),4.33(2H,t,J=5.6 Hz),4.41(2H,s)4.31(6H,s),4.55–4.61 (1H,m),4.76(2H,d,J=5.9 Hz),7.43–7.48(2H,m),7.51–7.57 (2H, m),7.71(2H,d,J=8.1 Hz),7.82–7.87(1H,m),7.92–7.95 (1H,m),7.99(1H,m,d,J=8.1 Hz),7.99–8.04(2H,m),8.06–8.09 (1H,m),8.68–8.80(4H, m),8.90(1H,d,J=6.1 Hz),8.91(1H,d, J=5.9 Hz),9.09(1H,s),9.12(1H, s),9.88(2H,brs),10.45(2H, brs).

EXAMPLE 66

Preparation of (S)-2-(4-(N-2-picolylaminomethyl)benzoylamino)-5-(N-2-picolylamino)valeric acid 3-(n-butoxy)propylamide [Compound No. 67]

Example 66-1

Synthesis of N$^α$-Fmoc-N$^δ$-Boc-L-ornithine methyl ester (Compound XLII-1)

Commercially available N$^α$-Fmoc-N$^δ$-Boc-L-ornithine (1.00 g), WSCI hydrochloride (0.633 g), and HOBt (0.446 g) were reacted in methanol (20 ml) for 23 hours at room temperature. After the reaction, methanol was removed and the residue was extracted with chloroform. The extract was washed with water, saturated aqueous solution of sodium hydrogencarbonate, and saturated brine, and dried over anhydrous sodium sulfate to remove water. Syrup obtained by removing the solvent was purified by silica gel column chromatography (50 g, chloroform/ethyl acetate=5/1) to obtain the title compound (1.06 g) as a white solid.

MS(FAB,Pos.): m/z=469[M+1]$^+$

Example 66-2

Synthesis of N$^\alpha$-(4-(N-Boc-N-(2-picolyl) aminomethyl)benzoyl)-N$^\delta$-Boc-L-ornithine methyl ester (Compound XLIV-1)

The compound obtained in Example 66-1 (0.300 g), diethylamine (0.136 ml), and DMF (5 ml) were reacted for one hour at room temperature. After removal of the solvent, the residue was dried under vacuum. The compound obtained in Example 1-2 (0.241 g), WSCI hydrochloride (0.184 g), HOBt (0.130 g), and DMF (5 ml) were added to the reaction mixture. Then, the resulting mixture was reacted for 25 hours at room temperature. After the reaction, the reaction solution was diluted with water and extracted with ethyl acetate. The extract was washed with saturated aqueous solution of sodium hydrogencarbonate and saturated brine, and dried over anhydrous sodium sulfate to remove water. Syrup obtained by removing the solvent was purified by silica gel column chromatography (50 g, chloroform/ethyl acetate=1/1) to obtain the title compound (0.337 g) as colorless oil.

MS(FAB,Pos.): m/z=571[M+1]$^+$ $^1$H-NMR(500 MHz, DMSO-d$_6$): δ=1.44 and 1.46(18H, 2s),1.56–1.60(2H, m),1.78–1.85(1H,m),1.97–2.04(1H,m),3.17–3.18(2H,m), 3.79(3H, s),4.46 and 4.51(2H, 2s),4.59(2H,brs),4.65(1H,br), 4.80–4.84 (1H,m),6.93(1H,m),7.17–7.19(2H,m),7.29–7.30 (1H,m),7.34–7.36 (1H,m),7.64–7.67(1H,m),7.78–7.79(2H, m),8.53(1H,d,J=4.2 Hz).

Example 66-3

Synthesis of (S)-2-(4-(N-Boc-N-(2-picolyl) aminomethyl)benzoyl)-5-(N-Boc-2-picolylamino) valeric acid methyl ester (Compound XLVI-1)

The compound obtained in Example 66-2 (0.337 g) was dissolved in methanol (5 ml) and 4 mol/l hydrochloric acid/dioxane solution (5 ml) was added. The mixture was stirred for 1.5 hours at room temperature. After the reaction, the solvent was removed by distillation. The residue was dissolved in methanol (5 ml). After the addition of 2-pyridine aldehyde (0.085 ml) and triethylamine (0.247 ml) to the solution, the mixture was reacted for 2 hours at room temperature. Next, the reaction solution was cooled over an ice-cooled bath. When the temperature was decreased to near 4° C., sodium borohydride (0.04 g) was added. After the reaction for 0.5 hour, methanol was removed to obtain a crude product. The product was dissolved in DMF (5 ml). After the addition of di-t-butyldicarbonate (0.256 g) and triethylamine (0.242 ml) to the solution, the mixture was reacted for 1.5 hours at room temperature. After the reaction, the reaction solution was diluted with a large amount of water and extracted with ethyl acetate. The extract was washed with saturated brine and treated with anhydrous sodium sulfate to remove water. The oily substance obtained by removing the solvent was purified by silica gel column chromatography (35 g, chloroform/MeOH=40/1) to obtain the title compound (0.236 g) as colorless oil.

MS(FAB,Pos.): m/z=662[M+1]$^+$ $^1$H-NMR(500 MHz, DMSO-d$_6$): δ=1.39, 1.44 and 1.46(18H, 3s),1.61–1.95 (4H, m),3.26–3.42(2H,m),3.76(3H,s),4.46–4.59(6H,m), 4.76–4.79 (1H,m),6.70(1H,brs),7.15–7.20(4H,m),7.23–7.35 (2H,m),7.64–7.67(2H,m),7.73–7.74(1H,m),7.81–7.82(1H, m),8.49(1H,m),8.53 (1H,d,J=4.2 Hz).

Example 66-4

Synthesis of (S)-2-(4-(N-Boc-N-(2-picolyl) aminomethyl)benzoyl)-5-(N-Boc-2-picolylamino) valeric acid (Compound XLVII-1)

The compound obtained in Example 66-3 (8.96 g) was dissolved in methanol (134.4 ml) and 1 N aqueous solution of sodium hydroxide (134.4 ml) was added. The mixture was stirred for 1 day. After confirming completion of the reaction with TLC, the reaction solution was concentrated under reduced pressure. The residue was dissolved in 1N aqueous solution of sodium hydroxide and washed with diisopropyl ether. 1 N hydrochloric acid aqueous solution was added to the resulting water layer to adjust the pH to 2–3. The solution was extracted with ethyl acetate and the organic layer separated was dried over anhydrous sodium sulfate, concentrated under reduced pressure, and dried under vacuum to obtain the title compound (8.04 g) as a light brown solid.

MS(FAB,Pos.): m/z=648[M+1]$^+$ $^1$H-NMR(500 MHz, CDCl$_3$): δ=1.44(9H,s),1.46(9H,s),1.62–2.04(4H, m),3.20–3.42(2H,m),4.38–4.84(7H,m),7.18–7.48(6H,m), 7.64–7.82(4H,m),8.42–8.56(2H,m).

Example 66-5

Synthesis of 2-(4-(N-2-picolylaminomethyl) benzoylamino)-5-(N-2-picolylamino)valeric acid 3-(n-butoxy)propylamide [Compound No. 67]

A solution of the compound obtained in Example 66-4 (0.600 g) in DMF (10 ml), a solution of HOBt (0.2508 g) in DMF (10 ml), and a solution of WSCI hydrochloride (0.3552 g) in DMF (50 ml) were prepared. 3-(n-butoxy) propylamine (19.7 mg) was charged into a test tube. The previously prepared DMF solution of the compound obtained in Example 59-5 (0.83 ml) and DMF solution of HOBt (0.83 ml) were added. The DMF solution of WSCI (4.2 ml) previously cooled at −20° C. with stirring was added. The mixture was allowed to become room temperature without dismantling the cooling bath. The mixture was stirred for 63.5 hours at room temperature. The reaction solution was concentrated by centrifugation as is. Chloroform (2 ml) was added to the residue and the resulting solution was washed with 1 N aqueous solution of hydrochloric acid (2 ml). The water layer was extracted with chloroform (2 ml), and the resulting organic layer washed with saturated aqueous solution of sodium hydrogencarbonate (2 ml), and dehydrated with Chem-Elut (manufactured by Varian Technologies Japan, Ltd.). The organic layer was concentrated. The residue was purified using a solid phase extraction column (Sep-Pak Vac silica (manufactured by Waters Corp.), 2 g, chloroform/benzene/methanol).

4 mol/l hydrochloric acid/dioxane solution (1.5 ml) and water (1.5 ml) were added to the resulting condensed product, and the mixture was stirred for 2 hours. The reaction solution was concentrated by centrifugation as is. The residue was azeotropicaly distilled with ethanol and dried under vacuum to obtain hydrochloride of the title compound (90.5 mg) as a white solid.

MS(FAB,Pos.): m/z=561[M+1]⁺ ¹H-NMR(500 MHz, DMSO-d₆): δ=0.86(3H,t,J=7.6 Hz),1.22–1.35(2H, m),1.42–1.50 (2H,m),1.60–1.70(2H,m),1.70–1.90(4H,m), 2.94–3.04(2H,m),3.08–3.16(2H,m), 3.30–3.40(4H,m),4.30 (6H,s), 4.40–4.48(1H,m),7.47(1H,t,J=7.8 Hz),7.48(1H,t,J= 7.6 Hz),7.60 (2H,t,J=8.3 Hz),7.67(2H,d,J=8.1 Hz), 7.90–7.95(2H,m),7.98(2H,d, J=8.3 Hz),8.17(1H,t,J=5.4 Hz),8.60–8.68(2H,m),9.39(2H,bs), 9.97(2H,bs)

EXAMPLE 67

Preparation of [Compound No. 68] to [Compound No. 82]

Hydrochlorides of the compounds shown below were prepared according to the same procedure as in Example 66-5.

Synthesis of (S)-2-(4-(N-2-picolylaminomethyl) benzoylamino)-5-(N-2-picolylamino)valeric acid tetrahydrofurfurylamide [Compound No. 68]

The same procedure was carried out using tetrahydrofurfurylamine (15.6 mg) to obtain hydrochloride of the title compound (9.0 mg) as a white solid.

MS(FAB,Pos.): m/z=531[M+1]⁺ ¹H-NMR(500 MHz, DMSO-d₆): δ=1.45–1.55(1H,m) 1.70–2.00(7H,m), 2.90–3.08 (2H,m),3.12–3.18(1H,m),3.50–3.56(1H,m), 3.68–3.78 (2H,m),3.80–3.86(1H,m),4.30(6H,s),4.45–4.52 (1H,m),7.42–7.48 (2H,m),7.54(2H,t,J=8.3 Hz), 7.66(2H,d, J=8.3 Hz),7.88–7.94(2H, m),7.97(2H,d,J=8.3 Hz),8.15(1H, t,J=6.1 Hz),8.58–8.68(3H,m), 9.24(2H,bs),9.82(2H,bs).

Synthesis of (S)-2-(4-(N-2-picolylaminomethyl) benzoylamino)-5-(N-2-picolylamino)valeric acid phenylhydrazide [Compound No. 69]

The same procedure was carried out using phenylhydrazine (16.7 mg) to obtain hydrochloride of the title compound (34.4 mg) as a white solid.

MS(FAB,Pos.): m/z=538[M+1]⁺ ¹H-NMR(500 MHz, DMSO-d₆): δ=1.74–2.00(4H,m),3.00–3.10(1H,m) 4.31(6H, s),4.40–4.46(1H,m),6.60–7.40(5H,m),7.44–7.50(2H, m),7.50–7.60(2H,m),7.60–7.74(2H,m),7.88–8.02(4H,m), 8.60–8.70(2H,m),9.41(2H,bs),9.99(2H,bs).

Synthesis of (S)-2-(4-(N-2-picolylaminomethyl) benzoylamino)-5-(N-2-picolylamino)valeric acid 2-(3-indolyl)ethylamide[Compound No. 70]

The same procedure was carried out using tryptamine (24.7 mg) to obtain hydrochloride of the title compound (45.7 mg) as a white solid.

MS(FAB,Pos.): m/z=590[M+1]⁺ ¹H-NMR(500 MHz, DMSO-d₆): δ=1.60–1.90(4H,m),2.80–3.10(4H,m) 3.20–3.40(2H,m),4.30(6H,s),4.40–4.55(1H,m),6.84–7.40 (5H,m), 7.40–7.56(4H,m),7.56–7.70(4H,m),7.84–8.06(4H, m),8.58–8.72 (2H,m),9.43(2H,bs),10.03(2H,bs).

Synthesis of (S)-2-(4-(N-2-picolylaminomethyl) benzoylamino)-5-(N-2-picolylamino)valeric acid (1-benzylpiperazin-4-yl)amide [Compound No. 71]

The same procedure was carried out using 4-amino-1-benzyl piperazine (–29.4 mg) to obtain hydrochloride of the title compound (40.5 mg) as a white solid.

MS(FAB,Pos.): m/z=620[M+1]⁺ ¹H-NMR(500 MHz, DMSO-d₆): δ=1.68–2.10(8H,m),2.94–3.08(4H,m), 3.24–3.34(2H,m),3.40–3.50(1H,m),3.64–3.80(2H,m), 4.20–4.33 (6H,m),4.41–4.48(1H,m),7.40–7.52(5H,m), 7.58–7.70(6H,m), 7.88–8.00(4H,m),8.45(1H,d,J=7.3 Hz), 8.60–8.70(2H,m),9.44 (2H,bs) 9.99(2H,bs)

Synthesis of (2S)-2-(4-(N-2-picolylaminomethyl) benzoylamino)-5-(N-2-picolylamino)valeric acid (1'S)-1'-(2-naphthyl)aminocarbonylphenethylamide [Compound No. 72]

The same procedure was carried out using phenylalanine 2-naphthylamide (44.8 mg) to obtain hydrochloride of the title compound (39.8 mg) as a white solid.

MS(FAB,Pos.): m/z=720[M+1]⁺ ¹H-NMR(500 MHz, DMSO-d₆): δ=1.60–1.95(4H,m),2.86–3.08(2H,m), 3.45–3.55 (1H,m),3.64–3.76(1H,m),4.48–4.55(1H,m), 4.70–4.77 (1H,m),7.14–7.25(3H,m),7.24(2H,d,J=7.3 Hz), 7.40–7.56(6H,m), 7.56–7.70(3H,m),7.76–8.10 (8H,m),8.46 (1H,d,J=7.8 Hz),8.60–8.72(4H,m),9.33(1H,bs), 9.93(1H, bs).

Synthesis of (S)-2-(4-(N-2-picolylaminomethyl) benzoylamino)-5-(N-2-picolylamino)valeric acid 4-hexadecylaminobenzylamide [Compound No. 73]

The same procedure was carried out using 4-hexadecylaminobenzylamine (53.5 mg) to obtain hydrochloride of the title compound (19.0 mg) as a white solid.

MS(FAB,Pos.): m/z=777[M+1]⁺ ¹H-NMR(500 MHz, DMSO-d₆): δ=0.85(3H,t,J=6.8 Hz),1.10–1.38(26H, m),1.65 (2H, quint., J=7.8 Hz),1.70–1.96(4H,m) 2.95–3.05(2H,m), 3.19(2H,t,J=7.8 Hz),8.30(8H,s),4.48–4.56(1H,m),7.38(2H, d,J=8.3 Hz),7.42–7.50(2H,m),7.59(2H,t,J=8.1 Hz),7.68(2H, d,J=8.3 Hz),7.86–7.94(2H,m),8.01(2H,d,J=8.3 Hz), 8.60–8.68(2H,m), 8.70–8.78(2H,m),9.39(2H,bs),9.96(2H, bs).

Synthesis of (S)-2-(4-(N-2-picolylaminomethyl) benzoylamino)-5-(N-2-picolylamino)valeric acid 4-(N-(1,2, 3,4-tetrahydro-1,4-dicarbonyl-phthalazin-6-yl)-N-ethylamino)butylamide [Compound No. 74]

The same procedure was carried out using N-(4-aminobutyl)-N-ethylisoluminol (42.7 mg) to obtain hydrochloride of the title compound (40.7 mg) as a white solid.

MS(FAB,Pos.): m/z=706[M+1]⁺ ¹H-NMR(500 MHz, DMSO-d₆): δ=0.85(3H,t,J=6.8 Hz),1.10–1.38(26H, m),1.65 (2H,quint.,J=7.8 Hz),1.70–1.96(4H,m),2.95–3.05(2H, m),3.19(2H,t,J=7.8 Hz),8.30(8H,s),4.48–4.56(1H,m),7.38 (2H, d,J=8.3 Hz),7.42–7.50(2H,m),7.59(2H,t,J=8.1 Hz), 7.68(2H,d,J=8.3 Hz),7.86–7.94(2H,m),8.01(2H,d,J=8.3 Hz),8.60–8.68(2H,m), 8.70–8.78(2H,m),9.39(2H,bs),9.96 (2H,bs).

Synthesis of (S)-2-(4-(N-2-picolylaminomethyl) benzoylamino)-5-(N-2-picolylamino)valeric acid 2,4,6-trichlorophenylhydrazide [Compound No. 75]

The same procedure was carried out using 2,4,6-trichlorophenylhydrazine (32.6 mg) to obtain hydrochloride of the title compound (61.4 mg) as a white solid.

MS(FAB,Pos.): m/z=640, 642, 644[M+1]⁺ ¹H-NMR(500 MHz,DMSO-d₆): δ=1.68–1.98(4H,m),2.92–3.08(2H,m), 4.31(6H,bs),4.56–4.60(1H,m),4.72–4.52(4H,m),7.50(2H,s), 7.59 (2H,t,J=8.3 Hz),7.66(2H,d,J=8.5 Hz),7.88–7.98(4H, m),8.60–8.68(2H,m),9.38(2H,bs),10.32(2H,bs).

Synthesis of (S)-2-(4-(N-2-picolylaminomethyl) benzoylamino)-5-(N-2-picolylamino)valeric acid 2-picolylamide [Compound No. 76]

The same procedure was carried out using 2-picolylamine (16.7 mg) to obtain hydrochloride of the title compound (61.5 mg) as a white solid.

MS(FAB,Pos.): m/z=538[M+1]⁺ ¹H-NMR(500 MHz, DMSO-d₆): δ=1.75–2.00(4H,m),2.95–3.06(2H,m), 4.31 (6H,bs),4.50–4.58(1H,m),4.66(1H,dd,J=17.0,5.6 Hz),4.72 (1H,dd,J=17.0,5.6 Hz), 7.46–7.56(2H,m),7.62–7.75(6H,m), 7.88–8.00(6H,m),8.05(2H,d,J=8.3 Hz), 8.53(1H,t,J=7.6 Hz),8.65–8.70 (2H,m),8.97(1H,d,J=7.8 Hz),9.13(1H,t,J=6.1 Hz),9.56(2H,bs),10.14 (2H,bs).

Synthesis of (S)-2-(4-(N-2-picolylaminomethyl) benzoylamino)-5-(N-2-picolylamino)valeric acid 2-(N,N-diethylamino)ethylamide [Compound No. 77]

The same procedure was carried out using N,N-diethylethylenediamine (17.9 mg) to obtain hydrochloride of the title compound (58.7 mg) as a white solid.

MS(FAB,Pos.): m/z=546[M+1]$^+$ $^1$H-NMR(500 MHz, DMSO-d$_6$): δ=1.21(3H,t,J=4.6 Hz),1.22(3H,t,J=4.6 Hz), 1.70–1.90(4H,m),2.95–3.05(2H,m),3.05–3.20(2H,m),3.44 (2H,q,J=7.1 Hz),2.46–2.56(6H,m),4.46(1H,q,J=4.4 Hz), 7.46–7.52 (2H,m),7.63(2H,d,J=7.8 Hz),7.66(2H,d,J=7.8 Hz),7.69(2H,d,J=8.5 Hz),7.90–7.98(2H,m),8.04(2H,d,J=8.3 Hz),8.55(1H,t,J=5.6 Hz), 8.64(1H,dt,J=3.2,1.0 Hz),8.67(1H, dt,J=3.9,1.0 Hz),8.87(1H,d,J=8.1 Hz),2.47(2H,bs),10.08 (2H,bs),11.01(1H,bs).

Synthesis of (S)-2-(4-(N-2-picolylaminomethyl) benzoylamino)-5-(N-2-picolylamino)valeric acid 3-(morpholin-1-yl)propylamide [Compound No. 78]

The same procedure was carried out using N-(3-aminopropyl)morpholine (22.3 mg) to obtain hydrochloride of the title compound (59.6 mg) as a white solid.

MS(FAB,Pos.): m/z=574[M+1]$^+$ $^1$H-NMR(500 MHz, DMSO-d$_6$): δ=1.70–1.95(6H,m),2.95–3.10(6H,m), 3.09 (2H,q,J=5.6 Hz),3.15(2H,q,J=6.6 Hz),3.38(2H,q,J=7.3 Hz), 3.82 (2H,td,J=12.2, 3.2 Hz),3.93(2H,d,J=12.5 Hz), 4.26–4.36(6H,m), 4.42(1H,q,J=5.1 Hz),7.50(1H,t,J=5.1 Hz),7.51(1H,t,J=4.9 Hz),7.64–7.74(4H,m),7.97(2H,td,J= 7.6,1.5 Hz),8.01(2H,d,J=8.3 Hz), 8.43(1H,t,J=5.9 Hz),8.66 (1H,d,J=4.9 Hz),8.68(1H,d,J=4.6 Hz),8.75 (1H,d,J=8.1 Hz), 9.56(2H,bs),10.10(2H,bs),11.22(1H,bs).

Synthesis of (S)-2-(4-(N-2-picolylaminomethyl) benzoylamino)-5-(N-2-picolylamino)valeric acid 2-(N,N-methylamino)ethylamide [Compound No. 79]

The same procedure was carried out using N,N-dimethylethylenediamine (13.6 mg) to obtain hydrochloride of the title compound (53.8 mg) as a white solid.

MS(FAB,Pos.): m/z=518[M+1]$^+$ $^1$H-NMR(500 MHz, DMSO-d$_6$): δ=1.70–2.00(4H,m),2.76(5H,d,J=4.9 Hz), 2.81 (1H,d,J=4.9 Hz),2.92–3.06(2H,m),3.15(2H,q,J=5.8 Hz), 3.30–3.60(2H,m),4.26–4.36(6H,m),4.50(1H,q,J=4.2 Hz), 7.49(1H, t,J=8.1 Hz),7.50(1H,t,J=7.8 Hz),7.64(1H,d,J=8.1 Hz),7.66(1H,d, J=8.5 Hz),7.69(2H,d,J=8.3 Hz),7.95(1H,td, J=7.6,1.7 Hz),7.97(1H, td,J=7.3,1.7 Hz),8.05(2H,d,J=8.3 Hz),8.48(1H,t,J=5.6 Hz),8.65 (1H,d,J=4.2 Hz),8.68(1H,d,J= 4.2 Hz),8.90(1H,d,J=8.3 Hz),9.48(2 H,bs),10.11(2H,bs), 10.62(1H,bs).

Synthesis of (S)-2-(4-(N-2-picolylaminomethyl) benzoylamino)-5-(N-2-picolylamino)valeric acid 4-(2,4-di-t-amylphenoxy)butylamide [Compound No. 80]

The same procedure was carried out using 4-(2,4-di-t-amylphenoxy)butylamine (47.2 mg) to obtain hydrochloride of the title compound (59.7 mg) as a white solid.

MS(FAB,Pos.): m/z=735[M+1]$^+$ $^1$H-NMR(500 MHz, DMSO-d$_6$): δ=0.53(3H,t,J=7.6 Hz),0.60(3H,t,J=7.3 Hz), 1.20(6H,s),1.28(6H,s),1.53–1.63(4H,m),1.68–1.88(8H, m),2.82–3.04(2H,m),3.10–3.20(2H,m),3.30(2H,t,J=6.1 Hz), 4.26–4.36(6H,m),4.44–4.52(1H,m),6.83(1H,d,J=8.3 Hz), 7.06(1H,d,J=7.8 Hz),7.07(1H,s),7.44–7.50(2H,m),7.60 (2H, t,J=8.5 Hz),7.67 (2H,d,J=8.3 Hz),7.92(1H,td,J=7.6,1.7 Hz), 7.93(1H,td,J=7.6,1.7 Hz),7.99(2H,d,J=8.3 Hz),8.25(1H,t,J= 5.6 Hz),8.63(1H,s),8.62–8.68(1H,m),8.67(1H,td,J=4.9,1.0 Hz),9.39(2H,bs),9.97(2H,bs)

Synthesis of (S)-2-(4-(N-2-picolylaminomethyl) benzoylamino)-5-(N-2-picolylamino)valeric acid 3-aminopropylamide [Compound No. 81]

The same procedure was carried out using 3-(Boc-amino) propylamine (26.9 mg) to obtain hydrochloride of the title compound (35.2 mg) as a white solid.

MS(FAB,Pos.): m/z=504[M+1]$^+$ $^1$H-NMR(500 MHz, DMSO-d$_6$): δ=1.65–1.95(2H,m),2.95–3.05(2H,m), 3.15 (2H,q,J=6.3 Hz),4.25–4.35(6H,m),4.35–4.45(1H,m), 7.44–7.54(2H,m),7.58–7.68 (2H,m),7.68(2H,d,J=8.3 Hz), 7.90–8.00(2H, m),8.00(2H,d,J=8.3 Hz),8.05(3H,bs),8.42 (1H,t,J=5.9 Hz),8.64(1 H,dd,J=4.2,0.7 Hz),8.67(1H,td,J= 3.4,0.7 Hz),8.73(1H,d,J=7.8 Hz), 9.50(2H,bs),10.06(2H,bs).

Synthesis of (S)-2-(4-(N-2-picolylaminomethyl) benzoylamino)-5-(N-2-picolylamino)valeric acid 5-indazoleamide [Compound No. 82]

The same procedure was carried out using 5-aminoindazole (20.6 mg) to obtain hydrochloride of the title compound (59.0 mg) as a white solid.

MS(FAB,Pos.): m/z=563[M+1]$^+$ $^1$H-NMR(500 MHz, DMSO-d$_6$): δ=1.75–1.95(4H,m),2.95–3.05(2H,m) 4.31(6H, bs),4.35–4.40(1H,m),7.36(1H,dd,J=8.8,2.0 Hz),7.48 (1H,t, J=6.8 Hz),7.49(1H,t,J=6.6 Hz),7.62(1H,d,J=9.3 Hz),7.64(1 H,d,J=8.1 Hz),7.65–7.70(3H,m),7.84(1H,dd,J=2,0.7 Hz), 7.92–7.96(2H,m),7.96(2H,d,J=8.3 Hz),8.19(1H,dd,J=8.3, 1.0 Hz),8.65 (1H,dq,J=4.9,0.7 Hz),8.68(1H,dq,J=4.9,0.7 Hz),8.80(1H,d,J=7.8 Hz),9.43(2H,bs),10.01(2H,bs),10.41 (2H,bs).

EXAMPLE 68

Preparation of (2S)-2-(2-(N-2-picolylaminomethyl) pyridin-5-ylcarbonyl)amino-5-(5,6,7,8-tetrahydroquinolin-8-yl)aminovaleric acid (1'S)-1'-(1-naphthyl)ethylamide [Compound No. 83]

Example 68-1

Synthesis of N$^α$-Fmoc-N$^δ$-Boc-ornithine (1'S)-1'-(1-naphthyl)ethylamide (Compound IX-4)

Commercially available N$^α$-Fmoc-N$^δ$-Boc-ornithine (3.00 g) was dissolved in DMF (60 ml), and WSCI hydrochloride (1.6784 g) and HOBt (0.9561 g) were added and dissolved. After the addition of (1S)-1-(1-naphthyl) ethylamine (0.165 ml), the solution was stirred for 3 days at room temperature. After the reaction, the solvent was removed by distillation. The residue was dissolved in chloroform and the resulting organic layer was washed with 1 mol/l aqueous solution of hydrochloric acid and saturated brine. The organic layer was dried over anhydrous sodium sulfate and the solvent was removed by distillation. The residue was dried under vacuum to obtain the title compound (3.6698 g) as a white solid.

MS(FAB,Pos.): m/z=608[M+1]$^+$

Example 68-2

Synthesis of N$^α$-(2-(N-Boc-N-2-picolylaminomethyl)pyridin-5-ylcarbonyl)-N$^δ$-Boc-L-ornithine (1'S)-1'-(1-naphthyl)ethylamide (Compound XI-11)

The compound obtained in Example 68-1 (502.5 mg) was dissolved in DMF (10 ml). After the addition of diethylamine (1.0 ml), the mixture was stirred for 4 hours at room temperature. After the reaction, the solvent was removed by distillation and the residue was dried under vacuum. The product was dissolved in DMF (10 ml), and WSCI hydrochloride (237.4 mg), HOBt (124.8 mg), and the compound obtained in Example 12–3 (305.2 mg) were added to the solution. The mixture was stirred for 21 hours at room temperature. After the reaction, the solvent was removed by distillation. The residue was dissolved in chloroform and the solution was washed with 1 mol/l aqueous solution of hydrochloric acid, 1 mol/l aqueous solution of sodium hydroxide, and saturated brine. The organic layer obtained was dried over anhydrous sodium sulfate and the solvent was removed by distillation. The residue was purified by silica gel column chromatography (35 g, chloroform/ methanol=25/1) to obtain the title compound (490 mg) as white foam.

MS(FAB,Pos.): m/z=711[M+1]$^+$ $^1$H-NMR(500 MHz, DMSO-d$_6$): δ=1.27–1.58(2H,m),1–0.31(9H,s),1.36(9H, s),1.51(3H,d,J=7.1 Hz),1.62–1.69(2H,m),2.83–2.95(2H,m), 4.45–4.68(5H,m),5.71(1H,quint.,J=7.1 Hz),6.78(1H,t,J=5.6 Hz),7.25–7.40(3H,m),7.46–7.58(4H,m),7.78(1H,td,J=7.8, 1.7 Hz),7.93–7.95(1H,m),8.10(1H,d,J=8.3 Hz),8.20(1H,d, J=8.1 Hz),8.50(1H,dd, J=4.9,1.7 Hz),8.60–8.67(2H,m),8.97 (1H,d,J=2.0 Hz).

Example 68-3

Synthesis of (2S)-2-(2-(N-2-picolylaminomethyl) pyridin-5-ylcarbonyl)amino-5-(5,6,7,8-tetrahydroquinolin-8-yl)aminovaleric acid (1'S)-1'-(1-naphthyl)ethylamide [Compound No. 83]

The compound obtained in Example 68-2 (209.6 mg) was dissolved in methanol (2 ml) and 4 mol/l hydrochloric acid/dioxane solution (2 ml) was added. The mixture was stirred for 8.5 hours at room temperature. After the reaction, the solvent was removed by distillation and the residue was dried under vacuum. The product was dissolved in methanol (4 ml). Then, triethylamine (0.119 ml), 5,6,7,8-tetrahydroquinolin-8-one (50.8 mg), and sodium cyanoborohydride (26.5 mg) were added. 25 drops of acetic acid was added to adjust the pH of the mixture to about 5. The mixture was stirred for 22 hours at room temperature. After the reaction, the solvent was removed by distillation. The residue was purified by silica gel column chromatography (5 g, chloroform/methanol/water=7/3/0.5) to obtain the title compound (108.7 mg) as a white solid.

MS(FAB,Pos.): m/z=642[M+1]$^+$ $^1$H-NMR(500 MHz, DMSO-d$_6$): δ=1.52(3H,d,J=6.8 Hz),1.65–2.02(7H,m), 2.24–2.35(1H,m),2.75–2.85(2H,m),2.90–3.01(1H,m), 3.02–3.13 (1H,m),4.38–4.50(1H,m),4.44(2H,s),4.50(2H,s), 4.58–4.65(1H, m),5.71(1H,quint.,J=6.8 Hz),7.35–7.41(1H, m),7.42–7.73(10H,m), 7.81(1H,d,J=8.3 Hz),7.92–8.00(2H, m),8.11(1H,d,J=8.5 Hz),8.35 (1H,d,J=8.1 Hz),8.45(1H,ddd, J=10.8,4.9,1.7 Hz),8.68(1H,ddd,J=4.9,1.7,1.0 Hz), 8.90–9.07(2H,m),9.13(1H,s),9.2(2H,br),9.9(2H, br).

EXAMPLE 69

Preparation of (2S)-2-(2-(N-2-picolylaminomethyl) pyridin-5-ylcarbonyl)amino-5 ((1-methyl-imidazol-2-yl)methylamino)aminovaleric acid (1'S)-1'-(1-naphthyl)ethylamide [Compound No. 84]

The compound obtained in Example 68-2 (150.1 mg) was dissolved in methanol (1.5 ml) and 4 mol/l hydrochloric acid/dioxane solution (1.5 ml) was added. The mixture was stirred for 2 hours at room temperature. After the reaction, the solvent was removed by distillation and the residue was dried under vacuum. The residue was dissolved in methanol (3 ml). After the addition of triethylamine (0.119 ml) and 1-methyl-2-imidazole carboaldehyde (23.6 mg), the mixture was stirred for 12 hours at room temperature. After the reaction, the solvent was removed by distillation. The residue was dried under vacuum. The residue was dissolved in anhydrous methanol (3 ml). Then, sodium borohydride (16 mg) was added and the mixture was stirred for 1.5 hours at room temperature. After the reaction, the solvent was removed by distillation. The residue was purified by silica gel column chromatography (5 g, chloroform/methanol/water=7/3/0.5) to obtain the title compound (110.7 mg) as a white solid.

MS(FAB,Pos.): m/z=605[M+1]$^+$ $^1$H-NMR(500 MHz, DMSO-d$_6$): δ=1.52(3H,d,J=6.8 Hz),1.74–1.95(4H,m), 3.02–3.17(2H,m),3.98(3H,s),4.44(2H,s),4.49(2H,s),4.53 (1H,s), 4.59–4.68(1H,m),5.71(1H,quint.,J=6.8 Hz), 7.45–7.58(6H,m), 7.65(1H,d,J=8.3 Hz),7.76–7.78(2H,m), 7.81(1H,d,J=8.1 Hz),7.90–7.96(2H,m),8.11(1H,d,J=8.3 Hz),8.39(1H,dd,J=8.3,2.2 Hz),8.67(1H,ddd,J=4.9,1.7,1.0 Hz),8.94(1H,d,J=8.3 Hz),8.95(1H,d,J=7.8 Hz), 9.14(1H,d, J=2.2 Hz),9.88(2H,br),10.25(2H,br).

EXAMPLE 70

Preparation of (2S)-2-(4-(N-2-picolylaminomethyl) naphthoyl)amino-5-(5,6,7,8-tetrahydroquinolin-8-yl) aminovaleric acid (1'S)-1'-(1-naphthyl)ethylamide [Compound No. 85]

Example 70-1

Synthesis of N$^α$-(4-(N-Boc-N-2-picolylaminomethyl)naphthoyl)-N$^δ$-Boc-L-ornithine (1'S)-1'-(1-naphthyl)ethylamide (Compound XI-12)

The compound synthesized in Example 68-1 (499.9 mg) was dissolved in DMF (10 ml). After the addition of diethylamine (1.0 ml), the mixture was stirred for one hour at room temperature. After the reaction, the solvent was removed by distillation and the residue was dried under vacuum. The product was dissolved in DMF (10 ml), and WSCI hydrochloride (239.0 mg), HOBt (123.7 mg), and the compound obtained in Example 43-2 (340.1 mg) we re added to the solution. The mixture was stirred for 24 hours at room temperature. After the reaction, the solvent was removed by distillation. The residue was dissolved in chloroform and the resulting solution was washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (30 g, chloroform/methanol=25/1) to obtain the title compound (349.1 mg) as white foam.

MS(FAB,Pos.): m/z=760[M+1]$^+$ $^1$H-NMR(500 MHz, DMSO-d$_6$): δ=1.33 and 1.37(18H, 2s),1.25–1.78(4H, m),1.55(3H,d,J=6.8 Hz),2.92(2H,m),4.36 and 4.44(2H, 2s), 4.50–4.59(1H,m),4.98 and 5.02(2H, 2s),5.75(1H,quint.,J= 6.8 Hz),6.80(1H,t,J=5.6 Hz),7.19–7.40(4H,m),7.49(1H,t,J= 7.8 Hz),7.51–7.62 (8H,m),7.77(1H,td,J=7.8,1.7 Hz),7.84 (1H,d,J=8.1 Hz),7.94–8.00 (2H,m),8.08–8.02(2H,m),8.26 (1H,d,J=7.8 Hz),8.52(1H,brs),8.61 (1H,d,J=8.1 Hz).

Example 70-2

Synthesis of (2S)-2-(4-(N-2-picolylaminomethyl) naphthoyl)amino-5-(5,6,7,8-tetrahydroquinolin-8-yl) aminovaleric acid (1'S)-1'-(1-naphthyl)ethylamide [Compound No. 85]

The compound obtained in Example 70-1 (200.0 mg) was dissolved in methanol (2 ml), and 4 mol/l hydrochloric acid/dioxane solution (2 ml) was added. The mixture was stirred for 2.5 hours at room temperature. After the reaction, the solvent was removed by distillation and the residue was dried under vacuum. The crude product was dissolved in methanol (4 ml). Then, 5,6,7,8-tetrahydroquinolin-8-one (51.6 mg) and sodium cyanoborohydride (27.1 mg) were added. 35 drops of acetic acid was added to adjust the pH of the mixture to about 5. The mixture was stirred for 13 hours at room temperature. After the reaction, the solvent was removed by distillation. The residue was purified by silica gel column chromatography (5 g, chloroform/methanol/ water=7/3/0.5) to obtain the title compound (83.7 mg) as a white solid.

MS(FAB,Pos.): m/z=691[M+1]$^+$ $^1$H-NMR(500 MHz, DMSO-d$_6$): δ=1.56(3H,d,J=6.8 Hz),1.64–2.02(7H,m), 2.28–2.35(1H,m),2.78–2.83(2H,m),2.92–3.01(1H,m), 3.05–3.20 (1H,m),4.35–4.47(1H,m),4.48(2H,s),4.65–4.70 (1H,m),4.78(2H, s),5.77(1H,quint.,J=6.8 Hz),7.38(1H,dd,J= 7.8,4.9 Hz),7.41–7.75(10H,m),7.80–7.87(2H,m),7.93–8.00 (2H,m),8.15(1H,d,J=8.5 Hz),8.28(1H,d,J=8.5 Hz),8.30(1H, d,J=8.3 Hz),8.48(1H,dd,J=4.6, 0.7 Hz),8.72(1H,dd,J=4.9, 1.0 Hz),8.70(1H,d,J=8.3 Hz),8.88(1 H,t, d=6.8 Hz),9.27(2H, br),9.96(2H,br).

EXAMPLE 71

Preparation of N$^\alpha$-(4-(N-2-picolylaminomethyl) benzoyl)-L-arginine (1'S)-1'-(1-naphthyl)ethylamide [Compound No. 86]

Example 71-1

Synthesis of N$^\alpha$-Fmoc-N$^G$-Pbf-L-arginine (1'S)-1'- (1-naphthyl)ethylamide (Compound XXVI-6)

Commercially available N$^\alpha$-Fmoc-N$^G$-Pbf-L-arginine (2.6467 g) was dissolved in DMF (53 ml), and WSCI hydrochloride (1.1830 g) and HOBt (0.6609 g) were added to the solution. After the addition of (1S)-1-(1-naphthyl) ethylamine (762.5 mg), the solution was stirred for 2 days at room temperature. After the reaction, the solvent was removed by distillation. The residue was dissolved in chloroform and the resulting solution was washed with 1 mol/l aqueous solution of hydrochloric acid and saturated brine. The organic layer was dried over anhydrous sodium sulfate and the solvent was removed by distillation. The residue was dried under vacuum to obtain the title compound (3.62 g) as a white solid.

MS(FAB,Pos.): m/z=802[M+1]$^+$

Example 71-2

Synthesis of N$^\alpha$-(4-(N-Boc-N-2-picolylaminomethyl)benzoyl)-N$^G$-Pbf-arginine (1'S)-1'-(1-naphthyl)ethylamide (Compound XXIX-10)

The compound obtained in Example 71-1 (624.7 mg) was dissolved in DMF (12.8 ml). After the addition of diethylamine (1.28 ml), the mixture was stirred for 2 hours at room temperature. After the reaction, the solvent was removed by distillation and the residue was dried under vacuum. The product was dissolved in DMF (12 ml) and WSCI hydrochloride (228.0 mg), HOBt (116.3 mg), and the compound obtained in Example 1–2 (284.5 mg) were added. The mixture was stirred for 12.5 hours at room temperature. After the reaction, the solvent was removed by distillation. The residue was dissolved in chloroform, and the resulting solution was washed with 1 mol/l aqueous solution of hydrochloric acid, 1 mol/l aqueous solution of sodium hydroxide, and saturated brine, and dried over anhydrous sodium sulfate. The residue was concentrated under reduced pressure and purified by silica gel column chromatography (30 g, chloroform/methanol 25/1) to obtain the title compound (582.5 mg) as yellow viscous oil.

MS(FAB,Pos.): m/z=904[M+1]$^+$ $^1$H-NMR(500 MHz, DMSO-d$_6$): δ=1.25–1.55(2H,m) 1.31(6H,s),1.37(9H, s),1.51(3H,d,J=7.1 Hz),1.60–1.81(2H,m),1.91(3H,s),2.40 (3H,s), 2.45(3H,s),2.90(2H,s),2.98–3.05(2H,m),4.35–4.40 (5H,m),5.70 (1H,quint,J=6.8 Hz),7.19–7.38(4H,m),7.47 (1H,t,J=7.8 Hz),7.49–7.58(3H,m),7.78(1H,td,J=7.8,1.7 Hz), 7.81(1H,d,J=8.1 Hz),7.86(2H,d,J=8.3 Hz),7.92–7.96(2H, m),8.08(1H,d,J=8.1 Hz),8.36(1H,d, J=8.1 Hz),8.52(1H,d,J= 4.9 Hz),8.65(1H,d,J=7.8 Hz).

Example 71-3

Synthesis of N$^\alpha$-(4-(N-2-picolylaminomethyl) benzoyl)-L-arginine (1'S)-1'-(1-naphthyl)ethylamide [Compound No. 86]

The compound obtained in Example 71-2 (250.3 mg) was dissolved in chloroform (2.5 ml) and trifluoroacetic acid (2.5 ml) was added. The mixture was stirred for 3.5 hours at room temperature. After the reaction, the solvent was removed by distillation. The residue was dried using a vacuum pump and purified by silica gel column chromatography (chloroform/methanol/water=7/3/0.5). Fractions obtained were concentrated. The obtained product was dissolved in 1 mol/l aqueous solution of hydrochloric acid, concentrated, and azeotropically distilled with ethanol to obtain hydrochloride of the title compound (59.5 mg) as a white solid.

MS(FAB,Pos.): m/z=552[M+1]$^+$ $^1$H-NMR(500 MHz, DMSO-d$_6$): δ=1.51(3H,d,J=7.1 Hz),1.41–1.59(2H,m), 1.68–1.85(2H,m),3.02–3.15(2H,m),4.31(4H,s),4.54–4.59 (1H,m), 5.71(1H,quint.,J=7.1 Hz),7.45(1H,ddd,J=7.6,4.5, 1.0 Hz),7.46–7.59(5H,m),7.64(2H,d,J=8.5 Hz),7.75(1H, brs),7.82(1H,d,J=8.3 Hz), 7.90(1H,td,J=7.8,1.7 Hz),7.94 (1H,d,J=7.8 Hz),7.98(2H,d,J=8.5 Hz),8.10(1H,d,J=8.3 Hz), 8.57(1H,d,J=8.1 Hz),8.66(1H,ddd,J=4.9,1.7,1.0 Hz),8.81 (1H,d,J=8.1 Hz),9.76(2H,brs).

EXAMPLE 72

Preparation of (2S)-2-(4-((1-methylimidazol-2-ylmethyl)aminomethyl)naphthoylamino-5-((1-methylimidazol-2-ylmethyl)amino)valeric acid (1'S)-1'-(1-naphthyl)ethylamide [Compound No. 87]

Example 72-1

Synthesis of N$^\alpha$-(4-(N-Boc-aminomethyl) naphthoyl)-N$^\delta$-Boc-L-ornithine (1' S)-1'-(1-naphthyl)ethylamide (Compound XVIII-11)

The compound obtained in Example 68-1 (503.1 mg) was dissolved in DMF (10 ml). After the addition of diethylamine (1.0 ml), the mixture was stirred for 1 hour at room temperature. After the reaction, the solvent was removed by distillation and the residue was dried under vacuum. The product was dissolved in DMF (10 ml), and WSCI hydrochloride (236.9 mg), HOBt (132.1 mg), and the compound obtained in Example 25-2 (268.6 mg) were added to the solution. The mixture was stirred for 2 days at room temperature. After the reaction, the solvent was removed by distillation. The residue was dissolved in chloroform and the resulting solution was washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (17 g, chloroform/ethyl acetate 1/1) to obtain the title compound (434.4 mg) as white foam.

MS(FAB,Pos.): m/z=669[M+1]$^+$ $^1$H-NMR(500 MHz, DMSO-d$_6$): δ=1.30–1.80(4H,m),1.37(9H,s),1.41(9H, s),1.54(3H,d,J=6.8 Hz),2.85–3.00(2H,m),4.55–4.62(1H,m), 4.60 (2H,d,J=6.1 Hz),5.75(1H,quint,J=6.8 Hz),6.80(1H,t,J= 5.6 Hz), 7.40 (1H,d,J=7.3 Hz),7.43–7.61(8H,m),7.84(1H,d, J=8.1 Hz),7.94–7.98(1H,m),8.13(1H,d,J=8.1 Hz),8.15(1H, d,J=8.3 Hz),8.24(1H,d, J=8.1 Hz),8.51(1H,d,J=8.1 Hz),8.60 (1H,d,J=7.6 Hz).

Example 72-2

Synthesis of (2S)-2 (4-((1-methylimidazol-2-ylmethyl)aminomethyl)naphthoylamino-5-((1-methylimidazol-2-ylmethyl)amino)valeric acid (1'S)-1'-(1-naphthyl)ethylamide [Compound No. 87]

The compound obtained in Example 72-1 (204.3 mg) was dissolved in methanol (2 ml) and 4 mol/l hydrochloric acid/dioxane solution (2 ml) was added. The mixture was stirred for 4 hours at room temperature. After the reaction, the reaction solution was concentrated and dried under reduced pressure. The crude product (109.8 mg) was dissolved in methanol (2 ml). After the addition of triethylamine (51.5 ml) and 1-methyl-2-imidazole carboaldehyde (72.2 mg), the mixture was stirred for 15 hours at room temperature. After the reaction, the reaction solution was concentrated. The residue was dried under reduced pressure and dissolved in anhydrous methanol (2 ml). The mixture was cooled to 0° C. Sodium borohydride 10. (46.2 mg) was added to the solution and the mixture was stirred for 0.5 hour at room temperature. After the reaction, the reaction mixture was concentrated. The residue was purified by silica gel column chromatography (10 g, chloroform/methanol/water= 7/3/0.5) and treated 15 with 1 mol/l aqueous solution of hydrochloric acid to obtain of hydrochloride of the title compound (156.4 mg) as a white solid.

MS(FAB,Pos.): m/z=657[M+1]$^+$ $^1$H-NMR(500 MHz, DMSO-$d_6$): δ=1.55(3H,d,J=6.8 Hz),1.70–1.97(4H,m), 3.07–3.20(2H,m),3.97(3H,s),3.99(3H,s),4.54(2H,s), 4.63–4.70 (1H,m),4.77(2H,s),4.90(2H,s),5.76(1H,d,J=6.8 Hz),7.50–7.80 (11H,m),7.54–7.60(3H,m),7.83(1H,d,J=8.3 Hz),7.86(1H,d,J=7.6 Hz),7.95–7.97(1H,m),8.14(1H,d,J=8.3 Hz),8.29(1H,d,J=8.3 Hz),8.35(1H,d,J=8.3 Hz),8.77(1H,d,J= 8.3 Hz),8.89(1H,d,J=7.8 Hz),10.19(2H,br)

EXAMPLE 73

Preparation of (2S)-2-(2-(N-2-picolylaminomethyl) pyridin-5-ylcarbonyl)amino-5-(N-methylpyrrol-2-ylmethyl)aminovaleric acid (1'S)-1'-(1-naphthyl) ethylamide [Compound No. 88]

The compound obtained in Example 68-2 (87.2 mg) was dissolved in methanol (1 ml) and 4 mol/l hydrochloric acid/dioxane solution (1 ml) was added. The mixture was stirred for 2 hours at room temperature. After the reaction, the solvent was removed by distillation and the residue was dried under vacuum and dissolved in methanol (2 ml). After the addition of triethylamine (0.069 ml) and N-methyl-2-pyrrole carboaldehyde (0.0145 ml), the mixture was reacted for 14 hours at room temperature. The solvent was removed by distillation. The residue was dried under reduced pressure and dissolved in anhydrous methanol (2 ml). The reaction solution was cooled with ice. After the addition of sodium borohydride (9.1 mg), the mixture was reacted for 5 hours at room temperature. After the reaction, the solvent was removed by distillation. The residue was purified by silica gel column chromatography (5 g, chloroform/methanol/ water=7/3/0.5) to obtain the title compound (65.0 mg) as a white solid.

MS(FAB,Pos.): m/z=604[M+1]$^+$ $^1$H-NMR(500 MHz, DMSO-$d_6$): δ=1.52(3H,d,J=6.8 Hz),1.65–1.84(4H,m), 2.84–2.93(2H,m),4.07(2H,t,J=5.6 Hz),4.44(2H,s),4.50(2H, s), 4.58–4.63(1H,m),5.71(1H,quint.,J=6.8 Hz),5.97(1H,dd, J=3.6, 2.7 Hz),6.23(1H,dd,J=3.6,2.0 Hz),6.78(1H,dd,J=2.7, 2.0 Hz), 7.43–7.58(5H,m),7.62(1H,d,J=7.8 Hz),7.66(1H,d, 8.1 Hz),7.81(1H, d,J=8.3 Hz),7.91–8.99(2H,m),8.11(1H,d, J=8.5 Hz),8.38(1H,dd,J=8.1,2.2 Hz),8.68(1H,ddd,J=4.9,1.7, 1.0 Hz),8.97(1H,d,J=7.8 Hz), 9.14(1H,d,J=2.2 Hz),9.20(2H, brs).

EXAMPLE 74

Preparation of N$^α$-(4-(N-(1-methylimidazol-2-yl) methylaminomethyl)-1-naphthalenecarbonyl)-L-arginine 2-(1-naphthyl)isopropylamide [Compound No. 89]

Example 74-1

Synthesis of Methyl 4-((1-methylimidazol-2-ylmethyl)aminomethyl)naphthalene-1-carboxylate (Compound V-6)

The compound obtained in Example 17-3 (0.8568 g) was dissolved in methanol (25 ml). After the addition of 1-methyl-2-imidazole carboxyaldehyde (0.526 g) and triethylamine (1.11 ml), the mixture was stirred for 63 hours. Then, sodium borohydride (0.329 g) was added, followed by stirring for 1.5 hours. The solvent was removed by distillation and the residue was purified by silica gel column chromatography (5 g, 3% methanol/47% chloroform/50% benzene) to obtain the title compound (0.9489 g) as light orange viscous oil.

MS(FAB,Pos.): m/z=310[M+1]$^+$ $^1$H-NMR(500 MHz, CDCl$_3$): δ=3.58(3H,s),3.94(2H,s),3.99(3H,s), 4.32(2H,s), 6.83(1H,d,J=1.2 Hz),6.95(1H,d,J=1.2 Hz),7.53–7.63 (3H, m),8.11(1H,d,J=7.6 Hz),8.16(1H,dd,J=7.8,0.7 Hz),8.93 (1H,d d,J=8.10.7 Hz).

Example 74-2

Synthesis of Methyl 4-(N-Boc-(1-methylimidazol-2-ylmethyl)aminomethyl)naphthalene-1-carboxylate (Compound VI-10)

The compound obtained in Example 74-1 (0.9452 g) was dissolved in DMF (10 ml). After the addition of di-t-butyldicarbonate (0.767 g) and triethylamine (0.464 g), the mixture was stirred for 22 hours. After the reaction, water was added and the solvent was removed by distillation. Chloroform and water was added to the residue. The organic layer separated was dried over anhydrous magnesium sulfate and the solvent was removed by distillation. The residue was purified by silica gel column chromatography (25 g, 50% ethyl acetate/hexane) to obtain the title compound (1.0569 g) as yellow viscous oil.

MS(FAB,Pos.): m/z=410[M+1]$^+$ $^1$H-NMR(500 MHz, CDCl$_3$): δ=1.42(9H,s),3.55 and 3.70(3H,bs),4.00 (3H,s), 4.45 and 4.59(2H,bs),6.82(1H,bs),6.93(1H,s),7.35(1H,bs), 7.55(1H,td,J=8.1, 1.2 Hz),7.62(1H,t,J=7.1 Hz),8.07 and 8.21 (1H, bs),8.13(1H,d,J=7.3 Hz),8.94(1H,d,J=8.1 Hz).

Example 74-3

Synthesis of 4-(N-Boc-(1-methylimidazol-2-ylmethyl)aminomethyl)naphthalene-1-carboxylic acid (Compound VII-14)

The compound obtained in Example 74-2 (1.0526 g) was dissolved in methanol (10 ml), and 1 N aqueous solution of sodium hydroxide (10 ml) and THF (10 ml) were added. The mixture was stirred for 2.5 hours. Part of the solvent was removed by distillation while adding water to the reaction solution. After adjusting the pH to 6, the water layer was extracted with chloroform. The extract was dried over anhydrous magnesium sulfate, the solvent was removed by distillation, and the residue was dried under vacuum to obtain the title compound (0.8551 g) as a pale yellow solid.

MS(FAB,Pos.): m/z=396[M+1]$^+$ $^1$H-NMR(500 MHz, CDCl$_3$): δ=1.51 and 1.58(9H,s),3.76 and 3.78(3H,s), 4.74 and 4.85(4H,s),6.95(1H,s),7.19 and 7.22(1H,s),7.33(1H,d, J=7.3 Hz),7.39–7.48(2H,m),7.92 and 8.19(1H,d,J=7.8 Hz), 8.01(1H,d, J=8.1 Hz),8.89 and 9.00(1H,d,J=7.8 Hz)

Example 74-4

Synthesis of 2-(1-naphthyl)propylamine

Cerium chloride hydrate (14.594 g) was dried while stirring for two hours at 150° C. (0.5 mm). Then, nitrogen was gradually introduced. After cooling over an ice bath, THF (80 ml) was added and the mixture was stirred for 1.5 hours at 25° C. Then, methyl lithium (0.861 g) was added to the mixture over 30 minutes while cooling at −50° C. or less. After the mixture was stirred for 30 minutes, a solution of 1-cyanonaphthalene (2 g) in THF (5 ml) was added. The mixture was stirred for a further two hours at room temperature. After the addition of concentrated aqueous ammonia (25 ml), the reaction solution was filtered through celite. The filtrate was dried over magnesium sulfate and the solvent was removed by distillation. The residue was dissolved in toluene (30 ml) and extracted with 1 mol/l hydrochloric acid. The water layer was adjusted to an alkaline pH with concentrated aqueous ammonia and extracted with chloroform. The extract was dried over magnesium sulfate and the solvent was removed by distillation. The residue was purified by silica gel column chromatography (10 g, 50% methanol/chloroform) to obtain the title compound (0.2640 g) as a light brown liquid.

MS(FAB,Pos.): m/z=186[M+1]$^+$ $^1$H-NMR(500 MHz, DMSO-d$_6$): δ=1.78(6H,s),7.40(1H,dd,J=8.1, 7.3 Hz), 7.46 (1H,ddd,J=8.1, 6.8, 1.2 Hz),7.50(1H,ddd,J=8.8, 7.1,1.7 Hz), 7.60 (1H,dd,J=7.3, 1.2 Hz),7.75(1H,d, 8.1 Hz),7.86(1H,dd, J=8.1,1.7 Hz),8.89(1H,dd,J=8.1,1.0 Hz)

Example 74-5

Synthesis of N$^α$-Fmoc-N$^G$-Pmc-L-arginine 2-(1-naphthyl)isopropylamide (Compound XXVII-7)

Commercially available N$^α$-Fmoc-N$^G$-Pmc-L-arginine (487.1 mg) was dissolved in DMF (10 ml), and WSCI hydrochloride (0.2516 g) and HOBt (0.1578 mg, 1.17 mmol) were added to the solution. After the addition of the compound obtained in Example 74-4 (119.8 mg), the solution was stirred for 13 hours at room temperature. After the reaction, the solvent was removed by distillation. The residue was dissolved in chloroform and the resulting solution was washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (25 g, chloroform/ethyl acetate=1/1) to obtain the title compound (348.8 mg) as white foam.

MS(FAB,Pos.): m/z=830[M+1]$^+$ $^1$H-NMR(500 MHz, DMSO-d$_6$): δ=1.23(6H,s),1.20–1.40(3H,m),1.50–1.62(1H, m),1.74(2H,t,J=6.8 Hz),1.77(3H,s),1.78(3H,s),2.02(3H, s),2.55(2H,t,J=6.8 Hz),2.89–3.01(2H,m),3.98–4.06(1H,m), 4.18–4.21(1H,m),4.21–4.29(2H,m),6.30–6.80(3H,br),7.21 (1H,d, J=8.5 Hz),7.27–7.31(2H,m),7.30–7.42(4H,m),7.52 (1H,d,J=7.3 Hz), 7.69(2H,dd,J=7.3,4.6 Hz),7.77(1H,d,J=8.1 Hz),7.82–7.90(3H,m), 8.40(1H,s),8.49(1H,d,J=9.3 Hz).

Example 74-6

Synthesis of N$^α$-(4-(N-Boc-N-(1-methylimidazol-2-yl)methylaminomethyl)-1-naphthalenecarbonyl)-N$^G$-Pbf-L-arginine 2-(1-naphthyl)isopropylamide (Compound XXIX-11)

The compound obtained in Example 74-5 (343.7 mg) was dissolved in DMF (7 ml). After the addition of diethylamine (0.7 ml), the mixture was stirred for 2 hours at room temperature. After the reaction, the solvent was removed by distillation and the residue was dried under vacuum, and dissolved in DMF (7 ml). WSCI hydrochloride (126.4 mg), HOBt (65.9 mg), and the compound obtained in Example 74-3 (179.3 mg) were added to the solution. The mixture was stirred for 16.5 hours at room temperature. After the reaction, the solvent was removed by distillation. The residue was dissolved in chloroform, and the resulting solution was washed with 1 mol/l aqueous solution of hydrochloric acid, 1 mol/l aqueous solution of sodium hydroxide, and saturated brine, and dried over anhydrous sodium sulfate. The solution was concentrated under reduced pressure and the resulting residue was purified by silica gel column chromatography (20 g, chloroform/methanol=30/1) to obtain the title compound (311.5 mg) as white foam.

MS(FAB,Pos.): m/z=985[M+1]$^+$

Example 74-7

Synthesis of N$^α$-(4-(N-(1-methylimidazol-2-yl) methylaminomethyl)-1-naphthalenecarbonyl)-L-arginine 2-(1-naphthyl)isopropylamide [Compound No. 89]

The compound obtained in Example 74-6 (308.7 mg) was dissolved in chloroform (3.1 ml) and trifluoroacetic acid (3.1 ml) was added. The mixture was stirred for 5 hours at room temperature. After the reaction, the solvent was removed by distillation and the residue was dried using a vacuum pump. 1 mol/l hydrochloric acid aqueous solution was added. The water layer was washed with chloroform and water was removed by distillation. The residue was dissolved in methanol. Acetone was added to the solution and the supernatant was removed by decantation. The obtained residue was treated with 1 mol/l aqueous solution of hydrochloric acid to obtain hydrochloride of the title compound (49.2 mg) as a white solid.

MS(FAB,Pos.): m/z=619[M+1]$^+$ $^1$H-NMR(500 MHz, DMSO-d$_6$): δ=1.40–1.65(3H,m),1.68–1.82(1H,m), 1.85 (6H,s),3.05–3.18(2H,m),3.96(3H,s),4.59–4.64(1H,m),4.73 (2H,s),2.96(2H,s),6.90(2H,br),7.20(1H,br),7.40–7.55(4H, m), 7.58–7.62(2H,m),7.64–7.81(6H,m),7.85(1H,d,J=7.7 Hz),8.11(1H, d,J=8.5 Hz),8.28(1H,d,J=8.3 Hz),8.51(1H,d, J=8.3 Hz),8.64(1H,d, J=8.5 Hz),8.79(1H,s).

EXAMPLE 75

Preparation of N$^α$-(2-(N-2-picolylaminomethyl) pyridin-5-ylcarbonyl)-L-arginine (1'S)-1'-(1-naphthyl)ethylamide [Compound No. 90]

Example 75-1

Synthesis of N$^α$-(2-(N-Boc-N-2-picolylaminomethyl)pyridin-5-ylcarbonyl)-N$^G$-Pbf-L-arginine (1'S)-1'-(1-naphthyl)ethylamide (Compound XXIX-12)

The compound obtained in Example 71-1 (504.2 mg) was dissolved in DMF (10 ml). After the addition of diethylamine (1 ml), the mixture was stirred for 2 hours at room temperature. After the reaction, the solvent was removed by distillation and the residue was dried under vacuum, and dissolved in DMF (12 ml). WSCI hydrochloride (180.3 mg), HOBt (96.0 mg), and the compound obtained in Example 12-3 (225.6 mg) were added. The mixture was stirred for 12.5 hours at room temperature. After the reaction, the solvent was removed by distillation. The residue was dissolved in chloroform, and the resulting solution was washed with 1 mol/l aqueous solution of hydrochloric acid, 1 mol/l aqueous solution of sodium hydroxide, and saturated brine, and dried over anhydrous sodium sulfate. The solution was concentrated under reduced pressure and the residue obtained was purified by silica gel column chromatography (30 g, chloroform/methanol=25/1) to obtain the title compound (404.6 mg) as yellow viscous oil.

MS(FAB,Pos.): m/z=906[M+1]$^+$

Example 75-2

Synthesis of N$^\alpha$-(2-(N-2-picolylaminomethyl)pyridin-5-ylcarbonyl)-L-arginine (1'S)-1'-(1-naphthyl)ethylamide [Compound No. 90]

The compound obtained in Example 75-1 (200.0 mg) was dissolved in chloroform (2 ml) and trifluoroacetic acid (2 ml) was added. The mixture was stirred for 12.5 hours at room temperature. After the reaction, the solvent was removed by distillation and the residue was dried using a vacuum pump. 1 mol/l hydrochloric acid aqueous solution was added to the residue. The water layer was washed with chloroform and water was removed by distillation. The residue was dissolved in methanol and acetone was added to the solution, followed by decantation. The obtained residue was dissolved in 1 mol/l aqueous solution of hydrochloric acid and the solution was concentrated. The residue was azeotropically distilled with methanol and dried to obtain hydrochloride of the title compound (114.2 mg) as a white solid.

MS(FAB,Pos.): m/z=553[M+1]$^+$ $^1$H-NMR(500 MHz, DMSO-d$_6$): δ=1.52(3H,d,J=7.1 Hz),1.41–1.60(2H,m), 1.66–1.87(2H,m),3.02–3.17(2H,m),4.44(2H,s),4.50(2H,s), 4.56–4.60(1H,m),5.72(1H,quint., J=7.1 Hz),6.9(2H,br),7.4 (1H,br),7.40–7.61(6H,m),7.65(1H,d,J=8.5 Hz),7.81(1H,d, J=8.1 Hz),7.86(1H, brs),7.91–7.96(2H,m),8.11(1H,d,J=8.3 Hz),8.38(1H,dd,J=8.1, 2.2 Hz),8.67(1H,ddd,J=4.9,1.7,1.0 Hz),8.88(1H,d,J=7.8 Hz),8.91 (1H,d,J=8.1 Hz),9.14(1H,d, J=2.2 Hz).

EXAMPLE 76

Preparation of (2S)-2-(4-(N-2-picolylaminomethyl)benzoyl)amino-5-(5,6,7,8-tetrahydroquinolin-8-yl)aminovaleric acid (1'S)-1'-(1-naphthyl)ethylamide [Compound No. 91]

Example 76-1

Synthesis of N$^\alpha$-(4-(N-Boc-N-2-picolylaminomethyl)benzoyl)-N$^\delta$-Boc-L-ornithine (1'S)-1'-(1-naphthyl)ethylamide (Compound XI-13)

The compound obtained in Example 68-1 (997.9 mg) was dissolved in DMF (20 ml). After the addition of diethylamine (2.0 ml), the mixture was stirred for 1.5 hours at room temperature. After the reaction, the solvent was removed by distillation and the residue was dried under vacuum, and dissolved in DMF (20 ml). WSCI hydrochloride (469.3 mg), HOBt (245.0 mg), and the compound obtained in Example 1–2 (598.9 mg) were added to the solution. The mixture was stirred for 21 hours at room temperature. After the reaction, the solvent was removed by distillation. The residue was dissolved in chloroform and the resulting solution was washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography (50 g, chloroform/methanol=30/1) to obtain the title compound (603.4 mg) as white foam.

MS(FAB,Pos.): m/z=710[M+1]$^+$ $^1$H-NMR(500 MHz, DMSO-d$_6$): δ=1.22–1.55(2H,m),1.31, 1.36 and 1.38(18H,s), 1.51(3H,d,J=7.1 Hz),1.60–1.72(2H,m),2.80–2.92(2H,m), 4.39–4.60(5H,m),5.70(1H,quint., J=7.1 Hz),6.78(1H,t,J=5.6 Hz),7.18–7.37(4H,m),7.46–7.57(4H,m), 7.78(1H,td,J=7.8, 1.7 Hz),7.82(1H,d,J=7.8 Hz),7.85(1H,d,J=8.3 Hz), 8.09(1H, d,J=8.1 Hz),8.34(1H,d,J=7.8 Hz),8.52(1H,d,J=4.8 Hz), 8.61 (1H,d,J=7.6 Hz).

Example 76-2

Synthesis of (2S)-2-(4-(N-2-picolylaminomethyl)benzoyl)amino-5-(5,6,7,8-tetrahydroquinolin-8-yl)aminovaleric acid (1'S)-1'-(1-naphthyl)ethylamide [Compound No. 91]

The compound obtained in Example 76-1 (408.9 mg) was dissolved in methanol (4 ml) and 4 mol/l hydrochloric acid/dioxane solution (4 ml) was added. The mixture was stirred for 3.5 hours at room temperature. After the reaction, the solvent was removed by distillation. The residue was dried under vacuum and dissolved in methanol (4 ml). Then, 5,6,7,8-tetrahydroquinolin-8-one (124.8 mg) and sodium cyanoborohydride (73.2 mg) were added. 50 drops of acetic acid was added to adjust the pH of the mixture to about 4–5. The mixture was stirred for 12.5 hours at room temperature. After the reaction, the solvent was removed by distillation. The residue was purified by silica gel column chromatography (chloroform/methanol/water=7/3/0.5) to obtain the title compound (211.5 mg) as a white solid.

MS(FAB,Pos.): m/z=641[M+1]$^+$ $^1$H-NMR(500 MHz, DMSO-d$_6$): δ=1.51(3H,d,J=6.8 Hz),1.68–2.02(7H,m), 2.22–2.33(1H,m),2.77–2.85(2H,m),2.90–3.00(1H,m), 3.01–3.15 (1H,m),4.31(2H,s),4.32(2H,s),4.38–4.47(1H,m), 4.57–4.63(1H, m),5.70(1H,quint.,J=6.8 Hz),7.37–7.41(1H, m),7.43–7.61(5H,m), 7.63–7.70(2H,m),7.68(2H,d,J=7.8 Hz),7.81(1H,d,J=8.1 Hz),7.94 (1H,d,J=7.8 Hz),7.97(1H,t,J= 7.8 Hz),7.99(2H,d,J=7.8 Hz),8.10(1 H,d,J=8.3 Hz),8.44(1H, m),8.64–8.67(2H,m),8.90(1H,d,J=7.1 Hz), 9.23(2H,br), 10.07(2H,br).

EXAMPLE 77

Preparation of (2S)-2-(4-(N-2-picolylaminomethyl)naphthoyl)amino-5-(5,6,7,8-tetrahydroquinolin-8-yl)aminovaleric acid 2-(3-indolyl)ethylamide [Compound No. 92]

Example 77-1

Synthesis of N$^\alpha$-(4-(N-Boc-N-2-picolylaminomethyl)naphthoyl)-N$^\delta$-Boc-L-ornithine 2-(3-indolyl)ethylamide (Compound XI-14)

The compound obtained in Example 17-5 (1.006 g) was dissolved in DMF (20 ml). After the addition of diethylamine (2.0 ml), the mixture was stirred for 4 hours at room temperature. After the reaction, the solvent was removed by distillation and the residue was dried under vacuum, and dissolved in DMF (20 ml). WSCI hydrochloride (499.0 mg), HOBt (255.2 mg), and the compound obtained in Example 43-2 (696.7 mg) were added to the solution. The mixture was stirred for 16 hours at room temperature. After the reaction, the solvent was removed by distillation. The residue was dissolved in chloroform and the resulting solution was washed with 1 mol/l aqueous solution of hydrochloric acid, 1 mol/l aqueous solution of sodium hydroxide, and saturated brine. The organic layer was dried over anhydrous sodium sulfate and the solvent was removed by distillation. The residue was purified by silica gel column chromatography. (50 g, chloroform/methanol=30/1) to obtain the title compound (860.9 mg) as white foam.

MS(FAB,Pos.): m/z=749[M+1]$^+$ $^1$H-NMR(500 MHz, DMSO-d$_6$): δ=1.25–1.80(4H,m),1.33, 1.37 and 1.43(18H, 2s),2.83–2.92(2H,m),2.92–3.02(2H,m),3.32–3.52(2H,m), 4.34–4.52(3H,m),4.95–5.08(2H,m), 6.82(1H,t,J=5.6 Hz), 6.98(1H,td,J=7.0,1.0 Hz),7.05(1H,td,J=7.0, 1.0 Hz),7.19 (1H,s),7.20–7.40(3H,m),7.34(1H,d,J=8.1 Hz),7.66–7.64 (4H,m),7.77(1H,td,J=7.6,1.7 Hz),8.09–8.21(2H,m), 8.24–8.31(1H,m),8.52–8.64(2H,m),10.83(1H,d,J=1.7 Hz).

Example 77-2

Synthesis of (2S)-2-(4-(N-2-picolylaminomethyl) naphthoyl)amino-5-(5,6,7,8-tetrahydroquinolin-8-yl) aminovaleric acid 2-(3-indolyl)ethylamide [Compound No. 92]

The compound obtained in Example 77-1 (469.7 mg) was dissolved in methanol (4.7 ml) and 4 mol/l hydrochloric acid/dioxane solution (4.7 ml) was added. The mixture was stirred for 2 hours at room temperature. After the reaction, the solvent was removed by distillation. The residue obtained was dried under vacuum and dissolved in methanol (4 ml). Then, 5,6,7,8-tetrahydroquinolin-8-one (143.9 mg) and sodium cyanoborohydride (78.7 mg) were added. 55 drops of acetic acid was added to adjust the pH of the mixture to about 5. The mixture was stirred for 17 hours at room temperature. After the reaction, the solvent was removed by distillation. The residue was dissolved in methanol, neutralized with the addition of Amberlite IRA-410, and concentrated. The obtained residue was purified by silica gel column chromatography (15 g, chloroform/methanol=10/2) to obtain the title compound (191.8 mg) as a white solid.

MS(FAB,Pos.): m/z=680[M+1]$^+$ $^1$H-NMR(500 MHz, DMSO-d$_6$): =1.50–1.73(4H,m),1.73–1.91(4H,m), 1.97–2.05 (1H,m),2.61–2.78(4H,m),2.83–2.94(2H,m),3.37–3.52 (2H, m),3.89(2H,s),4.20(2H,s),4.47–4.53(1H,m),6.98(1H,t,J=7.0 Hz),7.05(1H,t,J=7.0 Hz),7.13–7.22(2H,m),7.24–7.28(1H, m), 7.33(1H,d,J=8.1 Hz),7.43–7.61(7H,m),7.76(1H,td,J= 7.6,1.7 Hz), 8.08–8.17(1H,m),8.20–8.30(2H,m),8.34(1H,d, J=4.4 Hz),8.52(1H, ddd,J=4.9,1.7,1.0 Hz),8.62–8.72(1H,m), 10.85(1H,s).

EXAMPLE 78

Preparation of N$^\alpha$-4-(N-2-picolylaminomethyl) benzoyl-N$^G$-nitroarginine (1'S)-1'-(1-naphthyl) ethylamide [Compound No. 93]

Example 78-1

Synthesis of N$^\alpha$-Boc-N$^G$-nitroarginine (1'S)-1'-(1-naphthyl)ethylamide (Compound XXVII-8)

Commercially available N$^\alpha$-Boc-N$^G$-nitroarginine (3.00 g) was dissolved in dichloromethane, and triethylamine (3.96 ml) and (S)-1-(1-naphthyl)ethylamine (1.69 g) were added. The solution was cooled with ice and a solution of 2-chloro-1,3-dimethylimidazolinium chloride (DMC, 2.38 g) in dichloromethane (20 ml) was added dropwise over 60 minutes. After the addition, the reaction solution was allowed to become room temperature and stirred for 70 minutes. After the reaction, 1 mol/l aqueous solution of hydrochloric acid was added to the reaction solution and the mixture was extracted with chloroform. The organic layer was washed with saturated brine and dried over anhydrous sodium sulfate. Then, the solvent was removed by distillation. The residue was purified by silica gel column chromatography (chloroform/methanol=25/1) to obtain the target compound (4.10 g) as a white solid.

MS(FAB,Pos.): m/z=473[M+1]$^+$

Example 78-2

Synthesis of N$^\alpha$-4-(N-Boc-N-2-picolylaminomethyl) benzoyl-N$^G$-nitro-L-arginine (1'S)-1'-(1-naphthyl) ethylamide (Compound XXIX-13)

The compound obtained in Example 78-1 (1.0009 g) was dissolved in methanol, and 4 mol/l hydrochloric acid/dioxane solution was added. The mixture was stirred for 2 hours at room temperature. After the reaction, the reaction mixture was concentrated to dryness under vacuum, and dissolved in dichloromethane (20 ml). Triethylamine (1.25 ml) and the compound obtained in Example 1-2 (721.4 mg) were added, and the mixture was cooled with ice. A dichloromethane solution (5 ml) of DMC (439.1 mg) was added dropwise to the mixture over 20 minutes. The mixture was stirred for 20 minutes while cooling with ice. After the reaction, 1 mol/l aqueous solution of hydrochloric acid was added to the reaction solution and the mixture was extracted with chloroform. The organic layer was washed with saturated brine and dried over anhydrous magnesium sulfate. Then, the solvent was removed by distillation. The residue was purified by silica gel column chromatography (50 g, chloroform/acetone=2/1) to obtain the target compound (745.3 mg) as a white solid.

MS(FAB,Pos.): m/z=697[M+1]$^+$

Example 78-3

Synthesis of N$^\alpha$-4-(N-2-picolylaminomethyl) benzoyl-N$^G$-nitroarginine (S)-1-(1-naphthyl) ethylamide [Compound No. 93]

The compound obtained in Example 78-2 (204.1 mg) was dissolved in methanol (1 ml) and 4 mol/l hydrochloric acid/dioxane solution (1 ml) was added. The mixture was stirred for 2.5 hours at room temperature. After the reaction, the solvent was removed by distillation. The residue was azeotropically distilled with methanol and dried under reduced pressure to obtain the title compound (196.1 mg) as a white solid.

MS(FAB,Pos.): m/z=597[M+1]$^+$ $^1$H-NMR(500 MHz, DMSO-d$_6$): δ=1.51(3H,d,J=6.8 Hz),1.45–1.60(2H,m), 1.62–1.81(2H,m),3.09–3.23(2H,m),4.30(2H,s),4.31(2H,s), 4.51–4.58(1H,m),5.70(1H,quint.,J=6.8 Hz),7.42–7.58(6H, m),7.62(2H, d,J=8.1 Hz),7.82(1H,d,J=7.8 Hz),7.90(1H,td,J= 7.8,2.0 Hz),7.94(1H,d,J=7.8 Hz),7.96(2H,d,J=8.1 Hz),8.09 (1H,d,J=8.5 Hz),8.49(2H, brs),8.66(1H,ddd,J=4.9,1.7,1.0 Hz),8.73(1H,brs),9.60–9.78 (1H,br).

EXAMPLE 79

Preparation of (2R)-2-(4-(N-(imidazol-2-ylmethyl) aminomethyl)benzoyl)amino-5-(5,6,7,8-tetrahydroquinolin-8-yl)aminovaleric acid (1'S)-1'-(1-naphthyl)ethylamide [Compound No. 94]

Example 79-1

Synthesis of 4-(N-Boc-(N-imidazol-2-ylmethyl) aminomethyl)benzoic acid (Compound VII-12)

Commercially available methyl bromomethylbenzoate (10.01 g) was dissolved in DMF (100 ml). After the addition of potassium phthalimide (9.70 g), the mixture was stirred for 1.5 hours at room temperature. After the reaction, the reaction solution was concentrated. After the addition of water, the residue was extracted with chloroform. The extract was washed with saturated brine and dried over sodium hydrogensulfate, followed by removal of the solvent to obtain a white solid (12.91 g). Part of the white solid (7.56 g) was dissolved in methanol (100 ml). Hydrazine monohydrate (6.25 ml? was added and the mixture was stirred for 1.5 hours at 60° C. After the reaction, the deposited solid was separated by filtration and the solvent was removed by distillation. After the addition of water, the residue was extracted with chloroform. The extract was washed with 0.3 mol/l aqueous solution of sodium hydroxide and saturated brine and dried over anhydrous sodium sulfate. The solvent was removed by distillation. Methanol (120 ml) and 2-imidazole carboaldehyde (2.35 g) were added to the residue, and the mixture was stirred for 2 days at room temperature. After the reaction, the deposited solid was collected by filtration. The liquid layer was concentrated to dryness. The resulting solid was washed with anhydrous methanol (30 ml) and collected by filtration. The solid was combined with the previously collected solid and suspended in methanol (86 ml). Sodium borohydride (1.42 g) was added to the suspension while cooling with ice. Then, the mixture was stirred for one hour at room temperature and the solvent was removed by distillation. After adding water, the residue was extracted with chloroform. The organic layer was washed with saturated brine, dried over anhydrous sodium sulfate, concentrated under reduced pressure, and dried to obtain a colorless viscous liquid (4.32 g). Part of the colorless viscous liquid (4.28 g) was dissolved in DMF (65 ml). After the addition of di-t-butyldicarbonate (8.9 ml), the mixture was stirred for one hour at room temperature. After the reaction, the solvent was removed by distillation. The residue was dissolved in chloroform, washed with saturated brine, and dried over anhydrous sodium sulfate. After removal of the solvent by distillation, THF (43 ml), methanol (43 ml), and 1 mol/l aqueous solution of sodium hydroxide (43 ml) were added, and the mixture was stirred for 14 hours at room temperature. After the reaction, the solvent was removed by distillation. 1 mol/l aqueous solution of hydrochloric acid (5 ml) was carefully added and the deposited solid was collected by filtration and dried to obtain the title compound (4.87 g) as a white solid.

MS(FAB,Pos.): m/z=332[M+1]$^+$

Example 79-2

Synthesis of N$^\alpha$-(4-(N-(imidazol-2-ylmethyl) aminomethyl)naphthoyl)-N$^\delta$-Boc-D-ornithine (1'S)-1'-(1-naphthyl)ethylamide(Compound XI-15)

Commercially available (S)-1-(1-naphthyl)ethylamine (414.6 mg) was dissolved in DMF (10 ml). Commercially available N$^\alpha$-Fmoc-N$^\delta$-Boc-D-ornithine (1.0006 g), WSCI hydrochloride (414.6 mg), and HOBt (375.5 mg) were added to the solution. The mixture was stirred for 3 hours at room temperature. After the reaction, the solvent was removed by distillation. Chloroform was added to the residue and the mixture was washed with 1 mol/l aqueous solution of hydrochloric acid, 1 mol/l aqueous solution of sodium hydroxide, and saturated brine, and dried over anhydrous sodium sulfate. The solvent was removed by distillation to obtain a white solid (1.38 g). The white solid was dissolved in DMF (27 ml) and diethylamine (2.7 ml) was added thereto. The mixture was stirred for 40 minutes at room temperature, followed by removal of the solvent and drying under reduced pressure. The product was again dissolved in DMF (27 ml). Then, WSCI hydrochloride (633.5 mg), HOBt (335.9 mg), and the compound obtained in Example 79-1 (734.7 mg) were added. The mixture was stirred for 12 hours at room temperature. After the reaction, the solvent was removed by distillation. Chloroform was added to the residue. The resulting solution was washed with distilled water, 1 mol/l aqueous solution of sodium hydroxide, and saturated brine, and dried over anhydrous sodium sulfate. The solvent was removed by distillation and the residue was purified by silica gel column chromatography (55 g, chloroform/methanol=25/1) to obtain the title compound (906.2 mg) as a white solid.

MS(FAB,Pos.): m/z=699[M+1]$^+$ $^1$H-NMR(500 MHz, DMSO-d$_6$): δ=1.35 and 1.38(9H, 2s),1.35–1.60(2H,m), 1.50 (3H,d,J=6.8 Hz),1.68–1.82(2H,m),2.90–3.00(2H,m), 4.30–4.55(5H,m),5.70(1H,quint,J=6.8 Hz),6.84(1H,t,J=5.6 Hz),6.95(2 H,brs),7.19–7.31(2H,m),7.44–7.59(3H,m),7.60 (1H,d,J=7.1 Hz), 7.82(1H,d,J=8.1 Hz),7.84(2H,d,J=8.3 Hz), 7.93(1H,d,J=7.6 Hz),8.09 (1H,d,J=7.8 Hz),8.35(1H,d,J=7.8 Hz),8.55(1H,d,J=7.8 Hz).

Example 79-3

Synthesis of (2R)-2-(4-(N-(imidazol-2-ylmethyl) aminomethyl)benzoyl)amino-5-(5,6,7,8-tetrahydroquinolin-8-yl)aminovaleric acid (1'S)-1'-(1-naphthyl)ethylamide [Compound No. 94]

The compound obtained in Example 79-3 (504.9 mg) was dissolved in methanol (2.5 ml), and 4 mol/l hydrochloric acid/dioxane solution (2.5 ml) was added. The mixture was stirred for 1.5 hours at room temperature. After the reaction, the solvent was removed by distillation. The residue was dissolved again in methanol and neutralized with Amberlite IRA-410. The solvent was removed by distillation and the residue was dissolved again in methanol (50 ml). After the addition of 5,6,7,8-tetrahydroquinolin-8-one (0.1928 g), acetic acid (0.5 ml), and sodium cyanoborohydride (0.0861 g), the mixture was stirred for 3 days at room temperature. After the reaction, the solvent was removed by distillation. The residue was suspended in chloroform. The suspension was washed with 0.5 mol/l aqueous solution of sodium hydroxide and saturated brine. The organic layer was dried over anhydrous sodium sulfate and concentrated. The residue was purified by silica gel column chromatography (25 g, chloroform/methanol/water=7/3/0.5) to obtain the title compound (312.3 mg) as a white solid.

MS(FAB,Pos.): m/z=630[M+1]$^+$ $^1$H-NMR(500 MHz, DMSO-d$_6$): δ=1.48(3H,d,J=6.8 Hz),1.42–1.70(4H,m), 1.75–1.90(2H,m),1.80–1.93(1H,m),1.95–2.05(1H,m), 2.65–2.75(2H,m),2.70–2.80(2H,m), 3.66 (2H,s),3.71(2H,s), 3.62–3.70(1H,m),4.49–4.55(1H,m),5.69(1H,quint,J=6.8 Hz),6.81 and 6.99(2H,br),7.15–7.19(1H,m),7.40(1H,d,J=8.5 Hz),7.41(1H,d,J=8.8 Hz),7.44–7.55(2H,m),7.59(1H,d,J=7.3 Hz),7.79(1H,d,J=8.3 Hz),7.81(2H,d,J=8.5 Hz),7.92(1H,d,J= 7.6 Hz),8.09(1H,d,J=8.1 Hz),8.32–8.36(1H,m),8.38 and 8.45(1H,d,J=8.1 Hz),8.56 and 8.58(1H,d,J=8.1 Hz).

EXAMPLE 80

Preparation of N$^\alpha$-4-(N-2-(imidazol-2-ylmethyl) aminomethyl)benzoyl-L-arginine (1'S)-1'-(1-naphthyl)ethylamide [Compound No. 95]

Example 80-1

Synthesis of N$^\alpha$-(4-(N-Boc-N-(imidazol-2-ylmethyl) aminomethyl)benzoyl-N$^G$-pmc-L-arginine (1'S)-1'-(1-naphthyl)ethylamide (Compound XXIX-14)

The compound obtained in Example 71-1 (750.5 mg, 0.920 mmol) was dissolved in DMF (15 ml), and diethylamine (1.5 ml) was added. The mixture was stirred for 30 minutes at room temperature, followed by removal of the solvent and drying under reduced pressure. The residue was again dissolved in DMF (15 ml). Then, WSCI hydrochloride (269.0 mg), HOBt (140.4 mg), and the compound obtained in Example 79-1 (326.4 mg) were added. The mixture was stirred for 2 days at room temperature. After the reaction, the solvent was removed by distillation. Chloroform was added to the residue. The resulting solution was washed with 0.5 mol/l aqueous solution of sodium hydroxide and saturated brine, and dried over anhydrous sodium sulfate. The solvent was removed by distillation and the residue was purified by silica gel column chromatography (50 g, chloroform/methanol=20/1) to obtain the target compound (237.4 mg) as a white solid.

MS(FAB,Pos.): m/z=907[M+1]$^+$

Example 80-2

Synthesis of N$^\alpha$-4-(N-2-(imidazol-2-ylmethyl)aminomethyl)benzoyl-L-arginine (1'S)-1'-(1-naphthyl)ethylamide [Compound No. 95]

The compound obtained in Example 80-1 (210.1 mg) was dissolved in chloroform (4.2 ml), and methanesulfonic acid (0.45 ml) was added. The mixture was stirred for one day at room temperature. After the reaction, the reaction mixture was concentrated to dryness. The residue was washed with diethyl ether. After the addition of methanol, the solvent was again removed by distillation. The residue was purified by silica gel column chromatography (5 g, chloroform/methanol/water=7/3/0.5). The obtained fractions were concentrated and dried under reduced pressure to obtain methanesulfonate of the title compound (99.6 mg) as a white solid.

MS(FAB,Pos.): m/z=541[M+1]$^+$ $^1$H-NMR(500 MHz, DMSO-d$_6$): δ=1.41–1.61(2H,m),1.51(3H,d,J=6.8 Hz), 1.65–1.82(2H,m),2.38(12H,s),3.02–3.12(2H,m),4.34(2H,s), 4.48 (2H,s),4.52–4.58(1H,m),5.71(1H,quint,J=6.8 Hz), 6.7–7.4(4H, br),7.46–7.58(5H,m),7.60(1H,d,J=8.3 Hz),7.68 (2H,s),7.83(1H,d, J=8.3 Hz),7.95(1H,d,J=7.1 Hz),7.98(2H, d,J=8.3 Hz),8.10(1H,d,J=8.1 Hz),8.50(1H,d,J=8.1 Hz),8.70 (1H,d,J=7.6 Hz).

EXAMPLE 81

Preparation of (2S)-2-((1-methylimidazol-2-ylmethyl)aminomethyl)benzoylamino-5-(5,6,7,8-tetrahydroquinolyl-8-yl)aminovaleric acid 1-naphthalenemethyleneamide [Compound No. 96]

Example 81-1

Synthesis of Methyl 4-(N-Boc-N-(1-methylimidazol-2-yl)methylamino-methyl)benzoate (Compound VI-9)

Commercially available methyl aminomethylbenzoate (1.00 g) and 1-methyl-2-imidazole carboxyaldehyde (0.68 g) were dissolved in methanol (10 ml). Triacetoxy sodium borohydride (1.95 g) was added to the solution while stirring at 0° C. The mixture was stirred for one hour. The reaction mixture was allowed to become room temperature and stirred for a further 45 minutes. The reaction solution was concentrated and chloroform was added to the residue. The mixture was washed with a saturated aqueous solution of sodium hydrogencarbonate, distilled water, and saturated brine. The organic layer was concentrated and dried under reduced pressure. The residue was dissolved in DMF (30 ml). After triethylamine (0.61 g) was added dropwise, anhydrous di-t-butyldicarbonate was added dropwise at room temperature, followed by stirring for 3 hours. The reaction solution was concentrated and dried under reduced pressure. Chloroform was added to the residue. The resulting solution was washed with saturated aqueous solution of ammonium chloride, distilled water, and saturated brine. The organic layer was concentrated and dried under reduced pressure. The residue was purified by silica gel column chromatography (100 g, chloroform/methanol=50/1) to obtain the title compound (1.33 g) as yellow oil.

MS(FAB,Pos.): m/z=360[M+1]$^+$ $^1$H-NMR(500 MHz, CDCl$_3$): δ=1.47, 1.53(9H, 2s),3.49, 3.61(3H, 2s) 3.91(1H, s),4.47(2H,s),4.50(brs, 2H), 6.80(1H,brs),6.93(1H,d,J=1.2 Hz),7.22(1H,brs),7.95(1H,d,J=7.8 Hz),8.02(1H,s).

Example 81-2

Synthesis of N-Boc-N-(1-methylimidazol-2-yl)aminomethyl benzoic acid (Compound VII-13)

The compound obtained in Example 81-1 was dissolved in methanol (10 ml) and 1 mol/l aqueous solution of sodium hydroxide (10 ml) was added dropwise. The mixture was stirred for 3 hours at room temperature. Ion-exchange resin (CG 50) was added to the reaction solution. After adjusting the pH to around neutral, the resin was removed by filtration though a glass filter. The reaction solution was concentrated and dried under reduced pressure to obtain a crude product (1.39 g) as a yellow solid. The crude product was purified by silica gel column chromatography (100 g, chloroform/methanol=50/1) to obtain the title compound (1.33 g) as yellow oil.

Example 81-3

Synthesis of N$^\alpha$-(1-methylimidazol-2-ylmethyl)aminomethylbenzoyl-N-Boc-L-ornithine 1-naphthalenemethyleneamide (Compound XI-16)

The compound obtained in Example 23-1 (1.5.0 g) was dissolved in DMF (30 ml) and diethylamine (3.0 ml) was added dropwise at room temperature. After the reaction for 2 hours, the reaction solution was concentrated under reduced pressure and dried, and dissolved in DMF (30 ml). WSCI hydrochloride (0.73 g), DMAP (0.46 g), and the compound obtained in Example 81-2 (0.87 g) were added. After the reaction over night at room temperature, the reaction solution was concentrated to dryness under reduced pressure. The residue was dissolved in chloroform. The solution was washed with 1 mol/l hydrochloric acid, distilled water, and saturated brine, and purified by silica gel column chromatography (120 g, chloroform/methanol=20/1) to obtain the title compound (0.73 g) as yellow oil.

Example 81-4

Synthesis of (2S)-2-((1-methylimidazol-2-ylmethyl)aminomethyl)benzoylamino-5-(5,6,7,8-tetrahydroquinolyl-8-yl)aminovaleric acid 1-naphthalenemethyleneamide [Compound No. 96]

The compound obtained in Example 81-3 (0.19 g) was dissolved in methanol (4 ml). 4 mol/l hydrochloric acid/dioxane solution (4 ml) was added dropwise to the solution at room temperature, followed by stirring for 2 hours. The reaction solution was concentrated to obtain a crude product (0.20 g) as colorless oil. The colorless oil and 5,6,7,8- tetrahydroquinolinone (0.05 g) were dissolved in methanol (4 ml). Triethylamine (0.08 g) was added dropwise at room temperature. Acetic acid was added to the solution to adjust the pH to around 4. Sodium cyanoborohydride (0.07 g) was added to the solution. After stirring over night at room temperature, the reaction solution was concentrated under reduced pressure. The residue was purified by silica gel column chromatography (9 g, chloroform/methanol 5/1) and treated with 1 mol/l aqueous solution of hydrochloric acid to obtain hydrochloride of the title compound (0.07 g) as a white solid.

MS(FAB,Pos.): m/z=630[M+1]$^+$ $^1$H-NMR(500 MHz, DMSO-d$_6$): δ=1.73–1.84(3H,brs),1.86–1.91(3H, brs),1.98 (1H,brs),2.29(1H,brs),2.79(2H,m),2.95(1H,brs),3.08 (1H, m),3.97(3H,s),4.41(3H,brs),4.53–4.60(3H,brs),4.76(2H,d), 7.37(1H,m),7.46(2H,d), 7.54(2H,m),7.67(1H,d), 7.74(2H, d), 7.76 (2H,d), 7.84(1H,m),7.94(1H,m),8.00(2H,m),8.07 (1H,m),8.46(1H, m),8.69–8.74(2H,m),9.14(1H,brs),10.73 (1H,brs).

EXAMPLE 82

Preparation of N$^α$-(4-((N-(1-methylimidazol-2-ylmethyl)amino)methyl)naphthalene-1-carbonyl)-L-arginine (1'S)-1'-(1-naphthyl)ethylamide [Compound No. 97]

Example 82-1

Synthesis of N$^α$-(4-((N-Boc-N-(1-methylimidazol-2-ylmethyl)amino)methyl)naphthalene-1-carbonylamino)-N$^G$-Pmc-L-arginine(1'S)-1'-(1-naphthyl)ethylamide (Compound XXIX-15)

The compound obtained in Example 48-1 (0.3131 g) was dissolved in DMF (7 ml). After the addition of diethylamine (0.056 g), the mixture was stirred for 1.5 hours. The solvent was removed by distillation. The residue was dissolved in DMF (6 ml). The compound obtained in Example 74-3 (0.167 g), HOBt (0.0778 g), and WSCI hydrochloride (0.110 g) were added to the solution. The mixture was stirred for 19 hours at room temperature. Water was added to the mixture, and the solvent was removed by distillation. Chloroform was added to the residue. The mixture was washed with saturated aqueous solution of sodium hydrogencarbonate and dried over anhydrous magnesium sulfate. The solvent was removed by distillation and the residue was purified by silica gel column chromatography (15 g, 5% methanol/chloroform) to obtain the title compound (0.3137 g) as a white solid.

MS(FAB,Pos.): m/z=971[M+1]$^+$ $^1$H-NMR(500 MHz, CDCl$_3$): δ=1.28(6H,s),1.38–1.70(4H,m),1.43(9H, s),1.60 (3H,d,J=7.1 Hz),1.78(2H,t,J=6.8 Hz),2.07(3H,s),2.49(3H, s),2.58(2H,t,J=6.8 Hz),3.18–3.30(2H,m),3.54 and 3.68(3H, s), 4.39 and 4.53(2H,s),4.74–4.84(1H,m),4.96(2H,s),5.85 (1H, quint.,J=6.8 Hz),6.03 and 6.16(1H,bs),6.80(1H,s),6.83 (1H,s),7.24 (1H,d,J=8.5 Hz),7.39(1H,t,J=7.8 Hz),7.44–7.55 (5H,m),7.59(1H, d,J=7.3 Hz),7.74(1H,d,J=8.3 Hz),7.83(1H, d,J=7.3 Hz),8.01(2H,bs), 8.23(1H,d,J=6.1 Hz).

Example 82-2

Synthesis of N (4-((N-(1-methylimidazol-2-ylmethyl)amino)methyl)naphthalene-1-carbonyl)-L-arginine(1'S)-1'-(1-naphthyl)ethylamide [Compound No. 97]

The compound obtained in Example 82-4 (0.3099 g) was dissolved in chloroform (3.2 ml). The solution was cooled with ice, and then TFA (3.2 ml) was added. The mixture was stirred for 3.5 hours at room temperature, followed by removal of the solvent. After the reaction, 1 mol/l hydrochloric acid and chloroform were added and mixed. After the water layer was removed, the organic layer was washed with chloroform and the solvent was removed by distillation. The obtained residue was dissolved in 1 mol/l hydrochloric acid and the solvent was removed by distillation. A solid was reprecipitated from a mixture of water and acetone. The precipitate obtained was collected by filtration and dried to obtain hydrochloride of the title compound (0.2088 g) as a white solid.

MS(FAB,Pos.): m/z=[M+1]$^+$ $^1$H-NMR(500 MHz,DMSO-d$_6$): δ=1.50–1.62(2H,m),1.56(3H,d,J=7.1 Hz), 1.62–1.75 (1H,m),1.76–1.84(1H,m),3.08–3.15(2H,m),3.89(3H,s), 4.55–4.68(3H,m),4.80(2H,s),5.78(1H,quint.,J=7.1 Hz), 7.49–7.73(7H,m),7.78(1H,d,J=7.3 Hz),7.84(1H,d,J=8.3 Hz),7.96(1H,d, J=7.8 Hz),8.14(1H,d,J=8.3 Hz),8.26(1H,d, J=8.3 Hz),8.30(1H,d,J=8.3 Hz),8.70(1H,d,J=8.1 Hz),8.79 (1H,d,J=7.8 Hz).

EXAMPLE 83

Preparation of N$^α$-(4-((imidazol-2-ylmethyl)amino) methyl)naphthalene-1-carbonyl)L-arginine(1'S)-N-methyl-N-(1'-(1-naphthyl)ethyl)amide [Compound No. 98]

Example 83-1

Synthesis of N$^α$Fmoc-N$^G$-Pmc-L-arginine (1'S)-N-methyl-(1'-(1-naphthyl)ethyl)amide (Compound XXVII-9)

Commercially available N$^α$-Fmoc-N$^δ$-Pmc-arginine (1.000 g) was dissolved in DMF (20 ml). HOBt (0.224 g) was added to the solution. After the solution was cooled with ice, WSCI hydrochloride (0.318 g) was added. The mixture was stirred for 15 hours at room temperature. The reaction solution was concentrated and chloroform was added to the residue. The mixture was washed with saturated aqueous solution of sodium hydrogencarbonate. The water layer was extracted with chloroform. The obtained organic layer was dried over magnesium sulfate. The solvent was removed by distillation and the residue was purified by silica gel column chromatography (40 g, 2% methanol/chloroform) to obtain the title compound (0.5749 g) as a pale yellow viscous liquid.

MS(FAB,Pos.): m/z=830[M+1]$^+$ $^1$H-NMR(500 MHz, CDCl$_6$): δ=1.26(3H,s),1.27(3H,s),1.38–1.60(4H, m),1.62 (3H,d,J=7.1 Hz),1.77(2H,t,J=7.1 Hz),2.04(3H,s),2.45(3H, s),2.49(6H,s),2.56(2H,t,J=7.1 Hz),2.95–3.05(1H,m), 3.16–3.26(1H,m),4.21(1H,t,J=7.1 Hz),4.37(1H,dd,J=10.5, 7.1 Hz),4.43(1H, dd,J=10.5, 7.1 Hz),4.57(1H,t,J=8.3 Hz), 5.87(2H,bs),6.09(1H,d,J=8.3 Hz),6.52(1H,q,J=6.6 Hz),7.31 (1H,t,J=7.1 Hz),7.33(1H,t,J=7.1 Hz),7.38–7.51(6H,m),7.54 (1H,d,J=7.1 Hz),7.60(2H,t,J=6.8 Hz), 7.76–7.90(5H,m).

Example 83-2

Synthesis of N$^α$-(4-((N-Boc-N-(imidazol-2-ylmethyl)aminomethyl)naphthalene-1-carbonyl)-N$^G$-Pmc-L-arginine(1'S)-N-methyl-(1'-(1-naphthyl) ethyl)amide (Compound XXIX-16)

The compound obtained in Example 83-1 (0.2356 g) was dissolved in DMF (5 ml). After the addition of diethylamine (0.042 g), the mixture was stirred for 1.5 hours. The solvent was removed by distillation. The residue was dissolved in DMF (5 ml). The compound obtained in Example 17-4 (0.108 g), HOBt (0.0581 g), and WSCI hydrochloride (0.164 g) were added to the solution. The mixture was stirred for 6 days. Water was added to the reaction solution and the solvent was removed by distillation. Chloroform was added to the residue. The resulting solution was washed with saturated aqueous solution of sodium hydrogencarbonate and 1 mol/l aqueous solution of hydrochloric acid and dried over anhydrous magnesium sulfate. The solvent was removed by distillation and the residue was purified by silica gel column chromatography (20 g, 5% methanol/chloroform) to obtain the title compound (0.1814 g) as a pale yellow viscous liquid.

MS(FAB,Pos.): m/z=971[M+1]$^+$ $^1$H-NMR(500 MHz, CDCl$_3$): δ=1.27 and 1.28(9H,s),1.40–1.60(4H,m), 1.50(9H, s),1.67(3H,d,J=6.8 Hz),1.76(2H,t,J=6.6 Hz),2.04(3H,s), 2.50(6H,s),2.56(3H,s),2.57(2H,t,J=6.7 Hz),3.04–3.26(1H, m), 3.34–3.42(1H,m),4.36(2H,s),4.96(2H,s),5.14(1H,t,J= 6.1 Hz), 6.07 and 6.31(2H,bs),6.54(1H,q,J=7.1 Hz),6.96 (2H,s),7.33(2H, d,J=6.6 Hz),7.43–7.60(6H,m),7.68(2H,d,J= 7.3 Hz),7.83(2H,d,J=8.3 Hz),7.85(2H,d,J=8.1 Hz),7.88(2H, d,J=7.8 Hz),8.04(2H,d,J=7 3 Hz),8.35(2H,d,J=8.3 Hz).

Example 83-3

Synthesis of N$^α$-(4-((imidazol-2-ylmethyl)amino) methyl)naphthalene-1-carbonyl)L-arginine(1'S)-N-methyl-N-(1'-(1-naphthyl)ethyl)amide [Compound No. 98]

The compound obtained in Example 83-1 (0.1814 g) was dissolved in chloroform (1.8 ml), and TFA (1.8 ml) was added. The mixture was stirred for 5 hours at room temperature. The solvent was removed by distillation. 1 mol/l hydrochloric acid and chloroform were added to the residue. After the water layer was removed, the organic layer was washed with chloroform and the solvent was removed by distillation. The residue was caused to pass through silica gel column chromatography (2 g, chloroform/methanol/32% AcOH=7/3/0.5) and dissolved in 1 mol/l hydrochloric acid (2 ml). The solvent was removed by distillation. The residue was dissolved in water and acetone was added thereto. The obtained oily substance was collected by centrifugation. The supernatant was removed and the remaining solvent was removed by distillation. The resulting solid was again dissolved in a small amount of methanol. Ethyl acetate was added to the solution to cause a solid material to deposit. The solvent was removed by distillation to obtain hydrochloride of the title compound (0.0566 g) as a white solid.

MS(FAB,Pos.): m/z=605[M+1]$^+$ $^1$H-NMR(50 MHz, DMSO-d$_6$): δ=1.50–1.76(4H,m),1.61(3H,d,J=7.1 Hz), 2.61 (3H,s),3.00–3.15(2H,m),4.65(2H,s),4.82–4.92(1H,m),4.85 (2H,s),6.41(1H,q,J=6.8 Hz),7.50–7.62(4H,m),7.64–7.75 (9H,m), 7.83(1H,d,J=7.3 Hz),7.91(1H,d,J=8.1 Hz),7.94(1H, d,J=8.3 Hz),7.98(1H,d,J=7.8 Hz),8.30(1H,dd,J=7.1, 1.2 Hz), 8.33(1H,d,J=7.6 Hz), 9.01(1H,d,J=7.3 Hz).

EXAMPLE 84

Preparation of N$^α$-(4-(N-2-picolylaminomethyl) naphthoyl)-L-arginine(1'S)-1'-(1-naphthyl) ethylamide [Compound No. 99]

Example 84-1

Synthesis of N$^α$-(4-((N-Boc-N-2-picolylamino) methyl)naphthoyl)-N$^G$-Pmc-L-arginine (1'S)-1'(1-naphthyl)ethylamide (Compound XXIX-17)

The compound obtained in Example 48-1 (0.200 g) was dissolved in DMF (4 ml). After the addition of diethylamine (0.054 g), the mixture was stirred for two hours. The solvent was removed by distillation to obtain a viscous liquid. The compound obtained in Example 43-2 (0.0962 g) and HOBt (0.0497 g) were added to the viscous liquid. The mixture was dissolved in DMF (5 ml). WSCI hydrochloride (0.071 g) was added and the mixture was stirred for 16 hours. Water was added to the reaction solution and the mixture was concentrated. After the addition of chloroform, the mixture was processed through a solid layer extraction column, Chem-Elut (CE1003), permeated with a saturated aqueous solution of sodium hydrogencarbonate. The solvent was removed by distillation. The resulting mixture was purified by silica gel column chromatography (20 g, 4% methanol/chloroform) to obtain the title compound (0.1504 g) as white foam.

MS(FAB,Pos.): m/z=968[M+1]$^+$ $^1$H-NMR(500 MHz, CDCl$_3$): δ=1.29(6H,s),1.44 and 1.48(9H,s),1.40–1.70(4H, m),1.59(3H,d,J=5.4 Hz),1.78(2H,t,J=6.6 Hz),2.08(3H,s), 2.50(3H,s),2.51(3H,s),2.58(3H,t,J=6.3 Hz),3.20–3.30(2H, m), 4.38 and 4.53(2H,s),4.78–4.86(1H,m),4.99 and 5.03(2H, s),5.80–5.88(1H,m),5.92–6.00 and 6.10–6.22(2H,bs), 7.05–7.20(3H,m), 7.34–7.60(8H,m),7.73(1H,d,J=8.3 Hz), 7.83(1H,d,J=7.8 Hz), 7.94–8.06(2H,m),8.18–8.30(2H,m), 8.49(1H,s).

Example 84-2

Synthesis of N$^α$-(4-(N-2-picolylaminomethyl) naphthoyl)-L-arginine(1'S)-1'-(1-naphthyl) ethylamide [Compound No. 99]

The compound obtained in Example 84-1 (0.1448 g) was dissolved in chloroform (1.5 ml). After the solution was cooled with ice, TFA (1.44 ml) was added. The mixture was stirred for 4 hours at room temperature, and then the solvent was removed by distillation. The residue was dissolved in methanol and neutralized with an ion-exchange resin (Amberlite IRA-410). After filtration, the solvent was removed by distillation. 1 mol/l hydrochloric acid was added and the solvent was removed by distillation. After dehydration by azeotropic distillation with methanol, the residue was dried under vacuum and purified by silica gel column chromatography (3 g, chloroform/methanol/water=7/3/0.5) to obtain a solid. 1 mol/l hydrochloric acid was added to the solid obtained and-the solvent was removed by distillation. A residue obtained by azeotropic distillation with methanol was dissolved in methanol, followed by reprecipitation of a solid from acetone. The solvent was removed by distillation to obtain hydrochloride of the title compound (0.0981 g) as a white solid.

MS(FAB,Pos.): m/z=602[M+1]$^+$ $^1$H-NMR(500 MHz, DMSO-d$_6$): δ=1.50–1.64(2H,m),1.56(3H,d,J=6.8 Hz), 1.64–1.76(2H,m),1.80–1.90(2H,m),3.08–3.20(2H,m), 4.60–4.68(1H,m),4.77(2H,s),5.778(1H,quint.,J=7.1 Hz), 7.20–7.40(2H,bs), 7.48–7.72(9H,m),7.81(1H,d,J=7.3 Hz), 7.84(1H,d,J=8.3 Hz),7.90–8.00(3H,m),8.15(1H,d,J=8.1 Hz),8.26(1H,d,J=8.5 Hz),8.29(1H,d, J=8.3 Hz),8.71(1H,d, J=4.2 Hz),8.73(1H,d,J=8.1 Hz),8.86(1H,d,J=7.6 Hz),9.91 (2H,bs).

EXAMPLE 85

Preparation of methyl N$^α$-(4-(N-2-picolylaminomethyl)naphthalene-1-carbonyl)-L-arginine-D-3-(1-naphthyl)alanine [Compound No. 100]

Example 85-1

Synthesis of Methyl D-3-(1-naphthyl)alanine

Methanol (1 ml) was cooled to −10° C. and thionyl chloride (0.091 g) was gradually added while stirring. After 10 minutes, commercially available D-3-(1-naphthyl) alanine (0.04569 g) was added. After stirring for 21 hours at room temperature, the reaction mixture was concentrated under reduced pressure. Methanol (12 ml) was added and the solvent was removed by distillation. The mixture obtained by repeating this procedure twice was fractioned into portions dissolvable into saturated sodium hydrogencarbonate aqueous solution and chloroform. The water layer was extracted with chloroform. The organic layer was dried over anhydrous sodium sulfate. The solvent was removed by distillation to obtain the title compound (40.3 mg) as a colorless liquid.

MS(FAB,Pos.): m/z=230[M+1]$^+$ $^1$H-NMR(500 MHz, CDCl$_3$): δ=3.14(1H,dd,J=13.9, 8.8 Hz),3.69(1H,dd, J=13.9, 4.9 Hz),3.91(1H,dd,J=8.8,4.9 Hz),7.35(1H,d, 6.1 Hz),7.42 (1H,dd, 7.1,1.0 Hz),7.48–7.57(2H,m),7.78(1H,d,8.3 Hz), 7.87(1H, dd,J=8.1, 1.2 Hz),8.09(1H,d,J=8.5 Hz).

Example 85-2

Synthesis of Methyl N$^α$-Fmoc-N$^G$-Pmc-L-arginine-D-3-(1-naphthyl)alanine (Compound XXVII-10)

Commercially available N$^α$-Fmoc-N$^δ$-pmc-arginine (0.1258 g) was dissolved in DMF (2 ml). A reaction solution of HOBt (0.0233 g), WSCI hydrochloride. (0.0473 g), and the compound obtained in Example 85-1 (0.0377 g) in DMF (2 ml) was added. The mixture was stirred for 3 days. Water was added to the reaction solution, and the solvent was removed by distillation. The residue was dissolved in chloroform, washed sequentially with 1 mol/l aqueous solution of hydrochloric acid and saturated aqueous solution of sodium hydrogencarbonate, and dried over anhydrous sodium sulfate. The crude product obtained by evaporating the solvent was purified by silica gel column chromatography (7 g, 5% methanol/chloroform) to obtain the title compound (0.1497 g) as a white solid.

MS(FAB,Pos.): m/z=874[M+1]$^+$ $^1$H-NMR(500 MHz, DMSO-d$_6$): δ=1.25(3H,s),1.26(3H,s),1.28–1.46(3H, m),1.54–1.66(1H,m),1.73(2H,t,6.8 Hz),2.08(3H,s),2.56(3H, s), 2.57(2H,t,6.8 Hz),2.59(3H,s),3.02–3.22(2H,m),3.41(1H, dd,J=14.2, 8.8 Hz),3.63(3H,s),3.666(1H,dd,J=14.2,5.6 Hz), 4.09(1H,t, J=7.1 Hz),4.14–4.20(1H,m),4.24–4.33(2H,m), 4.90–4.96(1H,m), 5.75(1H,d,J=7.3 Hz),6.01(1H,bs), 7.20–7.30(4H,m),7.36(2H,t, J=7.6 Hz),7.44–7.53(4H,m), 7.67–7.69(1H,m),7.73(2H,d,J=7.6 Hz); 7.80(1H,d,J=7.8 Hz),8.052(1H,d,J=8.5 Hz).

Example 85-3

Synthesis of Methyl N$^α$-(4-((N-Boc-N-2-picolylamino)methyl)naphthalene-1-carbonyl)-N$^G$-Pmc-L-arginine-D-3-(1-naphthyl)alanine (Compound XXIX-18)

The compound obtained in Example 85-2 (0.142 g) was dissolved in DMF (5 ml). After the addition of diethylamine (0.036 g), the mixture was stirred for 1.5 hours. The solvent was removed by distillation to obtain a residue. The compound obtained in Example 43-2 (00.0701 g) and HOBt (0.0329 g) were added to the residue. The mixture was dissolved in DMF (5 ml). WSCI hydrochloride (0.0467 g) was added and the mixture was stirred for 38 hours. Water was added to the reaction solution, followed by concentration. The residue was dissolved in chloroform. The solution was washed with saturated aqueous solution of sodium hydrogencarbonate, and dried over anhydrous magnesium sulfate. The solvent was removed by distillation and the residue was purified by silica gel column chromatography (10 g, 4% methanol/chloroform) to obtain the title compound (0.1612 g) as a white solid.

MS(FAB,Pos.): m/z=1026[M+1]$^+$ $^1$H-NMR(500 MHz, CDCl$_3$): δ=1.28(6H,s),1–0.38–1.56(3H,m),1.43 and 1.47 (9H,s),1.64–1.76(1H,m),1.77(2H,t,J=6.8 Hz),2.08(3H,s), 2.50–2.62(8H,m),3.04–3.22(2H,m),3.40(1H,dd,J=13.9, 9.3 Hz), 3.64–3.72(1H,m),3.65(3H,s),4.37 and 4.51(2H,s),4.73 (1H,dd,J=13.7, 8.3 Hz),4.94–5.04(3H,m),6.08(2H,bs), 6.94–7.02(1H,m), 7.05–7.15(2H,m),7.20–7.36(6H,m), 7.42–7.62(7H,m),7.69(1H,d, J=8.1 Hz),7.80(1H,d,J=0.1 Hz),8.06(1H,d,J=8.5 Hz),8.20(1H,d,J=7.6 Hz),8.48(1H,bs).

Example 85-4

Synthesis of Methyl N$^α$-(4-(N-2-picolylaminomethyl)naphthalene-1-carbonyl)-L-arginine-D-3-(1-naphthyl)alanine [Compound No. 100]

The compound obtained in Example 85-3 (0.04066 g) was dissolved in chloroform (0.4 ml) and trifluoroacetic acid (0.20 ml) was added. The mixture was stirred for 8 hours at room temperature, then the solvent was removed by distillation. After azeotropic distillation twice with methanol, the residue was purified by silica gel column chromatography (3 g, chloroform/methanol/water=7/3/0.5) and treated with a hydrochloric acid-methanol solution. The solvent was removed by distillation to obtain hydrochloride of the title compound (0.0307 g) as a white solid.

MS(FAB,Pos.): m/z=660[M+1]$^+$ $^1$H-NMR(500 MHz, DMSO-d$_6$): δ=1.33–1.41(2H,m),1.45–1.53(1H,m) 1.60–1.67(1H,m),3.02–3.09(2H,m),3.35(1H,dd,J=14.2, 10 Hz), 3.66–3.70(1H,m),3.67(3H,s),4.47(2H,s),4.56(1H,dd,J= 8.3, 5.9 Hz),4.67–4.72(1H,m),4.77(2H,s),7.40(1H,dd,J=8.3, 7.1 Hz), 7.46–7.49(2H,m),7.52–7.71(7H,m),7.77(1H,d,J= 7.3 Hz),7.82(1H, d,J=8.3 Hz),8.12(1H,d,J=8.3 Hz),8.22(1H, dd,J=8.3, 1 Hz),8.29(1H, d,J=8.5 Hz),8.66(1H,d,J=8.1 Hz), 8.70(1H,d,J=4.9 Hz),8.80(1H,d, J=8.1 Hz),9.75(2H,bs).

EXAMPLE 86

Preparation of N$^α$-(4-(N-2-picolylaminomethyl) naphthalene-1-carbonyl)-L-arginine-D-3-(1-naphthyl)alanine [Compound No. 101]

The compound obtained in Example 85-3 (0.0727 g) was suspended in methanol (0.5 ml) and THF (1 ml). After the addition of 1 mol/l aqueous solution of sodium hydroxide (0.08 ml), the mixture was stirred for 1 hour at room temperature. After the solvent was removed by distillation, the residue was dissolved in methanol. The solution was treated with Amberlite CG-50. The solvent was removed by distillation and the residue was dissolved in chloroform (0.7 ml). After the addition of trifluoroacetic acid (0.7 ml), the mixture was stirred for 10 hours, followed by removal of the solvent. 1 mol/l hydrochloric acid was added and the mixture was washed twice with dichloromethane. After the solvent was removed, the water layer was treated with Amberlite CG-50. The solvent was removed by distillation and the residue was purified by silica gel column chromatography (500 mg, chloroform/methanol/water=7/3/0.5) to obtain the title compound (0.0507 g) as a pale yellow solid.

MS(FAB,Pos.): m/z=646[M+1]$^+$ $^1$H-NMR(500 MHz, DMSO-d$_6$): δ=1.32–1.42(2H,m),1.43–1.49(1H,m), 1.59–1.65(1H,m),3.00–3.11(2H,m),3.29(1H,dd,J=14.2, 10.3 Hz), 3.67–3.72(1H,m),4.465(2H,s),4.56–4.67(2H,m),4.77 (2H,s),7.40(1H,dd,J=8.1,6.8 Hz),7.46–7.55(3H,m), 7.58–7.64(4H,m),7.68(1H, ddd,J=8.3, 6.8, 1.2 Hz), 7.75–7.82(3H,m),7.90–7.95(2H,m),8.16 (1H,d,J=8.3 Hz), 8.22(1H,dd,J=8.5,1.0 HZ), 8.28(1H,d,J=8.5 Hz),8.63(1H,d, J=8.3 Hz),8.67(1H,d,J=8.5 Hz),8.70(1H,d,J=4.9 Hz),9.85 (2H,bs).

EXAMPLE 87

Preparation of (2S)-2-(8-2-picolylaminomethylquinoline-5-carbonyl)amino-5-(5,6,7,8-tetrahydroquinolin-8-yl)aminovaleric acid (1'S)-1'-(1-naphthyl)ethylamide [Compound No. 102]

Example 87-1

Synthesis of 5-iodine-8-methylquinoline (Compound II-1)

Commercially available 8-methylquinoline (5.002 g) and silver sulfate (5.446 g) were dissolved in concentrated sulfuric acid (50 ml). After the addition of water (6 ml), the mixture was heated to 80° C. Iodine (9.753 g) was added in several portions and the mixture was stirred for 5 hours. After the addition of silver sulfate (0.5446 g), the mixture was stirred for 0.5 hour. Iodine (0.9753 g) was added and the mixture was stirred for a further one hour. The reaction solution was cooled to room temperature and diluted with water. Excessive iodine was removed by the addition of sodium sulfite. A solid was separated by filtration using a glass filter. The filtrate was made into strong alkaline with an aqueous solution of sodium hydroxide. Produced precipitate was removed using a glass filter. The water layer was extracted with chloroform and the extract was dried over anhydrous magnesium sulfate, followed by removal of the solvent. The residue was purified by silica gel column chromatography (210 g, 30% chloroform/35% benzene/35% hexane) to obtain the title compound (8.2066 g) as a pale yellow solid.

MS(FAB,Pos.): m/z=270[M+1]$^+$ $^1$H-NMR(500 MHz, CDCl$_3$): δ=2.78(3H,s),7.30(1H,d,J=7.6 Hz),7.48(1H,dd,J= 8.5, 4.2 Hz),8.01(1H,d,J=7.6 Hz),8.38(1H,dd,J=8.5,1.7 Hz), 8.91(1H,dd,J=4.2,1.7 Hz).

Example 87-2

Synthesis of 8-methylquinoline-5-carboxylic acid (Compound II-2)

The compound obtained in Example 87-1 (4 g) was dissolved in diethyl ether (100 ml) under nitrogen atmosphere. The solution was cooled to −55° C. A n-butyl lithium/15% hexane solution (21.16 ml) was added dropwise to the solution at a temperature of −50° C. or less. The mixture was stirred for 20 minutes. The reaction mixture was allowed to become room temperature. After the addition of water, low polar components were extracted with chloroform. 1 mol/l hydrochloric acid was added to the water layer to cause a solid to precipitate. The solid was collected by filtration, washed with dilute hydrochloric acid, and dried under vacuum to obtain the title compound (1.8869 g) as a white solid.

MS(FAB,Pos.): m/z=188[M+1]$^+$ $^1$H-NMR(500 MHz, CDCl$_3$): δ=2.78(3H,d,J=0.6 Hz),7.66(1H,dd,J=8.7, 4 Hz), 7.71(1H,dd,J=7.5, 0.6 Hz),8.18(1H,d, 7.5 Hz),8.99(1H,dd, J=4.1,1.8 Hz),9.34(1H,dd,J=8.7,1.8 Hz),13.24(1H,bs).

Example 87-3

Synthesis of Methyl 8-methylquinoline-5-carboxylate (Compound III-3)

The compound obtained in Example 87-2 (1 g) was dissolved in methanol (25 ml). The solution was stirred for 15 hours while blowing hydrochloric acid gas, and the solvent was removed by distillation. The obtained residue was dissolved in water and 1 mol/l sodium hydroxide aqueous solution was added to cause a solid substance to precipitate. The solid was collected by filtration and the filtrate was extracted with chloroform. The extract was dried over anhydrous sodium sulfate and the solvent was removed by distillation to obtain a solid. The solid was combined with the previously collected solid and purified by silica gel column chromatography (20 g, chloroform) to obtain the title compound (0.7337 g) as a white solid.

MS(FAB,Pos.): m/z=202[M+1]$^+$ $^1$H-NMR(500 MHz, CDCl$_3$): δ=2.87(3H,s),3.99(3H,s),7.52(1H,dd,J=8.8, 3.9 Hz),7.60(1H,d,J=7.6 Hz),8.20(1H,d,J=7.6 Hz),8.98(1H,dd, J=3.9,1.7 Hz),9.39(1H,dd,J=8.8,1.7 Hz).

Example 87-4

Synthesis of Methyl 8-(N-Boc-N-2-picolylamino) methylquinoline-5-carboxylate (Compound VI-11)

The compound obtained in Example 87-3 (0.726 g) was dissolved in carbontetrachloride (15 ml). N-bromosuccinimide (0.676 g) and azobisisobutylonitrile (0.059 g) were added to the solution. The mixture was stirred for 3 hours at 70° C. After the reaction, the solid was removed from the reaction solution by filtration. The filtrate was washed with 1 mol/l aqueous solution of sodium hydroxide and saturated brine, and dried over anhydrous sodium sulfate. The solvent was removed by distillation. The residue was dissolved in DMF (10 ml) and 2-picolylamine (1.173 g) and potassium carbonate-(0.51 g) were added. The mixture was stirred for 17 hours at room temperature. After the reaction, the solvent was removed by distillation. The residue was dissolved in chloroform. The solution was washed with water, and dried over anhydrous magnesium sulfate. After the solvent was removed, the residue was dissolved in DMF (10 ml). Triethylamine (1.098 g) and di-t-butyldicarbonate (2.49 ml) were added and the mixture was stirred for one hour at room temperature. After the reaction, the solvent was removed by distillation. The residue was dissolved in chloroform. The solution was washed with saturated aqueous solution of sodium hydrogencarbonate, and dried over anhydrous magnesium sulfate. The solvent was removed by distillation and the residue was purified by silica gel column chromatography (60 g, ethyl acetate/hexane=2/3) to obtain the title compound (0.7372 g) as a light red solid.

MS(FAB,Pos.): m/z=408[M+1]$^+$ $^1$H-NMR(500 MHz, CDCl$_3$): δ=1.40 and 1.43(9H,2s),4.00 and 4.01(3H, 2s),4.70 and 4.77(2H,s),5.22 and 5.31(2H, 2s),7.15(1H,t,J=6.1 Hz), 7.24 and 7.36(1H,d,J=7.8 Hz),7.47–7.54(2H,m),7.60 and 7.73(1H,d, J=7.6 Hz),7.65 and 7.66(1H,t,J=7.6 Hz),8.29 and 8.50(1H,d,J=4.2 Hz),8.88(1H,d,J=3.9 Hz),9.35 and 9.38 (1H,d,J=8.5 Hz).

Example 87-5

Synthesis of 8-(N-Boc-N-2-picolylaminomethyl) quinoline-5-carboxylic acid (Compound VII-15)

The compound obtained in Example 87-5 (0.7308 g) was dissolved in THF (7 ml) and methanol (7 ml). After the addition of 1 mol/l aqueous solution of sodium hydroxide (7 ml), the mixture was stirred for 19 hours at room temperature. After the reaction, the solvent was removed by distillation. The residue was dissolved in distilled water and acidified with hydrochloric acid to precipitate a solid. The solid was collected by filtration and dried under reduced pressure to obtain the title compound (0.619 g) as a pale pink solid.

MS(FAB,Pos.): m/z=394[M+1]$^+$ $^1$H-NMR(500 MHz, CDCl$_3$): δ=1.43 and 1.53(9H,2s),4.80 and 4.91(2H, s),5.14 and 5.25(2H,2s),7.22–7.36(2H,m),7.47 and 7.49(1H,d,J=6.3 Hz),7.56 and 7.61 (1H,d,J=7.8 Hz),7.83 and 7.85(1H,t,J=7.8 Hz), 8.06 and 8.08(1H,d,J=7.6 Hz), 8.58(1H,d,J=4.6 Hz), 8.67(1H,d, J=3.9 Hz),9.02 and 9.10(1H,d,J=8.1 Hz).

Example 87-6

Synthesis of N$^α$-(8-(N-Boc-N-2-picolylaminomethyl)quinoline-5-carbonyl)-N$^δ$-Boc-L-ornithine(1'S)-1'-(1-naphthyl)ethylamide (Compound XI-17)

The compound obtained in Example 68-1 was dissolved in DMF (10 ml). After the addition of diethylamine (1 ml), the mixture was stirred for 3.5 hours at room temperature. After the reaction, the solvent was removed by distillation. The residue was dissolved in DMF (10 ml). After the addition of WSCI hydrochloride (0.237 g), HOBt (0.166 g), and the compound obtained in Example 87-5 (0.356 g), the mixture was stirred for 19 hours at room temperature. After the reaction, the solvent was removed by distillation. The residue was dissolved in chloroform. The solution was washed with saturated aqueous solution of sodium hydrogencarbonate and saturated brine, and dried over anhydrous magnesium sulfate. The solvent was removed by distillation and the residue was purified by silica gel column chromatography (45 g, chloroform/methanol 30/1) to obtain the title compound (0.660 g) as a pale pink solid.

MS(FAB,Pos.): m/z=761[M+1]$^+$

Example 87-7

Synthesis of (2S)-2-(8-2-picolylaminomethylquinoline-5-carbonyl)amino-5-(5,6,7,8-tetrahydroquinolin-8-yl)aminovaleric acid (1'S)-1'-(1-naphthyl)ethylamide [Compound No. 102]

The compound obtained in Example 87-6 (0.651 g) was dissolved in methanol (13 ml), and 4 mol/l hydrochloric acid/dioxane solution (13 ml) was added. The mixture was stirred for 2 hours at room temperature. After the reaction, the solvent was removed by distillation. The residue was dissolved again in methanol and neutralized with Amberlite IRA-410. The solvent was removed by distillation and the residue was dissolved in methanol. After the addition of 5,6,7,8-tetrahydroquinolin-8-one (0.151 g), sodium cyanoborohydride (0.108 g), and acetic acid (10 drops), the mixture was stirred for 16 hours at room temperature. After the reaction, the solvent was removed by distillation. The residue was purified by silica gel column chromatography (chloroform/methanol/water=7/3/0.5) and treated with hydrochloric acid to obtain hydrochloride of the title compound (0.1512 g) as a pale yellow solid.

MS(FAB,Pos.): m/z=692[M+1]$^+$ $^1$H-NMR(500 MHz, DMSO-d$_6$): δ=1.55(3H,d,J=7.1 Hz),1.64–2.05(7H,m), 2.28–2.36(1H,m),2.76–2.84(2H,m),2.90–3.04(1H,m), 4.36–4.50(1H,m),4.43(2H,s),4.60–4.70(1H,m),4.86(2H,s), 5.77(1H,quint, J=7.1 Hz),7.37–7.40(1H,m),7.46–7.63(6H, m),7.68–7.73(2H,m), 7.92–7.97(2H,m),8.03(1H,d,J=7.6 Hz),8.14(1H,d,J=8.5 Hz),8.47(1H,d,J=4.4 Hz),8.66(1H,d,J= 4.9 Hz),8.77(1H,dt,J=8.5,1.5 Hz),8.89–8.94(2H,m),9.04 (1H,dd,J=4.2,1.5 Hz).

EXAMPLE 88

Preparation of N$^α$-(4-((imidazol-2-ylmethyl)amino) methyl)naphthalene-1-carbonyl)L-arginine N-methyl-1-naphthylmethylamide [Compound No. 103]

Example 88-1

Synthesis of N$^α$-Fmoc-N$^G$-Pmc-L-arginine N-methyl-1-naphthylmethylamide (Compound XXVII-11)

Commercially available N$^α$-Fmoc-N$^G$-Pmc-arginine (1.0 g) was dissolved in DMF (20 ml), and WSCI hydrochloride (0.43 g), HOBt (0.31 g), and N-methyl-1-naphthylmethylamine (0.34 g) were added to the solution. The mixture was stirred for one day at room temperature. After the reaction, the solvent was removed by distillation. 1 mol/l hydrochloric acid was added to the residue. Insoluble substances were separated by filtration using a glass filter. The obtained solid was washed sequentially with 1 mol/l aqueous solution of sodium hydroxide and water to obtain the target compound (1.03 g) as a white solid.

MS(FAB,Pos.): m/z=816[M+1]$^+$ $^1$H-NMR(500 MHz, CDCl$_3$): δ=1.22 and 1.23(2s,6H), 1.41–1.79(6H,m), 2.00 and 2.01(2s,3H), 2.45 and 2.46(2s,6H), 2.50–2.60(2H,m), 2.95–3.10(4H,m),3.32(3H,s), 4.03–20(3H,m), 7.24–8.06 (15H, m).

Example 88-2

Synthesis of N$^α$-(4-((N-Boc-N-(imidazol-2-ylmethyl)aminomethyl)naphthalene-1-carbonyl)-N$^G$-Pmc-L-arginine N-methyl-1-naphthylmethylamide (Compound XXIX-19)

The compound obtained in Example 88-1 (428 mg) was dissolved in DMF (8.5 ml) and diethylamine (0.85 ml) was added. After the react-ion for one hour, the reaction solution was concentrated. The residue was dissolved in DMF (6.2 ml), and the compound obtained in Example 17-4 (200 mg), WSCI (151 mg), and DMAP (96 mg) were added. After the reaction for 15.5 hours at room temperature, the reaction solution was concentrated. 1 mol/l hydrochloric acid was added to the residue and the mixture was extracted with chloroform. The organic layer was washed with saturated brine, dried over anhydrous sodium sulfate, and concentrated. The residue was purified by silica gel column chromatography (15 g, chloroform/methanol=10/1) to obtain the title compound (530 mg) as a colorless viscous liquid.

MS(FAB,Pos.): m/z=957[M+1]$^+$

Example 88-3

Synthesis of N$^α$-(4-((imidazol-2-ylmethyl)amino) methyl)naphthalene-1-carbonyl)L-arginine N-methyl-1-naphthylmethylamide [Compound No. 103]

The compound obtained in Example 88-2 (530 mg) was dissolved in chloroform (5.3 ml) and trifluoroacetic acid (5.3 ml) was added. After the reaction for 15.5 hours, the reaction solution was concentrated and azeotropically distilled with chloroform. The residue was purified by silica gel column chromatography (15 g, chloroform/methanol/water=7/3/0.5) and treated with hydrochloric acid to obtain hydrochloride of the title compound (108 mg) as a white solid.

MS(FAB,Pos.): m/z=687[M+1]$^+$ $^1$H-NMR(500 MHz, DMSO-d$_6$): δ=1.50–1.90(4H,m),3.14(3H,s),3.10–3.25(2H, m),4.94–5.50(6H,m),7.20–8.20(16H,m),8.29–8.33(1H, m),8.92–9.00(1H,m).

EXAMPLE 89

Preparation of (2S)-2-(4-(2-pyridyl) aminomethylnaphthalene-1-carbonyl)amino-5-(5,6, 7,8-tetrahydroquinolin-8-yl)aminovaleric acid 1-naphthylmethylamide [Compound No. 104]

Example 89-1

Synthesis of 4-(2-pyridyl)aminomethylnaphthalene-1-carboxylic acid (Compound VII-16)

The compound obtained in Example 17-2 (1.6728 g) was dissolved in DMF (33 ml). After the addition of potassium carbonate (1.66 g) and 2-aminopyridine (0.68 g), the mixture was stirred for 15 hours at room temperature. After the reaction, the solvent was removed by distillation and the residue was dissolved in chloroform. The organic layer was washed with 1 mol/l aqueous solution of hydrochloric acid and saturated brine, and dried over anhydrous sodium sulfate. Then, the solvent was removed by distillation. The residue was dissolved in DMF (44 ml). Triethylamine. (1.58 ml) and di-t-butyldicarbonate (2.60 ml) were added and the mixture was stirred for 6 hours at room temperature. After the reaction, the solvent was removed by distillation. The residue was dissolved in ethyl acetate. The solution was washed with 0.5 mol/l aqueous solution of hydrochloric acid and saturated brine, and dried over anhydrous sodium sulfate. The solvent was removed by distillation. The residue was dissolved in methanol (6 ml), and 1 mol/l aqueous solution of sodium hydroxide (6 ml) was added. After the reaction for one day, the reaction solution was concentrated. The residue was dissolved again in methanol and neutralized with ion-exchange resin CG50. The resin was removed by filtration. The filtrate was concentrated. The residue was purified by silica gel column chromatography (15 g, chloroform/methanol=5/1) to obtain the title compound (159 mg) as a colorless viscous liquid.

MS(FAB,Pos.): m/z=379[M+1]$^+$

Example 89-2

Synthesis of (2S)-2-(4-(2-pyridyl) aminomethylnaphthalene-1-carbonyl)amino-5-(5,6, 7,8-tetrahydroquinolin-8-yl)aminovaleric acid 1-naphthylmethylamide [Compound No. 104]

The compound obtained in Example 23-1 (240 g) was dissolved in DMF (2.4 ml). After the addition of diethylamine (0.24 ml), the mixture was stirred for 2 hours at room temperature. After the reaction, the solvent was removed by distillation. The residue was dried under reduced pressure and dissolved in DMF (1.6 ml). The compound obtained in Example 89-1 (159 mg), WSCI hydrochloride (121 mg), and DMAP (77 mg) were added to the solution. The mixture was reacted for one day at room temperature. The reaction solution was concentrated. After the addition of 1 mol/l hydrochloric acid, the residue was extracted with chloroform. The organic layer was washed with saturated brine, dried over anhydrous sodium sulfate, and concentrated. The residue was purified by silica gel column chromatography (20 g, chloroform/methanol=0.20/1) to obtain a crude product. The crude product was dissolved in methanol (4.5 ml) and 4 mol/l hydrochloric acid/dioxane solution (4.5 ml) was added to the solution. After the reaction for one hour, the reaction solution was concentrated. The residue was dissolved in methanol (2.2 ml), and triethylamine (0.12 ml), 5,6,7,8-tetrahydroquinolin-8-one (40 mg), acetic acid (0.55 ml), and sodium cyanoborohydride (39 mg) were added. After the reaction for 3 days, the reaction solution was concentrated. The residue was purified by silica gel column chromatography (80 g, chloroform/methanol=20/1). The obtained compound was treated with hydrochloric acid to obtain hydrochloride of the title compound (20.7 mg) as a white solid.

MS(FAB,Pos.): m/z=663[M+1]$^+$ $^1$H-NMR(500 MHz, DMSO-d$_6$): δ=1.70–2.02(0.7H,m),2.28–2.34(1H,m), 2.76–2.83(2H,m),2.93–3.03(1H,m),3.04–3.16(1H,m), 4.57–4.64(1H,m),4.82(2H,t,J=5.5 Hz),5.15(2H,d,J=4.9 Hz), 6.93(1H,t,J=6.7 Hz),7.20(1H,d,J=8.8 Hz),7.38(1H,dd,J=4.7, 2.9 Hz),7.48(1H,dd, J=7.1, 8.1 Hz),7.52–7.70(8H,m),7.87 (1H,d,J=7.6 Hz),7.92–8.02 (3H,m),8.10(1H,d,J=6.8 Hz), 8.17(1H,d,J=8.3 Hz),9.13(2H,brs)

EXAMPLE 90

Preparation of (2S)-2-(4-(N-2-picolylaminomethyl) naphthalene-1-carbonyl)amino-5-((8S)-5,6,7,8-tetrahydroquinolin-8-yl)aminovaleric acid 1-naphthylmethylamide [Compound No. 105]

Example 90-1

Synthesis of (S)-8-amino-5,6,7,8-tetrahydroquinoline 5,6,7,8-tetrahydroquinolin-8-ol (16.586 g) was synthesized according to the method described in Journal of Medicinal Chemistry, vol. 20, No. 10, pp 1351–1354 (1977) and dissolved in benzene (160 ml). Phosphorus tribromide (31.7 ml) was added dropwise to the solution at 0° C. The reaction solution was stirred overnight and allowed to become room temperature. Aqueous solution of sodium hydroxide was added to the solution while cooling with ice to make pH of the mixture to 10. The mixture was extracted with chloroform. The organic layer was washed with saturated brine and dried over anhydrous sodium sulfate. The solvent was removed by distillation and the residue was dissolved in DMF (300 ml). Potassium phthalimide (14.5 g) was added to the solution and the mixture was stirred for 6.5 hours at room temperature. After the reaction, the solvent was removed by distillation and the residue was dissolved in chloroform. The resulting solution was washed with distilled water and saturated brine, and dried over anhydrous sodium sulfate. The solvent was removed by distillation. The residue was recrystallized from methanol to obtain a light brown solid (9.884 g). Part of the solid (2.98 g) was dissolved in methanol (29 ml). Hydrazine monohydrate (2.55 ml) was added and the mixture was stirred for 2 hours at room temperature. After the reaction, the solvent was removed by distillation. After the addition of water, the residue was extracted with chloroform. The organic layer was dried over anhydrous sodium sulfate. The solvent was removed by distillation. The residue was dissolved in methanol (8 ml). D-tartaric acid (1.58 g) was added to the solution. Then, chloroform (160 ml) was added to reprecipitate (RS)-8-amino-5,6,7,8-tetrahydroquinoline.D-tartrate as a white solid. Part of the white solid (1 g) was subjected to recrystallization from methanol three times to obtain the title compound (126.8 mg) as white needle-like crystals.

[α]25=+26.5°

Example 90-2

Synthesis of (2S)-2-(4-(N-Boc-N-2-picolylamino) methylnaphthalene-1-carbonyl)amino-5-((8S)-5,6,7, 8-tetrahydroquinolin-8-yl)aminovaleric acid 1-naphthylmethylamide (Compound XIII-16)

The compound obtained in Example 53-2 (34 mg) was dissolved in methanol (0.7 ml), and the compound obtained in Example 90-1 (24 mg), acetic acid (0.15 ml), and sodium cyanoborohydride (10 mg) were added to the solution. The mixture was stirred for 3 days at room temperature. After the reaction, the solvent was removed by distillation. The residue was purified by silica gel column chromatography (1.5 g, chloroform/methanol=10/1) to obtain the title compound (20 mg) as a pale yellow solid.

MS(FAB,Pos.): m/z=777[M+1]$^+$ $^1$H-NMR(500 MHz, CDCl$_3$): δ=1.45 and 1.49(9H,2s),1.70–2.12(6H,m), 2.14–2.25 (1H,m),2.33–2.43(1H,m),2.70–2.81(2H,m), 3.17–3.24(1H,m),3.46–3.53(1H,m),4.19–4.57(3H,m), 4.77–5.08(5H,m), 7.09–7.18(3H,m),7.38–7.63(10H,m),7.79 (1H,d,J=8.3 Hz),7.86(1H, d,J=8.3 Hz),7.99(1H,d,J=8.3 Hz), 8.08–8.19(2H,m),8.32(1H,brd, J=12.3 Hz),8.51(1H,s).

Example 90-3

Synthesis of (2S)-2-(4-(N-2-picolylaminomethyl) naphthalene-1-carbonyl)amino-5-((8S)-5,6,7,8-tetrahydroquinolin-8-yl)aminovaleric acid 1-naphthylmethylamide [Compound No. 105]

The compound obtained in Example 90-2 (14.2 mg) was dissolved in methanol (0.3 ml), and 4 mol/l hydrochloric acid/dioxane solution (0.3 ml) was added to the solution. After the reaction for 3.5 hours, the reaction solution was concentrated. The residue obtained was purified by silica gel column chromatography (0.5 g, chloroform/methanol/water=7/3/0.5) and treated with hydrochloric acid to obtain hydrochloride of the title compound (8.1 mg) as a white solid.

MS(FAB,Pos.): m/z=677[M+1]$^+$ $^1$H-NMR(500 MHz, DMSO-d$_6$): δ=1.60–1.95(6H,m),1.95–2.03(1H,m), 2.28–2.37(1H,m),2.81(2H,t,J=6.1 Hz),2.96–3.06(1H,m), 3.07–3.16(1H,m),4.60–4.67(1H,m),4.76–4.88(5H,m),7.39 (1H,dd,J=7.8,4.9 Hz),7.47–7.73(9H,m),7.81(1H,d,J=7.6 Hz),7.88(1H,d,J=8.1 Hz),7.93(1H,dt,J=1.8,5.9 Hz),7.95(1H, d,J=8.5 Hz),7.97(1H,d, J=9.5 Hz),8.11(1H,d,J=9.5 Hz), 8.26–8.33(3H,m),8.49(1H,d,J=3.7H), 8.71(1H,d,J=4.6 Hz), 8.74(1H,t,J=5.6 Hz),8.87(1H,d,J=7.8 Hz),9.14(2H,br),9.84 (2H,br).

EXAMPLE 91

Preparation of (2S)-2-(4-((N-imidazol-2-ylmethyl) aminomethyl)benzoylamino-5-(5,6,7,8-tetrahydroquinolin-8-yl)aminovaleric acid (1'S)-1'-(1-naphthyl)ethylamide [Compound No. 106]

Example 91-1

Synthesis of N$^α$-(4-(N-Boc-(N-imidazol-2-ylmethyl) amino)methyl)-N$^δ$-Boc-L-ornithine(1'S)-1'-(1-naphthyl)ethylamide (Compound XI-18)

The compound obtained in Example 68-1 (500 mg) was dissolved in DMF (10 ml). After the addition of diethylamine (1 ml), the mixture was stirred for 0.5 hour at room temperature. After the reaction, the solvent was removed by distillation to obtain a residue. The residue was dissolved again in DMF (15 ml). The compound obtained in Example 81-2 (312.4 mg), WSCI hydrochloride (246 mg), and HOBt (174 mg) were added to the solution, and the mixture was stirred for 15 hours at room temperature. After the reaction, the solvent was removed by distillation. The residue was dissolved in chloroform. The solusion was washed with saturated aqueous solution of sodium hydrogencarbonate and saturated brine, and dried over anhydrous sodium sulfate. The solvent was removed by distillation to obtain a residue and the residue was purified by silica gel column chromatography (15 g, ethyl acetate) to obtain the title compound (490.4 mg) as a colorless viscous liquid.

MS(FAB,Pos.): m/z=699[M+1]$^+$ $^1$H-NMR(500 MHz, CDCl$_3$): δ=1.32(9H,s),1.45(9H,s),1.40–1.72(6H, m),1.83–1.91(1H,m),2.95–3.06(1H,m),3.34–3.42(1H,m), 4.39(2H, s),4.49(2H,s),5.88–5.93(1H,m),7.23(1H,d,J=7.5 Hz),7.42–7.56 (4H,m),7.75–7.82(3H,m),7.87(1H,d,J=7.9 Hz),8.02(2H,s),8.08(1H,d,J=8.4 Hz).

Example 91-2

Synthesis of (2S)-2-(4-((N-imidazol-2-ylmethyl) aminomethyl)benzoylamino-5-(5,6,7,8-tetrahydroquinolin-8-yl)aminovaleric acid (1'S)-1'-(1-naphthyl)ethylamide [Compound No. 106]

The compound obtained in Example 91-1 (478 mg) was dissolved-in methanol (4.8 ml), and 4 mol/l hydrochloric acid/dioxane solution (4.8 ml) was added. The mixture was stirred for 2 hours at room temperature. The reaction solution was concentrated and neutralized with an ion-exchange resin. The residue was dissolved in methanol (10 ml). 5,6,7,8-tetrahydroquinolin-8-one (151 mg), acetic acid (2.5 ml), and sodium cyanoborohydride (129 mg) were added to the solution, and the mixture was stirred for 3 days at room temperature. After the solvent was removed by distillation, the residue was purified by silica gel column chromatography (chloroform/methanol=5/1) and treated with hydrochloric acid to obtain hydrochloride of the title compound (233.5 mg) as a pale yellow solid.

MS(FAB,Pos.): m/z=630[M+1]$^+$ $^1$H-NMR(500 MHz, DMSO-d$_6$): δ=1.51(3H,d,J=6.8 Hz),1.70–1.91(6H, m),1.91–2.01(1H,m),2.22–2.34(1H,m),2.76–2.84(2H,m), 2.88–3.00(1H,m),3.02–3.14(1H,m),4.35–4.45(1H,m),4.42 (2H,s),4.45–4.64(1H,m),4.59(2H,s),5.71(1H,quint.,J=6.8 Hz),7.35–7.40(1H, m),7.46–7.58(4H,m),7.67(1H,d,J=7.8 Hz),7.71(2H,d,J=8.3 Hz), 7.77(2H,s),7.82(1H,d,J=8.3 Hz), 7.94(1H,d,J=8.1 Hz),7.99(2H,d, J=8.3 Hz),8.10(1H,d,J=8.5 Hz),8.42–8.48(1H,m),8.62–8.67(1H,m), 8.83–8.92(1H,m), 9.12(2H,brs),10.70(2H,br).

EXAMPLE 92

Preparation of (2S)-2-(4-((N-1-methylimidazol-2-ylmethyl)aminomethyl)benzoylamino-5-(5,6,7,8-tetrahydroquinolin-8-yl)aminovaleric acid (1'S)-1'-(1-naphthyl)ethylamide [Compound No. 107]

Example 92-1

Synthesis of of N$^α$-(4-((N-1-methylimidazol-2-ylmethyl)aminomethyl)-N$^δ$-Boc-L-ornithine (1'S)-1'-(1-naphthyl)ethylamide (Compound XI-19)

The compound obtained in Example 68-1 (646.7 mg) was dissolved in DMF (12.9 ml). After the addition of diethylamine (1.29 ml), the mixture was stirred for 1 hour at room temperature. The reaction solution was concentrated under reduced pressure and dried under vacuum. The obtained crude compound was dissolved again in DMF (12.5 ml). The compound obtained in Example 81-2 (367.5 mg), WSCI hydrochloride (306.0 mg), and HOBt (215.7 mg) were added to the solution. The mixture was stirred for one day at room temperature. After the completion of the reaction, the reaction solution was concentrated under reduced pressure. Saturated aqueous solution of sodium bicarbonate was added to the residue and the mixture was extracted with chloroform. The extract was dried over anhydrous sodium sulfate, followed by concentration under reduced pressure. The residue was purified by silica gel column chromatography (30 g, chloroform/methanol=20/1) to obtain the title compound (758.6 mg) as a white solid.

MS(FAB,Pos.): m/z=713[M+1]$^+$ $^1$H-NMR(500 MHz, DMSO-d$_6$): δ=1.32(9H,s),1.45(9H,s),1.40–1.60(2H, m),1.66(3H,d,J=6.8 Hz),1.62–1.72(1H,m),1.82–1.91(1H, m),2.93–3.01(2H,m),3.61(3H,s),4.46(2H,s),4.49–4.65 (0.3H,m),4.91(1H,m), 5.91(1H,quint.,J=6.8 Hz),6.80(1H,s), 6.93(1H,s),7.18–7.29(4H, m),7.43–7.57(4H,m),7.69–7.76 (2H,m),7.78(1H,d,J=7.3 Hz),7.86(1H,d,J=8.1 Hz),8.08(1H, d,J=8.3 Hz).

Example 92-2

Synthesis of (2S)-2-(4-((N-1-methylimidazol-2-ylmethyl)aminomethyl)benzoylamino-5-(5,6,7,8-tetrahydroquinolin-8-yl)aminovaleric acid (1'S)-1'-(1-naphthyl)ethylamide [Compound No. 107]

The compound obtained in Example 92-1 (758.6 mg) was dissolved in methanol (15.2 ml) and 4 mol/l hydrochloric acid/dioxane solution (15.2 ml) was added. The mixture was stirred for one hour at room temperature. After the reaction, the reaction solution was concentrated under reduced pressure and the residue was dried under vacuum. The resulting crude product was dissolved again in methanol (16.4 ml). 5,6,7,8-tetrahydroquinolin-8-one (187.9 mg), sodium cyanoborohydride (133.7 mg), and triethylamine (0.445 ml) were added to the solution at room temperature. After adjusting the pH to 4–5 with the addition of acetic acid, the mixture was stirred for 3 days. After the reaction, the reaction solution was concentrated under reduced pressure. The residue was purified by silica gel column chromatography (20 g, chloroform/methanol/water=7/3/0.5) and treated with hydrochloric acid to obtain hydrochloride of the title compound (357.6 mg) as a white solid.

MS(FAB,Pos.): m/z=644[M+1]$^+$ $^1$H-NMR(500 MHz, DMSO-d$_6$): δ=1.51(3H,d,J=6.8 Hz),1.70–2.01(7H,m), 2.22–2.33(1H,m),2.75–2.82(2H,m),2.87–2.29(1H,m), 3.02–3.14(1H,m),3.98(3H,s),4.35–4.45(1H,m),4.42(2H,s), 4.53–4.68(1H, m),4.61(2H,s),5.71(1H,quint.,J=6.8 Hz), 7.35–7.40(1H,m),7.46–7.58(4H,m),7.67(1H,d,J=7.8 Hz), 7.73(2H,d,J=8.1 Hz),7.77(2H,s), 7.81(1H,d,J=8.1 Hz),7.94 (1H,dd,J=7.8,1.0 Hz),7.98(2H,d,J=8.3 Hz),8.11(1H,d,J=8.3 Hz),8.42–8.47(1H,m),8.67(1H,d,J=7.6 Hz), 8.88(1H,d,J= 5.6 Hz),9.20(2H,brs),10.29(1H,br),10.79(1H,br).

EXAMPLE 93

Preparation of (2S)-2-(4-(2-picolylaminomethyl) benzoyl-5-(imidazol-2-yl)aminovaleric acid (1'S)-1'-(1-naphthyl)ethylamide [Compound No. 108]

Example 93-1

Synthesis of N$^α$-(4-(N-Boc-N-2-picolylaminomethyl)benzoyl)-O-methyl-L-glutamic acid (1'S)-1'-(1-naphthyl)ethylamide (Compound XXXVII-2)

The compound obtained in Example 55-1 (3.0726 g) was dissolved in anhydrous methanol (30 ml) and 4 mol/l hydrochloric acid/dioxane solution (15 ml) was added. The mixture was stirred for 4 hours at room temperature. After the reaction, the solvent was removed by distillation under reduced pressure. The residue, the compound obtained in Example 1-2 (2.2554 g), and DMAP (1.1681 g) were dissolved in chloroform (30 ml). A solution of DCC (2.0902 g) in chloroform (10 ml) was slowly added to the solution, and the mixture was stirred for 16 hours at room temperature. After the precipitate was removed by filtration, the filtrate was made acidic with the addition of 1 mol/l hydrochloric acid and extracted with chloroform. The extract was washed with saturated aqueous solution of sodium hydrogencarbonate and saturated brine, and dried over anhydrous magnesium sulfate. After the solvent was removed by distillation under reduced pressure, the residue was purified by silica gel column chromatography (157.8 g, hexane/ethyl acetate=1/2) to obtain the title compound (3.4691 g) as a white solid.

MS(FAB,Pos.): m/z=639[M+1]$^+$ $^1$H-NMR(500 MHz, CDCl$_3$): δ=1.45(9H,brs),1.66(3H,d,J=6.8 Hz), 2.02–2.08 (1H,m) 2.10–2.18(1H,m),2.31–2.37(1H,m),2.55–2.60(1H, m),3.62(3H,s),4.49(2H,brs),4.60(2H,m),4.63–4.67(1H,m), 5.93(1H,quint,J=6.8 Hz),6.90(1H,d,J=8.3 Hz),7.17–7.19 (1H,m), 7.31(1H,d,J=7.3 Hz),7.35(1H,d,J=7.6 Hz), 7.46–7.56(4H,m),7.64–7.67(1H,dt,J=1.7, 6.0 Hz),7.76(2H, d,J=8.3 Hz),7.80(1H,d,J=8.3H z), 7.88(1H,d,J=8.1 Hz),8.09 (1H,d,J=8.6 Hz),8.53(1H,d,J=4.2 Hz).

Example 93-2

Synthesis of (2S)-2-(4-(N-Boc-N-2-picolylaminomethyl)benzoylamino)-5-hydroxyvaleric acid (1'S)-1'-(1-naphthyl)ethylamide (Compound XXXVIII-1)

The compound obtained in Example 93-1 (3.4477 g), sodium borohydride (821.4 mg), and calcium chloride (1.2154 g) were dissolved in a mixed solution of THF (30 ml) and ethanol (40 ml). The mixture was stirred for 2 hours at room temperature. After the reaction, 1 mol/l citric acid aqueous solution was added. The mixture was extracted with ethyl acetate. The extract was washed with saturated aqueous solution of sodium hydrogencarbonate and dried over anhydrous magnesium sulfate. The solvent was removed by distillation under reduced pressure and the residue was purified by silica gel column chromatography (170 g, ethyl acetate) to obtain the title compound (2.6203 g) as a white solid.

MS(FAB,Pos.): m/z=611[M+1]$^+$ $^1$H-NMR(500 MHz, CDCl$_3$): δ=1.45(9H,br),1.52–1.61(2H,m),1.65(3H, d,J=7.3 Hz),1.69–1.87(1H,m),1.88–1.95(1H,m),3.55–3.59(1H,m), 3.63–3.67(1H,m),4.49(2H,br),4.59(2H,br),4.78(1H,q,J=7.1 Hz), 5.93(1H,quint.,J=7.3 Hz),6.95(1H,d,J=8.1 Hz), 7.17–7.19(1H,m), 7.30(1H,d,J=7.8 Hz),7.34(1H,d,J=7.8 Hz),7.45–7.56(4H,m),7.66 (1H,dt,J=7.6,1.7 Hz),7.74–7.76 (2H,m),7.80(1H,d,J=8.1 Hz),7.88(1H,d,J=7.8 Hz),8.10(1H, d,J=8.5 Hz),8.53(1H,d,J=4.2 Hz).

Example 93-3

Synthesis of (2S)-2-(4-(N-Boc-N-2-picolylaminomethyl)benzoyl-5-(imidazol-2-yl) aminovaleric acid (1'S)-1'-(1-naphthyl)ethylamide (Compound XIII-17)

The compound obtained in Example 93-2 (0.700 g) was dissolved in chloroform (10 ml). After the addition of tetrabutylammonium chloride (31.9 mg), 2,2,6,6-tetramethyl-1-piperidyl oxide (17.9 mg), and N-chlorosuccinimide (195 mg), 0.5 mol/l aqueous solution of sodium hydrogencarbonate (10 ml) and 0.05 mol/l aqueous solution of potassium carbonate (10 ml) were added to the solution. The mixture was vigorously stirred for 5 hours at room temperature. After the reaction, the reaction solution was separated to a water layer and an organic layer. The water layer was extracted with chloroform. The extract was combined with the organic layer, washed with saturated brine, and dried over anhydrous sodium sulfate. The solvent was removed by distillation. The resulting residue was dissolved in methanol (14 ml). After the addition of 2-aminoimidazole 0.5 sulfate (0.17 g) and molecular sieve 3A, triethylamine was added to make pH of the reaction solution to 8. The mixture was stirred over night. Acetic acid was added to make pH of the mixture to 6–7. Then, sodium cyanoborohydride (0.22 g) was added and the mixture was stirred for 4 days. After removing insoluble components by filtration using a glass filter, the filtrate was concentrated under reduced pressure. The residue was purified by silica gel column chromatography (70 g, chloroform/methanol= 10/1) to obtain the title compound (0.15 g) as a white solid.

MS(FAB,Pos.): m/z=676[M+1]$^+$ $^1$H-NMR(500 MHz, DMSO-$d_6$): δ=1.31 and 1.38(9H,2s),1.51(3H,d,J=6.8 Hz), 1.69–1.78(2H, m),1.69–1.78(2H,m),3.15–3.30(2H,m),4.41 (1H,brs),4.50(2H, brs),4.55(2H,brs),5.71(1H,m),6.84(1H,s), 7.23(1H,m),7.28–7.36(4H,brs),7.45(1H,m),7.49–7.55(3H, m),7.76–7.82(2H,m), 7.93(1H,m),8.10(1H,m),8.32(1H,brs), 8.53(1H,brs),8.66(1H,brs).

Example 93-4

Synthesis of (2S)-2-(4-(2-picolylaminomethyl) benzoyl-5-(imidazol-2-yl)aminovaleric acid (1'S)-1'- (1-naphthyl)ethylamide [Compound No. 108]

The compound obtained in Example 93-3 (0.18 g, 0.27 mmol) was dissolved in methanol (4.0 ml). 4 mol/l hydrochloric acid/dioxane solution (4.0 ml) was added dropwise to the solution at room temperature, followed by stirring for 2 hours. The reaction solution was concentrated. The residue was purified by silica gel column chromatography (7 g, chloroform/methanol/water=7/3/0.5) and treated with 1 mol/l aqueous solution of hydrochloric acid to obtain hydrochloride of the title compound (0.09 g) as pale yellow foam.

MS(FAB,Pos.): m/z=576[M+1]$^+$ $^1$H-NMR(500 MHz, DMSO-$d_6$): δ=1.51(3H,d,m,J=6.8 Hz),1.61(1H,m), 1.75–1.82(2H,m),3.24(2H, d), 4.30(4H,brs),4.57(2H,m), 5.71(1H, m),6.93(2H,s),7.46(2H,m),7.49–7.59(4H,brs),7.65 (2H,d,J=8.5 Hz),7.80(1H,d,J=8.1 Hz),7.90–7.94(2H,m)8.00 (2H,d,J=8.3 Hz), 8.10(2H,m,J=8.3 Hz),8.61(1H,d,J=7.8 Hz),8.66(1H,m),8.86(2H,d, J=7.7 Hz),9.91(2H,brs).

EXAMPLE 94

Preparation of (2S)-2-(4-2-picolylaminomethyl) benzoyl-5-(pyridin-2-yl)aminovaleric acid (1'S)-1'- (1-naphthyl)ethylamide [Compound No. 109]

Example 94-1

Synthesis of (2S)-2-(4-(N-Boc-N-2- picolylaminomethyl)benzoyl-5-(pyridin-2-yl) aminovaleric acid (1'S)-1'-(1-naphthyl)ethylamide (Compound XIII-18)

The compound obtained in Example 93-2 (180 mg) was dissolved in chloroform (4 ml). Tetrabutylammonium chloride (8.2 mg), 2,2,6,6-tetramethyl-1-piperidyl oxide. (4.6 mg), and N-chlorosuccinimide (51 mg) were added to the solution, and further, 0.5 mol/l aqueous solution of sodium hydrogencarbonate (4 ml) and 0.05 mol/l aqueous solution of potassium carbonate (4 ml) were added. The mixture was vigorously stirred for 5 hours at room temperature. After the reaction, the reaction solution was separated to a water layer and an organic layer. The water layer was extracted with chloroform. The extract was combined with the organic layer, washed with saturated brine, and dried over anhydrous sodium sulfate. The solvent was removed by distillation. The residue was dissolved in methanol (4 ml). 2-aminopyridine (0.03 g) was added, followed by the addition of triethylamine to make pH of the reaction solution to 9. After the solution was stirred overnight, the pH of the solution was adjusted to 4 with acetic acid. Then, sodium cyanoborohydride (0.05 g) was added and the mixture was stirred overnight at room temperature. The reaction solution was concentrated under reduced pressure. The residue was purified by silica gel column chromatography (15 g, chloroform/ methanol=20/1) to obtain the title compound (0.04 g) as a white solid.

MS(FAB,Pos.): m/z=687[M+1]$^+$ $^1$H-NMR(500 MHz, DMSO-$d_6$): δ=1.31, 1.38(9H,2s),1.51(3H,d,J=6.8 Hz),1.56 (2H,1.75(2H,m),3.18(2H,m),4.40(1H,brs),4.48(2H,brs), 4.56(2H,brs),5.69(1H,m),6.42(1H,s),6.51(1H,m),7.23(1H, m), 7.26–7.35(4H,m),7.46(1H,m),7.54(3H,m),7.91(2H,m), 8.09(1H, d,J=7.5 Hz),8.39(1H,d,J=7.5 Hz),8.51(2H,brs), 8.65(1H,brs).

Example 94-2

Synthesis of (2S)-2-(4-2-picolylaminomethyl) benzoyl-5-(pyridin-2-yl)aminovaleric acid (1'S)-1'- (1-naphthyl)ethylamide [Compound No. 109]

The compound obtained in Example (0.03 g) was dissolved in methanol (0.5 ml), and 4 mol/l hydrochloric acid/dioxane solution (0.5 ml) was added dropwise. The mixture was stirred for 2 hours at room temperature. The reaction solution was concentrated. The residue was purified by silica gel column chromatography (7 g, chloroform/ methanol=5/1) and treated with 1 mol/l aqueous solution of hydrochloric acid to obtain of hydrochloride of the title compound (0.03 g) as pale yellow foam.

MS(FAB,Pos.): m/z=576[M+1]$^+$ $^1$H-NMR(500 MHz, DMSO-$d_6$): δ=1.51(3H,d,J=6.8 Hz) 1.56(1H,m), 1.61(1H, m),1.67–1.85(2H,m),4.30(4H,brs),4.60(1H,m),5.70(1H, m),6.84(1H,s),7.05(1H,brs),7.46(2H,brs),7.50–7.68(5H,m), 7.80(2H,d,J=8.3 Hz),7.91(5H,m),8.10(1H,d,J=8.5 Hz),8.60 (1H,d, J=7.1 Hz),8.66(1H,d,J=7.5 Hz),8.82(1H,brs).

EXAMPLE 95

Preparation of (S)-2-(4-((N-imidazol-2-ylmethyl) aminomethyl)benzoyl)amino-5-(4,5- dihydroimidazol-2-yl)aminovaleric acid (1'S)-1'-(1- naphthyl)ethylamide [Compound No. 110]

Example 95-1

Synthesis of (S)-5-phthalimide-2-Boc-aminovaleric acid (compound VIII-1)

Commercially available ornithine hydrochloride (13.35 g) was dissolved in water (135 ml) and basic copper (II) carbonate (10.4 g) was gradually added while stirring with heating in an oil bath at 100° C. After stirring for 10 minutes with heating, the reaction suspension was filtered.

The filtrate was diluted with water to make the total amount 270 ml. After the addition of sodium carbonate (13.2 g) and carboethoxy phthalimide (19.1 g), the mixture was stirred for 2 hours at room temperature. The reaction suspension was allowed to stand overnight while cooling at 2° C. The resulting light blue precipitate was collected by filtration and dried under reduced pressure. A mixed solution of. 4 mol/l hydrochloric acid (80 ml) and methanol (80 ml) was added to dissolve the precipitate. After washing with ether, the water layer was allowed to stand over night while cooling at 2° C. The resulting white precipitate was collected by filtration and dried under reduced pressure.

The precipitate was dissolved in DMF (100 ml), and triethylamine (23.7 ml) and di-t-butyldicarbonate (18.8 ml) were added. After the reaction overnight at room temperature, the reaction solution was concentrated. The residue was diluted with chloroform. The resulting solution was washed twice with saturated brine, and dried over anhydrous sodium sulfate. The solvent was removed by distillation. The, residue was purified by silica gel column chromatography (200 g, chloroform/methanol=10/1) to obtain the title compound (26.93 g) as a colorless viscous liquid.

MS(FAB,Pos.): m/z=363[M+1]$^+$

Example 95-2

Synthesis of (S)-5-phthalimide-2-Boc-aminovaleric acid (1'S)-1-(1-naphthyl)ethylamide (compound IX-5)

The compound obtained in Example 95-1 (19.4 g) was dissolved in DMF (194 ml). (S)-1-(1-naphthyl)ethylamine (9.17 g), WSCI hydrochloride (15.4 g), and HOBt (10.9 g) were added to the solution. After the reaction over a whole day and night, the reaction solution was concentrated. The residue was diluted with chloroform. To the solution was added saturated aqueous solution of sodium carbonate and the mixture was extracted with chloroform. The organic layer was washed with saturated brine, dried over anhydrous sodium sulfate, and concentrated. The residue was recrystallezed from ethyl acetate to obtain the title compound (20.96 g).

MS(FAB,Pos.): m/z=516[M+1]$^+$ $^1$H-NMR(500 MHz, CDCl$_3$): δ=1.44(9H,s),1.50–1.70(4H,m),1.71(3H, d,J=6 Hz),3.66–3.71(1H,m),3.81–3.90(1H,m),4.37–4.43(1H,m), 5.29(1H,d,J=8.3 Hz),5.85(1H, dq,J=6.8, 7.1 Hz),7.32(1H,t, J=7.1 Hz), 7.41(2H,t,J=7.3 Hz),7.52(1H,d,J=7.3 Hz), 7.56–7.62(2H,m), 7.63–7.70(2H,m),7.71(1H,d,J=7.8 Hz), 7.74(1H,d,J=8.3 Hz)7.96 (1H,d,J=8.5 Hz).

Example 95-3

Synthesis of (S)-2-(4-((N-Boc-N-imidazol-2-ylmethyl)aminomethyl)benzoyl)amino-5-phthalimide valeric acid (1'S)-1'-(1-naphthyl) ethylamide (Compound XI-20)

The compound obtained in Example 95-2 (19.3 g) was dissolved in methanol (100 ml), and to the solution were added dioxane (100 ml) and concentrated hydrochloric acid (20 ml). The mixture was stirred for 4 hours at 45° C. After the reaction, the solvent was removed by distillation and the residue was dissolved in DMF (200 ml). The compound obtained in Example 79-1 (13.64 g), WSCI hydrochloride (18.8 g), DMAP (9.40 g), and HOBt (7.60 g) were added to the solution. The mixture was stirred for 24 hours at room temperature. After the reaction, the solvent was removed by distillation. Chloroform was added to the residue, and the solution was washed with saturated aqueous solution of sodium hydrogencarbonate and saturated brine, and dried over anhydrous sodium sulfate. The solvent was removed by distillation and the residue was purified by silica gel column chromatography (chloroform/methanol=20/1) to obtain the title compound (26.24 g) as a white solid.

MS(FAB,Pos.): m/z=729[M+1]$^+$ $^1$H-NMR(500 MHz, CDCl$_3$): δ=1.50–1.82(16H,m),3.69–3.74(1H,m), 3.93–4.02 (1H,m)4.01(2H,s),4.50(2H s),5.00–5.07(1H,m),5.83–5.90 (1H,m),6.94(1H,d,J=8.3 Hz),6.98(2H,s),7.12(1H,d,J=8.3 Hz), 7.24(1H,d,J=8.5 Hz),7.37–7.43(2H,m),7.52–7.58(3H, m),7.64–7.69(2H,m),7.7.2(1H,d,J=8.1 Hz),7.75(1H,d,J=8.3 Hz),7.79(2H,d, J=8.3 Hz),7.98(1H,d,J=8.3 Hz),8.02(1H,s).

Example 95-4

Synthesis of (S)-2-(4-((N-Boc-N-imidazol-2-ylmethyl)aminomethyl)benzoyl)amino-5-aminovaleric acid (1'S)-1'-(1-naphthyl)ethylamide (Compound XII-3)

The compound obtained in Example 95-3 (26.13 g) was dissolved in 40% methylamine-methanol solution. The solution was stirred for 24 hours at room temperature. After the reaction, the reaction solution was concentrated under reduced pressure. The residue was dissolved in chloroform. The resulting solution was washed with distilled water and saturated brine, and dried over anhydrous sodium sulfate. The solvent was removed by distillation. The residue was purified by silica gel column chromatography (chloroform/methanol/water=7/3/0.5) to obtain the title compound (12.6 g) as a white solid.

MS(FAB,Pos.): m/z=599[M+1]$^+$ $^1$H-NMR(500 MHz, DMSO-d$_6$): δ=1.40(9H,brs),1.30–1.45(2H,m),1.51 (3H,s,J= 6.8 Hz),1.62–1.78(2H,m),2.45–2.55(2H,m),4.33(2H, brs), 4.43(2H,s),4.40–4.52(1H,m),5.71(1H,quint.,J=6.8 Hz), 6.84 (1H,s),7.05(1H,s),7.20–7.32(2H,m),7.47–7.57(4H,m) 7.82 (1H,d,J=8.1 Hz),7.84(2H,d,J=8.1 Hz),7.94(1H,d,J=7.6 Hz), 8.10(1H,d,J=8.1 Hz),8.48(1H,d,J=7.8 Hz),8.64(1H,d,J=7.8 Hz),11.8–12.0(1H,br)

Example 95-5

Synthesis of (S)-2-(4-((N-imidazol-2-ylmethyl) aminomethyl)benzoyl)amino-5-(4,5-dihydroimidazol-2-yl)aminovaleric acid (1'S)-1'-(1-naphthyl)ethylamide [Compound No. 110]

The compound obtained in Example 95-4 (212.1 mg), 2-(3,5-dimethylpyrazolyl)-4,5-dihydroimidazole hydrobromide (91.1 mg), and diisopropylamine (0.061 ml) were dissolved in DMF (1 ml). The solution was stirred for 24 hours at 80° C. After the reaction, the solvent was removed by distillation under reduced pressure. After the addition of water, the residue was extracted with chloroform. The resulting solution was dried over anhydrous magnesium sulfate and the solvent was removed by distillation under reduced pressure. The residue was purified by silica gel column chromatography (10 g, chloroform/methanol/water= 7/3/0.5). The compound obtained was dissolved in methanol and 4 mol/l hydrochloric acid/dioxane (0.13 ml) was added, followed by stirring for 7 hours at room temperature. After the reaction, the solvent was removed by distillation under reduced pressure to obtain the title compound (6.7 mg) as a white solid.

MS(FAB,Pos.): m/z=577[M+1]$^+$ $^1$H-NMR(500 MHz, DMSO-d$_6$): δ=1.47–1.56(2H,m),1.52(3H,d,J=6.8 Hz), 1.68–1.76(2H,m),3.11(2H,dd,J=7.1, 12.7 Hz),4.26(4H,br), 4.56(1H,dd,J=8.1, 13.9 Hz),5.71(1H,dd, J=6.8, 14.4 Hz), 7.50–7.57(6H,m),7.62(2H,d,J=8.1 Hz),7.84(1H, d,J=7.3

Hz),7.94–7.97(3H,m),8.11(1H,d,J=7.3 Hz),8.30–8.32(1H, m),8.55(1H,d,J=8.8), 8.78(1H,d,J=7.6 Hz).

EXAMPLE 96

Preparation of (S)-2-(4-((N-imidazol-2-ylmethyl) aminomethyl)benzoyl)amino-5-(pyrimidin-2-yl) aminovaleric acid (1'S)-1'-(1-naphthyl)ethylamide [Compound No. 111]

The compound obtained in Example 95-4 (202.7 mg), 2-bromopyrimidine (57.0 mg), and diisopropylamine (0.061 ml) were dissolved in DMF (2.4 ml). The solution was stirred for 45 hours at 80° C. After the reaction, the solvent was removed by distillation under reduced pressure. The residue was dissolved in chloroform. The solution was washed with saturated brine, and dried over anhydrous magnesium sulfate. The solvent was removed by distillation under reduced pressure and the residue was purified by silica gel column chromatography (18' g, chloroform/methanol= 9/1). The compound obtained was dissolved in methanol (1.2 ml) and 4 mol/l hydrochloric acid/dioxane (1.2 ml) was added, followed by stirring for 7 hours at room temperature. After the reaction, the solvent was removed by distillation under reduced pressure to obtain the title compound as reddish brown crystals.

MS(FAB,Pos.): m/z=577[M+1]$^+$ $^1$H-NMR(500 MHz, DMSO-d$_6$): δ=1.51(3H,d,J=6.8 Hz),1.53–1.62(2H,m) 1.71–1.79(2H,m),4.38(2H,brs),4.51(2H,brs),4.54–4.59(1H, m), 5.67–5.72(1H,quint.,J=6.8 Hz),6.69(1H,t,J=4.9 Hz), 7.46(1H,d, J=8.1 Hz),7.49–7.55(3H,m),7.67(2H,d,J=8.3 Hz),7.71(2H,s),7.81(1H,d,J=8.1 Hz),7.92–7.96(1H,m),7.96 (2H,d,J=8.5 Hz),8.09(1H, dd,J=2.2, 8.2 Hz),8.36(2H,d,J= 5.1 Hz),8.54(1H,d,J=8.1 Hz),8.74(1H,d,J=7.8 Hz).

EXAMPLE 97

Preparation of (S)-2-(4-((N-imidazol-2-ylmethyl) aminomethyl)benzoyl)amino-5-(3,4,5,6-tetrahydropyrimidine-2-yl)aminovaleric acid (1'S)-1'-(1-naphthyl)ethylamide [Compound No. 112]

The compound obtained in Example 96 (97.3 mg) was dissolved in acetic acid (8 ml) and concentrated hydrochloric acid (0.9 ml) was added. An acetic acid solution (7 ml) of 10% palladium-on-carbon (67.2 mg) was added and reacted for 2 hours under a hydrogen pressure of 2.9 kg/cm$^2$. The catalyst was removed and the solvent was removed by distillation under reduced pressure, followed by azeotropic distillation with toluene. The residue was purified by silica gel column chromatography (3 g, chloroform/methanol/ water=7/3/0.5) to obtain hydrochloride of the title compound (82.7 mg) as a white solid.

MS(FAB,Pos.): m/z=581[M+1]$^+$ $^1$H-NMR(500 MHz, DMSO-d$_6$): δ=1.42–1.60(2H,m),1.52(3H,d,J=6.8 Hz), 1.68–1.85(4H,m),3.01–3.11(2H,m),3.18–3.25(4H,m),4.32 (2H,s), 4.41(2H,s),4.52–4.58(1H,m),5.72(1H,quint.,J=6.8 Hz),7.46–7.60(6H,m),7.65(2H,d,J=8.3 Hz),7.76(1H,brs), 7.82(1H,d,J=8.1 Hz), 7.95(1H,d,J=7.3 Hz),7.98(2H,d,J=8.3 Hz),8.10(1H,d,J=8.1 Hz), 8.58(1H,d,J=8.1 Hz),8.80(1H,d, J=7.8 Hz).

EXAMPLE 98

Preparation of (S)-2-(4-(N-2-picolylaminomethyl) benzoyl)amino-5-(4,5-dihydroimidazol-2-yl) aminovaleric acid (1'S)-1'-(1-naphthyl)ethylamide [Compound No. 113]

Synthesis of (S)-2-(4-(N-Boc-N-2-picolylaminomethyl)benzoyl)amino-5-aminovaleric acid (1'S)-1'-(1-naphthyl)ethylamide (Compound XII-4).

The compound obtained in Example 95-1 (9.2827 g) was dissolved in DMF (93 ml). (1S)-1-(1-naphthyl)ethylamine (4.940 g), WSCI hydrochloride (7.4057 g), and HOBt (5.336 g) were added to the solution. The mixture was stirred for 16 hours at room temperature. After the reaction, the solvent was removed by distillation under reduced pressure. Saturated aqueous solution of sodium hydrogencarbonate and chloroform were added to the residue. The water layer separated was extracted with chloroform. The extract was combined with the organic layer, washed with saturated brine, and dried over magnesium sulfate. The solvent was removed by distillation under reduced pressure. The residue was dissolved in dioxane (80 ml). Methanol (80 ml) and concentrated hydrochloric acid (8 ml) were added to the solution, and the mixture was stirred for 2 hours at 45° C. The solvent was removed by distillation under reduced pressure. The residue was suspended in chloroform. The suspension was washed with 1 mol/l aqueous solution of sodium hydroxide, and dried over magnesium sulfate. The solvent was removed by distillation under reduced pressure and the residue was dissolved in DMF (110 ml). The compound obtained in Example 1-2 (9.6129 g), WSCI hydrochloride (7.4937 g), and HOBt (5.2943 g) were added to the solution, and the mixture was stirred for 16 hours at room temperature. After the reaction, the solvent was removed by distillation under reduced pressure. Saturated aqueous solution of sodium hydrogencarbonate and chloroform were added to the residue. The water layer separated was extracted with chloroform. The extract was combined with the organic layer., washed with saturated brine, and dried over magnesium sulfate. The solvent was removed by distillation under reduced pressure and the residue was purified by silica gel column chromatography (294 g, chloroform/ethyl acetate=2/1). 40% methylamine-methanol solution (100 ml) was added to the resulting compound, and the mixture was stirred for 40 hours at room temperature. After the reaction, the solvent was removed by distillation under reduced pressure. The residue was purified by silica gel column chromatography (572 g, chloroform/methanol/ water=7/3/0.5) to obtain the title compound (6.8058 g) as a white solid.

MS(FAB,Pos.): m/z=610[M+1]$^+$ $^1$H-NMR(500 MHz, CDCl$_3$): δ=1.34–1.42(2H,m),1.35(9H,br),1.51(3H, d,J=7.1 Hz),1.65–1.73(2H,m),3.16–3.44(2H,m),4.40(1H,brs), 4.49–4.56(4H,m),5.68–5.72(1H,quint.,J=7.1 Hz),7.20–7.34 (4H, m),7.42–7.57(4H,m),7.76–7.80(1H,m),7.82(1H,d,J= 7.8 Hz),7.86 (2H,d,J=8.3 Hz),7.94(1H,d,J=7.6 Hz),8.10(1H, d,J=8.1 Hz),8.52(1H,d,J=4.9 Hz).

Example 98-2

Synthesis of (S)-2-(4-(N-2-picolylaminomethyl) benzoyl)amino-5-(4,5-dihydroimidazol-2-yl) aminovaleric acid (1'S)-1'-(1-naphthyl)ethylamide [Compound No. 113]

The compound obtained in Example 98-1 (279.0 mg), 2-(3,5-dimethylpyrazolyl)-4,5-dihydroimidazole hydrobromide (178.1 mg), and diisopropylamine (0.127 ml) were dissolved in DMF (1.4 ml). The solution was stirred for 3.5 hours at 80° C. After the reaction, the solvent was removed by distillation under reduced pressure. The residue was purified by silica gel column chromatography (9 g, chloroform/methanol=10/1). The compound obtained was dissolved in chloroform (5 ml). Methanol (0.5 ml) and mesil acid (0.256 ml) were added to the solution. The mixture was stirred for 24 hours at room temperature. After the reaction, the solvent was removed by distillation under reduced pressure. The residue was purified by silica gel column chromatography (8 g, chloroform/methanol/water=7/3/0.5) to obtain mesilate of the title compound (218.9 mg) as a white solid.

MS(FAB,Pos.): m/z=578[M+1]$^+$ $^1$H-NMR(500 MHz, DMSO-d$_6$): δ=1.42–1.57(2H,m),1.52(3H,d,J=6.8 Hz), 1.64–1.78(2H,m),2.32(0.9H,s),3.10(2H,q,J=6.8 Hz),3.56 (4H,brs), 4.31(2H,brs),4.33(2H,brs),4.55(1H,dd,J=8.5, 14.2 Hz),5.72(1H, quint.,J=6.8 Hz),7.45–7.57(6H,m),7.62(2H,d, J=8.5 Hz),7.84(1H, d,J=8.1 Hz),7.91(1H,dt,J=1.7, 7.8 Hz), 7.94(1H,d,J=2.44 Hz),7.97(1H,d,J=8.3 Hz),8.10(1H,d,J=7.1 Hz),8.22(1H,q,J=5.4 Hz),8.52(1H,J=8.1 Hz),8.66–8.68(1H, m),8.70(1H,d,J=7.8 Hz),9.56(2H,brs)

EXAMPLE 99

Preparation of (S)-2-(4-(N-2-picolyl)aminomethyl) benzoyl)amino-5-(pyrimidin-2-yl)aminovaleric acid (1'S)-1'-(1-naphthyl)ethylamide [Compound No. 114]

The compound obtained in Example 98-2 (311.0 mg), 2-bromopyrimidine (97.1 mg), and diisopropylamine (0.106 ml) were dissolved in DMF (1.6 ml). The solution was stirred for 23 hours at 80° C. After the reaction, the solvent was removed by distillation under reduced pressure. The residue was dissolved in ethyl acetate. The resulting solution was washed with saturated brine, and dried over magnesium sulfate. The solvent was removed by distillation under reduced pressure and the residue was purified by silica gel column chromatography (18 g, chloroform/methanol=13/1).

The compound obtained was dissolved in methanol (2.8 ml) and 4 mol/l hydrochloric acid/dioxane solution (2.8 ml) was added to the solution. The mixture was stirred for 2 hours at room temperature. After the reaction, the solvent was removed by distillation under reduced pressure to obtain hydrochloride of the title compound (276.3 mg) as a white solid.

MS(FAB,Pos.): m/z=588[M+1]$^+$ $^1$H-NMR(500 MHz, DMSO-d$_6$): δ=1.51(3H,d,J=6.8 Hz),1.54–1.65(2H,m), 1.72–1.81(2H,m),3.30–3.38(2H,m),4.31(4H,brs),4.55–4.59 (1H, m),5.67–5.73(1H,quint.,J=6.8 Hz),6.79(1H,brs), 7.44–7.56(6H, m),7.64(2H,d,J=8.5 Hz),7.81(1H,d,J=8.1 Hz),7.90–7.94(2H,m), 7.97(2H,d,J=8.1 Hz),8.09(1H,d,J= 7.6 Hz),8.45(1H,d,J=4.2 Hz),8.55(1H,d,J=8.1 Hz),8.66(1H, dd,J=1.0, 3.9 Hz),8.77(1H,d,J=7.6 Hz), 9.80–9.86(2H,br).

EXAMPLE 100

Preparation of (S)-2-(4-(N-2-picolylaminomethyl) benzoyl)amino-5-(3,4,5,6-tetrahydropyrimidin-2-yl) aminovaleric acid (1'S)-1'-(1-naphthyl)ethylamide [Compound No. 115]

The compound obtained in Example 99 (202.0 mg) was dissolved in acetic acid (10 ml), and concentrated hydrochloric acid (1.8 ml) was added to the solution. An acetic acid suspension (10 ml) of 10% palladium-on-carbon (109.2 mg) was added and reacted for 2 hours under a hydrogen pressure of 2.85 kg/cm$^2$. After the reaction, the catalyst was removed and the solvent was removed by distillation under reduced pressure. After azeotropic distillation with toluene, the residue was purified by silica gel column chromatography (6 g, chloroform/methanol/water=7/3/0.5) to obtain the title compound (189.5 mg) as a white solid.

MS(FAB,Pos.): m/z=592[M+1]$^+$ $^1$H-NMR(500 MHz, DMSO-d$_6$): δ=1.40–1.60(2H,m),1.52(3H,d,J=6.8 Hz), 1.65–1.84(4H,m),3.00–3.10(2H,m),3.18–3.22(4H,m),4.30 (2H,s), 4.31(2H,s),4.53–4.58(1H,m),5.72(1H,quint.,J=6.8 Hz),7.44–7.57(6H,m),7.64(2H,d,J=8.3 Hz),7.79(1 H,brs) (1H,brs),7.82(1H,d,J=8.3 Hz),7.90(1H,td,J=7.8,1.7 Hz), 7.94(1H,d,J=7.6 Hz),7.99 (2H,d,J=8.3 Hz),8.11(1H,d,J=8.1 Hz),8.59(1H,d,J=8.1 Hz),8.66(1H,ddd,J=4.9,1.7,1.0 Hz), 8.82(1H,d,J=7.8 Hz),9.70–9.90(2H, br).

EXAMPLE 101

Preparation of [Compound No. 116] to [Compound No. 130]

Hydrochlorides of the compounds shown below were prepared according to the same procedure as in Example 66-5.

Synthesis of (S)-2-(4-(2-picolylaminomethyl)benzoyl)-5-(2-picolylamino)valeric acid 1'-(1-naphthyl)ethylamide [Compound No. 116]

The same procedure was carried out using 1'-(1-naphthyl) ethylamine (26.4 mg) to obtain hydrochloride of the title compound (46.6 mg) as a white solid.

MS(FAB,Pos.): m/z=601[M+1]$^+$ $^1$H-NMR(500 MHz, DMSO-d$_6$): δ=1.50(1.5H,d,J=6.8 Hz),1.51(1.5H,d, J=6.8 Hz), (1.68–1.94(4H,m),2.92–3.04(2H,m),4.24–4.36(6H,m), 4.52–4.60(1H,m),5.62–5.72 (1H,m),7.44–7.68(10H,m), 7.80–7.84(1H,m),7.88–8.02(5H,m),8.06–8.12(1H,m), 8.60–8.70(3H,m), 8.83(0.5H,d,J=7.8 Hz),8.88(0.5H,d,J=7.6 Hz),9.40(2H,bs),9.96(2H,bs).

Synthesis of (S)-2-(4-(2-picolylaminomethyl)benzoyl)-5-(2-picolylamino)valeric acid n-dodecylamide [Compound No. 117]

The same procedure was carried out using n-dodecylamine (28.6 mg) to obtain hydrochloride of the title compound (58.0 mg) as a white solid.

MS(FAB,Pos.): m/z=615[M+1]$^+$ $^1$H-NMR(500 MHz, DMSO-d$_6$): δ=0.85(3H,t,J=6.8 Hz),1.16–1.32(18H, m),1.32–1.44(2H,m),1.68–1.88(4H,m),2.94–3.08(4H,m), 4.28–4.38(6H,m),4.40–4.48(1H,m),7.44–7.50(2H,m), 7.58–7.62(2H,m), 7.66(2H,d,J=8.3 Hz),7.90–7.96(2H,m), 7.980(2H,d,J=8.3 Hz),8.14(1H,t,J=5.6 Hz),8.60–8.70(3H, m),9.36–9.44(2H,bs),9.90–10.02 (2H,bs).

Synthesis of (S)-2-(4-(2-picolylaminomethyl)benzoyl)-5-(2-picolylamino)valeric acid 3,5-ditrifluoromethylbenzylamide [Compound No. 118]

The same procedure was carried out using 3,5-ditrifluoromethylbenzylamine (37.5 mg) to obtain hydrochloride of the title compound (57.8 mg) as a white solid.

MS(FAB,Pos.): m/z=673[M+1]$^+$ $^1$H-NMR(500 MHz, DMSO-d$_6$): δ=1.70–1.96(4H,m),2.96–3.06(2H,m), 4.30–4.36(6H,m),4.40–4.58(3H,m),7.42–7.50(2H,m), 7.56–7.60 (2H,m),7.678(2H,d,J=8.3 Hz),7.90–7.96(2H,m), 7.96–8.06(5H,m), 8.63(1H,d,J=4.9 Hz),8.66(1H,d,J=4.9 Hz),8.80(1H,d,J=7.6 Hz),8.94 (1H,t,J=6.1 Hz),9.30–9.40 (2H,bs),9.88–10.00(2H,bs).

Synthesis of (S)-2-(4-(2-picolylaminomethyl)benzoyl)-5-(2-picolylamino)valeric acid (+)-dehydroabietylamide [Compound No. 119]

The same procedure was carried out using (+)-dehydroabietylamine (44.1 mg) to obtain hydrochloride of the title compound (65.9 mg) as a white solid.

MS(FAB,Pos.): m/z=715[M+1]$^+$ $^1$H-NMR(500 MHz, DMSO-d$_6$): δ=0.70–1.90(24H,m),2.18–2.30(1H,m), 2.66–2.84(4H,m),2.86–3.04(2H,m),3.06–3.14(1H,m), 4.24–4.36 (6H,m),4.50–4.56(1H,m),6.77(0.5H,s),6.86 (0.5H,s),6.90–6.98(1H,m),7.10–7.18(1H,m),7.44–7.52(2H, m),7.56–7.70(4H,m), 7.82–8.04(5H,m),8.58–8.70(3H,m), 9.36–9.50(2H,bs),9.90–10.08 (2H,bs).

Synthesis of (S)-2-(4-(2-picolylaminomethyl)benzoyl)-5-(2-picolylamino)valeric acid 2,3-dichlorobenzylamide [Compound No. 120]

The same procedure was carried out using 2,3-dichlorobenzylamine (27.0 mg) to obtain hydrochloride of the title compound (53.0 mg) as a white solid.

MS(FAB,Pos.): m/z=606,608,610[M+1]+ 1H-NMR(500 MHz,DMSO-d$_6$): δ=1.76–1.98(4H,m),2.98–3.06(2H,m), 4.30–4.36(6H,m),4.38(2H,d,J=5.9 Hz),4.51–4.61(1H,m), 7.34–7.36(2H,m),7.43–7.50(2H,m),7.53–7.62(3H,m),7.68 (2H,d,J=8.3 Hz),7.90–7.98(2H,m),8.01(2H,d,J=8.3 Hz), 8.63–8.67(2H,m), 8.77(1H,d,J=8.1 Hz),8.81(1H,t,J=5.9 Hz),9.40(1H,bs),9.97(1H,bs).

Synthesis of (S)-2-(4-(2-picolylaminomethyl)benzoyl)-5-(2-picolylamino)valeric acid 2-octylamide [Compound No. 121]

The same procedure was carried out using 2-octylamine (20.0 mg) to obtain hydrochloride of the title compound (45.1 mg) as a white solid.

MS(FAB,Pos.): m/z=559[M+1]+ 1H-NMR(500 MHz, DMSO-d$_6$): δ=0.82(1.5H,d,J=8.1 Hz),0.83(1.5H,d, J=8.1 Hz),1.02(3H,t,J=6.8 Hz),1.10–1.30(8H,m),1.30–1.44(2H, m), 1.68–1.86(4H,m),2.94–3.06(2H,m),3.64–3.78(1H,m), 4.24–4.38 (6H,m),4.40–4.48(1H,m),7.44–7.54(2H,m), 7.58–7.66(2H,m), 7.673(2H,d,J=8.3 Hz),7.90–8.02(5H,m), 8.56–8.62(1H,m),8.62–8.68(2H,m),9.40–9.50(2H,bs), 9.96–10.06(2H,bs).

Synthesis of (S)-2-(4-(2-picolylaminomethyl)benzoyl)-5-(2-picolylamino)valeric acid 3-(3-indolyl)-2-propylamide [Compound No. 122]

The same procedure was carried out using 3-(3-indolyl)-2-propylamine (27.0 mg) to obtain hydrochloride of the title compound (57.0 mg) as a white solid.

MS(FAB,Pos.): m/z=604[M+1]+ 1H-NMR(500 MHz, DMSO-d$_6$): δ=1.03 and 1.07(3H,d,J=6.6 Hz),1.50–1.82(4H, m),2.64–3.10(4H,m),4.04(1H,quint,J=6.6 Hz),4.20–4.40 (6H,m),4.32–4.54(1H,m),6.82–7.36(4H,m),7.40–7.50(2H, m), 7.50–7.70(5H,m),7.89–8.20(5H,m),8.54–8.67(3H,m), 9.34–0.52 (2H,bs),9.90–10.10(2H,brs).

Synthesis of (S)-2-(4-(2-picolylaminomethyl)benzoyl)-5-(2-picolylamino)valeric acid 2,2-diphenylethylamide [Compound No. 123]

The same procedure was carried out using 2,2-diphenylethylamine (30.5 mg) to obtain hydrochloride of the title compound (55.0 mg) as a white solid.

MS(FAB,Pos.): m/z=627[M+1]+ 1H-NMR(500 MHz, DMSO-d$_6$): δ=1.48–1.72(4H,m),2.80–2.92(2H,m), 3.62–3.70(1H,m),3.76–3.84(1H,m),4.20(1H,t,J=7.8 Hz), 4.24–4.34(6H,m),4.36–4.40(1H,m),7.14–7.20(2H,m), 7.22–7.30(8H,m), 7.46–7.50(2H,m),7.58(1H,d,J=7.8 Hz), 7.61(1H,d,J=7.8 Hz),7.66 (2H,d,J=8.3 Hz),7.90–7.98(4H, m),8.13(1H,t,J=5.4 Hz),8.52(1H,d, J=8.3 Hz),8.62–8.64 (1H,m),8.66–8.68(!H,m),9.30–9.40(2H,bs), 9.92–10.02(2H, bs).

Synthesis of (S)-2-(4-(2-picolylaminomethyl)benzoyl)-5-(2-picolylamino)valeric acid 4-t-butylcyclohexylamide [Compound No. 124]

The same procedure was carried out using 4-t-butylcyclohexylamine (24.0 mg) to obtain hydrochloride of the title compound (49.8 mg) as a white solid.

MS(FAB,Pos.): m/z=555[M+1]+ 1H-NMR(500 MHz, DMSO-d$_6$): δ=0.80(3H,s) 0.82(6H,s),0.88–1.34(4H, m),1.36–1.50(1H,m),1.66–1.86(8H,m),2.94–3.04(2H,m), 3.38–3.48(1H,m),4.26–4.36(6H,m),4.46–4.56(0.5H,m), 4.58–4.62(0.5H, m),7.44–7.50(2H,m),7.58–7.64(2H,m), 7.66(2H,d,J=8.3 Hz),7.90–8.00(4.5H,m),8.06(0.5H,d,J=7.8 Hz),8.57(0.5H,d,J=8.1 Hz),8.60–8.70(2.5H,m),9.36–9.46 (2H,bs),9.94–10.00(2H,bs).

Synthesis of (S)-2-(4-(2-picolylaminomethyl)benzoyl)-5-(2-picolylamino)valeric acid 2,4-dichlorobenzylamide [Compound No. 125]

The same procedure was carried out using 2,4-dichlorobenzylamine (27.2 mg) to obtain hydrochloride of the title compound (60.1 mg) as a white solid.

MS(FAB,Pos.): m/z=606,608,610[M+1]+ 1H-NMR(500 MHz,DMSO-d$_6$): δ=1.72–1.96(4H,m),2.96–3.06(2H,m) 4.26–4.38(8H,m),4.50–4.58(1H,m),7.38–7.44(2H,m), 7.46–7.52 (2H,m),7.58–7.66(3H,m),7.68(2H,d,J=8.3 Hz), 7.92–7.98(2H,m), 8.00(2H,d,J=8.3 Hz),8.64–8.68(2H,m), 8.76–8.82(2H,m),9.40–9.50(2H,bs),9.98–10.08(2H,bs).

Synthesis of (S)-2-(4-(2-picolylaminomethyl)benzoyl)-5-(2-picolylamino)valeric acid benzhydrylamide [Compound No. 126]

The same procedure was carried out using benzhydrylamine (28.3 mg) to obtain hydrochloride of the title compound (56.8 mg) as a white solid.

MS(FAB,Pos.): m/z=613[M+1]+ 1H-NMR(500 MHz, DMSO-d$_6$): δ=1.70–1.96(4H,m),2.94–3.06(2H,m) 4.26–4.36(6H,m),4.64–4.70(1H,m),6.11(1H,d, 8.5 Hz), 7.20–7.28 (2H,m),7.30–7.40(6H,m),7.40–7.50(3H,m),7.53 (1H,d,J=7.3 Hz), 7.58(2H,t,J=8.1 Hz),7.667(2H,d,J=8.3 Hz),7.88–7.96(2H,m),7.98 (2H,d,J=8.3 Hz),8.62(1H,d,J= 4.2 Hz),8.66(1H,d,J=4.4 Hz),8.71(1H,d,J=8.3 Hz),8.81(1H, d,J=8.5 Hz),9.36–9.42(2H,bs),9.88–9.96 (2H,bs).

Synthesis of (S)-2-(4-(2-picolylaminomethyl)benzoyl)-5-(2-picolylamino)valeric acid 3-chlorobenzylamide [Compound No. 127]

The same procedure was carried out using 3-chlorobenzylamine (21.9 mg) to obtain hydrochloride of the title compound (54.9 mg) as a white solid.

MS(FAB,Pos.): m/z=571,573[M+1]+ 1H-NMR(500 MHz, DMSO-d$_6$): δ=1.70–1.96(4H,m),2.96–3.06(2H,m), 4.24–4.38(8H,m),4.48–4.54(1H,m),7.23(1H,d,J=7.8 Hz), 7.26–7.36(3H,m),7.44–7.52(2H,m),7.58–7.66(2H,m),7.68 (2H,d,J=8.3 Hz),7.90–8.00(2H,m),8.00(2H,d,J=8.3 Hz), 8.62–8.68(2H,m), 8.84–8.90(2H,m),9.38–9.50(2H,bs), 9.96–10.06(2H,bs).

Synthesis of (S)-2-(4-(2-picolylaminomethyl)benzoyl)-5-(2-picolylamino)valeric acid 2-(4-methoxyphenyl)ethylamide [Compound No. 128]

The same procedure was carried out using 2-(4-methoxyphenyl)ethylamine (23.3 mg) to obtain hydrochloride of the title compound (46.7 mg) as a white solid.

MS(FAB,Pos.): m/z=581[M+1]+ 1H-NMR(500 MHz, DMSO-d$_6$): δ=1.66–1.84(0.4H,m),2.649(2H,t,J=7.3 Hz), 2.90–3.02(2H,m),3.18–3.30(2H,m),3.68(3H,s),4.22–4.38 (6H,m),4.40–4.46(1H,m),6.804(2H,d,J=8.5 Hz),7.11(2H, d,J=8.5 Hz),7.44–7.50(2H,m),7.58–7.64(2H,m),7.68(2H,d, J=8.3 Hz),7.90–7.96(2H,m),7.99(2H,d,J=8.3 Hz),8.21(1H,t, J=5.6 Hz),8.60–8.68(3H,m),9.36–9.46(2H,bs),9.96–10.06 (2H,bs).

Synthesis of (S)-2-(4-(2-picolylaminomethyl)benzoyl)-5-(2-picolylamino)valeric acid (4-(4-methylphenyl)oxy) phenylamide [Compound No. 129]

The same procedure was carried out using (4-(4-methylphenyl)oxy)phenylamine (38.0 mg) to obtain hydrochloride of the title compound (58.0 mg) as a white solid.

MS(FAB,Pos.): m/z=629[M+1]+ 1H-NMR(500 MHz, DMSO-d$_6$): δ=1.76–1.98(4H,m),2.30(3H,s),2.96–3.06(2H, m),4.26–4.38(6H,m),4.38–4.48(1H,m),6.94–6.98(2H,m), 7.04–7.08(2H,m.), 7.20–7.26(2H,m),7.38–7.40(2H,m), 7.44–7.50 (2H,m),7.58–7.64(2H,m),7.66–7.72(2H,m), 7.90–8.00(4H,m), 8.62–8.68(2H,m),8.80(0.5H,d,J=7.8 Hz), 8.96(0.5H,d,J=7.6 Hz), 9.38–9.48(2H,bs),9.96–10.06(2H, bs).

Synthesis of (S)-2-(4-(2-picolylaminomethyl)benzoyl)-5-(2-picolylamino)valeric acid 1-(1,2,3,4-tetrahydronaphthyl) amide [Compound No. 130]

The same procedure was carried out using 1-(1,2,3,4-tetrahydronaphthyl)amine (22.8 mg) to obtain hydrochloride of the title compound (52.2 mg) as a white solid.

MS(FAB,Pos.): m/z=577[M+1]$^+$ $^1$H-NMR(500 MHz, DMSO-d$_6$): δ1.64–1.94(8H,m),2.64–2.80(2H,m), 2.92–3.06 (2H,m),4.24–4.36(6H,m),4.46–4.56(1H,m),4.92–5.00(1H, m),7.06–7.22(4H,m),7.44–7.52(2H,m),7.56–7.82(4H,m), 7.88–8.02(4H,m),8.43(0.5H,d,J=8.8 Hz),8.50(0.5H,d,J=8.5 Hz), 8.58–8.70(2H,m),9.34–9.52(2H,bs),9.88–10.10(2H, bs).

Test results on the activity of the compounds of the present invention as an antiviral drug are described.

TEST EXAMPLE 1

HIV-1$_{IIIB}$ infected MT-4 cells were added to 96-well microtiter plates (3.0×10$^4$/well, MOI (Multiplicity of infection): 0.01), together with test compounds at different concentrations immediately after the infection. After culture for 5 days in a carbon dioxide incubator at 37° C., the number of surviving cells was counted by MTT (tetrazolium) method (Pawels et al., J. Virol. Methods, 20, 309–321, 1988). The antiviral activity was expressed in term of the concentration (μM) at which the compound inhibits 50% of cytotoxicity due to HIV infection (EC$_{50}$: 50% Effective Concentration).

TABLE 1

| Compound No. | EC$_{50}$ (μm) |
| --- | --- |
| 5 | 0.804 |
| 16 | 0.633 |
| 21 | 0.828 |
| 30 | 0.662 |
| 41 | 0.035 |
| 43 | 0.118 |
| 44 | 0.126 |
| 49 | 0.086 |
| 53 | 0.150 |
| 57 | 0.082 |
| 60 | 0.158 |
| 61 | 2.620 |
| 64 | 0.114 |
| 65 | 0.093 |
| 83 | 0.121 |
| 85 | 0.029 |
| 86 | 0.043 |
| 91 | 0.138 |
| 95 | 0.175 |
| 96 | 0.034 |
| 106 | 0.025 |
| 107 | 0.035 |
| 110 | 0.344 |
| 112 | 0.880 |

TEST EXAMPLE 2

The effect of the antiviral drug on SCID mice (immunodeficiency mice) was examined.

TMβ-1 (rat anti-mouse IL-2Rβ monoclonal antibody) was intraperitoneally administered to C.B-17 SCID mice (8 weeks-old, female, provided by CLEA Japan, Inc.) in the amount of 1 mg/mouse to exterminate NK cells. After 2 days, 1.5×10$^6$ human PBMCs were transplanted in the spleen together with human rIL-4 (0.2 μg/mouse). On the same day, the compound No. 86 (0.1 ml/2 mM solution/ mouse) or a medium (0.1 ml) (control) was intraperitoneally administered. After 1 day, HIV-1 (NL4-3) (0.2 ml/1×10$^4$ TCID$_{50}$/ml) was intraperitoneally administered to cause virus infection. The same amount of the compound No. 86 (or the medium) was intraperitoneally administered on each of 4 consecutive days thereafter. rIL-4 (0.2 μg) was also intraperitoneally administered 4 days after infection. 12 days after infection, blood plasma and abdominal cavity washing solutions were collected to measure the amount of HIV-1 P$^{24}$ using an ELISA kit. The results are shown in Table 2.

As shown in Table 2, administration of the antiviral drug decreased the P$^{24}$ level below the limit of detection, confirming the antiviral effect.

TABLE 2

| | | | p24 level (pg/ml) | |
| --- | --- | --- | --- | --- |
| SCID Mouse | Virus | Drug | Plasma | Abdominal cavity washing solution |
| 1 | mock | Medium | <5 | <5 |
| 2 | mock | Medium | <5 | <5 |
| 3 | mock | Medium | <5 | <5 |
| 4 | mock | Medium | <5 | <5 |
| 5 | NL4-3 | Medium | 20 | <5 |
| 6 | NL4-3 | Medium | 18 | 414 |
| 7 | NL4-3 | Medium | 24 | 1200 |
| 8 | NL4-3 | Compound No. 86 | <5 | <5 |
| 9 | NL4-3 | Compound No. 86 | <5 | <5 |

TEST EXAMPLE 3

Acute toxicity of the antiviral drug was examined. Three groups of 7 week-old, ICR male mice, each group consisting of 3 mice, were bred for one week. The compounds prepared in the Examples, dissolved in a physiological saline solution or distilled water, were intraperitoneally administered at a dose of 50 mg/kg, twice a day, for four days. After 5 days, the number of dead animals was examined. The results are shown in Table 3.

As shown in Table 3, no animals to which any tested compound was administered died, confirming non-acute toxicity of the antiviral drug.

TABLE 3

| Comound No. | Dead mouse |
| --- | --- |
| 39 | 0/3 |
| 41 | 0/3 |
| 49 | 0/3 |
| 57 | 0/3 |
| 65 | 0/3 |
| 86 | 0/3 |
| 92 | 0/3 |
| 96 | 0/3 |
| 97 | 0/3 |
| 99 | 0/3 |
| 106 | 0/3 |
| 107 | 0/3 |

PREPARATION EXAMPLE

A mixture of the compound No. 86 (34.6%), lactose (34.6%), cornstarch (17.3%), hydroxypropyl cellulose (7.3%), low substituted hydroxypropyl cellulose (6.2%), all compounds conforming to the specification of Japanese Pharmacopoeia except the compound No. 86, was sieved and thoroughly mixed in a polyvinyl chloride bag. Purified water, conforming to the specification of Japanese Pharmacopoeia, in the amount equivalent to these compounds was added. The mixture was kneaded using a biaxial kneader for 20 minutes to make a wet lump. The wet lump was granulated using an extruding granulator (cylinder pore size: 1 mm). Granules were dried in a fluid bed dryer (30 minutes at 40° C.). Dry granules were sieved. The sieved granules were thoroughly mixed with magnesium stearate at a ratio of 99:1 by weight, and processed using a tableting machine to obtain tablets with an average weight of 292 mg.

An undercoat liquid was prepared from hydroxypropyl methylcellulose 2910 (8%), macro-gall 6000 (1.6%), and purified water (balance to make the total amount 100%), all conforming to the specification of Japanese Pharmacopoeia. The undercoat liquid was sprayed onto the tablets in the amount of 5% of the tablets using a high coater. Undercoated tablets were prepared by drying the liquid for 20 minutes.

Hydroxypropyl methylcellulose acetate succinate (10%), conforming to the specification for drug additives, triethyl citrate (2%), titanium oxide (2%), and hydroxypropyl cellulose (0.05%), all conforming to the specification of Japanese Pharmacopoeia, were dissolved in purified water (balance to make the total amount 100%), thereby obtaining an enteric coating liquid. The enteric coating liquid was sprayed onto the tablets in the amount of 10% of the tablets using a high coater. Enteric-coated tablets were prepared by drying the liquid for 30 minutes. The enteric-coated tablets did not release the active drug component for two hours in the first solution of the Japanese Pharmacopoeia and released 80% or more of the active drug component within 30 minutes in the second solution of the Japanese Pharmacopoeia.

INDUSTRIAL APPLICABILITY

The novel nitrogen-containing compound or the salt thereof of present invention can provide a novel antiviral drug. The novel antiviral drug of the present invention exhibits antiviral activity and is useful as a treatment agent or preventive agent of AIDS and other diseases.

What is claimed is:

1. A nitrogen-containing compound of the following formula (I) or a salt thereof,

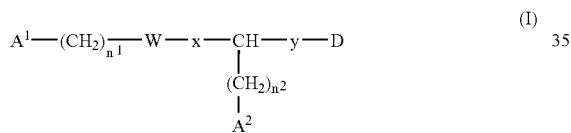

wherein $n^1$ is an integer of 0–3;
wherein $n^2$ is an integer of 0–4;
wherein $A^1$ represents $A^3$-$CH_2$—NH— or $A^3$-NH—, wherein $A^3$ represents a substituted or unsubstituted 5–6 member monocyclic heteroaromatic ring containing 1–2 nitrogen atoms;
wherein $A^2$ represents a substituted or unsubstituted guanidino group, $A^3$-$CH_2$—NH—, or $A^3$-NH—, wherein $A^3$ represents a substituted or unsubstituted 5–12 membered monocyclic or polycyclic heteroaromatic ring, optionally partially saturated, containing 1–2 nitrogen atoms;
wherein W represents a substituted or unsubstituted 6–15 member monocyclic or polycyclic aromatic ring, or a substituted or unsubstituted 5–15 member monocyclic or polycyclic heteroaromatic ring containing 1–3 oxygen atoms, 1–3 sulfur atoms, and/or 1–3 nitrogen atoms;
wherein D represents a:
4-hexadecylaminobenzylamino group,
3-butoxypropylamino group,
tetrahydrofuran-2-ylmethylamino group,
phenylhydrazino group,
1-benzylpiperidin-4-ylamino group,
1-(N-napthalene-2-ylcarbamoyl)-2-phenylethylamino group,
4-(N-(1,2,3,4-tetrahydro-1,4-dicarbonylphthalazin-6-yl)-N-ethyl)amino-butylamino group,
2,4,6-trichlorophenylhydrazino group,
2-(diethylamino)ethylamino group,
3-(morpholin-4-yl)propylamino group,
2-(dimethylamino)ethylamino group,
4-(2,4-di-t-amylphenoxy)butylamino group,
3-aminopropylamino group,
indazol-5-ylamino group,
2-(naphtalene-1-yl)-1-(methoxycarbonyl)ethylamino group,
2-(naphtalene-1-yl)-1-(carboxy)ethylamino group,
dodecylamino group,
dehydroabietylamino group,
2-octylamino group,
2,2-diphenylethylamino group,
4-t-butylcyclohexylamino group,
benzhydrylamino group,
4-(4-methylphenoxy)phenylamino group,
1,2,3,4-tetrahydronaphthalene-1-ylamino group, or
a functional group of the following formula (iii),

wherein R4 represents a hydrogen atom or a methyl group,
wherein $G^3$ represents a $C_1$ to $C_{10}$ linear or branched alkylene group,
wherein $G^3$ represents a substituted or unsubstituted 6–10 member monocyclic or polycyclic aromatic ring, or a substituted or unsubstituted 5–15 member monocyclic or polycyclic heteroaromatic ring containing 1–3 oxygen atoms, 1–3 sulfur atoms, and/or 1–3 nitrogen atoms;
wherein x represents —C(=O)—$NR^8$— or —$CH^2$—C(=O)—$NR^8$, wherein $R^8$ represents H or a substituted or unsubstituted $C_1$–$C_3$ alkyl group; and
wherein y represents —C(=O)—.

2. The compound or the salt according to claim 1, wherein $n^1$ represents an integer of 1 or 2 and $n^2$ represents an integer of 2 or 3.

3. The compound or the salt according to claim 1, wherein each nitrogen atom of $A^3$ is either substituted or unsubstituted, and
W is a monocyclic or dicyclic aromatic ring having 6–10 carbon atoms, or a monocyclic or dicyclic heteroaromatic ring having 5–10 carbon atoms.

4. An antiviral drug comprising a compound of claim 1 or a pharmaceutically acceptable salt thereof as an effective ingredient.

5. The compound or the salt according to claim 2 wherein each nitrogen atom of $A^3$ is either substituted or unsubstituted, and
W is a monocyclic or dicyclic aromatic ring having 6–10 carbon atoms, or a monocyclic or dicyclic heteroaromatic ring having 5–10 carbon atoms.

6. The compound or the salt according to claim 2 wherein $G^1$ represents a linear or branched alkylene group having 1–5 carbon atoms.

7. The compound or the salt according to claim 3 wherein $G^1$ represents a linear or branched alkylene group having 1–5 carbon atoms.

8. An antiviral drug comprising a compound of claim 2 or a pharmaceutically acceptable salt thereof as an effective ingredient.

9. An antiviral drug comprising a compound of claim 3 or a pharmaceutically acceptable salt thereof as an effective ingredient.

10. The compound or the salt according to claim 1, wherein $A^1$ represents $A^3$-$CH_2$—NH— and $A^3$ represents a pyridine group, a pyrazine group or an imidazole group.

11. The compound or the salt according to claim 1, wherein $A^2$ represents a guanidino group or $A^3$-$CH_2$—NH—, wherein $A^3$ represents a dicyclic, partially saturated or unsaturated, heteroaromatic ring.

12. The compound or the salt according to claim 1, wherein $A^2$ represents $A^3$-$CH_2$—NH— and $A^3$ represents a dicyclic, partially saturated or unsaturated, heteroaromatic ring containing 1 or 2 nitrogen atoms.

13. The compound or the salt according to claim 1, wherein W represents a phenyl group or a naphthyl group.

14. The compound or the salt according to claim 1, wherein $n^1$ represents an integer of 1 and $n^2$ represents an integer of 3.

15. The compound or the salt according to claim 1, wherein $G^3$ represents a substituted or unsubstituted 6–10 member dicyclic aromatic ring.

16. The compound or the salt according to claim 1, wherein $G^1$ represents a $C_1$ to $C_3$ linear or branched alkylene group.

17. The compound or the salt according to claim 13, wherein $G^3$ represents a naphthyl group.

18. The compound or the salt according to claim 13, wherein D represents a functional group of the following formula (iii), $$-NR^4\text{-}G^1\text{-}G^3 \qquad \text{(iii)}$$

wherein $R^4$ represents a hydrogen atom,
wherein $G^1$ represents a methylene group,
wherein $G^3$ represents a naphthyl group.

19. The compound or the salt, according to claim 1, wherein the compound is selected from the group consisting of:

(2S)-2-(4-(N-2-picolylaminomethyl)naphthoyl)amino-5-(5,6,7,8-tetrahydroquinolin-8-yl)aminovaleric acid (1'S)-1'-(1-naphthyl)ethylamide;

$N^8$-(4-(N-2-picolylaminomethyl)benzoyl)-L-arginine (1'S)-1'-(1-naphthyl)ethylamide; and (2S)-2-(4-((N-imidazol-2-ylmethyl)aminomethyl)benzoylamino-5-(5,6,7,8-tetrahydroquinolin-8-yl)aminovaleric acid(1)-1(1-naphthyl)ethylamide, and salts thereof.

* * * * *